US011315659B2

(12) United States Patent
Cradick et al.

(10) Patent No.: US 11,315,659 B2
(45) Date of Patent: Apr. 26, 2022

(54) METHODS AND SYSTEMS FOR IDENTIFYING NUCLEOTIDE-GUIDED NUCLEASE OFF-TARGET SITES

(71) Applicant: Georgia Tech Research Corporation, Atlanta, GA (US)

(72) Inventors: Thomas James Cradick, Atlanta, GA (US); Gang Bao, Mableton, GA (US); Peng Qiu, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 122 days.

(21) Appl. No.: 16/594,905

(22) Filed: Oct. 7, 2019

(65) Prior Publication Data

US 2020/0058373 A1    Feb. 20, 2020

Related U.S. Application Data

(63) Continuation-in-part of application No. 16/410,395, filed on May 13, 2019, now abandoned, which is a continuation of application No. 15/114,799, filed as application No. PCT/US2015/013134 on Jan. 27, 2015, now Pat. No. 10,354,746.

(60) Provisional application No. 61/932,003, filed on Jan. 27, 2014.

(51) Int. Cl.
*G16B 30/00* (2019.01)
*G06F 16/22* (2019.01)
*G06F 16/2458* (2019.01)
*G06N 7/00* (2006.01)

(52) U.S. Cl.
CPC ......... *G16B 30/00* (2019.02); *G06F 16/2228* (2019.01); *G06F 16/2468* (2019.01); *G06N 7/005* (2013.01)

(58) Field of Classification Search
CPC .................................................. G06F 16/2228
USPC .............................. 514/44 R, 44 A; 707/741
See application file for complete search history.

(56) References Cited

U.S. PATENT DOCUMENTS 9,938,521 B2 * 4/2018 Maeder ............. C12N 15/1024
10,354,746 B2  7/2019 Cradick et al.
(Continued)

FOREIGN PATENT DOCUMENTS

WO       2015/113063 A1     7/2015

OTHER PUBLICATIONS

"High Frequency off-target mutagenensis induced by CRISPR-Cas nucleases in human cells", Nature Biotechnology, vol. 31, No. 9, Sep. 2013.*

(Continued)

*Primary Examiner* — Hung T Vy
(74) *Attorney, Agent, or Firm* — Smith, Gambrell & Russell

(57) ABSTRACT

Methods and systems for searching genomes for potential nucleotide-guided nuclease off-target sites are provided. Also provided are methods of searching genomes for potential off-target deadCas9 binding sites. In some embodiments, the methods include ranking the potential off-target sites based on the number and location of mismatches, insertions, and/or deletions in the DNA, RNA, or DNA/RNA guide sequence relative to the genomic DNA sequence at a putative target site in the genome, allowing the selection of better target sites and/or experimental confirmation of off-target sites.

20 Claims, 37 Drawing Sheets

Specification includes a Sequence Listing.

(56) References Cited

U.S. PATENT DOCUMENTS

| | | | |
|---|---|---|---|
| 2012/0089339 A1* | 4/2012 | Ganeshalingam | G06F 19/22 702/19 |
| 2014/0068797 A1* | 3/2014 | Doudna | C12N 15/102 800/18 |
| 2016/0004814 A1 | 1/2016 | Stamatoyannopoulos | |
| 2019/0295689 A1 | 9/2019 | Cradick et al. | |

OTHER PUBLICATIONS

Perez, et al., "Establishment of HIV-1 resistance in CD4+ T cells by genome editing using zinc-finger nucleases," Nat. Biotechnol, 26:808-816 (2008).
Ramirez, et al., "Engineered zinc finger nickases induce homology-directed repair with reduced mutagenic effects," Nucleic Acids Res, 40:5560-5568 (2012).
Ran, et al., "Double nicking by RNA-guided CRISPR Cas9 for enhanced genome editing specificity," Cell, 154:1380-1389 (2013).
Ronda, et al., "Accelerating genome editing in CHO cells using CRISPR Cas9 and CRISPy, a web-based target finding tool," Biotechnol Bioeng. 11:1604-1616 (2014).
Rousseau, et al., "CRISPI: a CRISPR interactive database," Bioinformatics, 25: 3317-3318 (2009).
Sander, et al., "ZiFiT (Zinc Finger Targeter): an updated zinc finger engineering tool," Nucleic Acids Res, 38:W462-468 (2010).
Sapranauskas, et al., "The *Streptococcus thermophilus* CRISPR/Cas system provides immunity in *Escherichia coli*," Nucleic Acids Res., 39:9275-9282 (2011).
Shah, et al., "Protospacer recognition motifs: mixed identities and functional diversity," RNA Biol, 10:891-899 (2013).
Shmakov, S., et al., "Discovery and functional characterization of diverse Class 2 CRISPR-Cas systems", Mol Cell, 60(3):385-397 (2015).
Tesson, et al., "Knockout rats generated by embryo microinjection of TALENs" Nat Biotechnol, 29:695-696 (2011).
Tsai, et al., "Dimeric CRISPR RNA-guided FokI nucleases for highly specific genome editing," Nat Biotechnol, 32:569-576 (2014).
Vaquerizas, et al., "A census of human transcription factors: function, expression and evolution," Nature Genetics, 10:252-263 (2009).
Wang, et al., "One-step generation of mice carrying mutations in multiple genes by CRISPR/Cas-mediated genome engineering," Cell, 153:910-918 (2013).
Xiao, et al., "CasOT: A genome-wide Cas9/gRNA off-target searching tool," Bioinformatics, 30:1180-1182 (2014).
Xie, et al., "RNA-guided genome editing in plants using a CRISPR-Cas system," Mol Plant, 6 (2013).
Yu, et al., "Synthesis-dependent microhomology-mediated end joining accounts for multiple types of repair junctions," Nucleic Acids Res., 38:5706-5717 (2010).
International Preliminary Reporton Patentability received for PCT Patent Application No. PCT/US15/013134, dated Aug. 11, 2016, 9 pages.
International Search Report and Written Opinion received for PCT Patent Application No. PCT/US15/013134, dated May 11, 2015, 11 pages.
Ming Ma et al: "A Guide RNA Sequence Design Platform for the CRISPR/Cas9 System for Model Organism Genomes", Biomed Research International, vol. 31, No. 3, Jan. 1, 2013 (Jan. 1, 2013), p. 822-824.
Non-Final Rejection dated Jun. 1, 2018 for U.S. Appl. No. 15/114,799.
Notice of Allowance and Fees Due (PTOL-85) dated Feb. 13, 2019 for U.S. Appl. No. 15/114,799.
Prashant Mali et al: "CAS9 transcriptional activators for target specificity screening and paired nickases for cooperative genome engineering", Nature Biotechnology, vol. 31, No. 9, Aug. 1, 2013 (Aug. 1, 2013), pp. 833-838.
Thomas J Cradick et al: "COSMID: A Web-based Tool for Identifying and Validating CRISPR/Cas Off-target Sites", Molecular Therapy-Nucleic Acids, vol. 3, No. 12, Dec. 2, 2014 (Dec. 2, 2014), p. e214.

Non-Final Rejection received in corresponding application U.S. Appl. No. 16/410,395, dated Apr. 16, 2021 (11 pages).
Bae, et al., "Cas-OFFinder: a fast and versatile algorithm that searches for potential off-target sites of Cas9 RNA-guided endonucleases," Bioinformatics, 30:1473-1475 (2014).
Barrangou, et al., "CRISPR provides acquired resistance against viruses in prokaryotes," Science, 315:1709-1712 (2007).
Bolotin, et al., "Clustered regularly interspaced short palindrome repeats (CRISPRs) have spacers of extrachromosomal origin," Microbiology, 151 (Pt. 8): 2551-2561 (2005).
Brouns, et al., "Small CRISPR RNAs guide antiviral defense in prokaryotes," Science, 321: 960-964 (2008).
Chen, et al., "Cut site selection by the two nuclease domains of the Cas9 RNA-guided endonuclease," J. Biol Chem., 289(19):13284-94 (2014).
Cheng, et al., "Multiplexed activation of endogenous genes by CRISPR-on, an RNA-guided transcriptional activator system," Cell Res, 23: 1163-1171 (2013).
Cho, et al. "Targeted genome engineering in human cells with the Cas RNA-guided endonuclease," Nat. Biotechnol, 31:230-232 (2013).
Cong, et al., "Multiplexed Genome Engineering Using CRISPR/Cas Systems," Science, 339: 819-823 (2013).
Cornu, et al., "Quantification of zinc finger nuclease-associated toxicity," Methods Mol Biol, 649:237-245 (2010).
Cradick, et al., "ZFN-Site searches genomes for zinc finger nuclease target sites and off-target sites," BMC Bioinformatics, 12:152 (2011).
Cradick, et al., "CRISPR/Cas9 systems targeting β-globin and CCR5 genes have substantial off-target activity," Nucleic Acids Res, 41:9584-9592 (2013).
Fine, et al., "An online bioinformatics tool predicts zinc finger and TALE nuclease off-target cleavage," Nucleic Acids Res, 42:e42 (2013).
Fischer, et al., "An archaeal immune system can detect multiple protospacer adjacent motifs (PAMs) to target invader DNA," J Biol Chem, 287:33351-33363 (2012).
Fu et al., "High-frequency off-target mutagenesis induced by CRISPR-Cas nucleases in human cells," Nat Biotechnol, 31:822-826 (2013).
Fu, et al., "Improving CRISPR-Cas nuclease specificity using truncated guide RNAs," Nature Biotech. (3):279-84, (2014).
Gabriel, et al., "An unbiased genome-wide analysis of zinc-finger nuclease specificity," Nat. Biotechnol, 29:816-823 (2011).
Gaj, et al., "ZFN, TALEN, and CRISPR/Cas-based methods for genome engineering," Trends Biotechnol, 31:397-405 (2013).
Garneau, et al., "The CRISPR/Cas bacterial immune system cleaves bacteriophage and plasmid DNA," Nature, 468:67-71 (2010).
Gasiunas, et al., "Cas9-crRNA ribonucleoprotein complex mediates specific DNA cleavage for adaptive immunity in bacteria," Proc Natl Acad Sci USA, 109:E2579-E2586 (2012).
Geurts, et al., "Knockout rats via embryo microinjection of zinc-finger nucleases," Science, 325:433 (2009).
Gratz, et al., "Genome engineering of *Drosophila* with the CRISPR RNA-guided Cas9 nuclease," Genetics, 194:1029-1035 (2013).
Grissa, et al., "CRISPRFinder: a web tool to identify clustered regulary interspaced short palindromic repeats," Nucleic Acids Res, 35: W52-W57 (2007).
Grissa, et al., "The CRISPRdb database and tools to display CRISPRs and to generate dictionaries of spacers and repeats," BMC Bioinformatics, 8:172 (2007).
Guilinger, et al., "Fusion of catalytically inactive Cas9 to FokI nuclease improves the specificity of genome modification," Nat Biotechnol, 32: 577-582 (2014).
Gupta, et al., "Targeted chromosomal deletions and inversions in zebrafish," Genome Res., 23:1008-1017 (2013).
Guschin, et al., "A rapid and general assay for monitoring endogenous gene modification," Methods Mol. Biol., 649:247-256 (2010).
Hale, et al., "RNA-guided RNA cleavage by a CRISPR RNA-Cas protein complex," Cell, 139: 945-956 (2009).
Hockemeyer, et al., "Genetic engineering of human pluripotent cells using TALE nucleases" Nat Biotechnol, 29:731-734 (2011).
Horvath, et al., "Diversity, activity, and evolution of CRISPR loci in *Streptococcus thermophilus*," J Bacteriol, 190:1401-1412 (2008).

(56) References Cited

OTHER PUBLICATIONS

Horvath, et al., "CRISPR/Cas, file immune system of bacteria and Archaea," Science, 327: 167-170 (2010).
Hou, et al., "Efficient genome engineering in human pluripotent stem cells using Cas9 from Neisseria meningitidis," Proc Natl Acad Sci USA, 110: 15644-15649 (2013).
Hsu, et al., "DNA targeting specificity of RNA-guided Cas9 nucleases," Nat Biotechnol, 31: 827-832 (2013).
Hwang, et al., "Efficient genome editing in zebrafish using a CRISPR-Cas system," Nat. Biotechnol, 31:227-229 (2013).
Iseli, et al., "Indexing Strategies for Rapid Searches of Short Words in Genome Sequences," PLoS ONE, 2(6): e579 (2007).
Jiang, et al., "RNA-guided editing of bacterial genomes using CRISPR-Cas systems," Nat Biotechnol, 31: 233-239 (2013).
Jinek, et al., "A programmable dual-RNA-guided DNA endonuclease in adaptive bacterial immunity," Science, 337:816-821 (2012).
Jinek, et al., "RNA-programmed genome editing in human cells," Elife 2:e00471 (2013).
Lambert, et al., "The human transcription factors," Cell, 172:650-665 (2018).
Ledford, H., "Bacteria yield new gene cutter," Nature, 526(7571):17 (2015).
Lee, et al., "Targeted chromosomal deletions in human cells using zinc finger nucleases," Genome Res., 20:81-89 (2010).
Lin, et al., "CRISPR/Cas9 systems have off-target activity with insertions or deletions between target DNA and guide RNA sequences," Nucleic Acids Res, 42:7473-7485 (2014).
Makarova, et al., "A putative RNA-interference-based immune system in prokaryotes: computational analysis of the predicted enzymatic machinery, functional analogies with eukaryotic RNAi, and hypothetical mechanisms of action," Biol. Direct, 1:7 (2006).
Mali, et al., "Cas9 as a versatile tool for engineering biology," Nat. Methods, 10:957-963 (2013).
Mali, et al., "RNA-guided human genome engineering via Cas9," Science, 339: 823-826 (2013).
Marraffini, et al., "CRISPR interference: RNA-directed adaptive immunity in bacteria and archaea," Nat Rev Genet, 11:181-190 (2010).
Mojica, et al., "Short motif sequences determine the targets of the prokaryotic CRISPR defence system," Microbiology, 155 (Pt. 3): 733-740 (2009).
Montague, et al., "CHOPCHOP: a CRISPR/Cas9 and TALEN web tool for genome editing," Nucleic Acids Res, 42:W401-W407 (2014).
Mussolino, et al., "A novel TALE nuclease scaffold enables high genome editing activity in combination with low toxicity," Nucleic Acids Res, 39:9283-9293 (2011).
Pattanayak, et al., "High-throughput profiling of off-target DNA cleavage reveals RNA-programmed Cas9 nuclease specificity," Nat Biotechnol, 31: 839-843 (2013).
Pearson, W.R. and D.J. Lipman, "Improved tools for biological sequence comparison," Proc. Natl. Acad. Sci., 85:2444-2448 (1988).

* cited by examiner

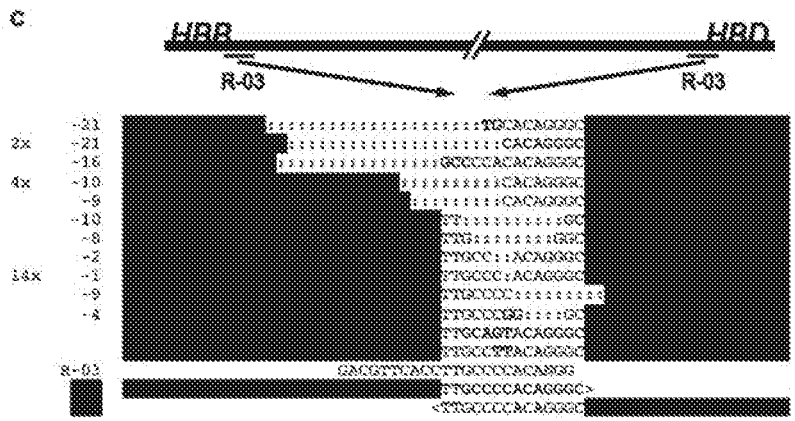
FIG. 4A, 4B, and 4C

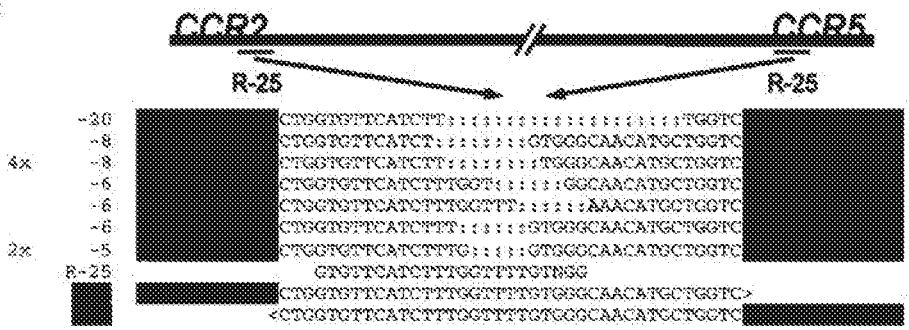
FIG. 5A, 5B, and 5C

 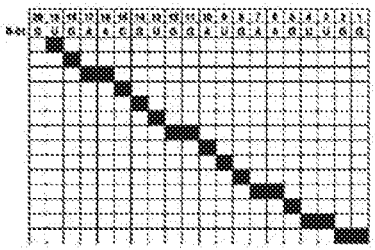 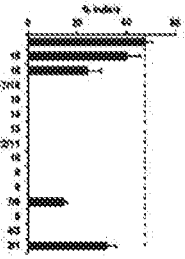
FIG. 9A  FIG. 9B  FIG. 9C
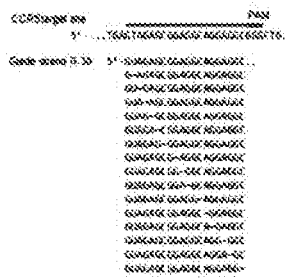 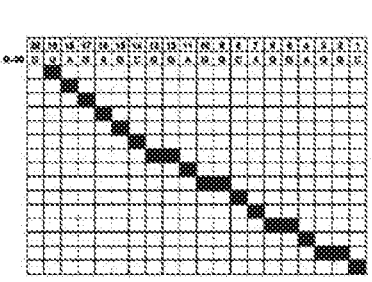 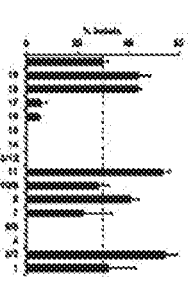
FIG. 10A  FIG. 10B  FIG. 10C

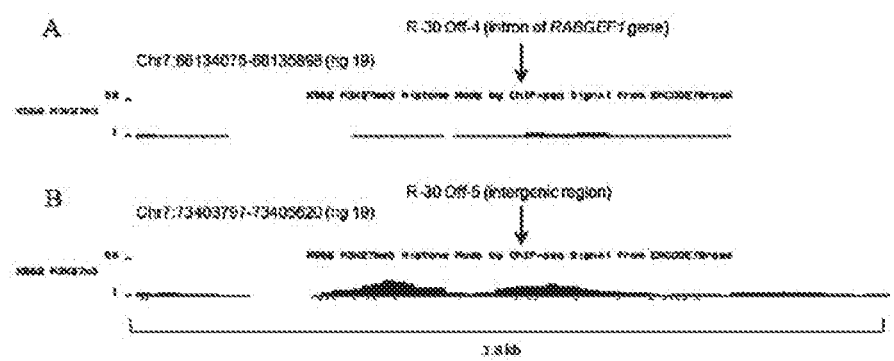
FIG. 20
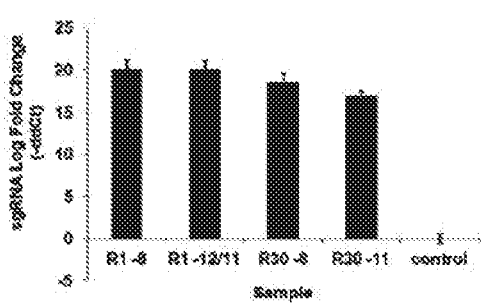
FIGS. 21A-21B
FIG. 22

To allow gRNA bulge = DNA is one-base shorter

DNA
gRNA

Search for genomic sequence using strings with each deletion:

```
T-AACGTGGATGAAGTTGGNRG
TG-ACGTGGATGAAGTTGGNRG
TGAA-GTGGATGAAGTTGGNRG
TGAAC-TGGATGAAGTTGGNRG
TGAACG-GGATGAAGTTGGNRG
TGAACGT-GATGAAGTTGGNRG
TGAACGTG-ATGAAGTTGGNRG
TGAACGTGG-TGAAGTTGGNRG
TGAACGTGGA-GAAGTTGGNRG
TGAACGTGGAT-AAGTTGGNRG
TGAACGTGGATG-AGTTGGNRG
TGAACGTGGATGAA-TTGGNRG
TGAACGTGGATGAAG-TGGNRG
TGAACGTGGATGAAGTT-GNRG
TGAACGTGGATGAAGTTGG-RG
TGAACGTGGATGAAGTTGGNR-
```

FIG. 26E

To allow DNA bulge = gRNA is one base shorter

DNA
gRNA

Search for genomic sequence using strings with each insertion added:

```
NGAACGTGGATGAAGTTGGNRG
GNAACGTGGATGAAGTTGGNRG
GANACGTGGATGAAGTTGGNRG
GAANCGTGGATGAAGTTGGNRG
GAACNGTGGATGAAGTTGGNRG
GAACGNTGGATGAAGTTGGNRG
GAACGTNGGATGAAGTTGGNRG
GAACGTGNGATGAAGTTGGNRG
GAACGTGGNATGAAGTTGGNRG
GAACGTGGANTGAAGTTGGNRG
GAACGTGGATNGAAGTTGGNRG
GAACGTGGATGNAAGTTGGNRG
GAACGTGGATGANAGTTGGNRG
GAACGTGGATGAANGTTGGNRG
GAACGTGGATGAAGNTTGGNRG
GAACGTGGATGAAGTNTGGNRG
GAACGTGGATGAAGTTNGGNRG
GAACGTGGATGAAGTTGNGNRG
GAACGTGGATGAAGTTGGNNRG
GAACGTGGATGAAGTTGGNNRG
GAACGTGGATGAAGTTGGNRNG
```

FIG. 26F

|  |  | Mis | Ins | Del |
|---|---|---|---|---|
| TAGAGCGGAGGCAGGAGGCNGG | -No Indel | | | |
| CAGGAGAGGAGGCAGGAGGCAGG | -Chr2:113487249 | 3 | 0 | 0 |
| -AGAGCGGAGGCAGGAGGCNGG | -Del 19 | | | |
| CAGGAGAGGAGGCAGGAGGCAGG | -Chr2:113487249 | 2 | 0 | 1 |
| TANGAGCGGAGGCAGGAGGCNGG | -Ins 17 | | | |
| CAGGAGAGGAGGCAGGAGGCAGG | -Chr2:113487249 | 2 | 1 | 0 |

FIG. 28A

|  |  | Mis | Ins | Del |
|---|---|---|---|---|
| TAGAGCGGAGGCAGGAGGCNGG | -No Indel | | | |
| TGTGAGCGGAGGCAGGAGGCAGG | -Chr2:241984714 | 2 | 0 | 0 |
| -AGAGCGGAGGCAGGAGGCNGG | -Del 19 | | | |
| TGTGAGCGGAGGCAGGAGGCAGG | -Chr2:241984714 | 1 | 0 | 1 |
| TNAGAGCGGAGGCAGGAGGCNGG | -Ins 18 | | | |
| TGTGAGCGGAGGCAGGAGGCAGG | -Chr2:241984714 | 1 | 1 | 0 |

FIG. 28B

METHODS AND SYSTEMS FOR IDENTIFYING NUCLEOTIDE-GUIDED NUCLEASE OFF-TARGET SITES

CROSS-REFERENCE TO RELATED APPLICATIONS

This application is a continuation-in-part application of U.S. patent application Ser. No. 16/410,395 filed May 13, 2019, which is a continuation of U.S. patent application Ser. No. 15/114,799, filed Jul. 26, 2016, which was a 371 application of International Application No. PCT/US2015/013134 filed Jul. 27, 2015, which claims the benefit of and priority to U.S. Ser. No. 61/932,003 filed Jan. 27, 2014 and which is incorporated by reference in its entirety.

STATEMENT REGARDING FEDERALLY SPONSORED RESEARCH

This invention was made with government support under Grant PN2EY018244 awarded by the National Institutes of Health. The government has certain rights in the invention.

SEQUENCE LISTING

The Sequence Listing submitted on Oct. 8, 2019, as a text file named "GTRC_6478_SL_txt.txt" created on May 13, 2019, and having a size of 271,348 bytes is hereby incorporated by reference pursuant to 37 C.F.R. § 1.52(e)(5).

FIELD OF THE INVENTION

The invention is generally directed to bioinformatics methods and systems for identifying nucleotide-directed nuclease on-target and putative off-target sites. The invention also includes systems for ranking and comparing nucleotide-directed nuclease on-target and putative off-target sites. These putative cleavage sites can have mismatches, insertions, and/or deletions compared to the guide strand. Determining the possible off-target sites allows better choice of guide strands and testing for effects from nuclease treatment. These methods are an improvement over partial search methods that fail to locate most, if not all cleavage sites.

BACKGROUND OF THE INVENTION

Genome editing has successfully created cell lines and animal models for biological and disease studies, and has a wide range of potential therapeutic applications (Gaj, et al., *Trends Biotechnol*, 31:397-405 (2013)). In particular, engineered nucleases creating DNA double-strand breaks or single-strand breaks ("nicks") at specific genomic sequences greatly enhance the rate of genomic manipulation. Double-strand breaks repaired by the cellular non-homologous end joining (NHEJ) pathway often induce insertions, deletions, and mutations, or other events, which are effective for gene disruptions and knockouts. Alternatively, when donor DNA is supplied, double-strand breaks and DNA nicks can be repaired through homologous recombination, which incorporates the donor DNA and results in precise modification of the genomic sequence. Regardless of the DNA repair pathway, it is important to minimize off-target cleavage in order to reduce the detrimental effects of mutations and chromosomal rearrangements. Although zinc finger nucleases and TAL effector nucleases potentially have a wide range of applications, they were found to cleave at off-target sites at detectible rates (Cornu, et al, *Methods Mol Biol*, 649:237-245 (2010); Ramirez, et al., *Nucleic Acids Res*, 40:5560-5568 (2012); Tesson, et al., *Nat Biotechnol*, 29:695-696 (2011); Hockemeyer, et al., *Nat Biotechnol*, 29:731-734 (2011); Mussolino, et al., *Nucleic Acids Res*, 39:9283-9293 (2011)). Clustered regularly interspaced short palindromic repeats (CRISPR), the bacterial defense system using RNA-guided DNA cleaving enzymes (Bolotin, et al., *Microbiology*, 151 (Pt. 8): 2551-2561 (2005); Barrangou, et al., *Science*, 315:1709-1712 (2007); Brouns, et al., *Science*, 321: 960-964 (2008); Hale, et al., *Cell*, 139: 945-956 (2009); Horvath, et al., *Science*, 327: 167-170 (2010); Marraffini, et al., *Nat Rev Genet*, 11:181-190 (2010); Garneau, et al., *Nature*, 468: 67-71 (2010)) is an exciting alternative to zinc finger nucleases and TAL effector nucleases due to the ease of directing the CRISPR-associated (Cas) proteins (such as Cas9) to multiple gene targets by providing guide RNA sequences complementary to the target sites (Jinek, et al., *Science*, 337: 816-821 (2012); Cong, et al., *Science*, 339: 819-823 (2013). Target sites for CRISPR/Cas9 systems can be found near most genomic loci; the only requirement is that the target sequence, matching the guide strand RNA, is followed by a protospacer adjacent motif (PAM) sequence in either orientation (Mojica, et al., *Microbiology*, 155 (Pt. 3): 733-740 (2009); Shah, et al., RNA Biol, 10:891-899 (2013); Horvath, et al., *J Bacteriol*, 190:1401-1412 (2008)). For *Streptococcus pyogenes* (Sp) Cas9, this is any nucleotide followed by a pair of guanines (marked as NGG). Studies on CRISPR/Cas9 systems indicate the possibility of high off-target activity due to nonspecific hybridization of the guide strand to DNA sequences with base pair mismatches at positions distal from the PAM region (Cong, et al., *Science*, 339: 819-823 (2013); Gasiunas, et al., *Proc Natl Acad Sci USA*, 109:E2579-E2586 (2012); Jinek, et al., *Elife* 2:e00471 (2013); Jiang, et al., *Nat Biotechnol*, 31: 233-239 (2013)).

For CRISPR/Cas9 systems, studies have confirmed levels of off-target cleavage comparable with the on-target rates (Fu, et al., *Nat Biotechnol*, 31: 822-826 (2013); Hsu, et al., *Nat Biotechnol*, 31: 827-832 (2013); Cradick, et al., *Nucleic Acids Res*, 41:9584-9592 (2013); Pattanayak, et al., *Nat Biotechnol*, 31: 839-843 (2013)), even with multiple mismatches to the guide strand in the region close to the PAM. RNA guide strands containing insertions or deletions in addition to base mismatches can result in cleavage and mutagenesis at genomic target site with levels similar to that of the original guide strand (Lin, et al., *Nucleic Acids Res*, 42:7473-7485 (2014)). These studies provide the first experimental evidence that genomic sites could be cleaved when the DNA sequences contain insertions or deletions compared with the CRISPR guide strand. These insertions or deletions have been described as RNA or DNA bulges (Lin, et al., *Nucleic Acids Res*, 42:7473-7485 (2014)). These non-alignments can be thought of as gaps or differences in DNA base stacking. In each case, these can be modeled as insertions and/or deletions in the nucleotide strings and used in the search process These results have demonstrated the need to identify potential off-target sites when choosing guide strand designs and examine off-target effects experimentally when using CRISPR/Cas systems in cells, plants and/or animals.

As mismatches and bulges/indels (insertions and deletions) are tolerated between the guide strand and target sequences, there may be embodiments where there are known or unknown differences between the guide stand and its complementary sequences. In some embodiments, the intended mismatches, truncations, indels or other non-complementary sequences may be included, such that the guide sequence will direct cleavage to the target site, although not a direct matching sequence.

In addition, other forms of nucleotide-guided nuclease gene editing are often utilized. One such platform is enzymatically inactive nucleotide guided endonucleases. Cas9 endonuclease dead, also known as dead Cas9 or dCas9, is a mutant form of Cas9 whose endonuclease activity is removed through point mutations in its endonuclease domain. dCas9 maintains the ability to bind DNA, but lacks the ability to cut DNA. It can however be manipulated to carry transcriptional activators and repressors, chromatic and epigenetic modifiers, and imaging agents to the target site on the nucleotide or DNA to invoke activation, repression, or visualization of the gene of interest. It is important to identify potential off-target sites for dCas9 to minimize the potential for inaccurate genetic modifications and subsequent effects of off-target genetic manipulation.

A number of CRISPR tools have been developed, including Cas Online Designer (Hsu, et al., *Nat Biotechnol*, 31: 827-832 (2013)), ZiFit,27 CRISPR Tools, (Hsu, et al., *Nat Biotechnol*, 31: 827-832 (2013)) and Cas OFFinder (Bae, et al., *Bioinformatics*, 30:1473-1475 (2014)), for different functions (Hsu, et al., *Nat Biotechnol*, 31: 827-832 (2013); Bae, et al., *Bioinformatics*, 30:1473-1475 (2014); Xiao, et al., *Bioinformatics*, 30:1180-1182 (2014); Grissa, et al., *Nucleic Acids Res*, 35: W52-W57 (2007); Grissa, et al., *BMC Bioinformatics*, 8:172 (2007); Rousseau, et al., Bioinformatics, 25: 3317-3318 (2009); Montague, et al., *Nucleic Acids Res*, 42:W401-W407 (2014)). However, none of these bioinformatics search tools has considered the off-target sites due to insertions or deletions between target DNA and guide RNA sequences, nor provide application-specific primers. Off-target cleavage could be detected in cells with 15 different insertions and deletions between the guide strand and genomic sequence, sometimes at rates higher than that of the perfectly matched guide strand (Lin, et al., *Nucleic Acids Res*, 42:7473-7485 (2014)).

Therefore, it is an object of the invention to provide a bioinformatics method and tools to identify potential off-target sites that have mismatches, insertions, and/or deletions between nucleotide-guide strand of choice and genomic sequences.

It is a further object of the invention to provide application-specific primers.

SUMMARY OF THE INVENTION

Methods and systems for searching genomes for potential nucleotide-guided nuclease off-target sites are provided. In some embodiments, the methods include ranking the potential off-target sites based on the number and location of mismatches, insertions, and/or deletions in the DNA, RNA, or DNA/RNA guide sequence relative to the genomic DNA sequence at a putative target site in the genome, allowing the selection of better target sites and/or experimental confirmation of off-target sites. In one embodiment, the nuclease is an enzymatically inactive nucleotide guided nuclease, for example dCas9. The disclosed computer-implemented methods and systems are used to identify potential on- and off-target dCas9 binding sites.

Also disclosed are computer-implemented methods for identifying cleavage locations of a nuclease, preferably a nucleotide-directed nuclease. In some embodiments, the nuclease is RNA-directed, DNA-directed, or directed by combinations of RNA, DNA or nucleotide-like molecules. These nucleotides can be natural or chemically modified. The chemical modifications can be to the individual units, alternative bonds between units. Additionally, modifications can be to the nucleotides or at ends of the nucleotide strings. The nuclease can cleave both nucleic acid strands, can be a single nickase, or a double nickase. In some embodiments, methods identify binding locations of a nucleotide-directed protein that binds to and/or interacts with DNA, but is not a nuclease are provided.

The methods can include, in a computer system, comparing a series of query sequences including a guide strand sequence (a guide sequence) and at least one variant sequence thereof including zero, one or more nucleotide insertions, zero, one or more nucleotide deletions, and/or zero, one or more nucleotide substitutions relative to the guide sequence, to genomic sequences and reporting target cleavage sites corresponding to locations in the genomic sequence having sequence identity to one or more of the query sequences.

The series of query sequences can include all possible guide strand sequence variants having between 0 and 10, preferable between 0 and 5, more preferably 0, 1, or 2 nucleotide insertions relative to the guide sequence; all possible guide strand sequence variants having between 0 and 10, preferable between 0 and 5, more preferably 0, 1, or 2 nucleotide deletions relative to the guide sequence; between 0 and 10, preferable between 0 and 5, more preferably 0, 1, 2, or 3 nucleotide mismatches (e.g., substitutions) relative to the guide sequence; and all possible combinations thereof. In some embodiments creating the query sequences is carried out through an interface, for example a computer implemented interface that allows the user to select the number of insertions, deletions, and/or mismatches. In some embodiments, the interface is a web-based interface. In particular embodiments, a web-based interface allows the user's choice of insertions or deletions of a single nucleotide, though other embodiments are possible, as described above. Larger number of nucleotides may be more applicable to other nucleases, particularly nucleotide-directed nucleases, with either longer guide strands or different binding arrangements. In a particular embodiment, the query guide sequences provide guide strand variant sequences having no indels and 0, 1, 2, or 3 mismatches; 1-base deletion, no insertions, and 0, 1, or 2 mismatches; 1-base insertion, no deletions, and 0, 1, or 2 mismatches; 1-base deletion, 1-base insertion, and 0, 1, or 2 mismatches; or any combination thereof.

The methods typically include comparing or searching one, or more, query sequence against one genome sequence(s) and reporting putative on- or off-target sites within the supplied criteria. In some embodiments an individual guide strand is searched against genomic DNA. In other embodiments multiple guide strands are searched, which can allow comparisons of the output or other testing. In other embodiments multiple strands are used at the same time. In the most preferred embodiments, a target site is reported if a genomic sequence is identified that matches the user-supplied search criteria, which can include the presence or lack of sites with no indel, with insertion(s), with deletion(s), with mismatch(es), or with combinations thereof. The user-supplied preferences typically include the number of allowed mismatches for each of the categories listed above. In each of these cases, the user can alternatively choose preferences from general or search type-specific defaults, or modify such preferences.

In the preferred embodiment, the output contains each site in the genome satisfying the search criteria. In other embodiments, particularly relevant with less well-sequenced genomes or DNA regions, the output can also include sites that might satisfy the search criteria if the ambiguous nucleotides were known. The output can contain exact matches to the query sequences and/or contain sites that differ (have mismatches) at, for example, 1-12 positions, that differ at 1-5 positions, or that differ at 1-3 positions. The percentage of the sequences matching can then vary depending on the length of the query sequence and the number of mismatches. In some embodiments, the search criteria can result in the reporting of genomic sequences that have approximately at least 80%, 85%, 90%, 95%, 96%, 97%, 98%, 99%, or 100% sequence identity to one or more of the sequences in the series of query sequences. The report can include the genomic location and preferably the genomic target sequence for each target site identified. The report can include the binding location of dCas9 or, in the case of CRISPR/Cas, the cleavage location and/or the genomic sequence that is cleaved.

The report can include a score indicating a proposed likelihood that the guide sequence will direct a CRISPR/Cas system to the DNA sequence and facilitate nuclease cleavage, or in the case of dCas9, DNA binding. The score can be used to rank the putative target sites in a list. The score can include additional information from experiments and/or databases, such as ENCODE, about the genomic context. For example, data on the histones, protein binding or confirmation of individual chromosomal regions can indicate if there is less or more likelihood of cleavage. In some embodiments, target cleavage locations including genomic sequences with higher sequence identity to the guide sequence receive a lower score relative to target cleavage locations having genomic sequences with lower sequence identity to the guide sequence. Typically, in such embodiments, increasing numbers of substitutions, deletions, and insertions at the target cleavage location increase the score, as do substitutions, deletions, and/or insertions closer to the PAM. The scoring mechanism and position weights can be changed to alter the scoring to better model certain CRISPR/Cas activities. For example, in some embodiments, the score is increased more for deletion(s) in the genomic sequence relative to the guide sequence (RNA bulges) than for insertions in the genomic sequence relative to the guide sequence (DNA bulges). The score can also reflect that sgRNA bulges are less tolerant to additional base mismatches, and vice versa.

In some embodiments, each query sequence in the series includes a protospacer adjacent motif (PAM) suffix. This adjacent sequence can be directly next to the target site, may be separated by 1, 2-5 nucleotides, or may be separated by a greater number. The spacing may be constant or variable. Exemplary suffixes include, but are not limited to, NGG, NAG, NGA, NGT, NAA, NRG, NNRG, NNAG, NNGG, NAGNRG, NNGRRT, NNNNRYAC, NNNNRYAC, NNNNGHTT, NNAGAAW, TTN, YTN, or any other set of 1-10 or more specific or ambiguous nucleotides. The PAM can be naturally occurring or engineered. In some embodiments, a target cleavage site having a NGG PAM guide strand is given a lower score than that of NAG PAM. Other PAMs can be included, or not included, and may be scored the same or differently. Some embodiments may include PAM flanking sequences that are deemed to affect binding. The adjacent binding sequence may be based on additional binding amino acids or an additional domain, such as a ZFP, TAL or additional nucleotide-based binding domain. The consensus or ambiguous binding sites for any of these could be similarly used. For example, a ZFP could be added and its target site used as a PAM following a range of Ns to indicate spacing.

In some embodiments, the scoring and ranking may be separated, with or without user input. The ranking can also be conducted using two steps, such as an initial ranking and then ranking or re-ranking, based on input weight factors. The ranking method may involve a series of weight scores or position weight matrix to total the scores of the individual weigh the positions of mismatch, insertions or deletions and influence the scoring based on their impact on the design criteria. The ranking can also include sequence specific features such that a match or mismatch weigh considers the interacting nucleotide. The sequence specific weight scores may correlate with hydrogen bonds, as with G-C verse A-T interactions, or may relate to sequence specificities at individual positions, possibly due to protein interactions. The design criteria can include binding, DNA cleavage rate, mutation rate, or other criteria.

In some embodiments, the ranking method is applied to genomic loci independently of the search method. In some embodiments, the ranking method is applied in combination with the search method.

In some embodiments, primer sequences suitable for amplifying the genomic sequence at the target cleavage site are reported. These primers may be suitable for PCR amplification or DNA preparation or isolation using other techniques, such as pull-down preparations. The primers may be used for Sanger sequencing, next generational sequencing (NGS), hybrid capture sequencing, mutation detection assays, such as the Surveyor (Cradick 2009 Thesis) and T7 Endonuclease I assays, and others.

The genome sequence or sequences that the series of query sequences are searched against typically makes up an organismal genome, preferably a complete or nearly complete organismal genome. In specific embodiments, the organismal genome is a mammalian genome for example a human genome, a rat genome, a mouse genome, or a rhesus macaque genome. In other embodiments, the searched sequence could be artificial sequences or a combination or artificial and genomic sequences. The searched sequences can be DNA. RNA, etc. In a particular embodiment the searched sequences are mRNA, for example, a transcriptome. In other embodiments, the organism can have inserted sequences or disease-specific changes.

The genomic sequence(s) can be DNA sequence converted into FASTA or similarly formatted files, then transformed into index entries that have all possible 25 bases-long tags in the DNA sequence. In other embodiments, other tagging schemes can be used including longer and shorter tags. The index entries can be sorted and the results stored as a binary main index file. The main index file can be divided into parts, each representing entries having about 12 nucleotides of the first nucleotides identical. In other embodiments, other lengths of index files may be used. A secondary index file can include the position in the main index file where each part starts added to the end of the index file. Searching genome sequence organized and indexed in such a way can improve the speed of the search, while allowing exhaustive searching. Preferred embodiments utilize index files, though other embodiments could use other index methods, similar expedited search strategies, or provide searching without index files, as done with linear searches through the full sequence space, though these would increase run times. A particular embodiment of the disclosed method is referred to herein as COSMID (CRISPR Off-target Sites with Mismatches, Insertions, and Deletions).

The disclosed methods and systems can aid the design and optimization of CRISPR guide strands by selecting the preferred target sites with minimum Cas-induced off-target cleavage and facilitate the experimental confirmation of off-target activity by providing both putative off-target sites and primer for testing cleavage that the sites in a CRISPR/Cas system. In some embodiments, the disclosed methods are more exhaustive and/or have a higher sensitivity for identifying putative and/or actual off-target sites than previously known methods or programs.

Exhaustive searches for possible off-target sites are important when choosing target sites, so that one can predict all putative sites. Exhaustive searches for off-target cleavage events are important for research experiments to rule out unintended DNA changes resulting in the observed effect. Exhaustive searches are important in the pre-clinical work on therapeutic targets and critical on treated cells to determine if there are unintended edits.

BRIEF DESCRIPTION OF THE DRAWINGS

FIG. 2B discloses SEQ ID NOS 697-702, respectively, in order of appearance.

FIGS. 3A-3C show R-03 (3A), R-04 (3B), or R-08 (3C) guide strand mutation rates at HBB (left-hand bar of each pair) and HBD (right-hand bar of each pair) loci when cells were transfected with 100, 200, 400, or 800 ng of CRISPR plasmid. FIGS. 3D-3E show R-25 (3D) or R-30 (3E) guide strand mutation rates at CCR5 (left-hand bar of each pair) and CCD2 (right-hand bar of each pair) loci when cells were transfected with 100, 200, 400, or 800 ng of CRISPR plasmid.

FIGS. 4A-4B are sequence alignments showing on-target loci (SEQ ID NOS 703-715, respectively, in order of appearance) (4A) and off-target loci (SEQ ID NOS 716-729, respectively, in order of appearance) (4B) for guide strands R-03 after transfection with the CRISPR plasmid. The regions were amplified with flanking PCR primers, cloned and Sanger sequenced. Sequencing reads are given for each guide strand and aligned to the wild-type sequence. The number of times each read occurred is indicated to the left of the alignment. Unmodified reads are indicated by 'WT'. Mutations, insertions, or deletions were detected in 70% of the reads at HBD and 62% of the reads in HBD. In FIG. 4B the guide strand mismatch is boxed. FIG. 4C depicts the sequence of chromosomal deletions as a sequence alignment (SEQ ID NOS 730-739, respectively, in order of appearance) showing PCR products of genomic DNA from cells treated with R-03, amplified using an HBD forward primer and reverse primer downstream of the HBB site, sequenced and aligned to 'HBB-HBD'. Sequencing detected that each product contained indels and mutations consistent with NHEJ, near the target sites for R-03. Insertions, point mutations, and deletions are illustrated.

FIGS. 5A-5B are sequence alignments showing on-target loci (SEQ ID NOS 740-745, respectively, in order of appearance) (5A) and off-target loci (SEQ ID NOS 746-754, respectively, in order of appearance) (5B) for guide strands R-25 after transfection with the CRISPR plasmid. The regions were amplified with flanking PCR primers, cloned and Sanger sequenced. Sequencing reads are given for each guide strand and aligned to the wild-type sequence. The number of times each read occurred is indicated to the left of the alignment. Unmodified reads are indicated by 'WT'. Mutations, insertions or deletions were detected in 50% of the reads at CCR5 and 32% of the reads in HCCR2. In FIG. 5B the guide strand mismatch is boxed. FIG. 5C depicts the sequence of chromosomal deletions as a sequence alignment (SEQ ID NOS 755-764, respectively, in order of appearance) showing PCR products of genomic DNA from cells treated with R-25, amplified using a CCR2 forward primer and reverse primer downstream of the CCR5 site, sequenced and aligned to 'CCR2-CCR5'. Sequencing detected that each product contained indels and mutations consistent with NHEJ, near the target sites for R-25. Insertions, point mutations, and deletions are illustrated.

FIGS. 6A-6C are sequence alignments showing on- and off-target sequencing (SEQ ID NOS 765-820, respectively, in order of appearance) after CRISPR transfection: R-02 targeted mutations at HBB (6A), R-02 mutations at off-target site 2, GRIN3A (6B), and R-30 off-target mutations at CCR2 (6C). Target loci in genomic DNA of HEK-293T cells transfected with each CRISPR construct were amplified, cloned, Sanger sequenced, and aligned to the reference gene, listed above the alignment, and shown aligned to the guide strand. After the guide strand name and genetic loci for each alignment, the number of clones with indels is shown, as is the total number of clones and percentage with indels. The alignment includes the reference gene and guide strand with mismatches boxed. The first column lists the number of times each read occurred and indel size change in basepairs. Unmodified reads are indicated by "WT". Insertions, point mutations, and deletions are illustrated.

FIG. 7 is a bar graph showing the indel spectra from CRISPR/Cas9 cleavage and NHEJ mis-repair. The change in number of base pairs resulting from each indel was calculated and compiled. The y-axis represents the percentage of each number of insertion or deletion.

FIG. 9A is a sequence alignment (SEQ ID NOS 826-840, respectively, in order of appearance) illustrating that a single nucleotide was deleted from the original R-01 sgRNA at all possible positions (dashes) throughout the guide sequence for sgRNA R-01 targeting HBB (SEQ ID NO: 825). FIG. 9B is a grid mapping the deletions, which in the case of repeated bases, can be thought to have been a deletion of either base. Semi-transparent squares in two positions in the same sgRNA indicate that deletions can be interpreted at either of adjacent positions (also marked by 'or') due to identical nucleotides at both positions. Sequence of the original sgRNA is in the top row of the grid. FIG. 9B discloses SEQ ID NOS 826-840, respectively, in order of appearance. FIG. 9C is a bar graph showing cleavage activity aligned to the corresponding sgRNA variants of 9A and 9B. The graph in FIG. 9C indicates cleavage activity for the corresponding sgRNA variants measured by T7EI assay in HEK293T cells at the HBB site for the sgRNA variants in (9A), and compares to the activity of the original full-length guide strand. Positions relative to PAM are labeled on the y-axis. The vertical dashed lines mark the activity levels of the original sgRNAs. Error bar, SEM (n=2).

FIG. 10A is a sequence alignment (SEQ ID NOS 842-857, respectively, in order of appearance) illustrating that a single nucleotide was deleted from the original sgRNA at all possible positions (dashes) throughout the guide sequence for sgRNA R-30 targeting CCR5 (SEQ ID NO: 841). FIG. 10B is a grid mapping the deletions, which in the case of repeated bases, can be thought to have been a deletion of either base. Semi-transparent squares in two positions in the same sgRNA indicate that deletions can be interpreted at either of adjacent positions (also marked by 'or') due to identical nucleotides at both positions. The sequence of the original sgRNA is in the top row of the grid. FIG. 10B discloses SEQ ID NOS 842-857, respectively, in order of appearance. The graph in FIG. 10C indicates cleavage activity for the corresponding sgRNA variants measured by T7EI assay in HEK293T cells at the HBB site for the sgRNA variants in (10A), and compares to the activity of the original full-length guide strand. FIG. 10C is a bar graph showing cleavage activity aligned to the corresponding sgRNA variants of 10A and 10B. Considerable activity, even higher than with the original guide strand was detected with deletions at a number of different positions. Positions relative to PAM are labeled on the y-axis. The vertical dashed lines mark the activity levels of the original sgRNAs. Error bar, SEM (n=2).

FIGS. 11A and 11B are alignments of −1 nt sgRNA variants (SEQ ID NOS 859-862, respectively, in order of appearance (FIG. 11A) and SEQ ID NOS 864-873, respectively in order of appearance (FIG. 11B)) to the HBB (SEQ ID NO: 858) (11A) and CCR5 (SEQ ID NO: 863) (11B) target loci showing mismatches instead of DNA bulge. Only the variants with detectable intracellular activities are shown. The target loci and index names of the sgRNA variants are indicated on the left of each alignment. Mismatches in the guide sequence and in the "NGG" PAM are marked with asterisks below each alignment. The alignment with the minimum number of mismatches is shown for each sgRNA variant. Nucleotide "U" in the guide RNA is replaced with 'T' for the ease of comparison to the target site. For example, modeling the cleavage of R-01 with a deletion at position 6 or 7 (11A) can either be modeled with a deletion and no mismatches or without a deletion, but with four mismatches close to the PAM (indicated by *), which would generally not be well tolerated, and prevent cleavage. Similarly, the CCR5 guide strand with a deletion at position 9 or 10 (11B) has considerable activity can either be modeled with a deletion and no mismatches or without a deletion. If this interaction was modeled without a deletion, there would be six mismatches close to the PAM (indicated by *), which would generally prevent cleavage.

FIGS. 15A and 15B are sequence alignments of +1 nt sgRNA variants (SEQ ID NOS 937-947, respectively, in order of appearance (FIG. 15A) and SEQ ID NOS 950-957, respectively, in order of appearance (FIG. 15B)) to the HBB (SEQ ID NO: 936) (15A) and CCR5 ('AGTAGAGCG-GAGGCAGGAGGCGGG' disclosed as SEQ ID NO: 948 and 'GTAGAGCGGAGGCAGGAGGCGGGC' disclosed as SEQ ID NO: 949) (15B) target loci without a bulge leads to many mismatches, instead of a sgRNA bulge. Only the variants with detectable intracellular activities are shown. The target loci and index names of the sgRNA variants are indicated on the left of each alignment. Mismatches in the guide sequence and in the "NGG" PAM are marked with asterisks below each alignment. The alignment with the minimum number of mismatches is shown for each sgRNA variant. Nucleotide "U" in the guide RNA is replaced with "T" for the ease of comparison to the target site.

FIGS. 17A and 17B show the larger bulges can also lead to activity.

FIGS. 18A and 18B show that bulges are tolerated in other CRISPR systems including the nickase nucleases, which only cut one strand.

FIG. 20 is a sequence alignment (SEQ ID NOS 1042-1044, respectively, in order of appearance) showing the effects of R-30 cleavage and miss-repair at the off-target site 5 (Off-5), quantified by Sanger sequencing. One of the 24 sequencing reads was not wild type with an inserted a in lowercase, the other 23 reads were wild type and are marked "WT".

FIGS. 21A and 21B are genetic maps showing the histone modification status and annotation of R30 Off-4 (21A) and Off-5 (21B) loci obtained from the UCSC genome browser.

FIG. 22 is a bar graph showing the results of quantitative PCR of sgRNA expression (sgRNA Log Fold Change (−ddCt)) levels in HEK293T cells for R-01 and R-30 variants.

FIG. 26B is an exemplary COSMID user interface for entering a query sequence (SEQ ID NO: 1058). FIG. 26C is an exemplary COSMID user interface for entering the protospacer motif (PAM) and selecting the type and number of mismatches and indels. FIG. 26D is an exemplary COSMID user interface entering primer design parameters. FIG. 26E is an alignment (SEQ ID NOS 1059-1074, respectively, in order of appearance) showing the tags generated and used to search the human genome when a COSMID user enters the guide sequence exemplified in FIG. 26A and 1-base deletion to allow gRNA bulge (e.g., DNA is base shorter than the guide sequence, as illustrated above the alignment). Deletions of either of consecutive bases result in the same sequence and are therefore omitted from the list. FIG. 26F is an alignment (SEQ ID NOS 1075-1095, respectively, in order of appearance) showing the tags generated and used to search the human genome when a COSMID user enters the guide sequence exemplified in FIG. 26A and allows 1-base insertion to allow DNA bulge (e.g., guide sequence RNA is one base short than DNA, as illustrated above the alignment). FIG. 26G discloses the 'processing input tag' as SEQ ID NO: 1096, the 'result' sequences as SEQ ID NOS 1097-1116, respectively, in order of appearance and the 'PCR primer' sequences as SEQ ID NOS 1117-1126, respectively, in order of appearance.

FIGS. 28A and 28B are sequence alignments showing two examples of genomic sites identified using different search queries for R-30. Both possible off-target sites can align to search strings without indels, with a deletion and with an insertion. Search strings are shown aligned to each identified chromosomal location. Mismatches are shaded, and insertions or deletions are illustrated with a dash ('-'). FIG. 28A discloses SEQ ID NOS 1127-1129, 1128, 1130 and 1128, respectively, in order of appearance. FIG. 28B discloses SEQ ID NOS 1131-1133, 1132, 1134 and 1132, respectively, in order of appearance.

FIGS. 29A and 29B display putative off-target sites with up to three mismatches and not indels. FIGS. 29C and 29D include the addition of sites with up to two mismatches and either an insertion or a deletion. Each vertical line represents each identified off-target site, plotted at its chromosomal location by the UCSC genome browser. The chromosome numbers are listed on edges of the plots.

DETAILED DESCRIPTION OF THE INVENTION

I. Definitions

Figures 1A, 1B, 1C:
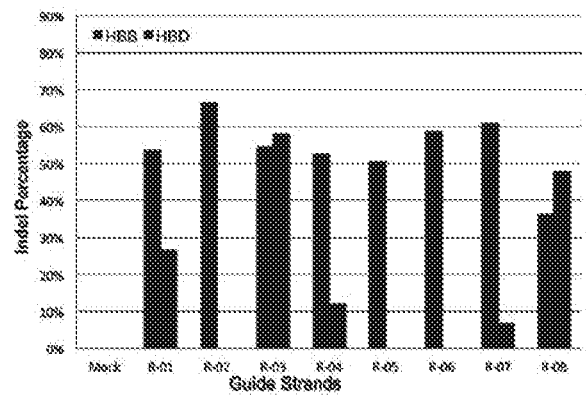
FIG. 1A is a sequence alignment of guide strands (SEQ ID NOS 670-677, respectively, in order of appearance) to their target sites in HBB (SEQ ID NO: 678) and aligned to the corresponding region in HBD (SEQ ID NO: 679). Forward direction guide strands (marked 'greater than') are shown adjacent to NGG, representing the PAM sequence. Guide strands complementary to the reverse strand (marked 'less than') are listed to the right of CCN. Asterisks between HBB and HBD indicate nucleotides that differentiate the two genes, whereas the other nucleotides are the same in both genes. The first base shown in HBB is the sickle cell anemia mutation site.
FIG. 1B is a sequence alignment (SEQ ID NOS 680-687, respectively, in order of appearance) showing the high levels of cleavage and mutation that can be found at off-target sites even with mismatch to the guide strands in the first 12 nucleotides closest to the PAM. The on- and off-target mutation rates are listed in decreasing order of the off-target mutation rates at HBD, and illustrate differences between the guide sequence and HBD. A lowercase g indicates that the first base in HBB does not match the guide strands' initial G (for all but R-01). The 12 bases closest to the PAM are boxed and numbered on top.
FIG. 1C is a bar graph showing the indel percentage in HBB (left-hand bar of each pair) and HBD (right-hand bar of each pair) for mock and guide strands R-01 through R-08 as determined by T7EI mutation detection assays.

As used herein, the terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. For example, an enhancer is a transcriptional regulatory sequence that is operatively linked to a coding sequence, even though they are not contiguous.

As used herein, an "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can include, for example, a functioning version of a malfunctioning endogenous molecule, a malfunctioning version of a normally-functioning endogenous molecule or an ortholog (functioning version of endogenous molecule from a different species).

As used herein, the terms "nucleic acid," "polynucleotide," and "oligonucleotide" are interchangeable and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general and unless otherwise specified, an analogue of a particular nucleotide has the same base-pairing specificity; i.e., an analogue of A will base-pair with T (or U in RNA).

As used herein, the terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

As used herein, the terms "cleavage" or "cleaving" of nucleic acids, refer to the breakage of the covalent backbone of a nucleic acid molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered "sticky" ends. In certain embodiments cleavage refers to the double-stranded cleavage between nucleic acids within a double-stranded DNA or RNA chain.

As used herein, the term "genome", refers to the nuclear DNA of an organism, though it can also include all the DNA in a given organism including mitochondrial DNA. The term "genomic DNA" refers to deoxyribonucleic acids that are obtained from the nucleus of an organism. The terms "genome" and "genomic DNA" encompass genetic material that may have undergone amplification, purification, or fragmentation. In some cases, genomic DNA encompasses nucleic acids isolated from a single cell, or a small number of cells, clones of cells or pools of cells. The "genome" in the sample that is of interest in a study may encompass the entirety of the genetic material from an organism, or it may encompass only a selected fraction thereof: for example, a genome may encompass one chromosome from an organism with a plurality of chromosomes. The genome may refer to the reference sequence for an organism or the sequence of one or more individuals. In some embodiments, the genomic sequence can contain or be comprised solely of man-made, altered or non-natural sequences, including, but not limited to, natural genomic sequences with the inclusion of knocked-in sequences, such as GFP expression cassettes or tags, or cDNA or other sequences for the expression of a gene of interest. In other embodiments, the genome may not consist of natural chromosomal sequences, but of sequences assembled by man.

As used herein, the terms "genomic region" or "genomic segment", as used interchangeably herein, denote a contiguous length of nucleotides in a genome of an organism. A genomic region may be of a length as small as a few kb (e.g., at least 5 kb, at least 10 kb or at least 20 kb), up to an entire chromosome or more.

As used herein, the terms "genome-wide" and "whole genome", are interchangeable and refer generally to the entire genome of a cell or population of cells and include the sequences normally found in those cells and introduced DNA such as knocked-in cDNAs, promoters, enhancer, tags or other naturally occurring, or man-made sequences or combinations of sequences. The terms "genome-wide" and "whole genome" will generally encompass a complete DNA sequence of all of an organism's DNA (chromosomal, mitochondrial, etc.). A sequence may represent the most common or earliest sequence found in an organism, while certain cells may have accumulated changes. Alternatively, the terms "genome-wide" or "whole genome" may refer to most or nearly all of the genome. For example, the terms "genome-wide" or "whole genome" may exclude a few portions of the genome that are difficult to sequence, do not differ among cells or cell types, are not represented on a whole genome array, or raise some other issue or difficulty that prompts exclusion of such portions of the genome. In some embodiments the genome is considered complete if more than 90%, more than 95%, more than 99%, or more than 99.9% of the base pairs have been sequenced. In some cases, less is known of a genome, but the known fraction, can be of use. The genome can refer to any organism for which a portion of the genome has been sequenced. In some embodiments the whole genome is a human genome, a rat genome, a mouse genome, a Zebrafish genome, an *Arabidopsis* genome, a yeast genome, a *D. melanogaster* genome, a *C. elegans* genome, a dog genome, a cow genome, an ape genome, or a pig genome. In some embodiments the "genome" will contain inserted or modified genomic sequences.

In some cases nucleotide sequences are provided using character representations recommended by the International Union of Pure and Applied Chemistry (IUPAC) or a subset thereof. IUPAC nucleotide codes used herein include, A=Adenine, C=Cytosine, G=Guanine, T=Thymine, U=Uracil, R=A or G, Y=C or T, S=G or C, W=A or T, K=G or T, M=A or C, B=C or G or T, D=A or G or T, H=A or C or T, V=A or C or G, N=any base, "." or "-"=gap. In some embodiments the set {A, C, G, T, U} for adenosine, cytidine, guanosine, thymidine, and uridine respectively. In some embodiments the set {A, C, G, T, U, I, X, Ψ} for adenosine, cytidine, guanosine, thymidine, uridine, inosine, uridine, xanthosine, pseudouridine respectively. In some embodiments the set of characters is {A, C, G, T, U, I, X, Ψ, R, Y, N} for adenosine, cytidine, guanosine, thymidine, uridine, inosine, uridine, xanthosine, pseudouridine, unspecified purine, unspecified pyrimidine, and unspecified nucleotide respectively. The modified sequences, non-natural sequences, or sequences with modified binding, may be in the genomic, the guide or the tracr sequences.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or MEGALIGN (DNAS-TAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y 100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A. Mismatches can be similarly defined as differences between the natural binding partners of nucleotides. The number, position and type of mismatches can be calculated and used for identification or ranking purposes.

As used herein, "mutation" encompasses any change in a DNA, RNA, or protein sequence from the wild type sequence or some other reference, including without limitation point mutations, transitions, insertions, transversions, translocations, deletions, inversions, duplications, recombinations, or combinations thereof. As used herein, in the context of alignments and identity between a CRISPR guide strand and each genomic on- or off-target site, the term "insertion" is used when the endogenous DNA sequence has one or more extra bases compared with the sequence of the guide strand (a DNA bulge). Similarly, in the context of alignments and identity between a CRISPR guide strand and a genomic target site, the term "deletion" is used when the endogenous DNA sequence has one or more missing bases compared with the guide strand (a RNA bulge). In the context of alignments and identity between a CRISPR guide strand and a genomic target site, the term "indels" indicates either insertions or deletions. Although insertions and deletions may be viewed as mismatches, as used herein in the context of alignments and identity between a CRISPR guide strand and a genomic target site, the term "mismatch" is used exclusively for base-pair mismatch when the guide strand and the potential off-target sequence have the same length, but differ in base composition. Guide strands and genomic sequences can have multiple mismatches, multiple insertions, multiple deletions or combination, such as one nucleotide inserted and two mismatches. In some cases, the alignment could be represented in several ways, such as with an indel and a few mismatches or without an indel but with a larger number of mismatches.

As used herein, the term "endonuclease", refers to any wild-type, engineered or variant enzyme capable of catalyzing the hydrolysis (cleavage) of bonds between nucleic acids within a DNA or RNA molecule, preferably a DNA molecule. Non-limiting examples of endonucleases include type II restriction endonucleases such as FokI, HhaI, HindIII, NotI, BbvCI, EcoRI, BglIII, and AlwI or these domains fused to other proteins. Endonucleases comprise also rare-cutting endonucleases when having typically a polynucleotide recognition site of about 12-45 basepairs (bp) in length, more preferably of 14-45 bp. Rare-cutting endonucleases induce DNA double-strand breaks (DSBs) at a defined locus. Rare-cutting endonucleases can for example be a homing endonuclease, a mega-nuclease, a chimeric Zinc-Finger nuclease (ZFN) or TAL effector nuclease (TALEN) resulting from the fusion of engineered zinc-finger domains or TAL effector domain, respectively, with the catalytic domain of a restriction enzyme such as FokI, other nuclease or a chemical endonuclease.

As used herein, the term "exonuclease", refers to any wild type or variant enzyme capable of removing nucleic acids from the terminus of a DNA or RNA molecule, preferably a DNA molecule. Non-limiting examples of exonucleases include exonuclease I, exonuclease II, exonuclease III, exonuclease IV, exonuclease V, exonuclease VI, exonuclease VII, exonuclease VII, Xm1, and Rat1.

In some cases an enzyme is capable of functioning both as an endonuclease and an exonuclease. The term nuclease generally encompasses both endonucleases and exonucleases, however in some embodiments the terms "nuclease" and "endonuclease" are used interchangeably herein to refer to endonucleases. i.e. to refer to enzyme that catalyze bond cleavage within a DNA or RNA molecule.

II. Methods

The systems and methods described herein for predicting off-target sites generally involve generating search criteria derived from input criteria, generating a list of target sites, and directing the list of target sites as output to the user. The input criteria will generally include information regarding the guide sequence, and optionally the PAM sequence, the number of allowed mismatches, the number of allowed insertions, the number of allowed deletions, the genome to be searched, etc. In preferred embodiments the output is provided in the form of a ranked-list wherein each of the target sites are assigned a numerical value, "score", that correlates with the likelihood of nuclease cleavage at that site. It will be appreciated that in many cases the practitioner knows the on-target location and although the methods and systems are designed to identify off-target locations, may nonetheless also include the on-target site(s). In some embodiments, the user may wish to determine if there are on- or off-target sites within different genomes. Therefore, in some embodiments, the list of target sites includes both on-target sites and off-target sites. In other embodiments, only off-site targets are provided. An example of genomic search for only off-target sites is when targeting non-genomic sequences, such as mutated sites, chromosomal rearrangements, introduced sequences (such as cDNA or other expression cassettes) or viral sequences. In some embodiments, the on-target site(s) can be subtracted or removed from the output.

In some embodiments, the methods and systems rank the target sites based on the likelihood of cleavage. The ranking can be based upon a scoring function for predicting nuclease activity based at least in-part on identity between the guide strand and each genomic target sequence and/or the ability of the guide sequence to hybridize to the complement thereof. In some embodiments the predictions can be based on the sequences and other known or predicted features such as accessibility, type of sequence, expression state or genomic context. In some embodiments the predictions will also include information about the cells in question, their development, tissue-type, chromatin, acetylation, or expression patterns. In some embodiments, the methods and systems provide PCR primer sequences that can be used for synthesizing oligonucleotide primers for testing cleavage in vivo.

A. Nucleotide-Guided Nucleases i. CRISPR Systems

CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example. Cong, *Science,* 15:339(6121):819-823 (2013) and Jinek, et al., *Science,* 337(6096):816-21 (2012)). By transfecting a cell with the required elements including a cas gene and specifically designed CRISPRs, the organism's genome can be cut and modified at virtually any desired location. A number of methods exist for expressing the guide strand or Cas protein, including inducible expression of one or both. A number of methods exist for introducing the guide strand and Cas protein into cells including viral transduction, injection or micro-injection, nano-particle or other delivery, uptake of proteins, uptake of RNA or DNA, uptake of combination of protein and RNA or DNA. Combinations of methods can also be used, simultaneously or in sequence. Multiple rounds of delivery of RNA, DNA or protein can occur with or without further protein expression. Methods of preparing compositions for use in genome editing using the CRISPR/Cas systems are described in detail in WO 2013/176772 and WO 2014/018423, which are specifically incorporated by reference herein in their entireties.

In general, "CRISPR" refers to clustered regularly interspaced short palindromic repeats or any of the DNA loci that serve to direct CRISPR associated proteins or similar nucleotide-directed nucleases. It also describes man-made, constructed, or selected systems derived using these frameworks or proteins. CRISPR systems and the related proteins vary among the currently described type I, type II and type III systems, though it is possible other analogous systems have yet to be described.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease. CRISPR systems can also include modified, swapped or engineered, guide, tracr or chimeric RNA sequences and the protein to which they interact (For example, Briner, et al., *Mol Cell* 56(2)333-9 (2014)). The methods disclosed herein may also be applicable to other, non-CRISPR nucleotide-directed nucleases.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Jinek, et al., *Science,* 337(6096):816-21 (2012)) and Cong, *Science,* 15:339(6121):819-823 (2013). A single fused crRNA-tracrRNA construct can also be referred to as a guide RNA or gRNA (or single-guide RNA (sgRNA)). Within a gRNA, the crRNA portion can be identified as the 'target sequence' and the tracrRNA is often referred to as the 'scaffold'. The target sequence can be perfectly complementary to a targeted site, as is often the case for an on-target site, or may also contain mismatches, insertions, deletions or be of different length than the cleaved intended or unintended sites.

In some embodiments, the tracrRNA can be modified in length, sequence or other composition. Similarly the guide portion or guide sequence can be modified in sequence and/or in length. The guide strand length varies between species. In some embodiments the length of the guide RNA is shortened, lengthened or further changed to alter the affinity to the complementary sequence in hopes of increase specificity or affecting the activity (Fu, et al., *Nature Biotech.* (3):279-84. (2014)).

When a gRNA and Cas9 are expressed together in a cell, a gRNA/Cas9 complex forms and is recruited to the genomic target sequence through binding to the PAM and/or the base-pairing between the gRNA sequence and the complement to the target sequence in the genomic DNA (Addgene, "CRISPR in the Lab: A Practical Guide," Addgene website, 2014). For Cas9 to successfully bind to a DNA sequence, the guide strand and target sequence must be sufficiently complementary, followed by a protospacer adjacent motif (PAM) sequence. Mismatches are tolerated in both the guide and in the PAM sequence (Fu, et al., *Nat Biotechnol,* 31: 822-826 (2013): Hsu, et al., *Nat Biotechnol,* 31: 827-832 (2013); Cradick, et al., *Nucleic Acids Res,* 41:9584-9592 (2013)). The specified nucleotides in the PAM may range in spacing from the protospacer, in some systems the PAM sequence is NGG, or can be further away as in NNNNGATT, where N is any nucleotide. The PAM sequence is present in the DNA target sequence, but not in the gRNA sequence. Any DNA sequence with the correct target sequence followed by the PAM sequence may be bound by Cas9, and may be cleaved. Other nucleotide-directed nucleases may be identified or engineered with minimal or no PAM requirements.

The binding of the gRNA/Cas9 complex localizes the Cas9 to the genomic target sequence. In one embodiment, wild type Sp Cas9 makes a double strand break 3-4 nucleotides upstream of the PAM sequence, which can be repaired by the Non-Homologous End Joining (NHEJ) DNA repair pathway, the Homology Directed Repair (HDR) pathway or alternative DNA repair pathways. Different nucleases can vary in the cut sites. The system can be manipulated to induce a variety of gene modifications including insertions and deletions causing frameshifts and/or premature stop codons, specific nucleotide changes, etc. In another embodiment, SpCas9 has mutations that make the nuclease a nickase. In such an embodiment, the mutations in SpCas9 are point mutations at key catalytic residues. Nickases retain the specificity of action of SpCas9 but only cleave one strand of the DNA. During gene editing with SpCas9 nickase, the individual nicks in the genome are repaired with high fidelity whereas double strand breaks induced by wild type SpCas9 are repaired by NHEJ or HDR activities of cells. In some embodiments, paired SpCas9 nickases can be used to make nicks on opposite DNA strands in close proximity to one another.

In another embodiment, the nickase is from a CRISPR system including but not limited to *Staphylococcus aureus* (Sa), *Streptococcus thermophilus* (St1 or St3), *Neisseria meningitidis* (Nm or Nme), *Campylobacter jejuni* (Cj), *Treponema denticola* (Td), or engineered variants. In one embodiment, the nickase cleaves zero, one, or both strands of DNA.

In other embodiments, the nuclease is directed by a single nucleotide, such as those employed by Cpf1 (Cas12) or the Cas13 family (Shmakov, S., et al., *Mol Cell,* 60(3):385-397 (2015); Ledford, Heidi, *Nature,* 526(7571):17 (2015)). Cpf1 is an RNA-guided endonuclease. Cpf1 recognizes T-rich PAM sites distal from the recognition region. Exemplary T-rich PAM sites include but are not limited to TTTA, TTTC, and TTTG.

In other embodiments, the CRISPR system can be *Staphylococcus aureus* (Sa), *Streptococcus thermophilus* (St1 or St3), *Neisseria meningitidis* (Nm or Nme), *Campylobacter jejuni* (Cj), *Treponema denticola* (Td), or engineered variants.

In some embodiments, one or more vectors driving expression of one or more elements of a CRISPR system are introduced into a target cell such that expression of the elements of the CRISPR system direct formation of a CRISPR complex. Although the specifics can vary between different engineered CRISPR systems, the overall methodology is similar. A practitioner interested in using CRISPR technology to target a DNA sequence can insert a short DNA fragment containing the target sequence into a guide RNA expression plasmid. The sgRNA expression plasmid contains the target sequence (generally about 20 nucleotides), a form of the tracrRNA sequence (the scaffold), as well as a suitable promoter and necessary elements for proper processing in eukaryotic cells. Such vectors are commercially available (see, for example, Addgene). Many of the systems rely on custom, complementary oligonucleotides that are annealed to form a double stranded DNA and then cloned into the sgRNA expression plasmid. These sequences can also be generated using PCR cloning or mutagenic strategies. Selection methodologies can also be used to isolate guide RNAs from pools of guide RNAs. Co-expression of the sgRNA and the appropriate Cas enzyme from the same or separate plasmids in transfected cells results in a single or double strand break (depending of the activity of the Cas enzyme) at the desired target site.

The literature also contains examples indicating the importance of off-target analysis. The Examples below show that levels of off-target cleavage using CRISPR/Cas9-based gene modification strategies can be comparable with the on-target rates, even when there are multiple mismatches to the guide strand in the region close to the PAM. The Examples also show that RNA guide strands containing insertions or deletions in addition to base mismatches can result in cleavage and mutagenesis at genomic target site with levels similar to that of the original guide strand. These studies provide experimental evidence that genomic sites can be cleaved when the DNA sequences contain insertions or deletions compared with the CRISPR guide strand. Accordingly, methods and systems for identifying target sites, and particularly off-target sites, of CRISPR/Cas guide strands are provided. Additionally, methods and systems for ranking target sites, and particularly off-target sites, of CRISPR/Cas guide strands are provided. The methods and systems can be used to prepare a list of off-target sites for a guide strand based on 1, 2, 3, or more mismatches, insertions, deletions, or combinations thereof.

Although, as discussed above, a chimeric guide RNA (gRNA), or single guide RNA (sgRNA) contains a target sequence, or guide sequence, and a tracrRNA sequence, with respect to the methods and systems disclosed herein, "guide", "guide strand", "guide strand sequence" and "guide sequence" are used interchangeably and refer to a gRNA or sgRNA sequence including, and preferably consisting of the target sequence of the gRNA that binds to a complementary genomic sequence at the target site (Jinek, et al., *Science,* 337:816-821 (2012)). In other embodiments, the guide sequence is not a chimeric sequence, but contains two parts: the guide portion and the tracrRNA. Alternative versions also exist in other embodiments with combinations of sequences, or replacements or modifications of portions of the tracrRNA or linking of RNA fragments, such as modifications to the lower or upper stem, nexus or hairpins, or the inclusion of additional sequences. The additional sequences may permit quantitation, binding to other nucleotides, linking to functional domains, other uses, or not provide a function. The guide sequence can be expressed from a plasmid, provided as RNA, or complexed with the Cas protein prior to adding to the cells. The sequence can be articulated as an RNA sequence or a cDNA sequence. With respect to the methods and systems discussed herein, for purposes of identity, homology, and other means of sequence comparison between gRNA sequence and genomic sequence, there is generally no "penalty" or other loss of identity for uracil (U) in the place of thymine (T). Therefore, the gRNA and genomic sequences can be compared as RNA-to-DNA or DNA-DNA and have the same sequence identity. In some embodiments, the disclosed systems and methods include converting an RNA sequence to DNA, or vice versa, so that sequences are compared as DNA-to-DNA, or RNA-to-RNA. In other embodiments other nucleotides, including non-natural nucleotides can be included.

As used herein, "target site" generally refers to a genomic location to which a guide strand might bind. The binding level may vary and may depend on context, accessibility or other factors. An "on-target" site generally refers to a genomic site to which a practitioner desires binding and/or cleavage to occur, while "off-target" refers to a genomic site to which a practitioner does not desire binding and/or cleavage to occur. The definition of target site or on-target site can be thought of as the intended binding or cleavage site, regardless of its level of identity, or number of mismatches, and regardless of how this site compares to other un-intended sites that may score below or higher in these indices. In the context of the CRISPR/Cas system, an on-target site can be a genomic site at which genetic modification is desired, while an off-target site can be a genomic site at which genetic modification is not required, not desired, or undesirable. On-target and off-target sites can have the same (e.g., identical), or different nucleotide sequences. A "cleavage site" is the site where the nuclease creates a single-strand break or double-stranded DNA breaks, in the CRISPR systems used in some embodiments, this is within the target site, 3 nucleotides from the PAM.

As used herein, "target sequence" and "target site sequence" are used interchangeable. The terms generally refer to the genomic DNA sequence at the target site and can optionally include the sequence of a PAM motif. It will be appreciated that the site is double-stranded genomic DNA, and therefore, the target sequence can be expressed or described by providing the sequence of either strand of DNA at the target site. For example, the target sequence can be expressed as the sequence of the strand of genomic DNA to which the guide sequence of a gRNA binds, or its complementary strand. Therefore, a target sequence can also be expressed as a sequence that is the same or similar to the gRNA sequence. In some instances a site can be cleaved using more than one guide strand on one or the other DNA strand. As discussed and exemplified in more detail below, the target sequence is most typically expressed as the same or similar sequence to the guide sequence so that the guide sequence can be aligned to the sequence of genomic DNA at the target site and establish the identity between the guide sequence and DNA sequence at the site.

ii. dCas9

Cas9 endonuclease dead, also known as dead Cas9 or dCas9, is a mutant form of Cas9 whose endonuclease activity is removed through point mutations in its endonuclease domain. Similar to its unmutated form, dCas9 is used in CRISPR systems along with gRNAs to target specific genes or nucleotides complimentary to the gRNA with PAM sequences that allow dCas9 to bind. Cas9 ordinarily has 2 endonuclease domains called the RuvC and HNH domains. The point mutations D10A and H840A change 2 important residues for endonuclease activity that ultimately results in its deactivation. Although dCas9 lacks endonuclease activity, it is still capable of binding to its guide RNA and the DNA strand that is being targeted because such binding is managed by other domains. In one embodiment, binding of dCas9 to its target alone is enough to attenuate or block transcription of the targeted gene if the gRNA positions dCas9 in a way that prevents transcriptional factors and RNA polymerase from accessing the DNA. This effect is reversible and can be used for temporary gene repression.

The ability of dCas9 to bind DNA can be exploited for example for the activation of genes, repression of genes, or visualization of genes. dCas9 has modifiable regions, typically the N and C terminus of the protein, that can be used to attach transcriptional activators, transcriptional repressors, chromatic and epigenetic modifiers, and imaging agents. In one embodiment, dCas9 conjugated with a transcriptional repressor, with the help of gRNA, targets a specific gene or nucleotide and effectively knocks down or inactivates the target genes. In another embodiment, the dCas9 conjugated with a transcriptional activator, with the help of gRNA, targets a specific gene or nucleotide and effectively activates the target genes. Transcription factors are known in the art. See for example Lambert, et al., *Cell*, 172:650-665 (2018) and Vaquerizas, et al., *Nature Genetics*, 10:252-263 (2009). In another embodiment, imaging agents can be transfixed to dCas9 to identify the target location of the gene of interest within a cell. Exemplary imaging agents include but are not limited to fluorescent probes, luminescent probes, colorimetric probes, radioactive probes, and magnetic probes.

The disclosed systems and methods can be used to determine possible off-target binding sites for enzymatically inactive nucleotide guided endonucleases, for example dCas9. Identifying off-target sites for dCas9 is important to ensure accurate gene editing. Binding of dCas9 to an off-target site could result in the activation, repression, or visualization of the wrong gene or nucleotide. This could lead to inaccurate data in a laboratory setting, or detrimental side effects on human subjects in a therapeutic setting. Therefore, it is critical to determine possible off-target sites for dCas9 nucleases early in development.

In other embodiments, the inactivated or partially inactivated nuclease is derived from other Cas9 or Cas family nucleases or orthologs. These can be naturally occurring, shuffled or re-engineered, such as with altered PAM-interacting domains.

B. Search Inputs

Figures 25A, 25B, 25C:
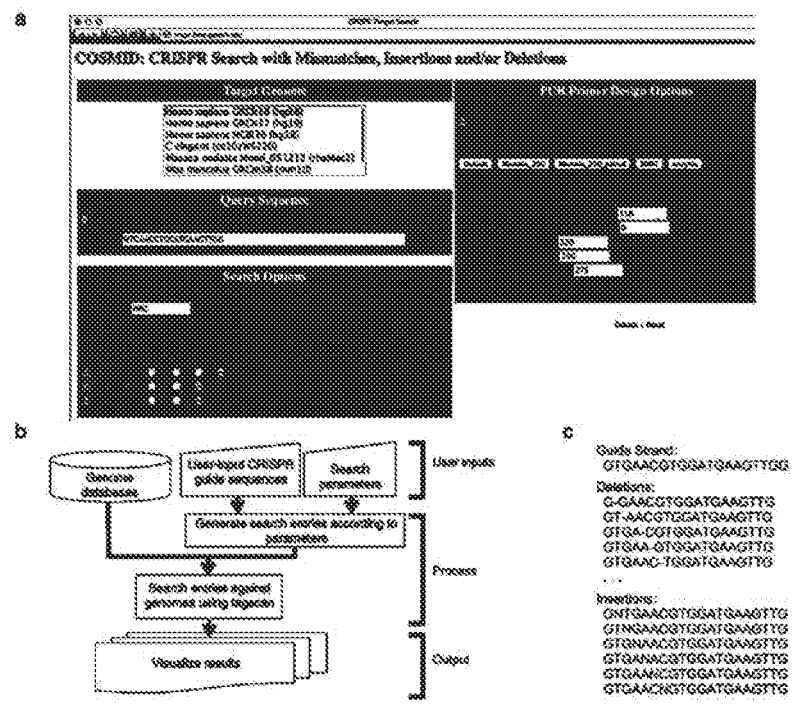
FIG. 25A is a screen-shot of an exemplary COSMID user input interface, including drop-down list of searchable genomes, a box to enter a query guide sequence (SEQ ID NO: 1045) of choice, a box to enter the type of PAM, radio buttons to select allowed number of mismatches, insertions and deletions, and both selection criteria and user input boxes to modify the primer design parameters.
FIG. 25B is a flow chart showing the COSMID software design and the major steps in performing a search.
FIG. 25C is a list of exemplary search strings (SEQ ID NOS 1046-1057, respectively, in order of appearance) with insertions or deletions in the first six possible positions demonstrating how the program searches for each insertion or deletion (if selected by user). Alternate deletions of repeated bases are synonymous.

Typically, to perform a search, user input can include the genome of interest, guide strand sequence, PAM sequence, and the number of base mismatches, insertions, and deletions allowed. To perform a search, a user chooses the genome of interest from the list, and enters the guide strand and optionally PAM sequences (FIG. 25A). Types of indel query include, for example, (i) the number of mismatches with no insertion or deletion (i.e., "No indels"); (ii) the number of mismatches in addition to a single-base deletion (i.e., "Del"); and (iii) the number of mismatches in addition to a single-base insertion (i.e., "Ins"). Typically, up to three mismatches without indels, and up to two mismatches together with a one-base insertion and/or one-base deletion can be selected. However, in some embodiments, 4, 5, 6, 7, 8, 9, 10, or more mismatches, insertions, deletions, or any combination thereof can be selected.

In some embodiments, PAM variants such as NRG or other PAM sequences can be entered in the suffix box. For example, the spacer (Ns) and required nucleotides are entered into the suffix box, and include genomic sites with any nucleotide at the N positions in the output. In other embodiments, a range of other sequences may constitute naturally occurring or modified PAM sequences. Exemplary spCas9 PAM variants include but are not limited to NGG, NAG, NGA, NGAN, NGNG, NGAG, NAAG, and NGCG. In one embodiment, the Cas9 enzyme is an ortholog from another bacterial species such as *Staphylococcus aureus* (Sa), *Neisseria meningitidis* (Nm or Nme), *Campylobacter jejuni* (Cj), *Streptococcus thermophilus* (St), or *Treponema denticola* (Td). Exemplary PAM variants for the above-mentioned bacterial species include but are not limited to NGRRT, NGRRN, NNNNGATT, NNNNRYAC, NNAGAAW, and NAAAAC. In another embodiment, the nuclease is Cpf1 and the PAM variant that is entered into the suffix box is TTA, TTC, TTG, TTTA, TTTC, or TTTG.

In some embodiments, the adjacent binding sequence may be based on additional binding amino acids or an additional domain, such as a ZFP, TAL or additional nucleotide-based binding domain. The consensus or ambiguous binding sites for an of these could be similarly used. For example, a ZFP could be added and its target site used as a PAM following a range of Ns to indicate spacing.

If primers are desired, primer design parameter settings and parameter templates can also be entered.

In other embodiments, parameters may be entered that correspond to cell type, culture conditions, animal age or growth, developmental state, genomic context, chromosomal or methylation state, DNA mutation repair, pathway choice and other features affecting cleavage and/or mutation rates. In one embodiment, the parameters are scored based on degree such as time, percent, or amount, and if they are positive or negative factors.

C. Processing

The disclosed methods for identifying off-target cleavage locations of a CRISPR/Cas nuclease typically computer-implemented methods that include scanning or searching the genomic sequence data for the target cleavage locations of the nuclease based on parameters selected from the group consisting of guide strand sequence, organismal genome, number of mismatches, insertions, and/or deletions, to return target cleavage location sequence and/or locations in the genome. Typically the target sites identified by the search are assigned a score that is used to rank the target cleavage locations based on the likelihood of target cleavage. This score may include other factors relating to the genomic context, chromatin, methylation, acetylation, proteins bound, etc.

The simplest mechanism for scoring locations in the genome is based on the sequence of the site and the adjacent PAM. A perfect match to the guide RNA would be given the highest score. The level of cutting decreases with mismatches between the guide RNA and the target site and each mismatch and/or bulge in the two sequences can be assigned individual scores that help predict the likelihood of cutting. The pairing between individual nucleotides helps predict the likelihood of pairing and/or binding and therefore can also be included in the scoring. More advanced scoring mechanisms take into consideration the number, spacing and exact pairing of the mismatches and/or bulges. These scoring mechanisms can also be used to predict the likelihood of the nuclease targeting RNA sequences based on the mismatches and bulges, their positions etc, plus the possibilities for RNA structures that may help or hinder cleavage.

In other embodiments, these scorings based on the sequences of the target and guide nucleotides also include factors relating to the genomic context, chromatin, methylation, acetylation, DNAse hypersensitivity sites, expression, proteins bound, and other factors. Genomic context, including nucleosomes and chromatin state, of each genomic locus significantly influences the cleavage efficiency (Chen, X. *Nucleic Acids Res,* 44:6482-6492 (2016)). Examples of sites with different levels of cleavage are shown in Tables 15 & 16. In other cell types, these may have different levels of cleavage and/or relative level changes. In some of these cases, the predicted or determined factors decrease the likelihood of the DNA being bound and/or cleaved. The nuclease may be blocked by transcription factors or other proteins or chromatin structures. In other cases, the predicted or determined factors increase the likelihood of the DNA being bound and/or cleaved. Numerous factors that influence the accessibility or likelihood of cleavage can be combined to predict the possibility of cleavage. Examples include the same sequence occurring in multiple locations across the genome. These other factors may predict in silico and may determine in the cell, how much each site is cleaved. Knowing that proteins or chromatin prevent binding or cutting may help scientist predict that certain sites will have less cutting before testing directly. Similarly, it has been described that sites can be cleaved at different rates (Cradick, et al. *Mol Ther Nucleic Acids,* 3(12):e214 (2014)). In each case, the scoring may include information on the features at a location and a scoring for each feature that may indicate the likelihood or strength of the scoring of that feature. For example, the proteins may be sometimes bound at that location, may be only bound in fraction of the cells or bound in portions of the cell cycle all of which may affect the scoring less than being bound at a higher amount, in more of the cells and a greater percentage of time.

In other embodiments the prime function is ranking sequences to a range of criteria.

1. Searching for Off-Target Sites

In the preferred embodiments, before performing a search, a series of search entries are constructed according to the user-specified guide strand and search criteria (FIG. 25B). The search entries include all insertions and deletions at each possible location (FIG. 25C, FIGS. 26E-26F).

Although multi-base deletions (RNA bulges) and insertions (DNA bulges) could be tolerated (Lin, et al., *Nucleic Acids Res,* 42:7473-7485 (2014), and search for a wide range of insertions and deletions will likely result in a very large number of returned sites. Therefore, in a preferred embodiment only searches for single-base insertions and deletions in the DNA sequence are compared with the guide strand (FIG. 25A). In other embodiments, larger number of nucleotide insertions or deletions, or multiple insertions and/or deletions can be accommodated, though this is likely to result in a longer list of sites output. Widening the scope of output sites may be particularly useful when trying to model the cause of verified off-target events that cannot be explained by stricter criteria. For the potential target sites, the search algorithm can allow some ambiguities (such as N for any nucleotide). Ambiguities included in the search string are not counted toward the user-specified mismatch limits. In certain embodiments, ranges of ambiguities can be employed, such as the codes for either of two nucleotides (R, W, S, K, R or Y) or three nucleotides (B, D, H, V), in addition to N. The use of ambiguities allows the inclusion of the matching genomic base with the output sequences. One possibility is to include an "N" in positions that can have substitutions, such as the first base in a guide strand that is often a G primarily to aid in transcription, but does not need to match the complementary target sequence (Hsu, et al., *Nat Biotechnol,* 31: 827-832 (2013); Cradick, et al., *Nucleic Acid Res,* 41:9584-9592 (2013); Mali, et al., *Science,* 339: 823-826 (2013)). One can leave off this base when performing a search, or include a 5' N in the search string, which allows output and alignment of the corresponding 5' bases at each locus to the "N."

In preferred embodiments, the search algorithm is based on sequence homology and identity, with the option to allow insertions or deletions a search method, a ranking method, or a combination thereof. The off-target site lists can be constructed using, for example, existing search algorithms such as FASTA or BLAST, or these methods modified to allow these types of exhaustive searches. In some embodiments, these types of existing or freshly generated lists can be ranked by the methods described here. The FASTA algorithm is described in W. R. Pearson, and D. J. Lipman (1988) *Proc. Natl. Acad Sci.,* 85:2444-2448 and D. J. Lipman, and W. R. Pearson (1989) *Science,* 227:1435-1441. The BLAST algorithm is described in S. Altschul, et al. (1990) *J. Mol. Biology,* 215:403-410. While FASTA, BLAST, mega-BLAST, BLAST Bowtie, and other later improvements can be used to construct a list of target sites, these are not the preferred approaches. In some embodiments, other search methods are used, then refined by using a ranking algorithm that can weigh the number and positions of mismatches, insertions, deletions and their combinations. The output from non-exhaustive search tools may not be considered to have all possible off-target sites.

In preferred embodiments, on-site and off-site targets of the CRISPR guide strands are determined by comparing the query sequence both with and without insertions, deletions, and/or mismatches at one or multiple positions using the FetchGWI search program (Iseli, et al., *PLoS ONE,* 2(6): e579 (2007). FetchGWI operates on indexed genome sequences that are precompiled and stored (FIGS. 26A-26G). It can identify genomic locations with sequences that match any of the series of search entries. FetchGWI saves run time by searching indexed files that represent the genome sequences, rather than the sequences themselves. There is one index entry for each nucleotide in the genome, which allows a rapid and exhaustive search. In other embodiments, other indexing strategies can be used. Exhaustive, complete searches are a key advantage over BLAST and other programs that scan nonoverlapping words and may miss potential off-target sites.

The guide strand sequence and/or variants thereof and/or other query sequences can be compared to an organismal genome, or any loaded sequence files. In preferred embodiments, the searched genome is human, mouse, *Caenorhabditis elegans*, or rhesus macaque genomes. In other embodiments, any genome, modified genome or sequence file can be searched. In the most preferred embodiments, the searchable genome is prepared using the genwin program (Iseli, et al., *PLoS ONE*, 2(6): e579 (2007)) to transform the DNA sequence from FASTA formatted files into unsorted index entries which have all possible 25 bases-long tags in the DNA sequence. After that, the sortGWI program is used to sort the index entries, and store the result as a binary index file. sortGWI subdivides the whole index file into parts, each representing entries having identical first 12 nucleotides. A secondary index, recording the position in the main index file where each part starts, is added to the end of the index file to enable faster search and reduce file size. The index files can be stored in a server.

When the search is initiated, the sequence tags can be used to generate a series of additional tags that contain indels if the insertion or deletion boxes are checked, or if defaults are used. Identical tags are removed if they are duplications for strings containing consecutive identical bases, or in other embodiments, these can be removed at other steps in the processing. The resulting tags are all searched against the user-selected genome. The working Examples include exemplary searches, for example, if guide strand R-01 is entered and one (1) insertion and one (1) deletion are selected, the tags illustrated in FIGS. 26E and 26F are generated and used to search a genome.

To search the query sequences against the user-selected genome, the FetchGWI program can be used (Iseli, et al., *PLoS ONE*, 2(6): e579 (2007). For example, if the user specifies a search with one or more mismatches, all possible sequence tags can be generated by replacing the specified number of nucleotides with all other possibilities. In the preferred embodiment, FetchGWI can search the genome allowing the user-specified number of mismatches. After that, FetchGWI can sort all the query tags and searches for matches in the index file, using binary search. FetchGWI can report the search results by appending the actual sequence tag found, along with the accession number and position offset within the sequence for each matched query tags. Programs, such as the TagScan algorithm can be used to minimize run times while still performing exhaustive genome searches. In other embodiments, other programs are used that can allow greater numbers of mismatches to the genomic sequences.

2. Exemplary Methods of Constructing Query Sequences

As discussed above, a series of guide sequence variants are constructed based on a user entered guide sequence and used to query the selected genome for potential target sites. The parameters used to construct the series of query guide sequences is typically prepared based on user entered parameters includes, the number of mismatches (e.g., 0, 1, 2, 3, etc.), insertions (e.g., 0, 1, 2, etc.), and/or deletions (e.g., 0, 1, 2, etc.) that are allowed at the target site relative to the guide sequence. In some embodiments, multiple insertions and/or deletions may be allowed. In some embodiments, duplicative query sequences are subtracted or culled from the series before the search such that each sequence in the series is unique and only searched once. In a particular embodiment, the query guide sequences provide guide strand variant sequences having no indels and 0, 1, 2, or 3 mismatches; 1-base deletion, no insertions, and 0, 1, or 2 mismatches; 1-base insertion, no deletions, and 0, 1, or 2 mismatches; 1-base deletion, 1-base insertion, and 0, 1, or 2 mismatches; or any combination thereof.

In specific embodiments, (1) if insertions are allowed:

a series of query guide sequences are generated that are variations of the original guide sequence. At each position in the guide sequence, (such as between the PAM and the closest nucleotide, between the first and second, second and third nucleotide, etc.) each nucleotide can be inserted generating different guide strand variations. As there are four natural nucleotides, in most embodiments, there will be four variations with A, C, G or T introduced in position in the four different variations. In the preferred embodiments, an "N" is inserted that will match any of these. If insertions of greater than one nt are allowed, then the single inserted N can also be replaced with two or more Ns, which can be inserted into each position to generate variations with one or more nt insertions.

(2) if deletions are allowed:

a series of query guide sequences are generated that are variations of the original guide sequence. At each position in the guide sequence, (such as between the PAM and the closest nucleotide, between the first and second, second and third nucleotide, etc.) each nucleotide can be deleted resulting in a guide strand that is one nt shorter. At positions where there are repeated nucleotides, deleting any one would result in the same variant. This is consistent if either is deleted when two nt are the same, or deleting any of a longer repeated string of nts. If deletions of greater than one nt are allowed, then the single nt deleted can also be replaced with two or more deleted nt that can be deleted at each position along the guide strand.

(3) if insertions and deletions are allowed:

a series of query guide sequences are generated that are variations of the original guide sequence. At each position in the guide sequence, (such as between the PAM and the closest nucleotide, between the first and second, second and third nucleotide, etc.) each nucleotide can be inserted generating different guide strand variations. As there are four natural nucleotides, in most embodiments, there will be four variations with A, C, G or T introduced in position in the four different variations. In the preferred embodiments, an "N" is inserted that will match any of these as with insertions alone. The resulting string of queries is then subjected to individual deletions as in (2) above resulting in variations that have inserted and deleted bases. Deleting an inserted base would result in the original sequence. Allowing more than one base inserted and/or deleted would introduce even more variations.

(4) if insertions are allowed with:

a series of query guide sequences are generated that are variations of the original guide sequence. At each position in the guide sequence, (such as between the PAM and the closest nucleotide, between the first and second, second and third nucleotide, etc) each nucleotide can be inserted generating different guide strand variations. As there are four natural nucleotides, in most embodiments, there will be four variations with A, C, G or T introduced in position in the four different variations. In the preferred embodiments, an "N" is inserted that will match any of these. In addition, other embodiments can allow the introduction of a second insertion at each point in the guide sequence.

(5) if deletions are allowed:

a series of query guide sequences are generated that are variations of the original guide sequence. At each position in the guide sequence, (such as between the PAM and the closest nucleotide, between the first and second, second and third nucleotide, etc) each nucleotide can be deleted resulting in a guide strand that is one nt shorter. At positions where there are repeated nucleotides, deleting any one would result in the same variant. This is consistent if either is deleted when two nt are the same, or deleting any of a longer repeated string of nts. In addition, other embodiments can allow the introduction of a second insertion at each point in the guide sequence.

(6) if insertions and deletions are allowed:

a series of query guide sequences are generated that are variations of the original guide sequence. At each position in the guide sequence, (such as between the PAM and the closest nucleotide, between the first and second, second and third nucleotide, etc) each nucleotide can be inserted generating different guide strand variations. As there are four natural nucleotides, in most embodiments, there will be four variations with A, C, G or T introduced in position in the four different variations. In the preferred embodiments, an "N" is inserted that will match any of these as with insertions alone. The resulting string of queries is then subjected to individual deletions as in (5) above resulting in variations that have inserted and deleted bases. Deleting an inserted base would result in the original sequence, though deleting one of the inserted bases may produce a variation already included in the output.

(7) if insertions are allowed with:

in other embodiments, other number of insertions may be allowed, leading to large combination of guide strand variations.

(8) if deletions are allowed:

in other embodiments, other number of deletions may be allowed, leading to large combination of guide strand variations, though the introduction of many would lead to shortening of the guide strand.

(9) if insertions and deletions are allowed:

variations can be derived as in (7 and 8) above, and also contain combinations as described in (6). The large number of variations output may not be feasible using current computer configurations and testing or sequencing methods, but advances may allow screening larger number of variations in other embodiments.

Once the variations with indels are created as in (1-9) above, these query sequences, or tags, are used to search the specified genome(s). In one embodiment, this is using FetchGWI to compare each variant to sequences throughout the genome and output the sites that match the user-specified guideline. In one embodiment, that is the number of mismatches for each condition: no indels, with insertions or with deletions. In other embodiments, the output contains other user-specified or default criteria to limit the sequences output. Example of this type of screenings are is the possibility of only including sites that appear to be in open chromatin, or only outputting sites with particular annotations, such as in exons, regulatory sequences or in defined oncogenic regions.

In specific embodiments the mismatches can similarly be added to the query sequences prior to searching,

(10) if one mismatch, zero insertions, and zero deletions is selected:

the series of query guide sequences includes the guide sequence and sequence variants thereof wherein each nucleotide position in the guide sequence is individually substituted by each of the alternative nucleotides, such that each of the query guide sequences in the series has zero or one mismatches, zero insertions, and zero deletions relative to the guide sequence;

(11) if two mismatches, zero insertions, and zero deletions is selected:

the series of query guide sequences includes the guide sequence and sequence variants thereof wherein each nucleotide position in the guide sequence is individually substituted by each of the alternative nucleotides, and guide sequence variants wherein each combination of two nucleotide positions in the guide sequence is substituted with each alternative nucleotide, such that each of the query guide sequences in the series has zero, one, or two mismatches, zero insertions, and zero deletions relative to the guide sequence:

(12) if three mismatches, zero insertions, and zero deletions is selected:

the series of query guide sequences includes the guide sequence and sequence variants thereof wherein each nucleotide position in the guide sequence is individually substituted by each of the alternative nucleotides, guide sequence variants wherein each combination of two nucleotide positions in the guide sequence is substituted with each alternative nucleotide, guide sequence variants wherein each combination of three nucleotide positions in the guide sequence is substituted with each alternative nucleotide, and such that each of the query guide sequences in the series has zero, one, two, or three mismatches, zero insertions, and zero deletions relative to the guide sequence;

(13) if zero mismatches, one insertion, and zero deletions is selected:

the series of query guide sequences includes the guide sequence and sequence variants thereof wherein each canonical nucleotide is individually inserted into each nucleotide position of the guide sequence, such that each of the query guide sequences in the series has zero mismatches, one insertion, and zero deletions relative to the guide sequence;

(14) if zero mismatches, two insertions, and zero deletions is selected:

the series of query guide sequences includes the guide sequence and sequence variants thereof wherein each canonical nucleotide is individually inserted into each nucleotide position of the guide sequence, and guide sequence variants wherein each combination of two canonical nucleotides are individually inserted into the guide sequence each combination of two positions in the guide sequence such that each of the query guide sequences in the series has zero mismatches, two insertions, and zero deletions relative to the guide sequence;

(15) if zero mismatches, zero insertions, and one deletion is selected:

the series of query guide sequences includes the guide sequence and sequence variants thereof wherein one nucleotide is individually deleted from each nucleotide position of the guide sequence, such that each of the query guide sequences in the series has zero mismatches, zero insertions, and one deletion relative to the guide sequence.

(16) if zero mismatches, zero insertions, and two deletions is selected:

the series of query guide sequences includes the guide sequence and sequence variants thereof wherein one nucleotide is individually deleted from each nucleotide position of the guide sequence, and guide sequence variants wherein two nucleotides are deleted from each combination of two nucleotide positions of the guide sequence such that each of the query guide sequences in the series has zero mismatches, zero insertions, and two deletions relative to the guide sequence;

(17) if one mismatch, one insertion, and zero deletions is selected:

the series of query guide sequences includes the guide sequence, and sequence variants thereof wherein each nucleotide position in the guide sequence is individually substituted by each of the alternative nucleotides; each canonical nucleotide is individually inserted into each nucleotide position of the guide sequence; and guide sequence variants having the combination thereof, such that each of the query guide sequences in the series has zero or one mismatches, zero or one insertions, and zero deletions relative to the guide sequence;

(18) if two mismatches, one insertion, and zero deletions is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each canonical nucleotide is individually inserted into each nucleotide position of the guide sequence; and guide sequence variants having combinations thereof, such that each of the query guide sequences in the series has zero, one, or two mismatches, zero or one insertions, and zero deletions relative to the guide sequence;

(19) if three mismatches, one insertion, and zero deletions is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each combination of three nucleotide positions in the guide sequence is substituted with each alternative nucleotide; each canonical nucleotide is individually inserted into each nucleotide position of the guide sequence; and guide sequence variants having combinations thereof, such that each of the query guide sequences in the series has zero, one, two, or three mismatches, zero or one insertions, and zero deletions relative to the guide sequence;

(20) if one mismatch, two insertions, and zero deletions is selected:

the series of query guide sequences includes the guide sequence, and sequence variants thereof wherein each nucleotide position in the guide sequence is individually substituted by each of the alternative nucleotides; each canonical nucleotide is individually inserted into each nucleotide position of the guide sequence; each combination of two canonical nucleotides are individually inserted into the guide sequence each combination of two positions in the guide sequence; and guide sequence variants having the combination thereof, such that each of the query guide sequences in the series has zero or one mismatches, zero, one, or two insertions, and zero deletions relative to the guide sequence;

(21) if two mismatches, two insertions, and zero deletions is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each canonical nucleotide is individually inserted into each nucleotide position of the guide sequence; each combination of two canonical nucleotides are individually inserted into the guide sequence each combination of two positions in the guide sequence; and guide sequence variants having combinations thereof, such that each of the query guide sequences in the series has zero, one, or two mismatches, zero, one, or two insertions, and zero deletions relative to the guide sequence;

(22) if three mismatches, two insertions, and zero deletions is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each combination of three nucleotide positions in the guide sequence is substituted with each alternative nucleotide; each canonical nucleotide is individually inserted into each nucleotide position of the guide sequence; each combination of two canonical nucleotides are individually inserted into the guide sequence each combination of two positions in the guide sequence; and guide sequence variants having combinations thereof, such that each of the query guide sequences in the series has zero, one, two, or three mismatches, zero, one, or two insertions, and zero deletions relative to the guide sequence;

(23) if one mismatch, zero insertions, and one deletion is selected:

the series of query guide sequences includes the guide sequence, and sequence variants thereof wherein each nucleotide position in the guide sequence is individually substituted by each of the alternative nucleotides; one nucleotide is individually deleted from each nucleotide position of the guide sequence; and guide sequence variants having the combination thereof, such that each of the query guide sequences in the series has zero or one mismatches, zero insertions, and zero or one deletions relative to the guide sequence;

(24) if two mismatches, zero insertions, and one deletion is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; one nucleotide is individually deleted from each nucleotide position of the guide sequence; and guide sequence variants having combinations thereof, such that each of the query guide sequences in the series has zero, one, or two mismatches, zero insertions, and zero or one deletions relative to the guide sequence;

(25) if three mismatches, zero insertions, and one deletion is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each combination of three nucleotide positions in the guide sequence is substituted with each alternative nucleotide; one nucleotide is individually deleted from each nucleotide position of the guide sequence; and guide sequence variants having combinations thereof, such that each of the query guide sequences in the series has zero, one, two, or three mismatches, zero insertions, and zero or one deletions relative to the guide sequence;

(26) if one mismatch, zero insertions, and two deletions is selected:

the series of query guide sequences includes the guide sequence, and sequence variants thereof wherein each nucleotide position in the guide sequence is individually substituted by each of the alternative nucleotides; one nucleotide is individually deleted from each nucleotide position of the guide sequence; two nucleotides are deleted from each combination of two nucleotide positions of the guide sequence; and guide sequence variants having the combination thereof, such that each of the query guide sequences in the series has zero or one mismatches, zero insertions, and zero, one, or two deletions relative to the guide sequence;

(27) if two mismatches, zero insertions, and two deletions is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; one nucleotide is individually deleted from each nucleotide position of the guide sequence; two nucleotides are deleted from each combination of two nucleotide positions of the guide sequence; and guide sequence variants having combinations thereof, such that each of the query guide sequences in the series has zero, one, or two mismatches, zero insertions, and zero, one, or two deletions relative to the guide sequence;

(28) if three mismatches, zero insertions, and two deletions is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each combination of three nucleotide positions in the guide sequence is substituted with each alternative nucleotide; one nucleotide is individually deleted from each nucleotide position of the guide sequence; two nucleotides are deleted from each combination of two nucleotide positions of the guide sequence; and guide sequence variants having combinations thereof, such that each of the query guide sequences in the series has zero, one, two, or three mismatches, zero insertions, and zero, one, or two deletions relative to the guide sequence;

(29) if one mismatch, one insertion, and one deletion is selected:

the series of query guide sequences includes the guide sequence, and sequence variants thereof wherein each nucleotide position in the guide sequence is individually substituted by each of the alternative nucleotides; each canonical nucleotide is individually inserted into each nucleotide position of the guide sequence; one nucleotide is individually deleted from each nucleotide position of the guide sequence; one nucleotide is individually deleted from each nucleotide position of the guide sequence; and guide sequence variants having the combination thereof, such that each of the query guide sequences in the series has zero or one mismatches, zero or one insertions, and zero or one deletions relative to the guide sequence;

(30) if two mismatches, one insertion, and one deletion is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each canonical nucleotide is individually inserted into each nucleotide position of the guide sequence; one nucleotide is individually deleted from each nucleotide position of the guide sequence; one nucleotide is individually deleted from each nucleotide position of the guide sequence; and guide sequence variants having combinations thereof, such that each of the query guide sequences in the series has zero, one, or two mismatches, zero or one insertions, and zero or one deletions relative to the guide sequence;

(31) if three mismatches, one insertion, and one deletion is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each combination of three nucleotide positions in the guide sequence is substituted with each alternative nucleotide; each canonical nucleotide is individually inserted into each nucleotide position of the guide sequence; one nucleotide is individually deleted from each nucleotide position of the guide sequence; one nucleotide is individually deleted from each nucleotide position of the guide sequence; and guide sequence variants having combinations thereof, such that each of the query guide sequences in the series has zero, one, two, or three mismatches, zero or one insertions, and zero or one deletions relative to the guide sequence;

(32) if one mismatch, two insertions, and one deletion is selected:

the series of query guide sequences includes the guide sequence, and sequence variants thereof wherein each nucleotide position in the guide sequence is individually substituted by each of the alternative nucleotides; each canonical nucleotide is individually inserted into each nucleotide position of the guide sequence; each combination of two canonical nucleotides are individually inserted into the guide sequence each combination of two positions in the guide sequence; one nucleotide is individually deleted from each nucleotide position of the guide sequence; and guide sequence variants having the combination thereof, such that each of the query guide sequences in the series has zero or one mismatches, zero, one, or two insertions, and zero or one deletions relative to the guide sequence;

(33) if two mismatches, two insertions, and one deletion is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each canonical nucleotide is individually inserted into each nucleotide position of the guide sequence; each combination of two canonical nucleotides are individually inserted into the guide sequence each combination of two positions in the guide sequence; one nucleotide is individually deleted from each nucleotide position of the guide sequence; and guide sequence variants having combinations thereof, such that each of the query guide sequences in the series has zero, one, or two mismatches, zero, one, or two insertions, and zero or one deletions relative to the guide sequence;

(34) if three mismatches, two insertions, and one deletion is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each combination of three nucleotide positions in the guide sequence is substituted with each alternative nucleotide; each canonical nucleotide is individually inserted into each nucleotide position of the guide sequence; each combination of two canonical nucleotides are individually inserted into the guide sequence each combination of two positions in the guide sequence; one nucleotide is individually deleted from each nucleotide position of the guide sequence; and guide sequence variants having combinations thereof, such that each of the query guide sequences in the series has zero, one, two, or three mismatches, zero, one, or two insertions, and zero or one deletions relative to the guide sequence;

(35) if one mismatch, one insertion, and two deletions is selected:

the series of query guide sequences includes the guide sequence, and sequence variants thereof wherein each nucleotide position in the guide sequence is individually substituted by each of the alternative nucleotides; each canonical nucleotide is individually inserted into each nucleotide position of the guide sequence; one nucleotide is individually deleted from each nucleotide position of the guide sequence; one nucleotide is individually deleted from each nucleotide position of the guide sequence; two nucleotides are deleted from each combination of two nucleotide positions of the guide sequence; and guide sequence variants having the combination thereof, such that each of the query guide sequences in the series has zero or one mismatches, zero or one insertions, and zero, one, or two deletions relative to the guide sequence;

(36) if two mismatches, one insertion, and two deletions is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each canonical nucleotide is individually inserted into each nucleotide position of the guide sequence; one nucleotide is individually deleted from each nucleotide position of the guide sequence; one nucleotide is individually deleted from each nucleotide position of the guide sequence; two nucleotides are deleted from each combination of two nucleotide positions of the guide sequence; and guide sequence variants having combinations thereof, such that each of the query guide sequences in the series has zero, one, or two mismatches, zero or one insertions, and zero, one, or two deletions relative to the guide sequence;

(37) if three mismatches, one insertion, and two deletions is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each combination of three nucleotide positions in the guide sequence is substituted with each alternative nucleotide; each canonical nucleotide is individually inserted into each nucleotide position of the guide sequence; one nucleotide is individually deleted from each nucleotide position of the guide sequence; one nucleotide is individually deleted from each nucleotide position of the guide sequence; two nucleotides are deleted from each combination of two nucleotide positions of the guide sequence; and guide sequence variants having combinations thereof, such that each of the query guide sequences in the series has zero, one, two, or three mismatches, zero or one insertions, and zero, one, or two deletions relative to the guide sequence;

(38) if one mismatch, two insertions, and two deletions is selected:

the series of query guide sequences includes the guide sequence, and sequence variants thereof wherein each nucleotide position in the guide sequence is individually substituted by each of the alternative nucleotides; each canonical nucleotide is individually inserted into each nucleotide position of the guide sequence; each combination of two canonical nucleotides are individually inserted into the guide sequence each combination of two positions in the guide sequence; one nucleotide is individually deleted from each nucleotide position of the guide sequence; two nucleotides are deleted from each combination of two nucleotide positions of the guide sequence; and guide sequence variants having the combination thereof, such that each of the query guide sequences in the series has zero or one mismatches, zero, one, or two insertions, and zero, one, or two deletions relative to the guide sequence;

(39) if two mismatches, two insertions, and two deletions is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each canonical nucleotide is individually inserted into each nucleotide position of the guide sequence; each combination of two canonical nucleotides are individually inserted into the guide sequence each combination of two positions in the guide sequence; one nucleotide is individually deleted from each nucleotide position of the guide sequence; two nucleotides are deleted from each combination of two nucleotide positions of the guide sequence; and guide sequence variants having combinations thereof, such that each of the query guide sequences in the series has zero, one, or two mismatches, zero, one, or two insertions, and zero, one, or two deletions relative to the guide sequence;

(40) if three mismatches, two insertions, and two deletions is selected:

the series of query guide sequences includes the guide sequence, and sequence variants thereof wherein each nucleotide position in the guide sequence is individually substituted by each of the alternative nucleotides; each combination of two nucleotide positions in the guide sequence is substituted with each alternative nucleotide; each combination of three nucleotide positions in the guide sequence is substituted with each alternative nucleotide; each canonical nucleotide is individually inserted into each nucleotide position of the guide sequence; each combination of two canonical nucleotides are individually inserted into the guide sequence each combination of two positions in the guide sequence; one nucleotide is individually deleted from each nucleotide position of the guide sequence; two nucleotides are deleted from each combination of two nucleotide positions of the guide sequence; and guide sequence variants having combinations thereof, such that each of the query guide sequences in the series has zero, one, two, or three mismatches, zero, one, or two insertions, and zero, one, or two deletions relative to the guide sequence.

The guide sequence and the series of query guide sequences can be modified to include one or more of the PAM sequence suffixes as discussed above. Next the guide sequence and the series of query guide sequences, with and/or with the PAM sequence suffix(es) is compared or aligned to a genome. As discussed above, in the most preferred embodiments, the genome is a user selected genome composed of indexed files that represent the genome sequences, rather than the sequences themselves.

A target site location in the genome is typically identified or reported in the output when the genomic sequence matches the user-specified criteria. For examples the number of mismatches is below the user-supplied limit, and it lacks indels in relation to the guide strand if only "no indels" is chosen. The maximal number of mismatches allowed can be 0, 1, 2, 3, 4, 5, 6, 7, 8, 9, 10, 12, 15 or longer depending on the guide strand length. Alternatively a site can be output if it does have an insertion or deletion and that type of search is chosen by the user, subject to the site having a direct match or having less mismatches than the user-specified limit. The maximal number of mismatches allowed can be 0, 1, 2, 3, 4, 5, 6, 7, 8, 9, 10, 12, 15 or longer depending on the guide strand length. The user can also specify one, two, three or more PAM sequences individually or using consensus or ambiguous sequences. Depending on the number of mismatches, number of indels, guide strand length, and PAM lengths, the genomic sequence may have at least 60, 65, 70, 80, 85, 90, 92, 95, 96, 97, 98, 99 or 100 percent identify to the guide strand.

Searching genomes with a longer guide strand or PAM sequences will decrease the number of sites output if using the same number of mismatches, therefore the genomic sites most similar to the guide strand my correspond to lower levels of identity, such as at least 60, 70, 80, 85, 90, 92, 95, 96, 97, 98, 99 or 100 percent identify to the guide strand. It may be important to query sequences throughout this range as tissue culture experiments have revealed that guide strands have been found to cleave sites with identities in this range.

In preferred embodiments, the level of matching is further or solely weighed based on sequence-dependent scoring, such that modified counts of the number of mismatches or indels or a modified percentage is determined by the sequence of the guide, the complementary genomic sequence or both. In some embodiments this may be weighed as the change in nucleotide affinity, the ability to tolerate mismatches or indels, or based on other modeling or data.

In other embodiments, other search programs are used to scan the genomes using the range of guide strand variants generated. Other index strategies can be used or whole genomic sequences can be scanned using perl, pyton, or other direct search programs or scripts. In some embodiments, the programs or scripts would identify sites that match the search criteria, though in other embodiments the sites would correspond to matching the guide strands and variants based on identity percentage. The sites output can be the highest percentages, or those sites above a calculated percentage (based on probability of finding sites after comparing the guide strand, PAM lengths and/or genome size).

A target site location in the genome is typically identified or reported when the genomic sequence has 10000 sequence identity with the guide sequence, or the highest percentage in the genome and/or one or more of the query guide sequences with or without one or more appended PAM sequences. In some alternative embodiments, the sequence identity between the genomic sequence and the guide sequence and/or one or more of the query guide sequences with or without one or more appended PAM sequences is at least 80, 85, 90, 92, 95, 96, 97, 98, or 99 percent. The target site or on-target site can be thought of as the intended cleavage site, regardless of its level of identity, or number of mismatches, if it includes indels related to the gRNA and regardless of how this site compares to other un-intended sites (i.e., off-target sites) that may score below or higher in these indices.

In other embodiments any search method using local alignment or index searches could be used, such as Eland, SOAP, SHRiMP, Bowtie, Q-pick, Maq, or BWA. The programs can vary in their speed and ability to locate all sites. Searches that fail to exhaustively locate all possible target sites, will not output the sites it fails to test, or fails to measure. For research settings, this may lead to failing to determine off-target events. The failure for exhaustive searching and testing are clearly needed in therapeutic settings. For this reason, other methods may be adopted to make the query searches more exhaustive, for example, by adding the possibility of bulges and differences in length between the guide and target sequences.

Other embodiments that fail to filter sites may produce very long lists of sites to sort through scoring and ranking. In some embodiments, the scoring and ranking methods is used to weigh ever site in a genome, and only output top sites or sites scoring above a specified threshold, or number of sites.

As discussed above, the guide sequences, variants thereof, query sequences, etc. can include one or more "N" and other symbolic nucleotides, such as those described herein, that refer to one or more nucleotides. It will be appreciated that in some embodiments, where variant and query sequences are constructed by adding (insertions) or substituting (mismatches) each nucleotide, or each alternative nucleotide as appropriate, relative to a parent sequence (e.g., the guide sequence(s)) at one or more positions, this can additionally or alternatively be accomplished by adding or substituting with an "N" and other symbolic nucleotides, and vice versa. Such symbols can be understood by the user and/or computational software, and thus reduce the total number of variant or query sequences that have to be prepared relative to adding or substituting each of the possible alternative nucleotides individually.

2. Constructing the Target Site List

If more than one target site is identified, the target sites are typically reported as a list, preferably a ranked list. Therefore, the disclosed methods and systems can rank the target sites. The ranking can be based on a score that reflects the expectation of how likely the target site will be cleaved by a CRISPR/Cas nuclease such as Cas9, and can be weighted based on one or more factors or attributes. The ranking can be based upon a scoring function for predicting nuclease activity based at least in-part on sequence identity between the guide strand and the genomic target sequence and/or complementarity between to the guide strand and complementary strand of the genomic target sequence. In some embodiments the scoring function is derived empirically or by incorporating various design rules. The rank can be determined based on the sum of scores corresponding to different design considerations. The ranking can include scoring systems that include the weights for mismatches, insertions, deletions and the combinations of these with particular weight corresponding to their location in the guide strand, based on nucleotide proximity or relative position, and or distance from the PAM. The ranking can include scoring systems with additive (or subtractive) weight factors and/or multiplicative factors and/or higher-order weights. In some embodiments, rankings will include features corresponding to the cell type, culture conditions, animal age and/or growth, developmental state, genomic context, chromosomal and/or methylation state, other features affecting cleavage rate, and combinations thereof. Therefore, the method is flexible and will be able to incorporate more design variables into the function as more information about the factors affecting nuclease activity at various target sites becomes available. In addition, the method can be re-applied to an enlarged training set of data once more experimental data become available. In some embodiments a range of different scoring functions is provided with some applying generally and others optimally for a specific guide strand sequence. FIG. 30 presents a flow chart of an exemplary target site prediction method (700) that generates search parameters (710) based upon an input query, constructs a list of on- and off-target sites (720) based upon the search parameters, and ranks (730) the target sites in the list before outputting the results. The score can also include consideration of the number and location of base mismatches, insertions, and/or deletions, when ranking of the more likely target sites. Other considerations include, but are not limited to, the distance between mismatch(es) and the PAM. The Examples below show that mismatches farther from the PAM are more likely to result in off-target cleavage. In some or all sequences, there are positions that may vary from this general trend.

Bioinformatics based ranking of CRISPR/Cas off-target sites may be hindered by the effects of genomic context and DNA modifications. Identical genomic sites and duplicated sites may have dramatic differences in off-target activity. The data presented in the Examples below shows that the indel rate at off-target site R-01_OT2 was 44%, though other loci with the same complementary sequence have much less, or no activity, possibly due to nuclease blocking or any of the other features described above. The accessibility of the genomic DNA may influence nuclease activity sites of similar sequence. Accordingly, in some embodiments, the score includes consideration of factors including chromatin condensation and/or DNA availability at the genomic location of the on- and off-target sites, alone or in combination with other factors in the search algorithm.

Typically, the results are sorted for unique sites with the lowest mismatch and indel score to locate the most likely target sites. In some embodiments, a low score correlates with a high likelihood of nuclease cleavage at the target site. For example, in a particular embodiment, one or more on-target sites are reported, generally first in the list, having a score of "0" and off-target sites are ranked in descending order of likelihood of cleavage based on ascending scores of greater than 0. By way of further illustration, the Examples below show an exemplary scoring paradigm wherein a binding site of a NGG PAM guide strand is typically ranked ahead of a binding site for the guide strand with a NAG PAM (by non-limiting example, +0.3 points can be added to the default scoring).

In other embodiments, a high score correlates with a high likelihood of nuclease cleavage at the target site. Other scoring schemes can be used in other embodiments, such as having 100 equal a perfect match or the top scoring site and scoring lower the less probable sites in accordance to mismatches, insertions and deletions, their combinations and positions.

In some embodiments, the mismatches, insertions, and/or deletions result in the addition to the score corresponding to their location in the guide strand, here in nucleotides from the PAM.

In some embodiments the location of each mismatch, insertion or deletion are added to make the score. For example, in an exemplary embodiment, for mismatches at or beyond position 13 the method adds 0.1, for positions 9-12, 0.5; for 7 and 8, 1.0; for position 6, 1.4; for position 5, 1.9; for position 4, 2.0; for position 1-3, 4; for mismatches in the PAM, 10. In other embodiments, there are multiplications of the individual scores, or combinations of additive scores and multiplication weights. In other embodiments, the weight scores are multiplied or they can be added/subtracted while other weights are multiplied to include score for individual or multiple mismatches or indels or multiple sets of mismatches or indels. In other embodiments, there are sequence specific weights in addition to position specific weights, and these weights can include the guide or complementary sequence or both. For example mismatches at G-C base pairing may be weighed differently than mismatches replacing A-T base pairs. Similarly the resulting mismatches may be weighed, such that G-A, G-T, C-A, or C-T can be scored differently depending on the orientation, the surrounding bases or other features. In other embodiments, other sequence-specific features are weighed such as the binding affinity, sequence patterns, GC or AT content, di-nucleotide pair usage or RNA secondary or tertiary structures or capacity to form such structures. Each of these embodiments may be used with each application, such that one scoring system may be applied to look for on- and off-target binding, on- and off-target binding when linked to effector domains, nuclease or nickase binding, nuclease or nickase cleavage, or other binding or functional effects.

Table 22 illustrates an exemplary of two scoring paradigms that can be used to analyze and rank target sites based on the location/position of the mismatch or indel, and its type (e.g., mismatch, deletion, or insertion). In the exemplary embodiment shown in the right column of Table 22

("scoring"), a "penalty" or "fine" of 0.5 is assessed for deletions, 0.6 for insertions, 0.3 for NAG PAM, and 20 for less preferred PAMs (anything outside NRG for *S. pyogenes* Cas9). This means there is a position penalty or fine for the insertions, then an additional penalty or fine for it being an indel instead of a mismatch. In another embodiment, the weights may be different, in some, or all positions.

In some embodiments the exact mismatches are weighed. For example, a DNA base adenine is scored differently when paired with adenine, guanine, and cytosine rather than its natural match uracil. Similarly, the different RNA or DNA bulges each would be scored differently. In each case, the position and mismatch would be scored.

Another embodiment is shown in the left column of Table 22 ("current"). In this embodiment, the weight scores are not decreasing as their distance varies from the PAM, but may be based on off-target data, biochemical or cellular testing, or other data or modeling. In other embodiments the total scoring is combinations of additive and/or multiplicative weight scores and may include factors weighing combinations of features, such as pairs of mismatches, or mismatches and indels. In other embodiments, the weights may include sequence-specific weights including combinations of features, such as pairs of mismatches, or mismatches and indels. In such an embodiment changing a given nucleotide to any of the others may result in different weight scores, depending on that sequence change and the sequence of the remainder of the guide and/or complementary sequence. There may be a number of concurrent embodiments based on the particular applications, or user-specified features or requirements.

In other embodiments, the scoring of any genomic site may include multiplicative scores that score combinations of mismatches and bulges using relative position weighting, multiplicative scoring based on empirical data, modelling or derived from other studies. This scoring may overlap with the scoring described above or may provide different scoring.

TABLE 22

Exemplary Scoring Paradigm

| Current | Position | Scoring |
|---------|----------|---------|
| 0.1 | >20 | 0.1 |
| 0.1 | 20 | 0.12 |
| 0.1 | 19 | 0.13 |
| 0.1 | 18 | 0.15 |
| 0.1 | 17 | 0.17 |
| 0.1 | 16 | 0.19 |
| 0.1 | 15 | 0.21 |
| 0.1 | 14 | 0.23 |
| 0.1 | 13 | 0.27 |
| 0.5 | 12 | 0.35 |
| 0.5 | 11 | 0.5 |
| 0.5 | 10 | 0.7 |
| 0.5 | 9 | 0.8 |
| 1 | 8 | 1.1 |
| 1 | 7 | 1.3 |
| 1.4 | 6 | 1.9 |
| 1.9 | 5 | 2.3 |
| 2 | 4 | 3 |
| 4 | 3 | 4 |
| 4 | 2 | 5 |
| 4 | 1 | 6 |
| 10 | PAM | 20 | plus additional for
deletions 0.51
insertions 0.7

Figure 34:
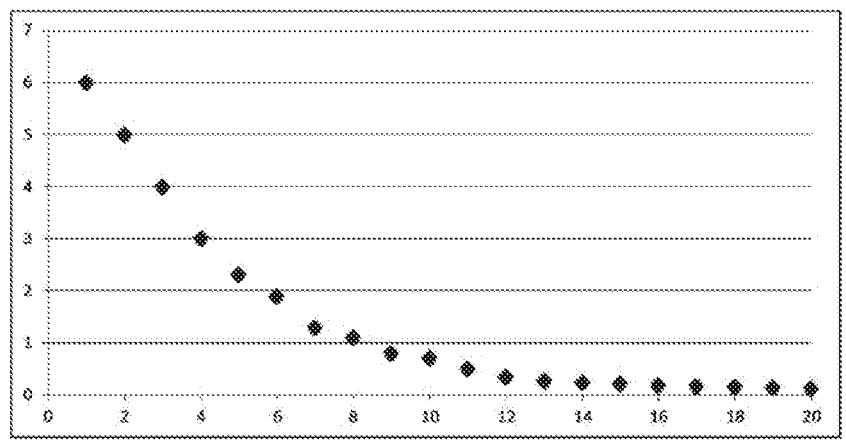
FIG. 34 is a curve illustrating the score (x-axis) as a function of the location/position of the mismatch or indel relative to the PAM (Y-axis).

FIG. 34 is a curve illustrating the score (x-axis) as a function of the location/position of the mismatch or indel relative to the PAM (y-axis) Mismatches in the PAM are not plotted. This graph displays one embodiment of the relationship between weight scores for the position of indels or mismatches. Lower scores under this scoring paradigm are believed to correlate with increased likelihood of nuclease activity at the target site with a mismatch or indel at this site. In this embodiment, weights scores or "fines" are added for multiple mismatches or indels according to these individual weights. Accordingly, in some embodiments under this paradigm, scores would be reported in ascending order with the target site believed to have the highest nuclease activity appearing first and others following in descending order.

D. Output

Output typically includes some or every genomic sequence that matches the user-supplied search criteria in comparison with the entered guide strand. The output method can be based on number of mismatches, indels, or as percentages. The output list of target sites allows a user to compare the number and score target sites for the input guide sequence. As discussed in more detail below, the output can include returning polymerase chain reaction primer sequences for amplification of the ranked cleavage site locations, returning a full nucleic acid sequence of an amplicon for detecting induced mutations; and designating each target cleavage location as being in an exon, intron, promoter, or regulatory or intergenic region. In addition, the output can return hyperlinks to internet resources on the genomic region of the cleavage locations.

1. Target Sites

In some embodiments, the output includes a ranked list of perfectly matched (on-target site and possibly other sites) and partially matched (potential off-target) sites in the genome, their ranking score, optionally along with reference sequences and primer designs that can be used for sequencing and/or mutation detection assays. In a particular embodiment, each line of the output file describes one genomic locus matching the search criteria. A locus may appear on multiple lines if it can be modeled and found in multiple ways.

In some embodiments, the output shows the genomic target site sequence ("hit"), preferably aligned to the query sequence (e.g., guide sequence) to highlight matches, mismatches, indels, etc. In particular embodiments, nucleotides that are not a direct match, including mismatches, insertions, and deletions, are colored or shaded differently or otherwise distinguished from matches. Ambiguities in the query sequence, such as the "N" in the PAM sequence NGG, are indicated differently or are similarly shown, though they do not count as mismatches.

The output can also include the query type, including (i) no deletion or insertion (No indel), (ii) deletions (Del), or (iii) insertions (Ins), with or without mismatches. This portion of the output can indicate if there are insertions or deletions, and specify the indel positions as the number of nucleotides away from the PAM.

The output can also include the number of mismatched bases between the guide sequence and target sequences. As illustrated in more detail in the Examples below, when two repeated bases appear in the guide strand, a deletion of either one of them in the target sequence gives the same query sequence, so the ambiguity can be noted in the output.

The output can also indicate if the PAM in the hit ends in RG, as NGG is the Cas9 PAM with the highest activity, followed by NAG. This portion of the output helps in ruling out genomic sites with unlikely PAMs. In other embodiments, individual PAMs or PAM-like sequences can each be given a different score.

Other information that can be provided in the output includes, but is not limited to, the chromosomal location of the matching sequence, its strand, and the chromosomal location of the cleavage site. This information may also include genomic context known for the particular type of cells, their development and other features. The predicted cleavage position is based on the fact that Cas9 primarily cleaves both DNA strands three nucleotides from the PAM for Sp Cas9. Other naturally occurring, or engineered Cas can have different cut sites. The output can include hyperlinks directed to the chromosomal sites one or more genomic websites or databases, for example, the UCSC genome browser. This allows determination of the gene that best matches the target sequence and if the target site is in an exon, intron, or other region. This information is helpful as mutations may be better tolerated in regions that are non-coding and nonfunctional. This information can also be included as part of the output.

In some embodiments, the output is grouped by query types, including (i) genomic sites with base mismatches, but no insertions or deletions (No indels), (ii) sites with deletions (Del), and (iii) sites with insertions (Ins) between the query and potential off-target sites (e.g., Table 12). Within each category, sites with mismatches further from the PAM are typically listed first, which are more likely to result in off-target cleavage. In some embodiments the scoring is the primary determinant of the order in the lists, though a number of tie-breaking criteria, such as lack of indels, or chromosomal location can be used.

The same genomic location may satisfy two or more search criteria, such as those sites that satisfy the mismatched base limit without and with an insertion or deletion. For example, mismatches at the base farthest from the PAM and deletions of this base will give the same set of genomic locations. This can also occur when the guide strand contains consecutively repeated bases. Since genomic locations can be specified through multiple criteria, they can be indicated as duplications in the output, for example, by listing in each of the corresponding groupings to aid further evaluation and scoring. In other embodiments, duplicate sites are removed or withheld in the output.

In some embodiments, the output lists the potential off-target sites according to attributes or by adding weight matrixes to rank the most likely off-target sites. The accumulation of additional experiments on CRISPR off-target activity will allow creation of a more predictive scoring system. It is believed that mutations in the PAM are least well tolerated followed by sites closest to the PAM; however, little is known about how the guide strand sequence influences these effects (Jinek, et al., *Elife* 2:e00471 (2013); Fu, et al., *Nat Biotechnol*, 31: 822-826 (2013); Hsu, et al., *Nat Biotechnol*, 31: 827-832 (2013); Cradick, et al., *Nucleic Acids Res*, 41:9584-9592 (2013)).

In some embodiments the output is in HyperText Markup Language (HTML). In some embodiments some or all of the output is exported into a spreadsheet, such as in Excel, text or comma, or tab separated formats. The spreadsheet can facilitate further processing by the user, such as sorting by attributes or adding weight matrixes to rank the most likely off-target sites. In some embodiments, the primary ranking is done in the spreadsheet to allow iterative tuning or ranking based on the default of user-supplied weight factors. In other embodiments, secondary, tertiary, or further ranking are done in the spreadsheet to add newer, alternative or other weight or multiplicative scores. The preferred embodiment allows the search method to greatly decrease the number of sites in the genome to a relatively low number, possibly hundreds, or to many thousands of loci to process in spreadsheets.

Table 10 shows an exemplary output in HTML. The output includes the genomic sites matching the user-supplied criteria in comparison to a user supplied guide strand sequence with chromosomal location. Scoring of the mismatches is provided for ranking, as are PCR primers and reference sequence. Other typical output elements (not illustrated in Table 12) include, but are not limited to, right and/or left primer sequences and links to test each primer pair using the UCSC in-silico PCR web site, amplicon sequence, and digest size (discussed in more detail below). The chromosomal location ("Chr. position") for each "hit" in Table 12 is provided as a hyperlink to genomic resources, e.g. UCSC genome browser, and to an output file as a spreadsheet for further manipulation and primer ordering. In other embodiments, links can be provided with genomic annotation, sequence viewers, in silico primer testing, and or pubmed links.

In Table 12, each hit is appropriately aligned to the query shown in the "Result" box. DNA bases corresponding to mismatches, indels, ambiguity codes, such as N, are shown in the query line to identify the matching genomic bases. To the right of the "Result" box are boxes with the query type, number of mismatches, chromosomal position, score, primers, and other features. A spreadsheet output allows the user to manipulate the output to evaluate the number and scores of the low-scoring sites that are predicted to be more likely off-target sites, which may provide important guidelines when evaluating and choosing guide strands and/or testing for true cleavage events using DNA samples from cells after CRISPR/Cas treatment.

2. PCR Primers

An automated primer pair design is sometimes included to design primers appropriate for target site validation assays, matching user input criteria. The primer design function can be used in combination with assays for off-target cleavage after cells or animals are treated with CRISPR guide strands and nuclease. Primers are designed that fit the criteria needed for the particular assay or sequencing platform using an automated primer pair design process. This greatly simplifies the standard method for primer design that requires iterative steps of primer design and verification of the resulting fragment sizes. In addition to speeding the primer design throughput, an automated design process allows the primers to be custom designed for the downstream assays or sequencing, and to be matched for high-throughput, full-plate PCR amplification. Primers can be designed according to specified criteria or to the defaults given for particular applications (FIG. 25A)

To optimize amplicons for different sequencing platforms, the primer pair design will sometimes provide for specifying the minimum distance from the edge of the amplicon to the nuclease site. The recommended parameters will in some cases include a separation distance between cleavage bands that is greater than 0, 20, 40, 60, 80, 100, 120, 140, 160, 180, or 200 base pairs. In some embodiments primer pairs are chosen such that the minimum separation between uncleaved and cleaved products is greater than 50, 75, 100, 125, 150, 175, or 200 base pairs. The primers may be optimally chosen for a variety of sequencing assays, such as appropriate for each sequencing platform.

In some embodiments, users can also input the number of bases the cleavage site must be from each amplicon's edge to ensure sequencing coverage depending on the different sequencing platforms. For single molecule, real-time (SMRT) sequencing, a set of exemplary recommended parameters are: Minimum Distance Between Cleavage Bands of 0 base pairs, Minimum Separation Between Uncleaved and Cleaved Products of 125 base pairs. In another example, for Surveyor assays, the primer design parameters can be specified to ensure that the nuclease site is placed in an optimal position within the amplicon to yield cleavage bands that can be easily distinguished from the parental band and each other using agarose, polyacrylamide, other gels or capillary apparatus. For example, exemplary recommended parameters for use in Surveyor assays resolved on 2% agarose gels are: Minimum Distance Between Cleavage Bands—100 bp, Minimum Separation Between Uncleaved and Cleaved Products—150 bp. In a particular embodiment, for resolution on a 2% agarose gel, the recommended parameters may be: Minimum Distance Between Cleavage Bands of 100 base pairs, Minimum Separation Between Uncleaved and Cleaved Products of 150 base pairs. The output primers can also easily modified in the spreadsheet, such as to add flanking sequences for additional amplification and/or barcodes for sequencing.

The primer pair design process implemented will in some cases use the following steps and considerations to yield primer pairs suitable for high-throughput PCR. In some embodiments the primer design process may take into account the potential secondary structure that could arise of the 3' end of a primer folding back; may take into account estimated physical properties including the temperature or length; may define targets for the content of specific bases in the primer; and may check to ensure for primers that are not self-complementary.

Outlined below is an example primer design process that may be employed in certain preferred embodiments.

Primer Design Process

Each possible position in the sequence 5' of the nuclease binding sites is considered as a possible 5' base for a primer (in some cases allowing for a user-specified minimum distance between the edge of the amplicon and the nuclease site).

For a given 5' starting position, a first number of bases in the 3' direction are taken as an initial sequence for the primer. The first number of bases may be any integer number of bases, but in some preferred embodiments the first number of bases chosen will be 15, 16, 17, 18, 19, or 20 bases. Then the following design loop begins:

Loop:
1) Check for potential secondary structure that could result from the 3' end folding back.
Check that the sequence of the primer up to the 4$^{th}$ most 3' base does not contain any exact matches to the reverse complement of the three most 3' bases.
Example:

```
Potential Primer Sequence:
                                              (SEQ ID NO: 1)
5'-ACATTGAGGCACTACTTG-3'

(SEQ ID NO: 2)
Check that the sequence CAA does not appear in

ACATTGAGGCACTA
```

If there is a match, lengthen the primer by one base in the 3' direction and repeat the loop.

2) Check the predicted melting temperature of the primer and GC content.
% GC—the percentage (not fraction) of G and C residues in the sequence i.e. 33 not 0.33
If the % GC content falls outside a specified range then lengthen the primer by one base in the 3' direction and repeat the loop. In some embodiments the specified range may be greater than 25, 30, 31, 32, 33, 34, 35, or 40% and less than 55, 60, 61, 62, 63, 64, 65, 70, or 75%.
The melting temperature can be approximated by a number of methods. In one embodiment it is approximated by the empirical relation below, where the % GC is the percentage of G and C residues and the length is the primer length in units of the number of nucleotides.

$$T_m = 56.7 + 0.44668 * \%GC - \left(\frac{479.7}{\text{Length}}\right) \quad (1)$$

If the predicted melting temperature falls outside of certain specified values, then lengthen the primer by one base in the 3' direction and repeat the loop. In preferred embodiments the predicted melting temperature is desirably less than 70, 65, 60, 59, 58, 57, 56, 55, 50 degrees when using the empirical formula above.
3) If the primer is longer than a specified maximum primer length, i.e. 30 base pairs, then exit the loop unsuccessfully—no primer for this position. In some cases the maximum primer length may be 20, 30, 35, 40, 50, 60, or 70 base pairs.
4) Check the primer sequence for high self-complementarity.
Ensure that all base pair sequences in the primer are not a perfect match to anywhere in the reverse complement sequence of the primer.
If any match is found, then exit the loop unsuccessfully—no primer for this position.
5) If all requirements are met, then exit the loop successfully and record the primer for this position.
End Loop After attempts to generate primers for all forward positions and all reverse positions are complete, pairs may then be made with each forward pair to each possible reverse pair. This list of pairs can then be pruned in some cases to remove any that would result in products where the distances between nuclease sites and the ends of the amplicon fall outside of some specified ranges. This list may further pruned to remove primer pairs that are somehow undesirable, i.e. could potentially form primer dimers as defined by having the final 3' bases of one primer match the reverse complement of the final 3' bases of the other primer.

The primer pairs may then be sorted by some selection criteria depending upon the application, for example how close the melting temperature is to a specified target melting temperature. Primer pairs may also be sorted and/or filtered by providing a preference, for instance for shorter amplicon lengths, or may be sorted alphabetically or any other acceptable manner.

In some embodiments, the primer pairs are then sorted by how close their melting temperature is to the target melting temperature (the default is 60° C.) by computing $$T_{diff} = (T_{m_{forward}} - 60)^2 + (T_{m_{reverse}} - 60)^2 \quad (2)$$

Take all pairs where the $T_{diff} < 2$ and apply further sorting criteria in order of priority:

1) Prefer shorter amplicon length

2) Prefer a shorter length of the longer primer sequence in the pair

3) As a final tie-break, son the primer sequences alphabetically

If no primer pairs are found acceptable under a specified set of criteria, the algorithm may selectively relax constraints in some embodiments to generate a minimum number of primer pairs. In a particular embodiment, the most lenient set of criteria still require a minimum % GC of 25, a maximum % GC of 70, a maximum length of 38, and a minimum melting temperature of 55° C.

The output can include returning polymerase chain reaction primer sequences for amplification of the ranked off-site cleavage locations alone, or in combination with a full nucleic acid sequence of an amplicon for detecting induced mutations.

In other embodiments, the output "primer sequences" can be used for other applications such as binding without amplification, pull-down sequences, probe sequences, or as sequence-specific tags.

3. Estimating Target Sites

Some embodiments provide an estimate of the number of expected target site based upon the search criteria, for example to provide the user with a guide for selecting appropriate search parameters or to prohibit queries that would generate such a large number of hits to be too time or resource intensive. In other embodiments these calculations are done to provide the default or suggested parameters.

Figure 30A:
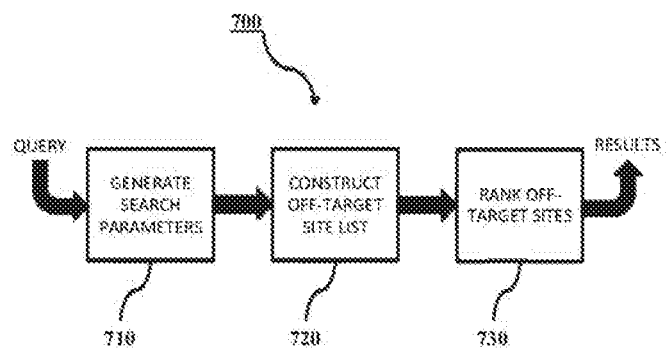
FIG. 30A is a flow chart of an exemplary method for generating a ranked list of off-target sites that could be implemented on a computer. A user query is used to generate search parameters used by the algorithm to construct a list of possible off-target cleavage sites. The possible off-target sites are ranked by their predicted off-target cleavage activity (or chance for activity) and output as results in a ranked list.
Figure 30B:
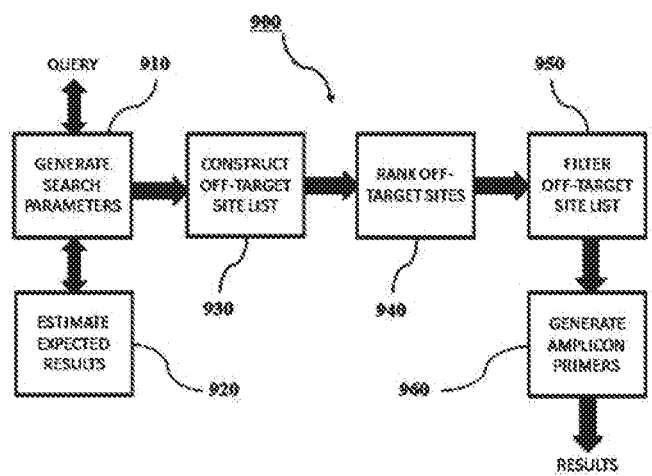
FIG. 30B is a flow chart of an additional exemplary method for generating a ranked list of off-target sites that could be implemented on a computer. This method includes estimating the results and generating a list of primers designed for amplifying and/or testing the mutations introduced at each site.

FIG. 30B depicts a flow chart for an exemplary method (900) for generating target sites. A query is obtained and search parameters are generated (910). Optionally, an estimate of the number of expected results is provided (920). The query may then be updated with a revised query, wherein a revised estimate is subsequently generated of the number of expected results. This process can be completed to obtain a desirable number of expected results. The query is then used to construct a target site list (930) using methods provided herein. The results in the target site list are ranked by score (940) and/or filtered by specified selection criteria (950). The list of target sites is then used to generate primer pairs (960) for generating test amplicons. The list of target sites and primer pairs is then output as results.

E. Exemplary Algorithm for Identifying and/or Ranking Targets Sites

Figure 30C:
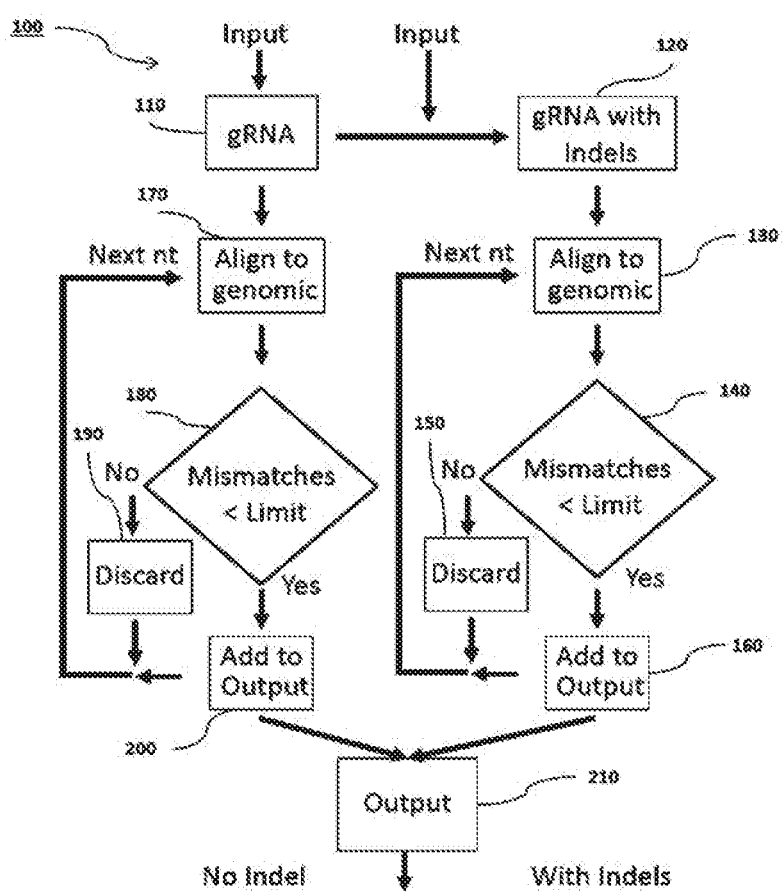
FIG. 30C is a flow chart illustrating an exemplary algorithm for executing the disclosed methods of identifying target sites and/or ranking or scoring target sites.
Figure 30C:
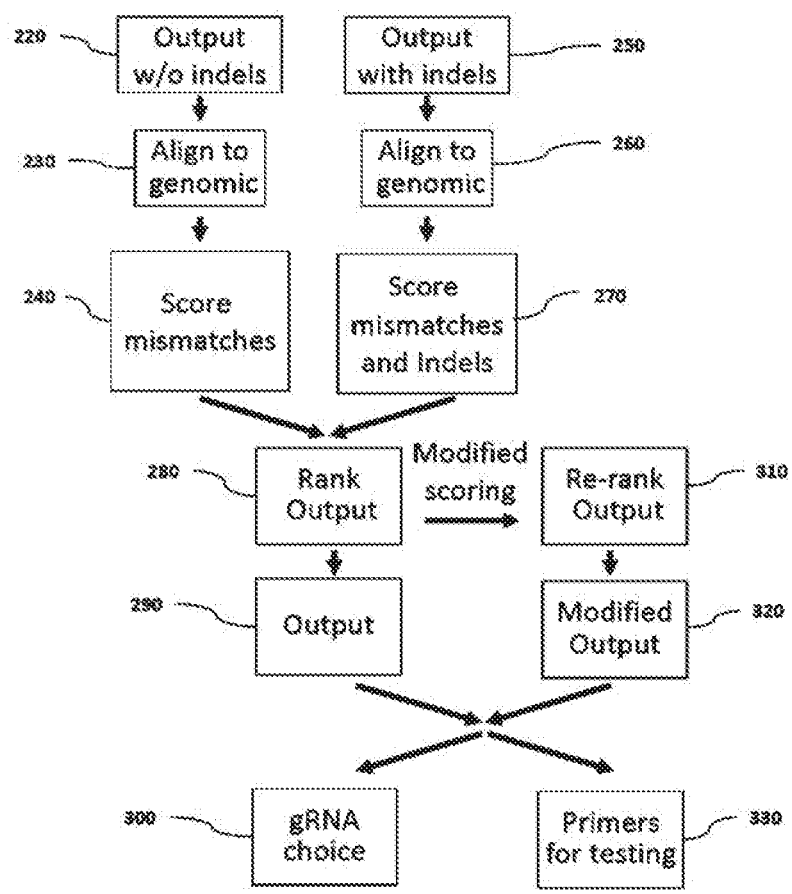

An exemplary decision tree for identifying and/or ranking putative target sites is illustrated in FIG. 30C (100). Following input of a guide strand sequence (gRNA) (110), based on the user-supplied inputs ("input"), variants of the guide RNA are generated that vary in insertion(s) and/or deletion(s) in each possible position. The collection of these variants without the original guide (or with the original guide, depending on embodiment) (120), are then aligned to the chosen genomic (or other) sequence (130). If specified, the required adjacent motif must be present within the supplied limits or mismatches. This can be a PAM or other type of sequence. At each site, the program can determine if each of the guides or variant guides matches within the user specified number of mismatches (140). If not, the sequence is not added to the output (150) and the search moves one nt further through the genome index, the specified sequence or file and searches again (130). The collection of sites matching the criteria and collected as output (160), whereas the sites not matching are not output (150), though they may be included in other output using other guide sequences or inputs, such as greater allowed number of mismatches.

The input guide strand sequence (gRNA) (110), can also be used to search the genomic or other sequences without the possible addition of indels, based on the user-supplied input (170). This process can occur in parallel, or as part of the search with variants, or it may occur prior or at other times than the search described above (130). At each site, the program can determine if each of the guides or variant guides matches within the user specified number of mismatches (180). If specified, the required adjacent motif must be present within the supplied limits or mismatches. This can be a PAM or other type of sequence. If not, the sequence is not added to the output (190) and the search moves one nt further through the genome index, the specified sequence or file and searches again (170). The collection of sites matching the criteria and collected as output (200), whereas the sites not matching are not output (190), though they may be included in other output using other guide sequences or inputs, such as greater allowed number of mismatches.

Each of the sites that was located through these processes is compiled into the collected output (210). The output can contain some or all of the following information or additional information: a list of genomic sequences, the genomic location, such as the chromosome number and base position in most genomes, and annotation on the nearest gene, if the site is in an exon, intron or other annotated sequence or other data from current or future data bases. In other embodiments an output without indels (220) and one that can include indels (250) remain separate. This data can be generated from the process listed above (110-210), or can be derived from other sources, and processed primarily in terms of ranking the output or sequences collected from any source. In other embodiments each site of a given length, sub-sequences, in a genome or other sequence can be scanned and given a ranking score using the algorithm described below (240, 270). Generally the user would request only the sub-sequences above a user-input or default cut-off, generally the sites that would likely be cut.

The listed sites are each individually compared to the guide sequence (220), or guide sequence allowing indels (260) with the ranking performed in any of a number of weighted methods (one embodiment described in Table 22). In the preferred embodiment the site is aligned to the genomic site and included in the output (230 or 260), whereas in other embodiments, the site can be iteratively compared to the genomic site with different combinations of mismatches, insertions and/or deletions (260, 270), or aligned across the full specified sequence or genomic indices. Based on the alignment, the differences are scored with weights for mismatches, insertions and/or deletions using one of the default or user-supplied ranking methods (240, 270). The results of the ranking are given as output (280), which can be combined with other annotated information and provided as HTML, graphical, text, spreadsheet and/or other forms of output (290). The output can be further processed based on the results of this output, such as the number of sites returned, based on newer or different data that emerged, based on alternative applications or other reasons. The output can therefore be re-ranked using independent scoring or scoring systems that incorporate the previously determined score. In one embodiment, this can be as simple as adding further weights for additional features, such as PAM mismatches. In other embodiments, re-ranking can be used to add data not in the original ranking such as chromosomal context, DNA accessibility, sequence specific features or known interactions (310). This output can be provided as HTML, graphical, text, spreadsheet and/or other forms of output (320).

The output in one preferred embodiment, allows one to avoid guide strands that may result in high off-target activity that may target important genes or may result in other off-target events (300). In other embodiments, this process allows the better choice of guide strands, but comparing the output between a ranking of guide strands, that may target the same gene, regions or otherwise be alternatives (300). After the guide strands are used in cells the genomic, plasmid or other DNA can be harvested to measure activity. In one embodiment, output primers are provided that can be used to determine cleavage, homologous recombination, mutation rates or the rates of other events at the on-target and putative off-target sites (330). Similarly, one can use the output primers or other methods to evaluate the on-target or off-target activity of the guide strands and then compare between the guide strands (330).

III. Systems

A. Computer Implemented Systems

Figure 31:
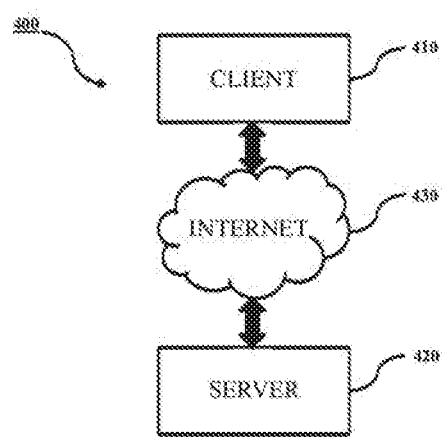
FIG. 31 is a block diagram of a preferred network-based implementation containing a computer server and one or more client computers in communication over a network.

The systems and methods provided herein are generally useful for predicting the location of CRISPR/Cas on- and off-target cleavage sites, particularly those due to insertions and/or deletions in the target DNA relative to the guide RNA sequences and vice versa. In certain embodiments the methods are implemented on a computer server accessible over one or more computer networks. FIG. 31 is a block diagram of a preferred network-based implementation (400) wherein a client computer system (410) is in communication with a server computer system (420) via a network (430), i.e. the Internet or in some cases a private network or a local intranet. One or both of the connections to the network may be wireless. In a preferred embodiment the server is in communication with a multitude of clients over the network, preferably a heterogeneous multitude of clients including personal computers and other computer servers as well as hand-held devices such as smartphones or tablet computers. In some embodiments the server computer is in communication, i.e. is able to receive an input query from or direct output results to, one or more laboratory automation systems, i.e. one or more automated laboratory systems or automation robotics that automate biochemical assays, PCR amplification, or synthesis of PCR primers. See for example automated systems available from Beckman Coulter.

Figure 32:
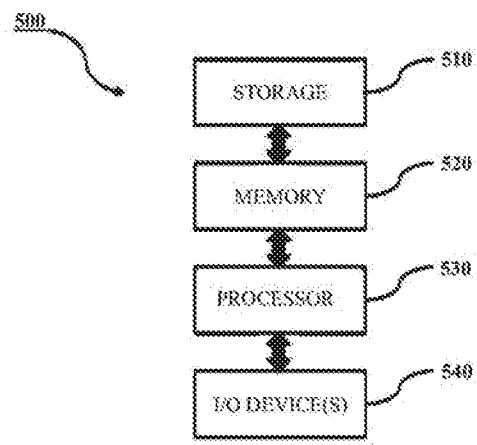
FIG. 32 is a block diagram of a computer server containing I/O device(s), a processor, memory, and storage.

The computer server where the methods are implemented may in principle be any computing system or architecture capable of performing the computations and storing the necessary data. The exact specifications of such a system will change with the growth and pace of technology, so the exemplary computer systems and components described herein should not be seen as limiting. FIG. 32 is a block diagram of the basic components of an exemplary computer server (500) on which the methods may be implemented. The systems will typically contain storage space (510), memory (520), one or more processors (530), and one or more input/output devices (540). It is to be appreciated that the term "processor" as used herein is intended to include any processing device, such as, for example, one that includes a CPU (central processing unit). The term "memory" as used herein is intended to include memory associated with a processor or CPU, such as, for example, RAM, ROM, etc. In addition, the term "input/output devices" or "I/O devices" as used herein is intended to include, for example, one or more input devices, e.g., keyboard, for making queries and/or inputting data to the processing unit, and/or one or more output devices, e.g., a display and/or printer, for presenting query results and/or other results associated with the processing unit. An I/O device might also be a connection to the network where queries are received from and results are directed to one or more client computers. It is also to be understood that the term "processor" may refer to more than one processing device. Other processing devices, either on a computer cluster or in a multi-processor computer server, may share the elements associated with the processing device. Accordingly, software components including instructions or code for performing the methodologies of the invention, as described herein, may be stored in one or more of the associated memory or storage devices (e.g., ROM, fixed or removable memory) and, when ready to be utilized, loaded in part or in whole into memory (e.g., into RAM) and executed by a CPU. The storage may be further utilized for storing program codes, databases of genomic sequences, etc. The storage can be any suitable form of computer storage including traditional hard-disk drives, solid-state drives, or ultrafast disk arrays. In some embodiments the storage includes network-attached storage that may be operatively connected to multiple similar computer servers that comprise a computing cluster.

B. Graphical User Interface

Figure 33:
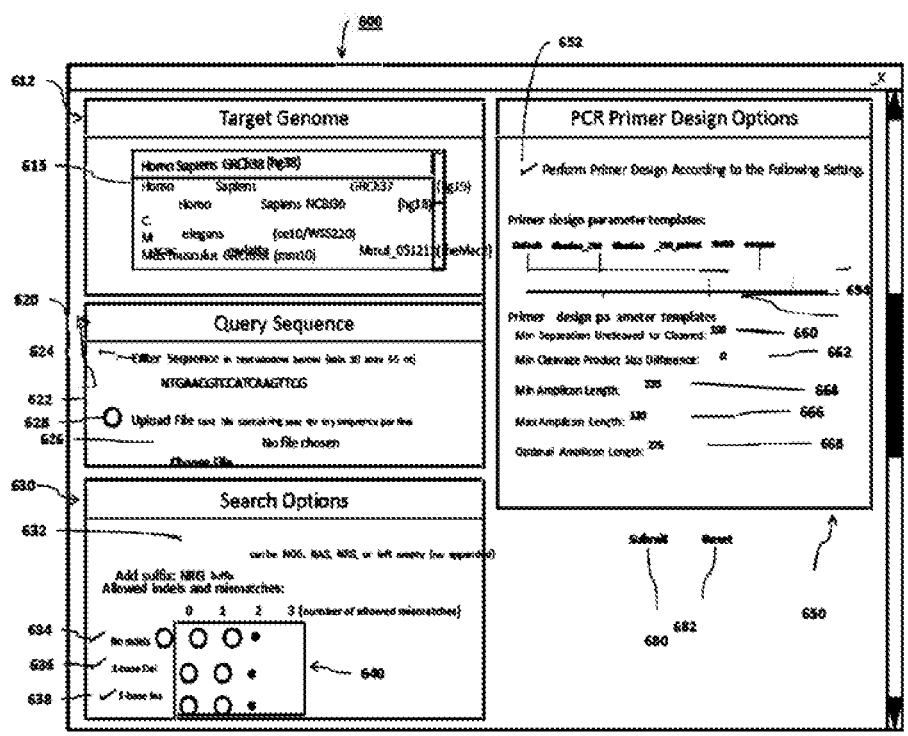
FIG. 33 is a schematic of a graphical user interface (GUI) for receiving input parameters for a computer-implemented off-target site search method. The GUI is displayed in a web browser and contains check boxes, drop-down lists, radio buttons, and text boxes for inputting the query sequence, modifying the search parameters, and customizing criteria design criteria for PCR primers that can be used to test off-target cleavage using the queried guide sequence.

In a preferred set of embodiments the computer server receives input submitted through a graphical user interface (GUI). The GUI may be presented on an attached monitor or display and may accept input through a touch screen, attached mouse or pointing device, or from an attached keyboard. In some embodiments the GUI will be communicated across a network using an accepted standard to be rendered on a monitor or display attached to a client computer and capable of accepting input from one or more input devices attached to the client computer. FIG. 33 depicts some of the components that may be found in an exemplary GUI for inputting parameters for target site searches capable of being rendered in a standard web browser window (600) on a client computer. In other embodiments, a phone interface can identify, read and or run entered sequences.

In the exemplary embodiment (600), the GUI contains a target genome selection region (612) where the user selects the genome to be searched. In this exemplary system a genome is indicated by clicking, touching, highlighting or selecting one of the genomes that are listed (615). In preferred embodiments, the target genome is selected from a drop-down list.

In the exemplary embodiment (600), the GUI contains in query sequence region (620) for entering or uploading one or more query guide sequences. The GUI typically includes a text box for the user to input a query guide strand sequence (622). In other embodiments, users may input any sequence or sequences for which they would like to design amplification primers. The GUI may additionally or alternatively contain an interface for uploading a text file containing one or more query sequences (628, 626). In a particular embodiment, the text file must contain only one query sequence per line. In embodiments that include both options, the GUI may also contain radio buttons that allow the user to select if the target sequence will be entered in a text box (624) or upload from a text file (628). The GUI may include a button for choosing the file (626), may allow a user to drag and drop the intended file, or other means of having the file uploaded. The GUI generally accepts a sequence of length acceptable for serving as a CRISPR/Cas guide strand sequence, for example between about 10 and about 55 nucleotides. In preferred embodiments this may range from 17-22 nucleotides. The input is typically a string of letters, each corresponding to a single letter designating a nucleotide, or other symbols allowing ambiguity at indicated positions (N, R, etc.), and together providing the nucleic acid sequence of the guide strand polynucleotide. The sequence will generally be entered using a combination of characters selected from the allowable characters and dependent upon the implementation may be limited to characters for the standard nucleotides, or may include non-standard nucleotides.

In the exemplary GUI embodiment (600), the GUI contains a region where the user selects search options (630). The region can include a text box for the user to input a target sequence protospacer adjacent motif (PAM) (632). The input is typically a string of three letters corresponding to the single letter code for the PAM. Exemplary PAMs include, but are not limited to, NGG, NAG, and NRG. Other PAMs that are considered include but are not limited to NGRRT, NGRRN, NNNNGATT, NNNNRYAC, NNAGAAW, NAAAAC, TTA, TTC, TTG, TTTA, TTTC, and TTTG.

The GUI also typically includes additional radio buttons, boxes, or/and other manners for the user to input the number of allowed mismatches, insertions, and/or deletions. In the exemplary GUI embodiment (600), the search options region (630) provides a check button for selecting if no indels should be included in the search (634), a check button for selecting if deletions should be included in the search (636), a check button for selecting if insertions should be included in the search (638), and radio buttons for entering how many mismatches (e.g., 0, 1, 2, or 3, etc.), deletions, (e.g., 0, 1, 2, etc.), insertions (e.g., 0, 1, 2, etc.), or a combination thereof should be searched. In some embodiments, the interface provides a check button to elect no indels in combination with radio buttons for selecting 0, 1, 2, or 3 mismatches; a check button to elect 1-base deletion in combination with radio buttons for selecting 0, 1, or 2 mismatches; and a check button to elect 1-base insertion in combination with radio buttons for selecting 0, 1, or 2 mismatches (640). In some embodiments, the number of mismatches, insertions, and/or deletions may be entered as individual numeric values, as a list of numeric values, or as a range of numeric values in a text box(es). For example, the input strings "0,1,2,3", "0,1–3", "0,1,2–3", or "0,1–2,3" would in some cases all be accepted inputs and would generate all possible alignments including 0, 1, 2, or 3 mismatches, insertions, or deletions.

The GUI can include options for the user to select pre-determined primer design options and/or to customize certain design parameters. In the exemplary GUI embodiment (600), the PCR primer design options region (650) includes a check box (652) or radio button that allows the user to select whether or not primer sequences should be included with the output. The GUI can include radio buttons or tabs (654) that allow the user to select a preferred primer design strategy, for example, default, Illumina 250, Illumina 250—paired. SMRT, or enzyme. Additionally, or alternatively, the GUI can include text boxes that allow the user to customize primer parameter settings including, for example, the minimum separation of uncleaved to cleaved (660), minimum cleavage product size difference (662), minimum amplicon length (664), maximum amplicon length (666), optimal amplicon length (668), etc. The user input for each text box is typically an integer, for example, between about 0 and 100,000 inclusive, preferably between about 0 and 10,000 inclusive, or between 0 and 1,000 inclusive. In the absence of user input or user editing, the text boxes can be populated with default setting before or after the user submits the query. The user can also elect not to include primer sequence as part of the output, which can reduce the runtime associated with the query.

The GUI also typically includes an interface for the user to initiate a search. The exemplary GUI embodiment (600) includes a submit button or tab (680) that when selected initiates a search according to the user entered or default criteria. The GUI can also include a reset button or tab (682) that when selected removes that user input and/or restores the default settings.

The GUI will in some embodiments have an example button that, when selected by the user populates all of the input fields with default values. The option selected by the example values may in some embodiments coincide with an example described in detail in a tutorial, manual, or help section. The GUI will in some embodiments contain all or only some of the elements described above. The GUI may contain any graphical user input element or combination thereof including one or more menu bars, text boxes, buttons, hyperlinks, drop-down lists, list boxes, combo boxes, check boxes, radio buttons, cycle buttons, data grids, or tabs.

FIGS. 26A-26G and Table 14 (below) illustrate an exemplary search string processed according to the disclosed methods and include examples showing the input, and portions of a web result and spreadsheet output for a search of the human genome using guide strand R-01.

Figure 26A:
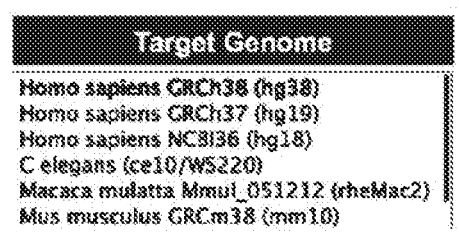
FIG. 26A is an exemplary COSMID user interface for selecting a searchable genome.
Figures 26B, 26C, 26D:
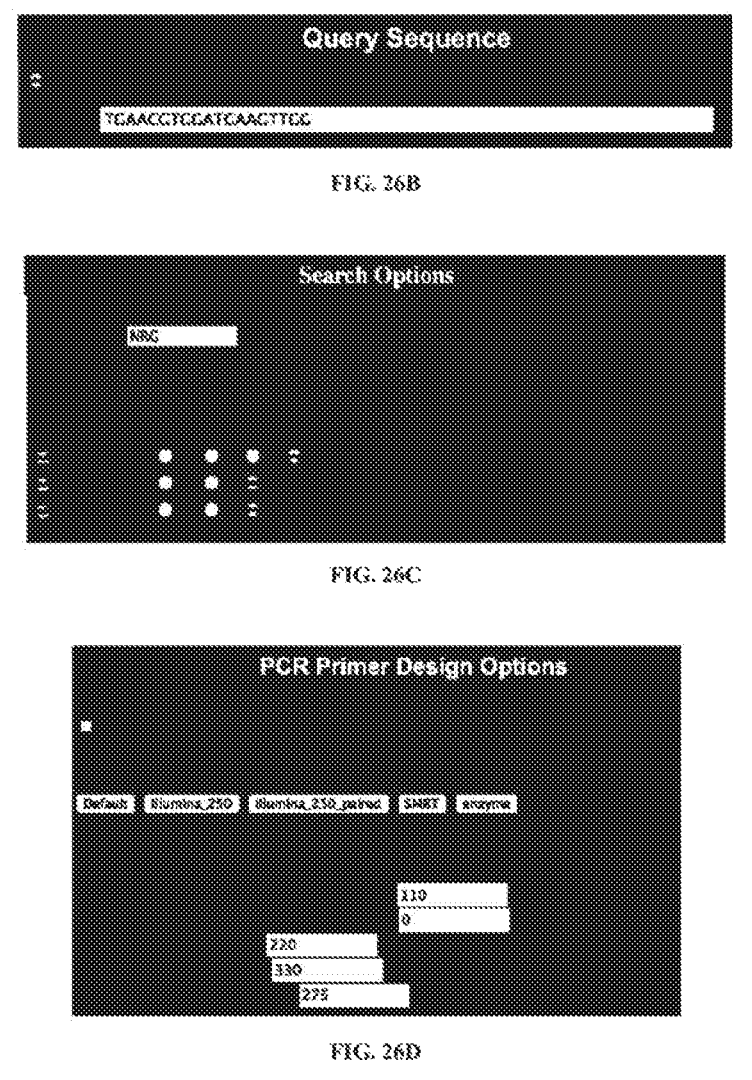

The genome of interest is chosen from the Target Genome list (FIG. 26A). The target sequence is entered into the Query Sequence box (FIG. 26B). The required protospacer adjacent motif (PAM) is entered into the 'Add suffix' Box of the Search Options section (FIG. 26C). The spacers (Ns) and required bases are included, such as NGG or NRG.

The boxes in the 'Allowed indels and mismatch' of the Search Options section are checked to indicate if genome sites to be searched include genomic sites that have No indels (with ≤3 mismatches but the same length), have 1-base Del (are 1-base shorter), or have 1-base Ins (are 1-base longer) (FIG. 26C).

The boxes in the PCR Primer Design Options section are chosen, which allow COSMID to design primers matching the specific application. Primer design parameters are set by pressing the button for 'Default', 'Illumina 250', 'Illumina 250 paired', 'SMRT' or 'enzyme' (when using other enzymes). Any of the parameters can be entered by hand to further customize.

IV. Experimental Methods

The methods provided herein will in some cases completely replace the need for experimentally screening nuclease target sites or nuclease activities, allowing for the design of CRISPR/Cas guide strands in a completely in-silico manner. In some cases the tools provided herein will serve as an essential first step in the design process by screening and selecting only the few potential guide strands that are predicted to have the desired cleavage-mediating activity at the on-target site, with limited off-site cleavage. In some cases, the tool will prevent the use of guide strands that have medium or high probability of cleaving an off-target site or cleaving multiple sites in the genome. This will allow for far less experimental time and resources being applied to preparing and testing guide strands that do not have the desired features.

In some cases the methods provided herein for predicting off-target sites are used without the need for experimental data. In some cases the methods provided herein for predicting off-target sites are parameterized to correlate with experimentally determined values. In some embodiments the methods provided herein for predicting off-target sites are used to screen candidate guide strands wherein a much smaller subset are subsequently tested experimentally.

The methods of predicting off-target sites can be used in combination with experimental methods for measuring both on-target and/or off-target cleavage activity. In some embodiments this includes using the results from one or more experiments to guide the search for guide strand with the desired activity at the target site and little or no activity on off-target sites. The experimental methods can include any method capable of measuring the cleavage activity or identifying off-target active sites of a guide stand in combination with a CRISPR/Cas nuclease.

Non-limiting exemplary experimental methods are described below. For example, mutation detection assays can be used to determine if off-target cleavage occur at putative off-target sites identified by according to the disclosed methods. Suitable assays, such as enzyme mismatch assays, are known in the art, see, for example. Guschin, et al., *Methods Mol. Biol.*, 649:247-56 (2010), which describes a procedure for quantifying mutations that result from DNA double-strand break repair via non-homologous end joining: and Huang, et al., *Electrophoresis*, 33(5):788-96 (2012), which describes a T7 endonuclease I-based assay. The assays are typically based on the ability of a nuclease to selectively cleave distorted duplex DNA formed via cross-annealing of mutated and wild-type sequence. Briefly, using primers, such as primers designed according to the methods described herein, PCR is used to amplification of the genomic loci of putative target sites after transfecting test cells with the elements of the CRISPR/Cas system (e.g., a plasmid expressing Cas9 and a test guide strand). Sanger sequencing can be used to observe mutations. Deep sequencing can also be used to detect and quantitate nuclease induced mutations in CRISPR/Cas-treated cell populations.

EXAMPLES

Example 1: CRISPR Guide Strands can Exhibit Off-Target Activity at Similar Levels as On-Target Activity, Even with Mismatches within First 12 Nucleotides Materials and Methods
CRISPR Design and Testing There were no CRISPR target sites in the human HBB gene sequence with their proximal 12 bases unique in the human genome (Cong, et al., *Science*, 339:819-823 (2013)); therefore, CRISPR/Cas9 guide strands targeting HBB were chosen by comparing the similar regions in the human hemoglobin δ (HBD) gene. Eight 20-base guide strands were designed to target sites near the sickle mutation in the HBB gene (FIG. 1A), each adjacent to a PAM sequence that contains the canonical trinucleotide NGG. Five guide strands were also designed to target two segments in the human CCR5 gene (FIG. 2A), and tested the corresponding CRISPR/Cas9 systems to determine their on-target cleavage and potential off-target activity at the human C—C chemokine receptor type 2 (CCR2) gene. Herein the name of the guide strand (such as R-03) is used to represent the CRISPR/Cas9 system with the specified guide strand.

CRISPR plasmids were generated by kinasing and annealing oligonucleotides containing a G followed by 19 additional bases of the guide strand plus sticky ends, ligating into the pX330 plasmid that contains a U6 promoter-driven chimeric +85-bp guide strand and a CHb promoter-driven Cas9 expression cassette, and expressed together from the 8.5-kb Cas9 gene expression plasmid, pX330 (provided by Dr. Feng Zhang, and also available through Addgene 42230) (Hsu, et al., *Nat. Biolechnol*, 31:827-832 (2013)). In a 24-well plate, 80,000 HEK-293T cells/well were seeded and cultured in Dulbecco's modified Eagle medium supplemented with 10% fetal bovine serum (FBS) and 2 mM fresh L-glutamine, 24 h prior to transfection. Cells were transfected with 100, 200, 400 or 800 ng of CRISPR plasmids (normalized to 800 ng with pUC18) using FuGENE HD (Promega). The genomic DNA was harvested after 3 days using QuickExtract (EpiCentre). Targeted cleavage was measured at the endogenous loci by the rate of mutations through mis-repair, detected using amplification of these sites using bar-coded or traditional primers (Table 1) and the T7EI assay. The fragments were separated on agarose gels and quantitated using ImageJ: the mutation frequencies were calculated and averaged. To better determine the mutation rate, amplification bands were cloned using the TOPO® TA kit [Invitrogen], Sanger sequenced and aligned to the genomic sequence to observe the individual mutations and determine the mutational spectra. Sanger sequencing was chosen to ensure the detection of large insertions and deletions, as well as effectively detect single base indels, both of which can be problematic with the next-generation sequencing methods.

TABLE 1

Sequence of primers used to amplify endogenous loci for the T7EI assay, sequencing and quantitative PCR

| Gene | SEQ ID NO: | Primer Sequence |
|---|---|---|
| CCR5-F | 3 | GCACAGGGTGGAACAAGATGG |
| CCR5-R | 4 | GACCACCCCAAAGGTGACCGT |
| CCR2-F | 5 | TTGAACAAGGACGCATTTCCCCAG |
| CCR2-R | 6 | CAAAGACCCACTCATTTGCAGCAG |
| HBB-F | 7 | CCAATAGGCAGAGAGAGTCAGTG |
| HBB-R | 8 | AGCCAGGGCTGGGCATAAAAG |
| HBD-F | 9 | GAGGTTGTCCAGGTGAGCCAGGCCATCAC |
| HBD-R | 10 | CTGCTGAAAGAGATGCGGTGGGGAGATATGTA |
| HBD-521F | 11 | AAGGCAGGGCAGAGTCGA |
| HBB-308R | 12 | CACATGCCCAGTTTCTATTGGT |
| HBB-mid99 | 13 | GCAAGGTGAACGTGGATGA |

Off-Target Analysis

Figures 6A, 6B:
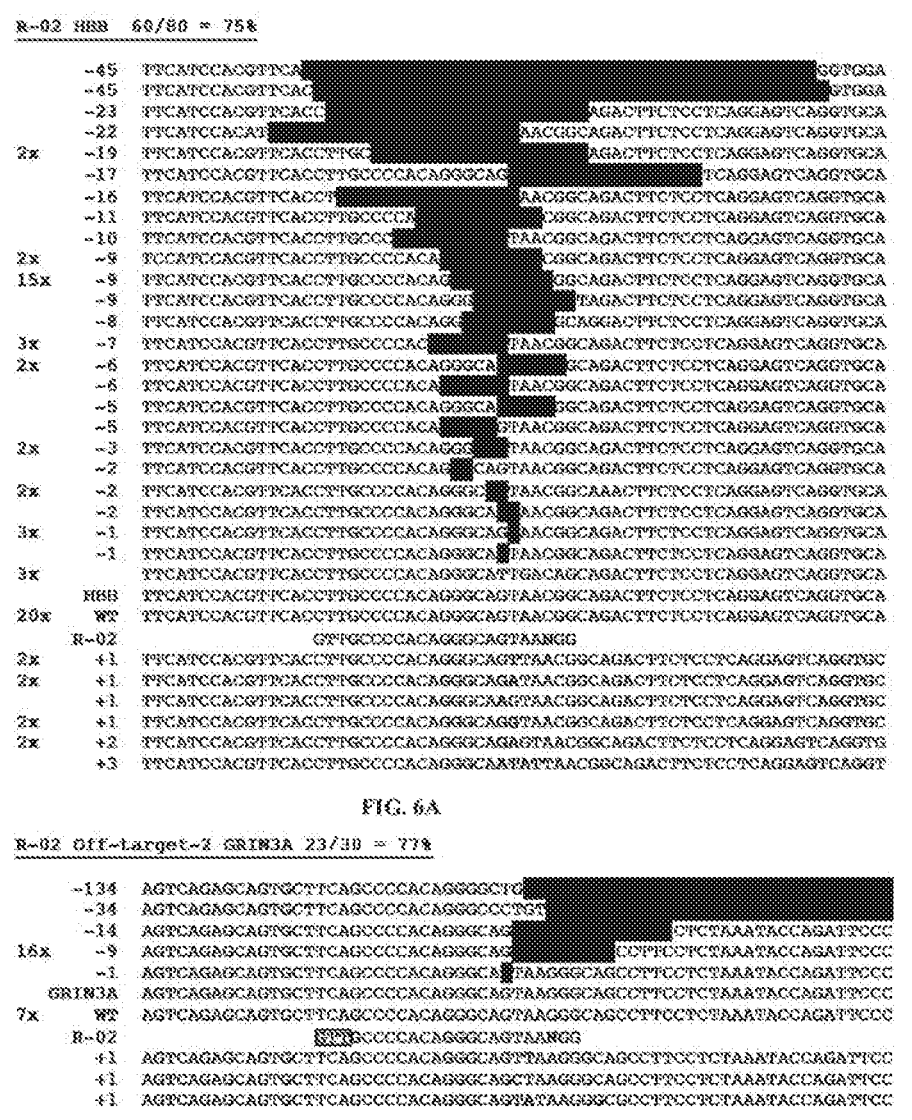

Off-target analysis was performed using a bioinformatics-based search tool to select potential off-target sites, which were evaluated using the T7EI mutation detection assay. Sanger sequencing was used to confirm the gene modification frequencies for the CRISPR/Cas9 systems, including guide strand R-02 at GRIN3A (see FIG. 6B) and compared to the on-target rate (FIG. 6A).

Results

The ability to precisely edit endogenous DNA sequences has greatly facilitated the creation of cell lines and animal models for biological and disease studies, and led to unprecedented opportunities in therapeutics. For example, engineered zinc finger nucleases (ZFNs) and transcription activator-like effector nucleases (TALENs) have generated hundreds of animal models for disease studies (Perez, et al., Nat. Biotechnol, 26:808-816 (2008); Geurts, et al., Science, 325:433 (2009), and nuclease-based treatment strategies are currently undergoing clinical trials. The discovery of a bacterial defense system that uses RNA-guided DNA cleaving enzymes and clustered, regularly interspaced, short palindromic repeats (CRISPR) (Bolotin, et al., Microbiology, 151:2551-2561 (2005): Horvath, Science, 327:167-170 (2010); Marraffini, et al., Nat. Rev. Genet., 11:181-190 (2010); Garneau, et al., Nature, 468:67-71 (2010); Hale, et al., Cell, 139:945-956 (2009)) may provide an exciting alternative to ZFNs and TALENs, as the CRISPR-associated (Cas) protein remains the same for different gene targets: only the short sequence of the guide RNA needs to be changed to redirect the site-specific cleavage (Cong, et al., Science, 339:819-823 (2013)).

Potential off-target cleavage by engineered nucleases poses concerns both for adverse events in therapeutic applications and confounding variables in biological studies. ZFNs (Pattanayak, et al., Nat. Methods, 8:765-770 (2011): Gabriel, et al., Nat. Biotechnol, 29:816-823 (2011)) have been shown to lack exquisite specificity and may cleave sequences in addition to their intended targets, which often induces unwanted mutations and/or toxicity (Comu, et al., Methods Mol. Biol., 649:237-245 (2010); Ramirez, et al., Nucleic Acids Res., 40:5560-5568 (2012)). Although reports indicate that TALENs have better specificity than ZFNs, off-target activities have been found for TALENs as well (Tesson, et al., Nat. Biotechnol, 29:695-696 (2011); Hockemeyer, et al., Nat. Biotechnol, 29:731-734 (2011); Mussolino, et al., Nucleic Acids Res., 39:9283-9293 (2011)). Previous in vitro studies indicate that CRISPR/Cas9 systems have a high potential for off-target activity, as they have more promiscuous binding abilities at positions distal from the protospacer-adjacent motif (PAM) region (Cong, et al., Science, 339:819-823 (2013); Gasiunas, et al., Natl Acad. Sci. USA, 109:E2579-E2586 (2012); Jinek, et al., Elife, 2:e00471 (2013); Jiang, et al., Nat. Biotechnol, 31:233-239 (2013)). Further, because the guide RNA strands typically target a DNA sequence of ~20 bp, relatively short compared with the ≥36 bp targeted by TALENs, many potential off-target sites may exist in large genomes, such as in mammals. Additionally, because non-Watson-Crick base pairing is known to occur (Jiang, et al., Nat. Biotechnol, 31:233-239 (2013)), it is possible that CRISPR/Cas9 systems have more off-target activities compared with corresponding ZFNs and TALENs.

To determine the off-target effects of CRISPR/Cas9 systems in the context of the human genome, a series of CRISPR/Cas9 systems were constructed with guide RNA strands targeting the human hemoglobin β (HBB) and C—C chemokine receptor type 5 (CCR5) genes, expressed them in human embryonic kidney 293T (HEK-293T) cells, and quantified their on- and off-target activities using the T7 endonuclease I (T7EI) mutation detection assay and Sanger sequencing. Special attention was placed on the effects of mismatches between the guide strands and the complementary target sequences. This allowed a direct evaluation of the impact of the location and number of mismatches within the 12 bases nearest the PAM region, as well as those in the PAM region (that usually match the canonical NGG motif, or NAG) (Table 2) on potential off-target activities (Cong, et al., Science, 339:819-823 (2013); Sapranauskas, et al., Nucleic Acids Res., 39:9275-9282 (2011)). The results show that the CRISPR/Cas9 systems targeting the human HBB and CCR5 genes had significant off-target cleavage activities, especially at the HBD and CCR2 genes, which have high sequence homology with HBB and CCR5, respectively.

TABLE 2

CRISPR on- and off-target cleavage rates (Table 2 discloses SEQ ID NOS 14-34, respectively, in order of appearance)

| Guide strand | Mis-matches(a) | Indel % by sequencing (%) | Indel % by T7E1 (%) | (b) 210987654321nGG | Region | Gene |
|---|---|---|---|---|---|---|
| R-01 | 0 | 67 | 54 | GTGAACGTGGATGAAGTTGGtGG | Exon | HBB |
|  | 1 | 30 | 27 | GTGAACGTGGATGcAGTTGGtGG | Exon | HBD |
| R-02 | 1 | 75 | 66 | cTTGCCCCACAGGGCAGTAAcGG | Exon | HBB |
|  | 3 | 77 | 33* | tcaGCCCCACAGGGCAGTAAcGG | Intergenic | GRIN3A |
| R-03 | 1 | 70 | 55 | cACGTTCACCTTGCCCCACAgGG | Exon | HBB |
|  | 2 | 62 | 58 | cACGTTCACtTTGCCCCACAgGG | Exon | HBD |
| R-04 | 1 | 47 | 53 | cCACGTTCACCTTGCCCCACaGG | Exon | HBB |
|  | 2 | 10 | 12 | cCACGTTCACtTTGCCCCACaGG | Exon | HBD |
| R-05 | 1 |  | 51 | aGTCTGCCGTTACTGCCCTGnGG | Exon | HBB |
| R-06 | 1 |  | 59 | cGTTACTGCCCTGTGGGGCAnGG | Exon | HBB |
| R-07 | 1 | 68 | 61 | aAGGTGAACGTGGATGAAGTtGG | Exon | HBB |
|  | 2 |  | 7 | aAGGTGAACGTGGATGcAGTtGG | Exon | HBD |
| R-08 | 1 | 38 | 36 | cCTGTGGGGCAAGGTGAACGtGG | Exon | HBB |
|  | 2 |  | 48 | cCTGTGGGGCAAaGTGAACGtGG | Exon | HBD |
| R-25 | 0 | 50 | 46 | GTGTTCATCTTTGGTTTTGTgGG | Exon | CCR5 |
|  | 0 | 32 | 20 | GTGTTCATCTTTGGTTTTGTgGG | Exon | CCR2 |
| R-26 | 0 | 76 | 74 | GCTGCCGCCCAGTGGGACTTtGG | Exon | CCR5 |

TABLE 2-continued

CRISPR on- and off-target cleavage rates (Table 2 discloses SEQ ID
NOS 14-34, respectively, in order of appearance)

| Guide strand | Mis-matches(a) | Indel % by sequencing (%) | Indel % by T7E1 (%) | (b) 210987654321nGG | Region | Gene |
|---|---|---|---|---|---|---|
| R-27 | 0 | 78 | 77 | GGCAGCATAGTGAGCCCAGAgGG | Exon | CCR5 |
| R-29 | 0 |  | 65 | GTGAGTAGAGCGGAGGCAGGnGG | Exon | CCR5 |
| R-30 | 0 |  | 21 | GTAGAGCGGAGGCAGGAGGCgGG | Exon | CCR5 |
|  | 2 |  | 5 | GTAGAGCGGAGGCAGGAGttgGG | Exon | CCR2 |

(a) Number of base differences between the guide strand and complementary sequence, including the 5' nucleotide.
(b) Base pair positions from the PAM are numbered above the loci. The differences between the guide strand and complementary sequences are indicated in lowercase underlined nucleotides. The first of the three nucleotides in the PAM sequence is also indicated in lowercase.
*T7EI was performed in duplicate for this off-target site, not triplicate as with all other cases.

Table 2 summarizes the on- and off-target cleavage rates in which, for each CRISPR/Cas9 system, the complementary sequence of the guide strand, the number of mismatches within the guide strand and the name and genetic region of the on- and off-target activities are provided. Specifically, in Table 2, the third and fourth columns list, respectively, the indel percentages determined by Sanger sequencing and T7EI.

Guide strands directed toward HBB resulted in high rates of on-target activity, with an average mutation frequency of 54% measured by the T7EI assay (FIG. 1B-1C). Because the T7EI assay may not cleave the PCR product completely and assumptions must be made about the indel diversity to calculate the mutation percentages (Guschin, et al., *Methods Mol. Biol.*, 649:247-256 (2010)), the mutation frequencies were verified using Sanger sequencing. It was determined that for some guide strands and loci, Sanger sequencing gave much higher mutation frequencies than the T7EI measurements. For example, Sanger sequencing of the HBB loci indicated that R-02 and R-03 resulted, respectively, in 60 of 80 (75%) and 31 of 44 (70%) sequences with insertions or deletions (indels) indicative of the error-prone nonhomologous end-joining (NHEJ) DNA repair pathway (FIG. 1A-C, FIG. 4A-C,). Similarly. HEK-293T cells transfected with CRISPR constructs containing guide strands targeting CCR5 resulted in high rates of on-target activity, with an average of 57% mutation frequency measured by the T7EI assay (FIG. 2A-C, FIG. 5A-C).

Some CRISPR/Cas9 systems with guide strands targeting HBB also cleaved HBD (some at high rates), even though there are mismatches between the guide strands and the complementary HBD sequences. For example, guide strands having just one-base mismatch with the complementary HBD sequences, located at positions 4 (R-07), 7 (R-01), 8 (R-08), 10 (R-04) and 11 (R-03) bases from the PAM sequence, resulted in off-target mutation rates ranging from 7 to 58%, roughly corresponding to the distance between the mismatch location and the PAM sequence, with R-04 as an exception (FIG. 1B). Note that two off-target sites at HBD had mutation rates even higher than the on-target rates at HBB, especially R-08, which induced a mutation rate of 48% at HBD, much higher than that at HBB (36%).

To allow RNA transcription by the U6 polymerase, the guide strand is typically preceded by a guanine (Cong, et al., *Science*, 339:819-823 (2013)). Results show that it is not necessary for the guanine base to match the target site for efficient cleavage, as seven guide strands without a guanine at this position induced mutations in HBB (R-02 to R-08) and four guide strands (R-03, R-04, R-07, R-08) induced mutations in HBD (FIG. 1B).

Figures 2A, 2B, 2C:
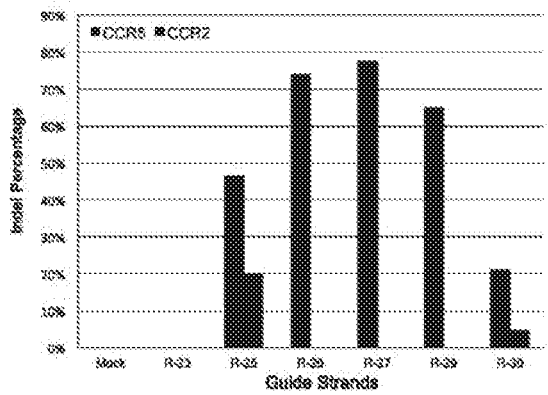
FIG. 2A is a sequence alignment of guide strands (SEQ ID NOS 688-690 and 693-694, respectively, in order of appearance) to their target sites in CCR5 (SEQ ID NOS 691 and 695, respectively, in order of appearance) (shown below the guide strands) and aligned to corresponding region in CCR2 (SEQ ID NOS 692 and 696, respectively, in order of appearance) (shown below CCR2). Forward direction guide strands (marked 'greater than') are shown adjacent to NGG, representing the PAM sequence. Guide strands complementary to the reverse strand (marked 'less than') are listed to the right of CCN. Asterisks between CCR5 and CCR2 indicate nucleotides that differentiate the two genes.
FIG. 2B is an illustration showing that cleavage can occur at off-target sites even with mismatch to the guide strands in both of the first two nts closest to the PAM (R-30). The first two guide strands in the list are in ranked order of the off-target mutation rates at CCR2. By sequence comparison, one can identify the differences between the guide strand sequence and complementary sequence in CCR2. The 12 bases closest to the PAM are boxed and numbered on top.
FIG. 2C is a bar graph showing the indel percentage in CCR5 (left-hand bar of each pair) and CCR2 (right-hand bar of each pair) for mock and guide strands R-01 through R-08 as determined by T7EI mutation detection assays.
Figure 3A:
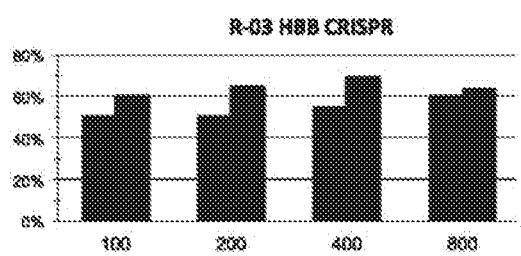
FIGS. 3A-3E are bar graphs illustrating how the transfection dosage variability effects on- and off-target mutation rates (%).
Figure 3B:
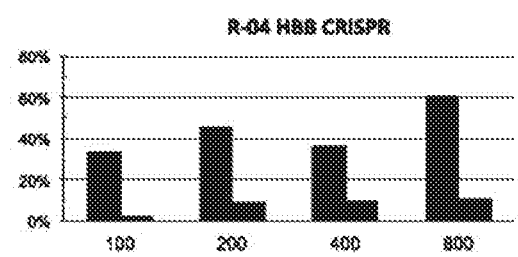
Figure 3C:
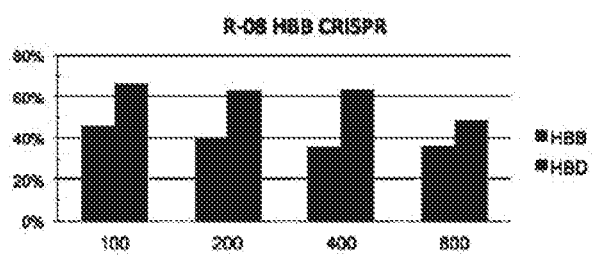
Figure 3D:
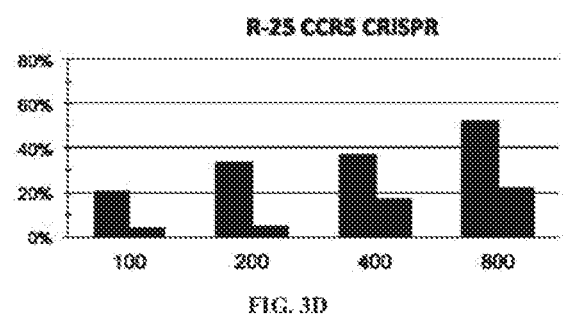
Figure 3E:
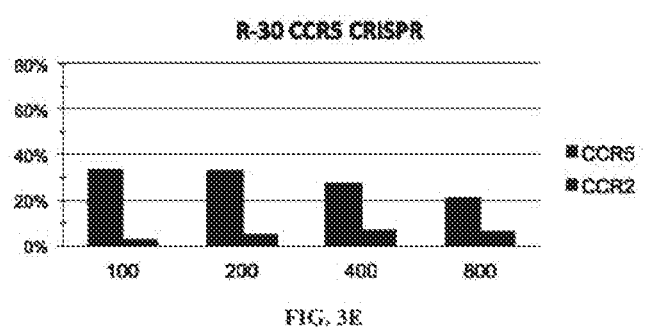

To a lesser extent, CCR5-targeting CRISPR/Cas9 systems also induced off-target cleavage on CCR2, with mutation rates of 5% and 20% (FIG. 2B-2C). Specifically, guide strand R-25 was designed with two identical genomic targets in CCR5 and CCR2 genes to identify the influence of factors beyond sequence homology, such as genomic context. The CRISPR/Cas9 system with R-25 showed a >2-fold difference in mutation rate at these two sites (46% versus 20% mutation rate, FIG. 2c). These results indicate that other features such as genomic context may play an important role in cleavage activity. Although guide strand R-30 had two mismatches with CCR2 at the two bases proximal to the PAM region, it induced mutations in CCR2 at a rate of 5% as measured by T7EI with 800 ng of plasmid in transfection (FIG. 2B). R-30 transfections with 1100 ng of plasmid induced mutations of 21% quantified by sequencing (FIG. 6C), but only 6% by T7EI (FIG. 3E); part of the difference is likely because of the incomplete cleavage of PCR products by T7EI.

A distinct feature of CRISPR off-target activity as related to mismatches in the guide strand is that mismatches in the PAM region can prevent off-target cleavage (Hsu, et al., *Nat. Biotechnol*, 31:827-832 (2013)). For example, R-06, which has a one-base mismatch in the PAM, did not induce detectable mutations at HBD, although it has a perfect match of the 14 bases proximal to the PAM (FIG. 1B-1C). Further, R-02 did not induce cleavage at HBD because of the one-base mismatch in the PAM and two mismatches at positions 2 and 4 from the PAM (FIG. 1B). Similarly, there was no off-site mutagenesis detected at CCR2 by the CCR5-targeting CRISPR/Cas9 systems with guide strands R-27 and R-29 that had NTG and NGT PAM substitutions, respectively. In particular, although R-29 had a perfect match with the 18-bp sequence proximal to the PAM, a one-base mismatch in the PAM region prevented cleavage of CCR2 (FIG. 2B-2C). Clearly, off-target cleavage could also be prevented without any mismatch in the PAM, by having multiple mismatches between the guide strand and the complementary target sequence proximal to the PAM, as demonstrated by R-05 (FIG. 1B) and R-26 (FIG. 2B).

To quantify the change in CRISPR/Cas9 cleavage activity with transfection conditions, CRISPR plasmids were transfected at doses from 100 to 800 ng, and corresponding on- and off-target activities measured by T7EI (FIG. 3A-3E).

With the dose decreases, R-04 and R-25 gave lower on- and off-target activities, whereas R-30 resulted in increased on-target activity and decreased off-target activity; the on- and off-target activities of R-03 and R-08 remained roughly the same. In general, transfection with the lowest dose (100 ng) increased the ratio of on-target to off-target activities for R-04, R-25 and R-30, although not for R-03 and R-08. These findings expand the results of a study where no appreciable changes in on- and off-target rates were found with two CRISPR guide strands at two doses (Fu, et al., *Nat. Biotechnol*, 31:822-826 (2013)).

Example 2: CRISPR-Targeted Loci Showed a Wide Variety of Insertions, Deletions and Point Mutations Materials and Methods Chromosomal Deletion Analysis To assay for gross chromosomal deletions, genomic DNA from cells transfected with R-03 was amplified using the HBD forward primer and the reverse primer downstream of the HBB site. Genomic DNA from cells transfected with R-25 or R-30 were similarly amplified using the CCR2 forward and the CCR5 reverse primers. Agarose gels were used to confirm that the polymerase chain reaction (PCR) product sizes were consistent with chromosomal deletions between these sites. The R-03, R-25 and R-30 PCR products were cloned and the individual colonies Sanger sequenced and aligned.

Quantitative PCR

Quantitative PCR determination of the percentage of HBD-HBB chromosomal deletions. HEK-293 cells were transfected in triplicate with CRISPR plasmids containing guide strands R-02 or R-03, or mock transfected cells. Genomic DNA was harvested using QuickExtract (EpiCentre), per manufacturer's protocol. Amplification reactions contained 1 ul of genomic DNA added to mastermix aliquots containing: 0.1 ul of each 10 uM primer, 3.8 ul of water and 5 ul of iTaq Universal SYBR Green 2× Supermix. The reactions were analysed on an Mx3005P qPCR System (Stratagene) using MxPro qPCR software. As the genomic DNA could not be normalized, the total amount of HBB and the amount of HBD to HBB deletions were measured to determine the percentage of chromosomal deletions. Total HBB was measured using primers HBB-308R and HBB-mid99 that generated a 99 bp product from unmodified HBB or from chromosomal DNA with HBD to HBB deletions, as the primers bind outside the cleavage site. The HBD-HBB chromosomal deletion was measured using primers HBB-308R and HBD-520F and generates a 225 bp product that spans the cleavage site. The HBB product was seen in mock transfections, as HBB was unmodified. Mock transfection DNA did not amplify using HBB-308R and HBD-520F, indicating a lack of these chromosomal deletions. The no-template controls for each primer set were negative.

Results

As revealed by Sanger sequencing, CRISPR-targeted loci showed a wide variety of insertions, deletions and point mutations. Because HBD is located ~7 kb upstream of HBB on chromosome 11, cleavage at both sites raises the possibility of chromosomal rearrangements, including a deletion of the intervening segment (Lee, et al., *Genome Res.*, 20:81-89 (2010); Gupta, et al., Genome Res., 23:1008-1017 (2013); Xiao, et al., *Nucleic Acids Res.*, 41:e141 (2013); Gratz, et al., *Genetics*, 194:1029-1035 (2013)). These gross chromosomal deletions are seen with guide strand R-03, which cleaves both HBB and HBD at high rates, even though it has a mismatch to HBD (FIGS. 4A and 4B). PCR amplification and sequence analysis revealed gross chromosomal deletions resulting from rejoining the DNA double-strand break ends induced by two cleavage events in (or near) the conserved region of the HBB and HBD (FIG. 4C). Each of these joined HBD-HBB clones amplified from cells transfected with R-03 had an indel consistent with NHEJ.

Figure 4D:
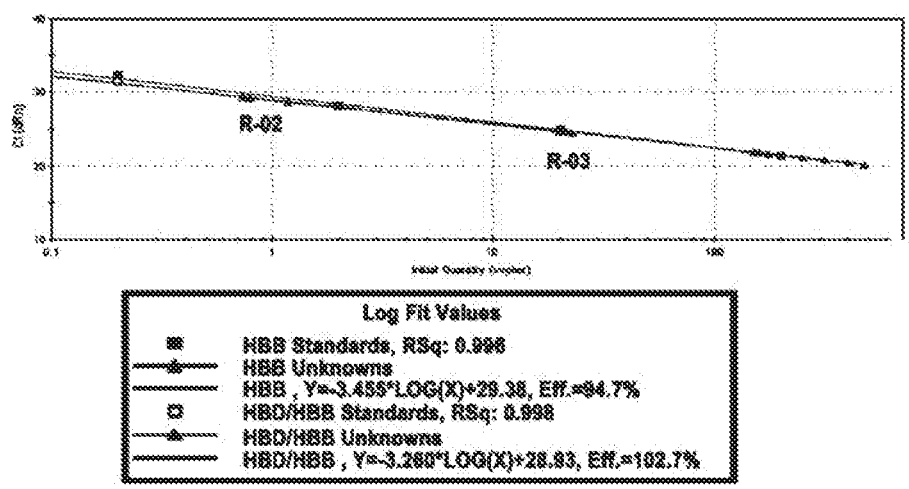
FIG. 4D is a line graph depicting the Quantitative PCR determination of the percentage of HBD-HBB chromosomal deletions at R-03, and the lower amount after transfection or R-02.

Quantitative PCR was used to estimate the number of HBB alleles containing the chromosomal deletion with HBD. Standard curves were made using serial dilutions of cloned HBD-HBB deletion fragment, so that the standard curves of both sets of primers could be compared (FIG. 4D). Quantities were very similar across this standard curve using either the HBB pair of primers or the HBD-HBB pair of primers, which allowed comparison of the total amount of HBB and the amount of HBD to HBB deletions. The groupings of three HBD/HBB samples for R-02 and R-03 are labelled (FIG. 4D). Genomic DNA from the cells transfected with guide strand R-03 contained HBD-HBB chromosomal deletions equal to 12.6% of the copies of total HBB (Table 3). This was compared to genomic DNA from the cells transfected with guide strand R-02, which had higher HBB cleavage, but low HBD cleavage. The R-02 treated genomic DNA contained HBD-HBB chromosomal deletions equal to 0.4% of the copies of total HBB.

TABLE 3

Results of quantitative PCR analysis

|  | Total HBB | HBD-HBB | HBD-HBB/ Total HBB | AVG | ST DEV |
|---|---|---|---|---|---|
| R-02a | 251.80 | 0.7 | 0.3% | | |
| R-02b | 318.20 | 1.2 | 0.4% | 0.4% | 0.001 |
| R-02c | 159.20 | 0.8 | 0.5% | | |
| R-03a | 176.20 | 21.1 | 11.9% | | |
| R-03b | 201.00 | 22.8 | 11.4% | 12.6% | 0.016 |
| R-03c | 151.20 | 21.8 | 14.4% | | |
| mock | 479.80 | 0.0 | 0.0% | | |
| mock | 404.90 | 0.0 | 0.0% | 0.0% | 0.000 |
| mock | 175.60 | 0.0 | 0.0% | | |

Similarly, CCR5 is located ~8 kb upstream of CCR2 on chromosome 3: thus, chromosomal rearrangements may occur with cleavages at both CCR5 and CCR2. These gross chromosomal deletions were detected with the R-25 CRISPR/Cas9 system, which cleaved both genes at high rates (FIGS. 5A and 5B). Here again, PCR amplification and sequence analysis revealed two cleavage events in (or near) a conserved region of the CCR5 and CCR2 genes, as indicated by indels consistent with NHEJ (FIG. 5C). Cells transfected with the R-30 CRISPR/Cas9 system also had chromosomal deletions between CCR5 and CCR2 (FIG. 5C).

Figures 6C, 7:
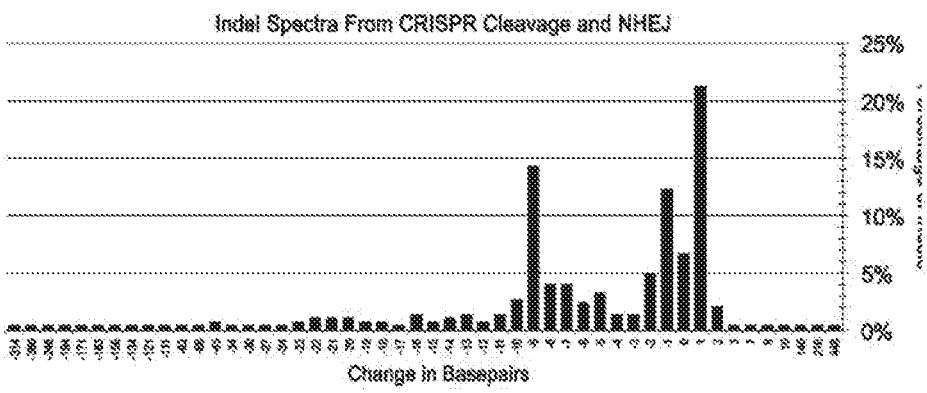

Sequencing the on- and off-target loci revealed a range of different indels as a result of CRISPR/Cas9-induced DNA cleavage and mis-repair. Cleavage followed by correct repair is more difficult to detect, as the sequence does not change. The changes include three large insertions (140, 216 and 448 bp), and a range of deletions. Some sequencing reads had mutations and indels and some with only mutations, but no change in length. Specifically, the results indicated that one-base insertions and deletions occurred frequently, usually several bases from the PAM sequence, consistent with the reported cleavage between the third and fourth bases from the PAM (Jinek, et al., *Science*, 337:816-821 (2012)). As shown in FIG. 7, the frequency of cleavage-induced gene modifications varied significantly with indels of different sizes, though 21% were one-base insertions and 12% one-base deletions. Interestingly, a common indel size was a 9-bp deletion that occurred in 14% of the clones, possibly due to micro-homologies in the sequence. Because the range of indels is influenced by sequence differences, microhomologies and/or palindromes in the area being cleaved (Yu, et al., *Nucleic Acid Res.*, 38:5706-5717 (2010)), and the results were primarily from a limited number of overlapping target sites, further sequence analysis is needed to ensure a more general distribution.

Although CRISPR/Cas9 systems can induce high rates of gene modification in mammalian cells, they do not have perfect specificity, similar to previous observations with ZFNs and TALENs. The results presented in Examples 1 and 2 demonstrate that CRISPR/Cas9 systems can have significant off-target activities even if 10 or 11 of the 12 bases proximal to the PAM sequence match. Therefore, it is likely that there are many more potential off-target sites in the human genome than previously thought (Cong, et al., *Science*, 339:819-823 (2013); Mali, et al., *Science*, 339:823-826 (2013)), if cleavage occurs when any permutation of 10 of the 12 bases in the guide strand matches a genomic sequence. The results indicate that mismatches in, or proximal to, the PAM sequence could block cleavage, as seen by others (Hsu, et al., *Nat. Biotechnol*, 31:827-832 (2013); Fu, et al., *Nat. Biotechnol*, 31:822-826 (2013); Mali, et al., *Science*, 339:823-826 (2013)). However, there are contrary examples, such as R-30 that cleaves CCR2 with mismatches in the two PAM-proximal bases (FIG. 2B, FIG. 6C).

The importance of the PAM sequence (Mojica, et al., *Microbiology*, 155:733-740 (2009)) was corroborated by the lack of cleavage at some complementary sequences similar to the guide strand, but with PAM sequences differing from NGG (FIGS. 1B and 2B). An example is guide strand R-06 that cleaved HBB at 59%, but had no detectable cleavage at HBD, presumably due to the NGA in the PAM sequence. Similarly, R-29 cleaves CCR5 at 65% efficiency. R-29 failed to cleave at CCR2 possibly due to the less tolerated, adjacent NGT PAM sequence, although the R-29 guide strand matches the 18 bases closest to the PAM sequence at CCR2.

Although Cas9 is thought to generate blunt ends (Gasiunas, et al., *Natl Acad. Sci. USA*, 109:E2579-E2586 (2012); Jinek, et al., *Science*, 337:816-821 (2012)), the results presented in Examples 1 and 2 indicate that CRISPR-directed on- and off-target cleavage can induce a wide range of indels, with a large number of one-base insertions and a few large deletions. The high rate of off-target cleavage may result in large indels, causing a significant potential of mutagenesis and chromosomal rearrangements. For example, if two or more cleavage sites are on the same chromosome, it may lead to gross chromosomal deletions, as seen with R-03 (FIG. 4C), and R-25 (FIG. 5C). These chromosomal deletions and the high levels of on- and off-target cleavage indicate that there might be other chromosomal rearrangements, translocations and inversions. Although the ability of engineered CRISPR/Cas9 systems to target multiple sites/genes with different guide strands is an exciting feature (Cong, et al., *Science*, 339:819-823 (2013); Mali, et al., *Science*, 339:823-826 (2013); Wang, et al., *Cell*, 153:910-918 (2013)), each system may lead to off-target cleavage. The effect of having multiple guide strands on off-target cleavage and its effect on rates of chromosomal rearrangement have yet to be thoroughly studied (Wang, et al., *Cell*, 153:910-918 (2013)). A CRISPR/Cas9 system may cause chromosomal rearrangements with one guide strand inducing cleavage at two defined locations, or with a pair of guide strands inducing deletion between the target sites (Xiao, et al., *Nucleic Acids Res.*, 41:e141 (2013)): in both cases the off-target effects of each guide strand must be assayed. Therefore, multiplexed gene editing using CRISPR/Cas9-based approaches might have limitations unless optimal design of the guide strands can be performed to reduce or even eliminate the potential for gross chromosomal rearrangements.

As demonstrated in this work and elsewhere (Hsu, et al., *Nat. Biotechnol*, 31:827-832 (2013); Fu, et al., *Nat. Biotechnol*, 31:822-826 (2013)), CRISPR/Cas9 systems may have high rates of off-target cleavage: therefore, care must be taken when choosing and evaluating target sites. Even with diligent choice of target sites, in most genome editing applications, quantifying the off-target activities is necessary to identify unintended cleavage and mutagenesis. Transfection conditions, including plasmid dosage, may be optimized to decrease off-target cleavage, although the effects may vary with guide strands (FIGS. 3A-3E). The variety of on- and off-target cleavage rates induced by CRISPR/Cas9 systems raises hope that better selection of target sites, possibly through rational design and/or screening in cells, can result in gene editing with improved specificity. Advanced genome searches may be needed in choosing optimal target sites by minimizing the number of potential off-target sites corresponding to different mismatches. More extensive off-target analysis of the CRISPR/Cas9 systems, with a combination of bioinformatics and experimental approaches, may reveal patterns and design guidelines that better predict the target sites that can be effectively cleaved with high specificity.

Example 3: sgRNA Variants Containing Single-Base DNA Bulges Induce Cas9 Cleavage Materials and Methods CRISPR/Cas9 Plasmid Assembly DNA oligonucleotides containing a G followed by a 19-nt guide sequence (Table 3) were kinased, annealed to create sticky ends and ligated into the pX330 plasmid that contains the +85 chimeric RNA under the U6 promoter and a Cas9 expression cassette under the CBh promoter (available at Addgene) (Hsu, et al., *Nat Biotechnol*, 31 (2013)).

TABLE 4

Protospacer target sites for the sgRNAs used in Examples 3-8 (Table 4 discloses SEQ ID NOS 35-61, respectively, in order of appearance)

| Gene | Storage Index | Protospacer Target (5' to 3') | PAM |
| --- | --- | --- | --- |
| HBB | R-01 | GTGAACGTGGATGAAGTTGG | TGG |
| HBB | R-03 | GACGTTCACCTTGCCCCACA | GGG |
| HBB | R-04 | GCACGTTCACCTTGCCCCAC | AGG |
| HBB | R-05 | GGTCTGCCGTTACTGCCCTG | TGG |
| HBB | R-06 | GGTTACTGCCCTGTGGGGCA | AGG |
| HBB | R-07 | GAGGTGAACGTGGATGAAGT | TGG |
| HBB | R-08 | GCTGTGGGGCAAGGTGAACG | TGG |
| EGFP | R-19 | GGTGGTGCAGATGAACTTCA | GGG |
| EGFP | R-20 | GACCAGGATGGGCACCACCC | CGG |

TABLE 4-continued

Protospacer target sites for the sgRNAs used in Examples 3-8 (Table 4 discloses SEQ ID NOS 35-61, respectively, in order of appearance)

| Gene | Storage Index | Protospacer Target (5' to 3') | PAM |
|---|---|---|---|
| CCR5 | R-25 | GTGTTCATCTTTGGTTTTGT | GGG |
| CCR5 | R-26 | GCTGCCGCCCAGTGGGACTT | TGG |
| CCR5 | R-27 | GGCAGCATAGTGAGCCCAGA | AGG |
| CCR5 | R-29 | GTGAGTAGAGCGGAGGCAGG | AGG |
| CCR5 | R-30 | GTAGAGCGGAGGCAGGAGGC | GGG |
| ERCC5 | R-31 | GCCAAGCACTTAAAGGAGTC | CGG |
| ERCC5 | R-33 | GCAAGCACTTAAAGGAGTCC | GGG |
| ERCC5 | R-35 | GTGAGTTCCCATGGCGATCC | CGG |
| ERCC5 | R-36 | GCTATTGAAGAAACAGACTT | TGG |
| ERCC5 | R-38 | GATTTTCTATTGAGTTCCCA | TGG |
| ERCC5 | R-39 | GGAAACAAAGTGAGAAGATG | AGG |
| ERCC5 | R-40 | GCCTATTTTTGTGTTTGATG | GGG |
| TARDBP | R-41 | GCAGAGCAGTTGGGGTATGA | TGG |
| TARDBP | R-42 | GGCAGCACTACAGAGCAGTT | GGG |
| TARDBP | R-43 | GCAGCACTACAGAGCAGTTG | GGG |
| TARDBP | R-44 | GCCTGACTGGTTCTGCTGGC | TGG |
| HPRT1 | R-52 | GTTTGTGTCATTAGTGAAA | TGG |
| HPRT1 | R-53 | GCAACTTGAACTCTCATCTT | AGG |

Variants of sgRNAs were constructed and tested with one or more nucleotides inserted or deleted Table 5.

TABLE 5 sgRNA variants (Table 5 discloses SEQ ID NOS 62-227, respectively, in order of appearance)

| Index | Guide sequence | % indel | s.e.m |
|---|---|---|---|
| R-01 -1 nt | | | |
| R-01 variant -19 | G-AACGUGGAUGAAGUUGG | 40.1 | 5.4 |
| R-01 variant -18 | GU-AACGUGGAUGAAGUUGG | 24.3 | 5.5 |
| R-01 variant -17/16 | GUGA-CGUGGAUGAAGUUGG | nd | |
| R-01 variant -15 | GUGAA-GUGGAUGAAGUUGG | nd | |
| R-01 variant -14 | GUGAAC-UGGAUGAAGUUGG | nd | |
| R-01 variant -13 | GUGAACG-GGAUGAAGUUGG | nd | |
| R-01 variant -12/11 | GUGAACGUG-AUGAAGUUGG | nd | |
| R-01 variant -10 | GUGAACGUGG-UGAAGUUGG | nd | |
| R-01 variant -9 | GUGAACGUGGA-GAAGUUGG | nd | |
| R-01 variant -8 | GUGAACGUGGAU-AAGUUGG | nd | |
| R-01 variant -7/6 | GUGAACGUGGAUG-AGUUGG | 14.3 | 1.5 |
| R-01 variant -5 | GUGAACGUGGAUGAA-UUGG | nd | |
| R-01 variant -4/3 | GUGAACGUGGAUGAAG-UGG | nd | |
| R-01 variant -2/1 | GUGAACGUGGAUGAAGUU-G | 31.9 | 3.7 |
| R-01 5' truncation | | | |
| R-01 d1 (variant 19) | GGAACGUGGAUGAAGUUGG | 40.1 | 5.4 |
| R-01 d2 | GAACGUGGAUGAAGUUGG | 39.3 | 17.3 |
| R-01 d3 | GACGUGGAUGAAGUUGG | nd | |
| R-01 d4 | GCGUGGAUGAAGUUGG | nd | |
| R-01 d5 | GGUGGAUGAAGUUGG | nd | |
| R-01 d6 | GUGGAUGAAGUUGG | nd | |
| R-30 -1 nt | | | |
| R-30 variant -19 | G-ACAGCGGAGGCAGGAGGC | 44.0 | 45 |
| R-30 variant -18 | GU-GAGCGGAGGCAGGAGGC | 43.8 | 1.3 |
| R-30 variant -17 | GUA-AGCGGAGGCAGGAGGC | 5.7 | 2.2 |
| R-30 variant -16 | GUAG-GCGGAGGCAGGAGGC | 4.8 | 0.5 |
| R-30 variant -15 | GUAGA-CGGAGGCAGGAGGC | nd | |
| R-30 variant -14 | GUAGAG-GGAGGCAGGAGGC | nd | |
| R-30 variant -13/12 | GUAGAGCG-AGGCAGGAGGC | nd | |
| R-30 variant -11 | GUAGAGCGG-GGCAGGAGGC | 53.4 | 3.0 |
| R-30 variant -10/9 | GUAGAGCGGA-GCAGGAGGC | 26.4 | 3.9 |
| R-30 variant -8 | GUAGAGCGGAGG-AGGAGGC | 40.8 | 3.3 |
| R-30 variant -7 | GUAGAGCGGAGGC-GGAGGC | 22.1 | 11.2 |
| R-30 variant -6/5 | GUAGAGCGGAGGCA-GAGGC | nd | |

TABLE 5-continued sgRNA variants (Table 5 discloses SEQ ID NOS 62-227, respectively, in order of appearance)

| Index | Guide sequence | % indel | s.e.m |
|---|---|---|---|
| R-30 variant -4 | GUAGAGCGGAGGCAGG-GGC | nd | |
| R-30 variant -3/2 | GUAGAGCGGAGGCAGGA-GC | 54.5 | 4.7 |
| R-30 variant -1 | GUAGAGCGGAGGCAGGAGG- | 32.1 | 10.7 |
| R-08 -1 nt | | | |
| R-08 variant -19 | G-UGUGGGGCAAGGUGAACG | 13.0 | 0.3 |
| R-08 variant -18 | GC-UGGGGCAAGGUGAACG | 23.5 | 1.4 |
| R-08 variant -17 | GCU-UGGGGCAAGGUGAACG | 30.8 | 3.5 |
| R-08 variant -16 | GCUG-GGGCAAGGUGAACG | nd | |
| R-08 variant -15/14/13/12 | GCUGU-GGGCAAGGUGAACG | 0.3 | 0.3 |
| R-08 variant -11 | GCUGUGGGG-AAGGUGAACG | nd | |
| R-08 variant -10/9 | GCUGUGGGCA-GGUGAACG | nd | |
| R-08 variant -8/7 | GCUGUGGGCAA-GUGAACG | 1.1 | 0.9 |
| R-08 variant -6 | GCUGUGGGCAAGG-GAACG | nd | |
| R-08 variant -5 | GCUGUGGGCAAGGU-AACG | nd | |
| R-08 variant -4/3 | GCUGUGGGCAAGGUG-ACG | nd | |
| R-08 variant -2 | GCUGUGGGCAAGGUGAA-G | 2.2 | 0.5 |
| R-08 variant -1 | GCUGUGGGCAAGGUGAAC- | 1.5 | 0.5 |
| R-25 -1 nt | | | |
| R-25 variant -19 | G-GUUCAUCUUUGGUUUUGU | nd | |
| R-25 variant -18 | GU-UUCAUCUUUGGUUUUGU | nd | |
| R-25 variant -17/16 | GUG-UCAUCUUUGGUUUUGU | nd | |
| R-25 variant -15 | GUGUU-AUCUUUGGUUUUGU | nd | |
| R-25 variant -14 | GUGUUC-UCUUUGGUUUUGU | nd | |
| R-25 variant -13 | GUGUUCA-CUUUGGUUUUGU | nd | |
| R-25 variant -12 | GUGUUCAU-UUUGGUUUUGU | nd | |
| R-25 variant -11/10/9 | GUGUUCAUC-UUGGUUUUGU | nd | |
| R-25 variant -8/7 | GUGUUCAUCUUU-GUUUUGU | nd | |
| R-25 variant -6/5/4/3 | GUGUUCAUCUUUGG-UUUGU | nd | |
| R-25 variant -2 | GUGUUCAUCUUUGGUUUU-U | nd | |
| R-25 variant -1 | GUGUUCAUCUUUGGUUUUG- | nd | |
| R-01 +1 nt | | | |
| R-01 variant U +20/19 | GUUGAACGUGGAUGAAGUUGG | 28.2 | 21.4 |
| R-01 variant G +19/18 | GUGGAACGUGGAUGAAGUUGG | 30.9 | 4.1 |
| R-01 variant U +18 | GUGUAACGUGGAUGAAGUUGG | nd | |
| R-01 variant U +17 | GUGAUACGUGGAUGAAGUUGG | nd | |
| R-01 variant U +16 | GUGAAUCGUGGAUGAAGUUGG | 39.9 | 4.1 |
| R-01 variant A +18/17/16 | GUGAAACGUGGAUGAAGUUGG | nd | |
| R-01 variant C +16/15 | GUGAACCGUGGAUGAAGUUGG | 44.7 | 6.7 |
| R-01 variant U +15 | GUGAACUGUGGAUGAAGUUGG | 53.5 | 1.5 |
| R-01 variant A +15 | GUGAACAGUGGAUGAAGUUGG | 37.5 | 4.9 |
| R-01 variant G +15/14 | GUGAACGGUGGAUGAAGUUGG | 17.1 | 11.2 |
| R-01 variant C +14 | GUGAACGCUGGAUGAAGUUGG | nd | |
| R-01 variant A +14 | GUGAACGAUGGAUGAAGUUGG | nd | |
| R-01 variant U +14/13 | GUGAACGUUGGAUGAAGUUGG | 39.7 | 3.0 |
| R-01 variant A +13 | GUGAACGUAGGAUGAAGUUGG | nd | |
| R-01 variant C +13 | GUGAACGUCGGAUGAAGUUGG | 9.0 | 0.2 |
| R-01 variant G +13/12/11 | GUGAACGUGGGAUGAAGUUGG | 41.3 | 0.7 |
| R-01 variant C +12 | GUGAACGUGCGAUGAAGUUGG | 56.5 | 3.8 |
| R-01 variant C +11 | GUGAACGUGGCAUGAAGUUGG | nd | |
| R-01 variant A +11/10 | GUGAACGUGGAAUGAAGUUGG | nd | |
| R-01 variant U +10/9 | GUGAACGUGGAUUGAAGUUGG | nd | |
| R-01 variant G +9/8 | GUGAACGUGGAUGGAAGUUGG | nd | |
| R-01 variant A +8/7/6 | GUGAACGUGGAUGAAAGUUGG | nd | |
| R-01 variant G +6/5 | GUGAACGUGGAUGAAGGUUGG | nd | |
| R-01 variant U +5/4/3 | GUGAACGUGGAUGAAGUUUGG | nd | |
| R-01 variant G +3/2/1 | GUGAACGUGGAUGAAGUUGGG | nd | |
| R-30 +1 nt | | | |
| R-30 variant U +20/19 | GUUAGAGCGGAGGCAGGAGGC | 37.5 | 2.3 |
| R-30 variant A +19/18 | GUAAGAGCGGAGGCAGGAGGC | 15.5 | 6.9 |
| R-30 variant G +18/17 | GUAGGAGCGGAGGCAGGAGGC | 16.4 | 1.1 |
| R-30 variant C +17 | GUAGCAGCGGAGGCAGGAGGC | 2.9 | 1.4 |
| R-30 variant U +17 | GUAGUAGCGGAGGCAGGAGGC | nd | |
| R-30 variant A +17/16 | GUAGAAGCGGAGGCAGGAGGC | 23.8 | 3.2 |
| R-30 variant U +16 | GUAGAUGCGGAGGCAGGAGGC | 44.2 | 6.9 |
| R-30 variant C +16 | GUAGACGCGGAGGCAGGAGGC | 24.5 | 5.1 |
| R-30 variant G +16/15 | GUAGAGGCGGAGGCAGGAGGC | 23.4 | 0.5 |
| R-30 variant A +15 | GUAGAGACGGAGGCAGGAGGC | 35.8 | 3.3 |

TABLE 5-continued sgRNA variants (Table 5 discloses SEQ ID NOS 62-227, respectively, in order of appearance)

| Index | Guide sequence | % indel | s.e.m |
|---|---|---|---|
| R-30 variant U +15 | GUAGAGUCGGAGGCAGGAGGC | 37.8 | 14.7 |
| R-30 variant C +15/14 | GUAGAGCCGGAGGCAGGAGGC | 23.8 | 7.4 |
| R-30 variant A +14 | GUAGAGCAGGAGGCAGGAGGC | nd | |
| R-30 variant U +14 | GUAGAGCUGGAGGCAGGAGGC | nd | |
| R-30 variant G +14/13/12 | GUAGAGCGGGAGGCAGGAGGC | 17.8 | 1.1 |
| R-30 variant U +13 | GUAGAGCGUGAGGCAGGAGGC | 27.2 | 8.5 |
| R-30 variant U +12 | GUAGAGCGGUAGGCAGGAGGC | 45.4 | 1.6 |
| R-30 variant A +12/11 | GUAGAGCGGAAGGCAGGAGGC | 9.4 | 2.9 |
| R-30 variant G +11/10/9 | GUAGAGCGGAGGGCAGGAGGC | 3.4 | 0.6 |
| R-30 variant C +9/8 | GUAGAGCGGAGGCCAGGAGGC | 10.6 | 0.6 |
| R-30 variant U +8 | GUAGAGCGGAGGCUAGGAGGC | 11.7 | 5.7 |
| R-30 variant G +8 | GUAGAGCGGAGGCGAGGAGGC | 13.9 | 7.6 |
| R-30 variant A +8/7 | GUAGAGCGGAGGCAAGGAGGC | 7.4 | 2.1 |
| R-30 variant G +7/6/5 | GUAGAGCGGAGGCAGGGAGGC | 1.7 | 0.5 |
| R-30 variant A +5/4 | GUAGAGCGGAGGCAGGAAGGC | nd | |
| R-30 variant G +4/3/2 | GUAGAGCGGAGGCAGGAGGGC | nd | |
| R-30 variant C +2/1 | GUAGAGCGGAGGCAGGAGGCC | nd | |
| R-08 +1 nt | | | |
| R-08 variant U +20 | GUCUGUGGGGCAAGGUGAACG | 17.0 | 0.7 |
| R-08 variant U +19/18 | GCUUGUGGGGCAAGGUGAACG | 13.4 | 2.3 |
| R-08 variant C +18 | GCUCGUGGGGCAAGGUGAACG | 27.4 | 0.5 |
| R-08 variant U +17/16 | GCUGUUGGGGCAAGGUGAACG | 15.5 | 2.7 |
| R-08 variant C +16 | GCUGUCGGGGCAAGGUGAACG | 3.2 | 0.2 |
| R-08 variant U +15 | GCUGUGUGGGCAAGGUGAACG | 26.3 | 0.3 |
| R-08 variant U +14 | GCUGUGGUGGCAAGGUGAACG | nd | |
| R-08 variant U +13 | GCUGUGGGUGCAAGGUGAACG | 11.0 | 1.4 |
| R-08 variant U +12 | GCUGUGGGGUCAAGGUGAACG | 25.2 | 0.8 |
| R-08 variant U +11 | GCUGUGGGGCUAAGGUGAACG | 16.5 | 2.6 |
| R-08 variant U +10 | GCUGUGGGGCAUAGGUGAACG | nd | |
| R-08 variant U +9 | GCUGUGGGGCAAUGGUGAACG | nd | |
| R-08 variant U +8 | GCUGUGGGGCAAGUGUGAACG | nd | |
| R-08 variant U +7/6 | GCUGUGGGGCAAGGUUGAACG | nd | |
| R-08 variant C +6 | GCUGUGGGGCAAGGUCGAACG | nd | |
| R-08 variant U +5 | GCUGUGGGGCAAGGUGUAACG | nd | |
| R-08 variant U +4 | GCUGUGGGGCAAGGUGAUACG | nd | |
| R-08 variant U +3 | GCUGUGGGGCAAGGUGAAUCG | nd | |
| R-08 variant U +2 | GCUGUGGGGCAAGGUGAACUG | nd | |
| R-25 +1 nt | | | |
| R-25 variant U +20/19 | GUUGUUCAUCUUUGGUUUUGU | nd | |
| R-25 variant C +19 | GUCGUUCAUCUUUGGUUUUGU | nd | |
| R-25 variant U +18/17/16 | GUGUUUCAUCUUUGGUUUUGU | nd | |
| R-25 variant C +17 | GUGUCUCAUCUUUGGUUUUGU | nd | |
| R-25 variant C +16/15 | GUGUUCCAUCUUUGGUUUUGU | nd | |
| R-25 variant U +15 | GUGUUCUAUCUUUGGUUUUGU | nd | |
| R-25 variant U +14/13 | GUGUUCAUUCUUUGGUUUUGU | nd | |
| R-25 variant C +13/12 | GUGUUCAUCCUUUGGUUUUGU | nd | |
| R-25 variant U +12/11/10/9 | GUGUUCAUCUUUUGGUUUUGU | nd | |
| R-25 variant C +11 | GUGUUCAUCUCUUGGUUUUGU | nd | |
| R-25 variant C +10 | GUGUUCAUCUUCUGGUUUUGU | nd | |
| R-25 variant C +9 | GUGUUCAUCUUUCGGUUUUGU | nd | |
| R-25 variant U +8 | GUGUUCAUCUUUGUGUUUUGU | nd | |
| R-25 variant U +7/6/5/4/3 | GUGUUCAUCUUUGGUUUUUGU | nd | |
| R-25 variant C +6 | GUGUUCAUCUUUGGUCUUUGU | nd | |
| R-25 variant C +5 | GUGUUCAUCUUUGGUUCUUGU | nd | |
| R-25 variant C +4 | GUGUUCAUCUUUGGUUUCUGU | nd | |
| R-25 variant C +3 | GUGUUCAUCUUUGGUUUUCGU | nd | |
| R-25 variant U +2/1 | GUGUUCAUCUUUGGUUUUGUU | nd | |
| R-01 And R-30 +2 nt to +5 nt or -2 nt | | | |
| R-01 variant +15 +16 | GUGAACuuGUGGAUGAAGUUGG | 1.7 | 0.1 |
| R-01 variant +12 +13 | GUGAACGUGuuGAUGAAGUUGG | 41.2 | 5.1 |
| R-30 variant +15 +16 | GUAGAGuuCGGAGGCAGGAGGC | 31.7 | 6.5 |
| R-30 variant +12 +13 | GUAGAGCGGuuAGGCAGGAGGC | 26.5 | 6.7 |
| R-01 variant -6 -7 | GUGAACGUGGAUG--GUUGG | nd | |
| R-01 variant -1 -2 | GUGAACGUGGAUGAAGUU-- | nd | |
| R-30 variant -9 -10 | GUAGAGCGGA--CAGGAGGC | nd | |
| R-30 variant -7 -8 | GUAGAGCGGAGG--GGAGGC | nd | |
| R-01 variant +15 +16 +17 | GUGAACuuuGUGGAUGAAGUUGG | nd | |
| R-01 variant +12 +13 +14 | GUGAACGUGuuuGAUGAAGUUGG | 34.5 | 0.8 |

TABLE 5-continued sgRNA variants (Table 5 discloses SEQ ID NOS 62-227, respectively, in order of appearance)

| Index | Guide sequence | % indel | s.e.m |
|---|---|---|---|
| R-30 variant +15 +16 +17 | GUAGAGuuuCGGAGGCAGGAGGC | 5.6 | 1.2 |
| R-30 variant +12 +13 +14 | GUAGAGCGGuuuAGGCAGGAGGC | 37.9 | 7.4 |
| R-01 variant +12 +13 +14 +15 | GUGAACGUGuuuuGAUGAAGUUGG | nd | |
| R-30 variant +15 +16 +17 +18 | GUAGAGuuuuCGGAGGCAGGAGGC | nd | |
| R-30 variant +12 +13 +14 +15 | GUAGAGCGGuuuuAGGCAGGAGGC | 8.9 | 2.4 |
| R-01 variant +12 +13 +14 +15 +16 | GUGAACUGuuuuuGAUGAAGUUGG | nd | |

Index names correspond to the index in FIGS. 6A-6H and FIGS. 2A-5C.
Dashes indicate deleted nucleotides.
"nd" means activity was not detected in the T7EI assay.

The annealed oligonucleotides have 4-bp overhangs that are compatible with the ends of BbsI-digested pX330 plasmid. Constructed plasmids were sequenced to confirm the guide strand region using the primer CRISPR_seq 5'-CGATACAAGGCTGTTAGAGAGATAATTGG-3' (SEQ ID NO; 228).

T7 Endonuclease I (T7EI) Mutation Detection Assay for Measuring Endogenous Gene Modification Rates The cleavage activity of RNA-guided Cas9 at endogenous loci was quantified based on the mutation rates resulting from the imperfect repair of double-stranded breaks by NHEJ. In a 24-well plate, 60 000 HEK293T cells per well were seeded and cultured in Dulbecco's Modified Eagle Medium (DMEM) media supplemented with 10% Fetal Bovine Serum (FBS) and 2 mM fresh L-glutamine, 24 h prior to transfection. Cells were transfected with 750 ng (sgRNA variants) or 1000 ng of CRISPR plasmids using 3.4 µl FuGene HD (Promega), following manufacturer's instructions. Each sgRNA plasmid was transfected as biological duplicates in two separate transfections. All subsequent steps, including the T7EI assay were performed independently for the duplicates. A HEK293T-derived cell line containing stably integrated EGFP gene was used for sgRNAs targeted to the EGFP gene. This cell line was constructed by correcting the mutations in the EGFP gene in the cell line 293/A658 (Jinek, et al., Science, 337:816-821 (2012)) (kindly provided by Dr Francesca Storici). The genomic DNA was harvested after 3 days using QuickExtract DNA extraction solution (Epicentre), as described in (Yu, et al., Nucleic Acids Res., 38:5706-5717 (2010)). T7EI mutation detection assays were performed, as described previously (Mali, et al., Science, 339:823-826 (2013)) and the digestions separated on 2% agarose gels. The cleavage bands were quantified using ImageJ. The percentage of gene modification=100×(1−(1−fraction cleaved)0.5), as described (28). Unless otherwise stated, all polymerase chain reactions (PCRs) were performed using AccuPrime Taq DNA Polymerase High Fidelity (Life Technologies) following manufacturer's instructions for 40 cycles (94° C., 30 s; 60° C., 30 s; 68° C., 60 s) in a 50 µl reaction containing 1.5 µl of the cell lysate, 3% Dimethyl sulfoxide (DMSO) and 1.5 µl of each 10 µM target region amplification primer (Tables 6 and 7) or off-target region amplification primer (Tables 8 and 9).

TABLE 6

Primers for Target PCR

Primers for target PCR

| Gene | sgRNA | Forward primer name | Reverse primer name | special PCR condition |
|---|---|---|---|---|
| HBB | R-01, R-03, R-04, R-05, R-06, R-07, R-08 | B-glo-Fwd | B-glo-Rev | |
| EGFP | R-19, R-20 | T7 | SSA-Cell-R4 | annealed at 50° C. |
| CCR5 | R-25, R-26, R-27, R-29, R-30 | CSR5_1_10_1_F | CCR5_1_10_1_R | |
| ERCC5 | R-31, R-33, R-35, R-36, R-38, R-39, R-40 | ERCC5-F2 | ERCC5-R2 | |
| TARDBP | R-41, R-42, R-43, R-44 | TAR-F | TAR-R | |
| HPRT1 | R-52, R-53 | HPRTe9-F | HPRTe9-R | |

Primer for qPCR

| Gene | Forward primer name | Reverse primer name |
|---|---|---|
| sgRNA | CRI-qPCR-F | CRI-qPCR-R |

TABLE 7

Primer sequence (SEQ ID NOS 229-242, respectively, in order of appearance)

| Primer Name | Primer sequence (5' to 3') |
|---|---|
| B-glo-Fwd | CCAACTCCTAAGCCAGTGCCAGAAGAG |
| B-glo-Rev | AGTCAGTGCCTATCAGAAACCCAAGAG |
| T7 | TAATACGACTCACTATAGGG |

TABLE 7-continued

Primer sequence (SEQ ID NOS 229-242, respectively, in order of appearance)

| Primer Name | Primer sequence (5' to 3') |
|---|---|
| SSA-Cell-R4 | TGCCGTCCTCGATGTTGTGGCG |
| CCR5_1_10_1_F | GCACAGGGTGGAACAAGATGG |
| CCR5_1_10_1_R | ACCACCCCAAAGGTGACCGT |
| ERCC5-F2 | TGAGGATGAAGAGAAAATCCCGGAG |
| ERCC5-R2 | ATCATTGTACCCATGATGAACTCTCATAAAAC |
| TAR-F | CAATAGCAATAGACAGTTAGAAAGAAGTGGAAG |
| TAR-R | GCTGCACCAGAATTAGAGCCACTATAAGAG |
| HPRTe9-F | CAATCCGCCCAAAGGGAACTGATAG |
| HPRTe9-R | TGCTTTGTTTTCAAAAGATACACTCCCCA |
| CRI-qPCR-F | GTTTTAGAGCTAGAAATAGCAAGTTAAAATAAGGC |
| CRI-qPCR-R | AAAGCACCGACTCGGTGCCAC |

Sequences of primers used to amplify endogenous loci for testing the on-target activities of sgRNAs, and primers for qPCR. Target gene, sgRNAs using the primers, special PCR conditions are listed with each pair of primers in Table 6. The primer sequences are listed in the lower portion of Table 7.

TABLE 8

Human genomic loci tested for off-target activity using T7EI-18 target-site insertions (DNA bulges) (Table 8 discloses the 'Potential Off-Target' sequences as SEQ ID NOS 243-278, respectively, in order of appearance and the 'Primer' sequences as SEQ ID NOS 279-314, respectively, in order of appearance.)

| Index | Potential Off-target Sites | Inserted (DNA bulge) Position | Chromosomal Coordinates [start..end] (hg 19) | Strand | Primer | Primer Sequence |
|---|---|---|---|---|---|---|
| R-01 Off-1 | TTGTAACATGATGAAGTTGAGG G N G | Ins 18 | Chr2: 186524309-186524332 | + | R1off-F1<br>R1off-R1 | TCAGTCTTTTACTCGGGATACCAA<br>TTCATCTATCGTAACGCTTGCAAT |
| R-01 Off-2 | CTGCAACGTGGATGAAGCTGGAGG G N T N | Ins 18 | Chr21: 16223748-16223771 | − | R1off-F2<br>R1off-R2 | GAACAGAATGATGAGGAAGGAAGA<br>AACCTAGATGCCCATCAATAGTGGA |
| R-05 Off-1 | GCTCTGCCGTTTACTGCCCTGTGG G N | Ins 10, 11, or 12 | Chr1: 162859322-162859345 | + | R5off-F1<br>R5off-R1 | TTGAGATGCCGTTGTTTCATGCCAA<br>ATTGCTCACACACATCAGAAAGCC |
| R-07 Off-1 | AAGATGAACGTGGAGTGAAGTTGGG G G N N | Ins 7 | Chr9: 116503487-116503510 | + | R7off-F1<br>R7off-R2 | CCAGGCATCCTGCTGATCTTTTGTT<br>TTAGGGTTAAAGGGCTTGCTGTG |
| R-20 Off-1 | CGCCAAGATGGGCAGCCACCCCGG GA G N N | Ins 7 | Chr20: 21687581-21587604 | + | R20off-F1<br>R20off-R1 | GACGGCGTCTGCAGACAAGTACAATG<br>GAGGTCTTACAAAAGGCCCAGGA |
| R-20 Off-2 | ATCCAGGATGGGCACCACCACCGGG GA N | Ins 3 | Chr15: 570067704-570067727 | − | R20off-F2<br>R20off-R2 | GGTACCTTGGAGGGATCTATTGCCT<br>CTGACACTTCTGCAGCCTTGGGTAG |
| R-25 Off-1 | ATGTTCTTCTTTGGCTTTTGTTGG G A N N | Ins 7 | Chr10: 59053283-59053306 | − | R25off-F1<br>R25off-R1 | TGACCAATGAGCAAAGAAATTATCCACA<br>ACATCCCAAAGAATGAAGTTGGAGA |
| R-25 Off-2 | TATTTCATCTTTGGTTTTAGTTGGG GTG N | Ins 3 | Chr13: 23183816-23183839 | + | R25off-F2<br>R25off-R2 | GCACACTAGTGACTACTCAGGGTAT<br>ACAGGCATATCATATTGTATGTCAGAGTG |
| R-25 Off-3 | AGGTTCAACTTTGGTTTTGGTGGG GT T N | Ins 2 or 3 | Chr15: 37967958-37967981 | − | R25off-F3<br>R25off-R3 | AAGAAACAGGGATCCCTGCATAAAT<br>AATTTCTTTGTTGGAAAACCCTGGA |
| R-25 Off-4 | ATGTTCATATTTGGTTTTGTGTGG G C NN | Ins 1 | Chr2: 22543732-22543755 | + | R25off-F4<br>R25off-R4 | CATTGATTGTTTCATCCCGACAGTT<br>GGCTAAGGTGAAAAACAAAGCCAAT |
| R-26 Off-1 | TTTGCCCCCAGTGGGACATTTGG GC G N N | Ins 3 | Chr3: 52498409-52496432 | − | R26off-F1<br>R26off-R1 | GCTACATCTGGTTCTGGTTTGAGGC<br>TCCACCCTATCCAATGTCAGCAACA |
| R-30 Off-1 | GTGTGAGGCGGAGGCAGGAGGCAGG NA N | Ins 19 | Chr2: 241904712-241904735 | + | R30off-F1<br>R30off-R1 | AGGAATGCTTTAGCGAGGAGGAAG<br>CTCTCCACTCCTCCTCTGGTTCTC |
| R-30 Off-2 | GTAGGAGGAGGCAGGCAGGAGGCAGG N C | Ins 17 or 18 | Chr19: 35843790-35843813 | + | R30off-F2<br>R30off-R2 | TGATGGACTTGAGGACAGCTACTCT<br>TGTGCCTGGCTTCAAATATGTCTTA |
| R-30 Off-3 | CCAGAAGCGGAGGCAGGAGGCTGG GT N | Ins 16 or 17 | Chr9: 139753254-139753277 | − | R30off-F3<br>R30off-R3 | CCACTTTGCCTCTTTGAAACTGG<br>AACACGATCTGATGGAGAAGGAAAG |
| R-30 Off-4 | GTAGAGAGGAGGCAGGAGGCGGG C N | Ins 5, 6, or 7 | Chr7: 66134975-66134998 | − | R30off-F4<br>R30off-R4 | CTCGGGAAATGGCACCATCATCATC<br>CAGGTCATGTGAACCTCAGAGCTA |

TABLE 8-continued

Human genomic loci tested for off-target activity using T7EI-18 target-site insertions (DNA bulges) (Table 8 discloses the 'Potential Off-Target' sequences as SEQ ID NOS 243-278, respectively, in order of appearance and the 'Primer' sequences as SEQ ID NOS 279-314, respectively, in order of appearance.)

| Index | Potential Off-target Sites | Inserted Position (DNA bulge) | Chromosomal Coordinates [start..end] (hg 19) | Strand | Primer | Primer Sequence |
|---|---|---|---|---|---|---|
| R-30 Off-5 | GTAGAGAGGAGGCAGGAGGCGGG<br>C      N    N | Ins 5, 6, or 7 | Chr7: 73404697-73404720 | − | R30off-F5<br>R30off-R5 | TTCTGTAATTCTGAGCCCACGGAG<br>TGATGAACCTCAGAGCCATTTGGGG |
| R-31 Off-1 | ACCAAGCACTTAAAGGAGTGCTGG<br>G      N    N | Ins 2 | Chr9: 86698731-86598754 | − | R31off-F1<br>R31off-R1 | ACCTCCCACATGTACCTTGCTTTTT<br>GCCTTTCATGTCTGAACATTTTTG |
| R-42 Off-1 | TCCAGCACTACAGAGCAGATTTGG<br>GG     N    N | Ins 3 | Chr10: 48593036-48593059 | − | R42off-F1<br>R42off-R1 | CCAACCTCAAAAGGACCTTGCTGTC<br>TTCACTTTCCAGAGAAGAGTCCTCC |

TABLE 9

Human genomic loci tested for off-target activity using T7EI-62 target-site insertions (sgRNA bulges) (Table 9 discloses the 'Potential Off-Target' sequences as SEQ ID NOS 315-438, respectively, in order of appearance and the 'Primer' sequences as SEQ ID NOS 439-562, respectively, in order of appearance.)

| Index | Potential Off-target Sites | Deleted (sgRNA bulge) Position | Chromosomal Corrdinates [start ... end] (hg) | Strand | Primer | Primer Sequence |
|---|---|---|---|---|---|---|
| R-01 Del-1 | GGGAA^TTGGATGAAGTTGGGG<br>T ^G N | Del 15 | Chr7:85607600-85607621 | + | R1_del_1_F<br>R1_del_1_R | GAATGCAGTAAATTAAAAGCCCAAGG<br>CATCACAGAACACCAGAAGAGACAGC |
| R-01 Del-2 | CTGAA^GTGGATAAAGTTGGTG<br>G ^ G N | Del 15 | Chr4:44622064-4622085 | + | R1_del_2_F<br>R1_del_2_R | GCAAATCTGGGTGGATGTACTGTTG<br>CCTGCACFATCTCACTATGTCTTGC |
| R-01 Del-6 | GGGAACG^GGATGAAGTGGTGG<br>T ^ T N | Del 13 | Chr8:37261849-37261870 | − | R1_del_6_F<br>R1_del_6_R | TTTACATGTGGAGGACAGGACTTC<br>CCAATGATGATTATCTCCGTGACTG |
| R-03 Del-1 | CACCTTCACC^TGCCCCACACGG<br>G G ^ N | Del 9 or 10 | Chr7:134252717-134252738 | − | R5_del_1_F<br>R5_del_1_R | AATTCACTTTCCTTCCTTCTTTTG<br>CTCACACTCCCAGGTTCAAACAATC |
| R-04 Del-1 | TCACCTTC^CCTTGCCCCACAGG<br>G G ^ N | Del 12 | Chr4:570928889-57092910 | − | R7_del_1_F<br>R7_del_1_R | GTTGAAATTTGATCCCCAGCATTG<br>AGAGAGGTGTGAAGGAGGAGGAAAG |
| R-06 Del-1 | GGCTACTGCCCTG^GGGGCAGGG<br>T ^ N | Del 7 | Chr14:100616656-100616677 | − | R11_del_1_F<br>R11_del_1_R | TTGATGCCGTCTGTGTACTCAAGCA<br>GTTTGGTCTCTTTGGAAGGGGAAGC |
| R-07 Del-1 | GCAGTG^ACGTGGATGAAGTTCC<br>AG ^ N | Del 13 or 14 | Chr3:161230477-161230498 | − | R13_del_1_F<br>R13_del_1_R | GTTCCCATTGTGTTGTTGGTTTTCTG<br>TGCTACTATAAAGACGCATGCACAC |
| R-07 Del-2 | GTGGGG^ACGTGGATGAAGTTGG<br>A T ^ N | Del 13 or 14 | Chr8:106659900-106659921 | − | R13_del_2_F<br>R13_del_2_R | GTGAGTGAGAACATGTGGTGTTCA<br>TGGTGCTATTCACAACAGCAAAGAG |
| R-07 Del-3 | GAGG^GAACGTGGATGAAGCTGG<br>^ TN | Del 16 | Chr2:116826850-116826871 | + | R13_del_3_F<br>R13_del_3_R | AGACGTGAATCACACACAAATGCCC<br>ACAGATGTGCGATGTCAAGATCACC |
| R-08 Del-1 | GATGAGGGG^AAGGTGAACGTGG<br>C T ^ N | Del 11 | Chr23:6739538-6739559 | − | R15_del_1_F<br>R15_del_1_R | ATAGAGACTGCTTGGGAAAGCGTGTG<br>AGCCTTACCGAGGACTCCTTTTACC |
| R-08 Del-2 | GCTG^GGGGCAACGTGAACGTGG<br>G ^ N | Del 16 | Chr17:38953488-38953509 | − | R15_del_2_F<br>R15_del_2_R | CTGAGTCGTGGGAGATCTGTTGCTTG<br>ATACACCTGACCCGCAAACTTTGAGAC |
| R-19 Del-1 | GGTGGT^CAGATCAACTTCAGGG<br>G ^ N | Del 14 | Chr10:79211096-79211117 | − | R19_del_1_F<br>R19_del_1_R | CCCTGAGATACAAGAGGAGCCTGAC<br>CGTCCCTGAACTTCAATTGCCCTG |
| R-20 Del-1 | GACCAGGA^GGGCAGCACCCAGG<br>^ C N | Del 12 | Chr14:24535619-24535640 | + | R20_del_1_F<br>R20_del_1_R | GAATGACATGGAGATGCTAGAGCAGA<br>AGAGGCTTTCCATACCTATGTGCCA |

TABLE 9-continued

Human genomic loci tested for off-target activity using T7EI-62 target-site insertions (sgRNA bulges) (Table 9 discloses the 'Potential Off-Target' sequences as SEQ ID NOS 315-438, respectively, in order of appearance and the 'Primer' sequences as SEQ ID NOS 439-562, respectively, in order of appearance.)

| Index | Potential Off-target Sites | Deleted (sgRNA bulge) Position | Chromosomal Coordinates [start ... end] (hg) | Strand | Primer | Primer Sequence |
|---|---|---|---|---|---|---|
| R-25 Del-1 | GTCTTC^TCTTTGGTTTTGTAGG<br>G N | Del 14 | Chr7:121693943-121693964 | + | R25_del_1_F<br>R25_del_1_R | TGCCCAGTAAGCATTGGCTATAATAATC<br>GTCCCATATCATCCTCCAGAAATCC |
| R-25 Del-10 | GTGTTCATCTT^GGTTTTGTACG<br>^ NC | Del 9, 10, or 11 | Chr4:70483200-70483221 | – | R25_del_10_F<br>R25_del_10_R | GCTTTAGGATCTGCTGCCCTCCTAT<br>CGTCTTAATGGACCCTGTATGTTGCT |
| R-25 Del-2 | ATGCTC^TCTTTGGTTTTGTTGG<br>G T ^ N | Del 14 | Chr2:230663047-230663068 | – | R25_del_2_F<br>R25_del_2_R | GACCCGGCTGCTTAAATTACAAATG<br>TTGTTCCAGACAAGGAAAAGCTGAC |
| R-25 Del-3 | ATGGTC^TCTTTGGTTTTGTAGG<br>G T ^ N | Del 14 | Chr17:59233856-59233877 | + | R25_del_3_F<br>R25_del_3_R | TGTTTCTTTTGGGGAAACTTAGAG<br>TTTCTTACCAAATGATGAAACTCGAC |
| R-25 Del-4 | ATGTTCAT^TTTGGTTTTGTTGG<br>G ^ N | Del 12 | Chr21:27369860-27369881 | – | R25_del_4_F<br>R25_del_4_R | GAGAACATAATCTAAAACAAAAAGAGAAAC<br>GCAAGAAATCCTCTCTGTTAAGAAACC |
| R-25 Del-5 | TTATTCAT^TTTGGTTTTGTGGG<br>G G ^ N | Del 12 | Chr6:131504701-131504722 | – | R25_del_5_F<br>R25_del_5_R | ACAAAAAGGGATTTTGGAGGTAGG<br>CAGTGCTCTCCAGGCTCACTCTC |
| R-25 Del-6 | GGTTTCAT^TTTGGTTTTGTAGG<br>TG ^ N | Del 12 | Chr18:8673547-8673568 | – | R25_del_6_F<br>R25_del_6_R | CAGAAGATGTTCAGAAACAAGCAAGG<br>ATTCTGTCTGTGAGGCGTGTCTTTC |
| R-25 Del-8 | GTGTTCA^CTTTGGTCTGTAGG<br>^ T N | Del 13 | Chr5:74921783-74921804 | + | R25_del_8_F<br>R25_del_8_R | CTCACCATTGCAGGAGGAGAGAACT<br>GAATGGGAAGAAGGAATCTGGCTGC |
| R-25 Del-9 | GTGTTCTTCTT^GGTTTTGTTGG<br>A ^ N | Del 9, 10, or 11 | Chr8:114654423-114654444 | – | R25_del_9_F<br>R25_del_9_R | AAGTTACTCACCTGTCCCCTAGAGTA<br>ATTTTGCCTGAGCTGGCCTTCATA |
| R-27 Del-1 | GGAAGCA^AGTGAGCCCAGAGG<br>C ^ N | Del 13 | Chr13:95847651-95847672 | + | R27_del_1_F<br>R27_del_1_R | GAACACGGGAGTTGGTTGGAAAT<br>ATAGGTGATTGTGAAAAGAAGC |
| R-27 Del-3 | GAAAGCATAGTGA^CCCAGAGGG<br>GC ^ N | Del 7 | Chr7:51295518-51205539 | – | R27_del_3_F<br>R27_del_3_R | AATTACTCACTGATTTTACTGAGAACTG<br>ACTGGGCTATTGTTAATATGATGG |
| R-27 Del-4 | GGCA^CATAFTGAGCCAAGATGG<br>^ C N | Del 16 | Chr5:99191677-99191698 | + | R27_del_4_F<br>R27_del_4_R | GACCCAGCCATCCATTACTTGGTA<br>TCTGAAAAGCGCAATATTCGGGTGG |
| R-27 Del-5 | GGCAGC^TAGTGAGCCCAGAGA<br>^ N G | Del 14 | Chr1:164837564-164837585 | + | R27_del_5_F<br>R27_del_5_R | CATCCGTGCACAATACCAGGCTAAG<br>GCTGCTTGCAAATCAACCAGGTTTC |
| R-27 Del-6 | GGCAGCA^AGTGAGGCCAGAAGG<br>C ^ N | Del 13 | Chr13:19571247-19571268 | + | R27_del_6_F<br>R27_del_6_R | AGTCCAAGTCAGATGGTCAGAAAGCA<br>TCCTTGCATGCCAAGACAGAGATT |

TABLE 9-continued

Human genomic loci tested for off-target activity using T7EI-62 target-site insertions (sgRNA bulges) (Table 9 discloses the 'Potential Off-Target' sequences as SEQ ID NOS 315-438, respectively, in order of appearance and the 'Primer' sequences as SEQ ID NOS 439-562, respectively, in order of appearance.)

| Index | Potential Off-target Sites | Deleted (sgRNA bulge) Position | Chromosomal Corrdinates [start ... end] (hg) | Strand | Primer | Primer Sequence |
|---|---|---|---|---|---|---|
| R-29 Del-1 | GAGTGT^GAGCGGAGGCAGGAGG<br>T A ^ N | Del 14 | Chr2:238918342-238918303 | - | R29_del_1_F<br>R29_del_1_R | CAATAGCTGTCATTGTGCCTTTGTC<br>CCTGGAAGTGACATCCTATGCAAAC |
| R-29 Del-2 | CTGAGGAG^GCCGAGGCAGGAGG<br>G T ^ N | Del 12 | Chr7:8334655-8334676 | - | R29_del_2_F<br>R29_del_2_R | CAGGCCAGAAGTATATTCCTACGTG<br>CCTGGGCAACAAAGTGAGACC |
| R-29 Del-5 | GTGAGTAGAG^GGAGGAGGAGG<br>A ^ N | Del 10 | Chr8:83327062-83327083 | - | R29_del_5_F<br>R29_del_5_R | ATATACCAGCCAACTTGGGATGCCT<br>ACAAGTTTCAGTGAGGGAGGGAA |
| R-30 Del-11 | GAAGGGCGGAG^AGGAGGCAGG<br>T A ^ N | Del 8 | Chr16:30382121-30382142 | + | R30_del_11_F<br>R30_del_11_R | AGGGCTGTAAGACCAATCAGAGAC<br>ACCTCCTCCCCTTTTCATTCC |
| R-30 Del-12 | GGAGAGGGAGG^AGGAGGCAGG<br>T C ^ N | Del 8 | Chr3:194821292-194821313 | - | R30_del_12_F<br>R30_del_12_R | CAGAGTTCTTCTGCCCTGGCATC<br>AGAAGGGCACCACAGCCTCAG |
| R-30 Del-14 | GCAAAGCGGAGGC^GGAGGCAGG<br>T G ^ N | Del 7 | Chr6:105436556-105436577 | - | R30_del_14_F<br>R30_del_14_R | AGCCACTTGGCCTGTAGTTTTCTT<br>GAGGTCAGGAGTTTGAGAACAGCCT |
| R-30 Del-15 | GCAGCGCCGAGGC^GGAGGCGGG<br>T A ^ N | Del 7 | Chr9:132372864-132372885 | + | R30_del_15_F<br>R30_del_15_R | CCTAGCAATTTTGGGCTCAACAAC<br>AAACTTCTCAGCCTCTCGCTCCAG |
| R-30 Del-16 | CTAGGGCGGAGC^GGAGGCGGG<br>G A ^ N | Del 7 | Chr9:96108620-96108641 | - | R30_del_16_F<br>R30_del_16_R | GCTGGGCTGGAGAGAAGGTG<br>GTCCTTGCAAACTCCCGTTCC |
| R-30 Del-17 | GTGGAG^GGAGGCAGGAGGCAGG<br>A ^ N | Del 14 | Chr3:128063055-128063078 | - | R30_del_17_F<br>R30_del_17_R | TGTGTGCAGAGTGAGATCCTATGAG<br>GGACCTGGGTTCGTAGGAAGAAAAC |
| R-30 Del-2 | GAAG^GAGGAGGCAGGAGGCTGG<br>T ^ C | Del 16 | Chr6:74322905-74322926 | + | R30_del_2_F<br>R30_del_2_R | AGGCGCTGACCACAGTGCCTAC<br>GGAGTTTATTCCCTCCTCTTGAAGC |
| R-30 Del-4 | GGAG^GTCCAGGCAGGAGGCTGG<br>T ^ C | Del 16 | Chr20:55620115-55620136 | - | R30_del_4_F<br>R30_del_4_R | AACTTGTGAGTGCGGTGACTCTGAAG<br>AGCACACCTCGCTCTCATGGAC |
| R-30 Del-6 | GGTGAG^GGAGGCAGGAGGCAGG<br>TA ^ N | Del 14 | Chr7:132937943-132937964 | + | R30_del_6_F<br>R30_del_6_R | TTGGCTTCCTTGGAGCCTAGC<br>CAAGGAGGAAAGGGGAGAGCAG |
| R-30 Del-0 | GCAGGGCGG^GGCAGGAGGCTGG<br>T A ^ N | Del 11 | Chr10:70883851 70883872 | + | R30_del_0_F<br>R30_del_9_R | GTAATTGCCCGCCCCTC<br>CCCTACTCCACTCCTCTTCCCTCAG |
| R-31 Del-1 | GGCTAGCA^TTAAAGGAGTCAGG<br>C A ^ N | Del 12 | Chr23:8280850-8280871 | + | R31_del_1_F<br>R31_del_1_R | TGTGTAACAAATTGCCACAAATTTAGC<br>GATGTTGATAGCTGCAAGAAACTGG |

TABLE 9-continued

Human genomic loci tested for off-target activity using T7EI-62 target-site insertions (sgRNA bulges) (Table 9 discloses the 'Potential Off-Target' sequences as SEQ ID NOS 315-438, respectively, in order of appearance and the 'Primer' sequences as SEQ ID NOS 439-562, respectively, in order of appearance.)

| Index | Potential Off-target Sites | Deleted (sgRNA bulge) Position | Chromosomal Corrdinates [start ... end] (hg) | Strand | Primer | Primer Sequence |
|---|---|---|---|---|---|---|
| R-33 Del-1 | GCAAG^ACTTAAAGCAGTCCGGG<br>     ^                  G    N | Del 15 | Chr15:70302028-70302049 | − | R33_del_1_F<br>R33_del_1_R | CTCATGGGCAAATGGTCTTCAACC<br>CCCCATCACATGAGAGAATGTGGGT |
| R-35 Del-1 | GTGAGGTCCCA^GGCGATCCTGG<br>           T ^                  N | Del 9 | Chr1:47674820-47674841 | + | R35_del_1_F<br>R35_del_1_R | GACGCTGAGACACATAGAATCCT<br>GTGTTCAATGGGCTATCAGGCTTCC |
| R-36 Del-2 | GCTAGT^AAGAAAACAGACTTAGG<br>      T ^                       N | Del 14 | Chr2:34787318-34787339 | + | R36_del_2_F<br>R36_del_2_R | TCTCATTGATCCTCATTGCACTCTG<br>AAAGCAAATGTCTTTGGCCACATTG |
| R-38 Del-5 | GATTTTCT^TTGAGGTCCCAAGG<br>        ^  T                 N | Del 12 | Chr15:67922643-57922664 | + | R38_del_5_F<br>R38_del_5_R | GGCTTCTCCATAAATGCCCCATTG<br>CACCGGGTAGGAAGTCTATCCACAG |
| R-30 Del-2 | GGAATCAAA^TGAGAAGATGTGG<br>         A ^                 N | Del 11 | Chr6:171806850 171806880 | − | R30_del_2_F<br>R30_del_2_R | AATGCACACCAATGCCAATACACC<br>GGCCTATAGGAGCCACTTTCAAGC |
| R-39 Del-3 | GAAGACAAAG^GAGAAGATGAGG<br>G  A      ^                 N | Del 10 | Chr19:8322816-8322837 | − | R39_del_3_F<br>R39_del_3_R | TGGTCCCATCCTATAGCACCTTCTC<br>AGGCAGTTCCTGGAATCTCAGACAC |
| R-39 Del-4 | AGAATCAAAG^GAGAAGATGAGG<br>G  A      ^                 N | Del 10 | Chr20:17602724-17602745 | + | R39_del_4_F<br>R39_del_4_R | GAAGGTGTTCAGCTGTGGAGGTG<br>TGACCCAGTATGCTCCTTTCATCAG |
| R-39 Del-5 | GGAAA^AAAGTGAGAACATGTGG<br>     ^                      G    N | Del 15 | ChrX:71641287-71641308 | + | R39_del_5_F<br>R39_del_5_R | GTAAACGTCTGCCATGCTGGTCTG<br>AGCAGTGGAACTGAATAATAGCAGAGT |
| R-39 Del-6 | GGAAACAAAG^GAGAAGATGTGC<br>          ^                    N G | Del 10 | Chr2:96791029-96791050 | − | R39_del_6_F<br>R39_del_6_R | CCCACTTCAGATCACTCCCACCTAC<br>TATCAAGATGGTGAGCATGGGAGCA |
| R-39 Del-7 | GGAAACAAAGT^AGAAGAAGAGG<br>          ^                T  N | Del 9 | Chr20:16523350-16623371 | + | R39_del_7_F<br>R39_del_7_R | ATATGAACAAAGACCTGAACGGGC<br>GGATGCATCTCCATTCCTGTACCCT |
| R-30 Del-8 | CCAAACAAAATCA^AACATCACC<br>             ^               N | Del 7 | Chr10:2106 648 21061660 | + | R30_del_8_F<br>R39_del_8_R | AACGCCAGCAATTGTTGTAAGCACATTTCT<br>TGGCAAGATTAACCAATTAGCTACCCAC |
| R-40 Del-1 | GCCTGTTTTT^TGTTTGATGTGG<br>           A ^               N | Del 10 | Chr8:32701225-32701246 | + | R40_del_1_F<br>R40_del_1_R | TAGTCACTGTTGTTGGTAAGCACATTTCT<br>AGCCCAAACTCCAATGGTAAAGCA |
| R-40 Del-2 | GCCTATTTTG^GTTTGAAGGGG<br>          ^                T  N | Del 9 | Chr3:104520703-104520724 | + | R40_del_2_F<br>R40_del_2_R | AACACGTCTAGGGTGCATACACCATGTCA<br>TCGTTGGTTGAACATCTTTCTCAGTCT |
| R-41 Del-1 | GCAGA^CAGTTGGGGTGTGAATGG<br>     ^                   A    N | Del 15 | Chr11:11580913-11580934 | − | R41_del_1_F<br>R41_del_1_R | AATAACAGCACCTCCTTCACAGGCT<br>CATGAGATTGTAGATGGTGTCAGGTCC |

TABLE 9-continued

Human genomic loci tested for off-target activity using T7EI-62 target-site insertions (sgRNA bulges) (Table 9 discloses the 'Potential Off-Target' sequences as SEQ ID NOS 315-438, respectively, in order of appearance and the 'Primer' sequences as SEQ ID NOS 439-562, respectively, in order of appearance.)

| Index | Potential Off-target Sites | Deleted (sgRNA bulge) Position | Chromosomal Coordinates [start ... end] (hg) | Strand | Primer | Primer Sequence |
|---|---|---|---|---|---|---|
| R-42 Del-1 | TCCAGC^CTACAGAGCAGTTTGG GG N | Del 14 | Chr9:31067668-31067689 | − | R42_del_1_F R42_del_1_R | ATGAGACCACTCCCAAACGAATTG TGACCAAATTCTATCAGGTTTATACCAC |
| R-42 Del-2 | GGCAGCAG^ACAGAGCAGATTGG T N | Del 12 | Chr4:69223620-69223641 | − | R42_del_2_F R42_del_2_R | TACCACAGAATGCAGCCTTGAATCC ACAAAAATTAGCCAGGCATGGTGGT |
| R-42 Del-3 | GGCAGCACTA^AGAGCAGTCGGG TN | Del 10 | Chr20:17812309-17812330 | − | R42_del_3_F R42_del_3_R | GGTCTCGGGAAAGGAGCATTTTGAC AAGTCCCAGTCTGCAGTAACAAGT |
| R-43 Del-1 | CCAGAA^TACAGAGCAGTTGGGG G C ^ N | Del 14 | Chr22:37278975-37278996 | + | R43_del_1_F R43_del_1_R | CAGCTAGGACACAGGCTTTGAGG ATCACCTCAGCTGTCCATCTAGGG |
| R-44 Del-1 | GCCTG^CTGGTGCTGCTGGCAGG T N | Del 15 | Chr17:72942981-72943002 | + | R44_del_1_F R44_del_1_R | ACTGAGTACTGCCTCATCTGCTGTG CAATGGCCACGATCCAGAAATAGGC |
| R-52 Del-1 | GTTTT^TGTCATTAGTGAAATGGG CN | Del 15 | Chr13:31515245-31515288 | + | R52_del_1_F R52_del_1_R | ATTGAAAAGTGGAGTATTGGTAAGACCAT CCCAGTTACGGACTCACTGGGATAG |
| R-53 Del-2 | ACAAGTTG^ACTCTCATCTTGGG G C ^ N | Del 11 or 12 | Chr14:78919187-78919208 | − | R53_del_2_F R53_del_2_R | TGGGCTTATTAATCAATGGCATCAG ACACATGAGGCATTATTGGACTTGG |

Sanger Sequencing of Gene Modifications Resulted from Cas9

To validate the mutation rates measured by T7EI assay, the PCR products used in the T7EI assays were cloned into plasmid vectors using TOPO TA Cloning Kit for Sequencing (Life Technologies) or Zero Blunt TOPO PCR Cloning Kit (Life Technologies), following manufacturer's instructions. Plasmid DNAs were purified and Sanger sequenced using a M13F primer (5'-TGTAAAACGACGGCCAGT-3' (SEQ ID NO: 563)). The mutation rates were determined by comparing each sequence read to the genomic sequence.

Results

Advances with engineered nucleases allow high-efficiency, targeted gene editing in numerous organisms, primary cells and cell lines. Gene editing was used to create user-defined cells, model animals and gene-modified stem cells with novel characteristics that can be used for gene functional studies disease modeling and therapeutic applications. Clustered regularly interspaced short palindromic repeats (CRISPR) and CRISPR-associated (Cas) proteins constitute a bacterial defense system that cleaves invading foreign nucleic acids (Bolotin, et al., *Microbiology*, 151: 2551-2561 (2005); Horvath, et al., *Science*, 327:167-170 (2010); Marraffini, et al., *Nat. Rev. Genet.*, 11:181-190 (2010); Garneau, et al., *Nature*, 468:67-71 (2010); Hale, et al., *Cell*, 139:945-956 (2009); Makarova, et al., *Biol. Direct*, 1:7 (2006); Barrangou, et al., *Science*, 315:1709-1712 (2007); Brouns, et al., *Science*, 321:960-964 (2008)). Chimeric single-guided RNAs (sgRNAs) based on CRISPR (Jinek, et al., *Science*, 337:816-821 (2012)) have been engineered to direct the Cas9 nuclease to cleave complementary genomic sequences when followed by a 5'-NGG protospacer-adjacent motif (PAM) in eukaryotic cells (Mali, et al., *Nat. Methods*, 10:957-963 (2013); Cong, et al., *Science*, 339:819-823 (2013); Mali, et al., *Science*, 339:823-826 (2013)). Since gene targeting by CRISPR/Cas9 is directed by base pairing, such that only the short 20-nt sequence of the sgRNA needs to be changed for different target sites, CRISPR/Cas systems enable simultaneous targeting of multiple deoxyribonucleic acid (DNA) sequences and robust gene modification (Jinek, et al., *Science*, 337: 816-821 (2012); Mali, et al., *Nat. Methods*, 10:957-963 (2013); Cong, et al., *Science*, 339:819-823 (2013); Yang, et al., *Cell*, 154:1370-1379 (2013); Xie, et al., *Mol Plant*, 6 (2013); Hwang, et al., *Nat. Biotechnol*, 31:227-229 (2013); Cho, et al., *Nat. Biotechnol*, 31:230-232 (2013); Li, et al., *Nat. Biotechnol*, 31:681-683 (2013); Shan, et al., *Nat. Biotechnol*, 31:686-688 (2013).

Endogenous DNA sequences followed by a PAM sequence can be targeted for cleavage by designing a ~20-nt sequence of the sgRNA complementary to the target. However, other sequences in the genome may also be cleaved non-specifically, and such off-target cleavage by CRISPR/Cas systems remains a major concern. Generally speaking, there is a partial match between the on- and off-target sites and the differences between the on- and off-target sequences can be grouped into three cases: (a) same length but with base mismatches; (b) off-target site has one or more bases missing ('deletions'): (c) off-target site has one or more extra bases ('insertions'). Recent studies have shown that CRISPR/Cas9 systems non-specifically cleave genomic DNA sequences containing base-pair mismatches (case a) generating off-target mutations in mammalian cells with considerable frequencies (Fu, et al., *Nat. Biotechnol*, 31:822-826 (2013); Hsu, et al., *Nat. Biotechnol*, 31:827-832 (2013); Pattanayak, et al., *Nat. Biotechnol*, 31:839-843 (2013); Cradick, et al., *Nucleic Acids Res.*, 41:9584-9592 (2013); Mali, et al., *Nat. Biotechnol*, 31:833-838 (2013): Cho, et al., *Genome Res.*, 24:132-141 (2014)). Mismatches in the PAM sequence are less tolerated, although Cas9 also recognizes an alternative NAG PAM with low frequency (Hsu, et al., *Nat. Biotechnol*, 31:827-832 (2013); Mali, et al., *Nat. Biotechnol*, 31:833-838 (2013); Jiang, et al., *Nat. Biotechnol*, 31:233-239 (2013)). In addition, Cas9 off-target cleavage at a similar gene sequence with a base pair mismatch may lead to gross chromosomal deletions with high frequencies, as demonstrated by the deletion of the 7-kb sequence between two cleavage sites in HBB and HBD, respectively (Cradick, et al., *Nucleic Acids Res.*, 41:9584-9592 (2013)). These results indicate that, although Cas9 specificity extends past the 7-12 bp seed sequence (Hsu, et al., *Nat. Biotechnol*, 31:827-832 (2013); Pattanayak, et al., *Nat. Biotechnol*, 31:839-843 (2013)), off-target effects may limit the applications of Cas9-mediated gene modification, especially in large mammalian genomes that contain multiple DNA sequences differing by only a few mismatches. One report revealed that 99.96% of the sites previously assumed to be unique Cas9 targets in human exons may have potential off-target sites containing a functional (NAG or NGG) PAM and one single-base mismatch compared with the on-target site (Mali, et al., *Nat. Biotechnol*, 31:833-838 (2013)).

Figure 8A:
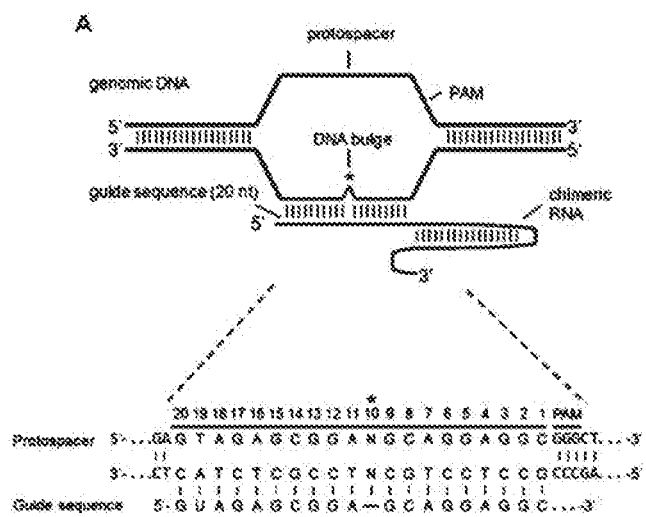
FIGS. 8A and 8B are diagrams showing that CRISPR can cleave at genomic sites with mismatches to the guide strand and with insertions or deletions relative to the guide strand, for example at off-target sites with a 1-bp insertion (DNA bulge) (8A) or a 1-bp deletion (RNA bulge) (8B). The 20-nt guide sequence in the sgRNA is shown aligned with the genomic target sequence (protospacer) containing single-base DNA bulge (8A, asterisk) or single-base sgRNA bulge (8B, Δ). The zoom-in nucleotide sequences of protospacer and PAM (SEQ ID NOS 821 and 823, respectively, in order of appearance) are shown above the sgRNA guide sequence (SEQ ID NOS 822 and 824, respectively, in order of appearance). Positions of nucleotides in the target are numbered 3' to 5' starting from the nucleotide next to PAM.
Figure 8B:
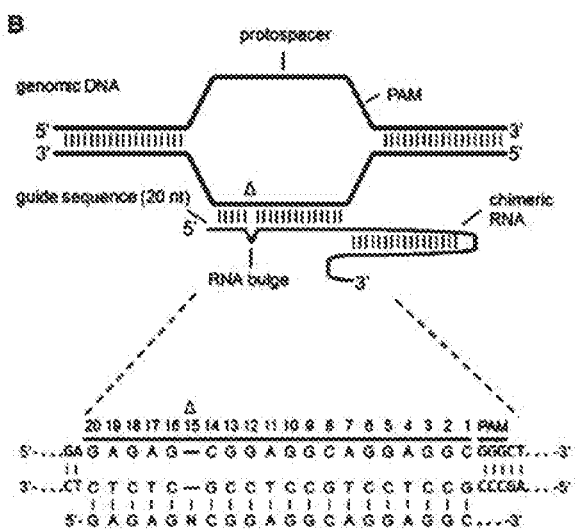

Examples 3-8 examine the above-mentioned cases (b) and (c) of potential CRISPR-Cas9 off-target cleavage in human cells by systematically varying sgRNAs at different positions throughout the guide sequence to mimic insertions or deletions between off-target sequences and RNA guide strand. To avoid confusion, for single-base insertions, a 'DNA bulge' was used to represent the extra, unpaired base in the DNA sequence compared with the guide sequence. Similarly, for single-base deletions, an 'RNA bulge' was used to represent the extra, unpaired base in the guide sequence compared with the DNA sequence (FIGS. 8A-8B). Therefore, adding a base into the guide RNA would result in an RNA bulge, while removing a base in the guide strand can be used to model a DNA bulge. The cleavage activity of RNA-guided Cas9 at endogenous loci in HEK293T cells transfected with plasmids encoding Cas9 and sgRNA variants was quantified as the mutation rates induced by Non-Homologous End Joining (NHEJ). The results below show that off-target cleavage resulted from the sgRNA variants occurred with DNA bulge or sgRNA bulge at multiple positions in the guide strands, sometimes at levels comparable to or even higher than those of original sgRNAs. Cas9-mediated mutagenesis was also examined at 114 potential off-target loci in the human genome carrying single-base DNA bulges or sgRNA bulges together with a range of base mismatches, and the results confirmed 15 off-target sites with mutation frequencies up to 45.5%. The results illustrate the need to search for genomic sites with base-pair mismatches, insertions and deletions compared with the guide RNA sequence in analyzing CRISPR/Cas9 off-target activity and in designing RNA guide strands for targeting specific genomic sites.

To determine if CRISPR/Cas9 systems tolerate genomic target sites containing single-base DNA bulges (FIG. 8A), the sgRNA-DNA interfaces of two sgRNAs. R-01 and R-30, targeting the HBB and CCR5 genes, respectively, were used as a model system (Cradick, et al., *Nucleic Acids Res.*, 41:9584-9592 (2013)). Systematically removing single nucleotides at all possible positions throughout the original 19-nt guide sequences of R-01 and R-30 resulted in single-base DNA bulges at their original HBB and CCR5 target sites that model single-base insertion at potential off-target sites in the genome (FIGS. 9A and 10A).

Cleavage of the genomic DNA in HEK293T cells was quantified using the T7EI mutation detection assay. For both groups of sgRNA variants (generated from R-01 and R-30 respectively), single-base DNA bulges at certain positions in the DNA sequences were well tolerated (e.g. still had Cas9 induced cleavage), though variants of R-30 had higher cleavage activity at more locations (FIGS. 9B-9C and 10B-10C). For both groups, it was clear that Cas9 tolerated DNA bulges in target sites in three regions: seven bases from PAM, the 5'-end (PAM-distal) and the 3'-end (PAM-proximal). Specifically, "−1 nt" variants of R-01 induced Cas9 cleavage activity when a single-base DNA bulge is present at positions 1 or 2, 6 or 7, 18 and 19 of the target DNA sequence from the PAM (FIG. 9B-9C). Due to the presence of consecutive identical nucleotides at positions 1 and 2, 6 and 7, removing either one of the identical nucleotides in the sgRNA at these adjacent positions would give the same sequence and have the same sgRNA-DNA interface (their position is therefore marked as 'or' in FIGS. 9B-9C and 10B-10C).

In contrast, "−1 nt" variants of R-30 induced variable cleavage activity at more positions throughout the guide sequence: positions 1, 2 or 3, 7, 8, 9 or 10, 11, 16, 17, 18 and 19 from the PAM (FIG. 10B-10C). Seven R-30 variants have activities comparable to or even higher than that of the original sgRNA. These variants correspond to DNA bulges at positions 1, 2 or 3, 8, 9 or 10, 11, 18 and 19 from the PAM (FIG. 10B-10C). Consistent with previous studies showing that the specificity of CRISPR/Cas9 systems is guide-strand and target-site dependent (Fu, et al., Nat. Biotechnol, 31:822-826 (2013); Hsu, et al., Nat. Biotechnol, 31:827-832 (2013); Cradick, et al., Nucleic Acids Res., 41:9584-9592 (2013)), the positions in R-01 sgRNA variants where DNA-bulges were tolerated are different from that in R-30 sgRNA variants. However, these positions seem to group in the 5'-end, middle and 3'-end regions of the target loci, as in both R-01 and R-30 sgRNA-DNA interfaces, single-base DNA-bulges at the following five positions seems to be tolerated: positions 1, 2, 7, 18 and 19. Although additional studies are needed to determine if these positions are common for different target sequences, the data support a conclusion that single-base DNA-bulges at the target sites corresponding to these positions are worth investigating when performing off-target analysis for CRISPR/Cas9 systems.

Figure 11A:
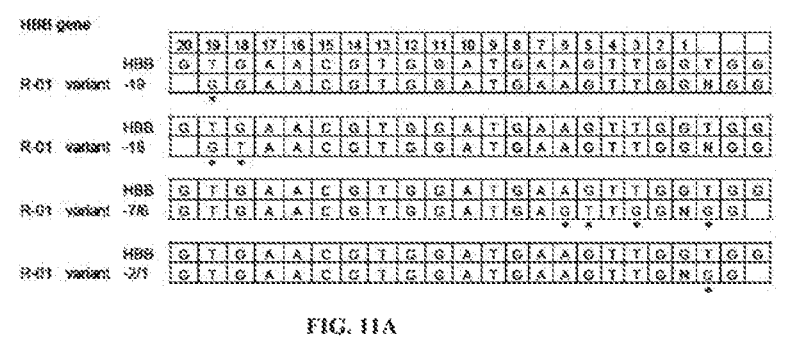
Figure 11B:
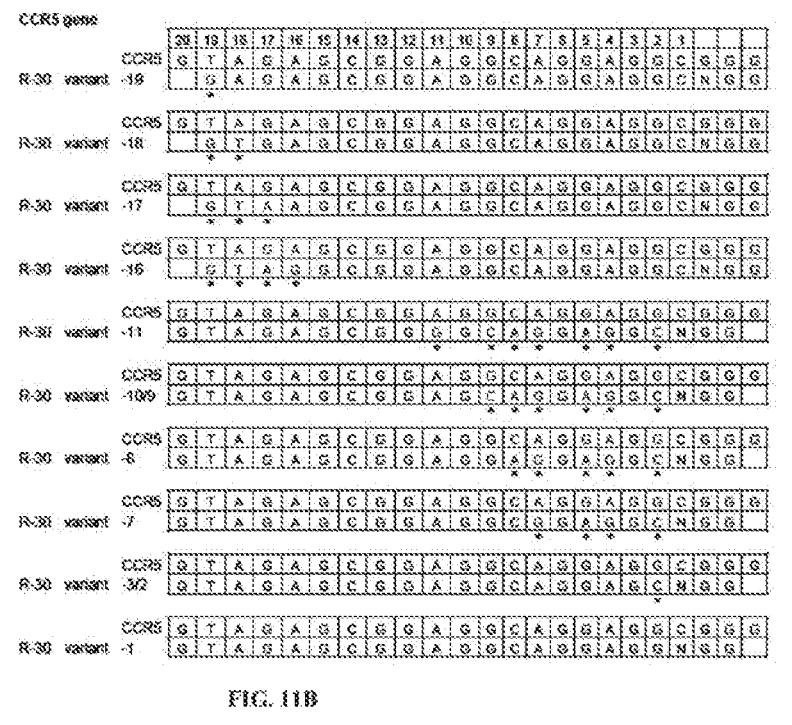

In certain cases, off-target sites with DNA bulges may also be interpreted as sequences having various base mismatches with guide sequence and/or PAM (FIG. 11A-11B). For example, the sgRNA-DNA interfaces corresponding to removing 5'-end bases in the guide sequences (positions 18 and 19 of the R-01 interface and 16-19 of the R-30 interface) can be viewed as having DNA bulges or having mismatches in the 5'-end region of sgRNA, which have been shown to be better tolerated compared to the 3'-end region (Cong, et al., Science, 339:819-823 (2013); Fu, et al., Nat. Biotechnol, 31:822-826 (2013): Hsu, et al., Nat. Biotechnol, 31:827-832 (2013)). Therefore, the Cas9 cleavage activities induced by these guide strands may be interpreted as tolerance of base mismatches at the 5'-end of the guide RNA. In addition, the position-1 variant of R-30 results in a shift in the adjacent PAM from GGG to CGG (another canonical PAM), which could explain why the activity of this guide sequence variant was similar to the original R-30. However, off-target activities associated with most other DNA bulges for the R-01 and R-30 interfaces cannot be attributed to base mismatch tolerance, since a base removal in the sgRNAs (corresponding to a DNA bulge) could result in many base mismatches or mutation in the PAM sequence. For example, the cleavage activity induced by the R-01 variant at position 2/1 may be alternatively interpreted as Cas9 cleavage with a GTG PAM (FIGS. 9B-9C and FIG. 11A), which is highly unlikely according to previous studies (Hsu, et al., Nat. Biotechnol, 31:827-832 (2013), Pattanayak, et al., Nat. Biotechnol, 31:839-843 (2013)). Further, a R-30 guide strand variant at position 11 would contain at least seven mismatches if modeled without a bulge. This guide strand resulted in a 1.8-fold higher cleavage activity compared to the original R-30 (FIGS. 10B-10C and FIG. 11B), which cannot be readily explained by the high level of base mismatches (which should prohibit cleavage), and thus should be attributed to the tolerance of DNA bulges. This is a good example of the case of a sequence-verified off-target site with a bulge that could modeled as mismatches without indels, though the number and position of mismatches would likely not allow cleavage.

Figure 12A:
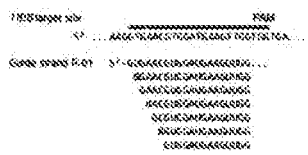
FIG. 12A is a sequence alignment showing 1-6 bp truncations at the 5' end of the guide sequence R-01 (SEQ ID NOS 875-881, respectively, in order of appearance) targeted to the HBB gene (SEQ ID NO: 874).
Figure 12B:
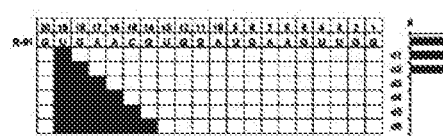
FIG. 12B is a grid showing cleavage activity for the corresponding sgRNA variants measured by T7EI assay in HEK293T cells at the HBB site for the sgRNA variants (SEQ ID NOS 876-881, respectively, in order of appearance) in (12A). Truncated positions are highlighted in the grid. Sequence of the original sgRNA is in the top row of the grid.
Figure 12C:
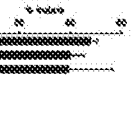
FIG. 12C is a bar graph showing cleavage activity aligned to the corresponding sgRNA variants of 12A and 12B. The number of deleted nucleotides is labeled on the y-axis. The vertical dashed lines mark the activity levels of the original sgRNAs. Error bar, SEM (n=2).

Studies were also designed to determine if sgRNAs with small truncations at the 5'-end retain cleavage activity. One to six nucleotides were deleted from the 5' end of R-01 except for the nucleotide at position 20, because the guanine here is required for the expression under the U6 promoter (FIG. 12A). For these guide sequence truncations, it was discovered that 1- to 2-bp 5' truncations could still induce cleavage activities similar to the full-length sgRNA (FIG. 12B-12C).

Figure 13A:
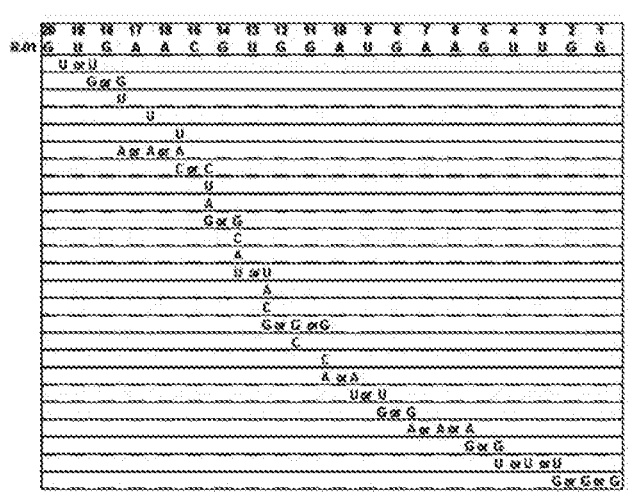
FIG. 13A is a grid showing the activity of Cas9 at the HBB target site carrying single-base sgRNA bulges associated with different variants of the original sgRNAs R-01 (SEQ ID NOS 882-907, respectively, in order of appearance). Each variant shown has a single nucleotide, A, G, C, or U inserted into the original sgRNA at the positions shown throughout the guide sequence. Sequence of the original sgRNA is in the top row of the grid. Positions of the original guide sequence are shaded, while the inserted positions are white. Due to identical nucleotides at adjacent positions, some inserted nucleotides can be in multiple positions (marked by 'or').
Figure 13B:
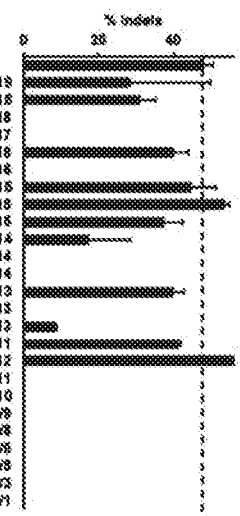
FIG. 13B is a bar graph showing corresponding cleavage activities quantified by T7EI assay in HEK293T cells. Positions relative to PAM and the single nucleotides added are labeled on the y-axis. Error bar, SEM (n=2).
Figure 14A:
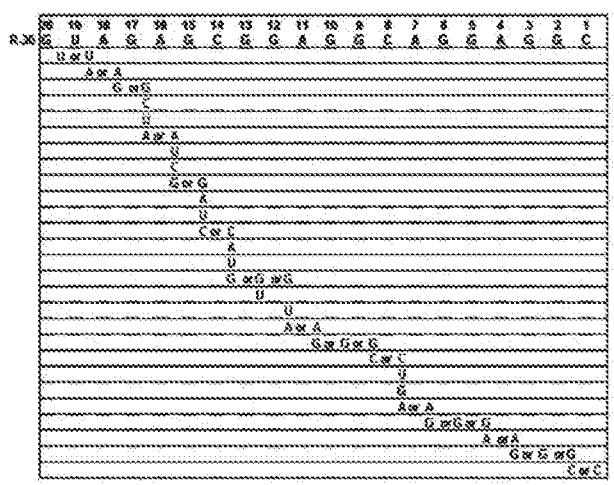
FIG. 14A is a grid showing the activity of Cas9 at the CCR5 target site resulting from treatment with different variants of R-30 with single-base bulges (SEQ ID NOS 908-935, respectively, in order of appearance). A single nucleotide, A, G, C, or U, was inserted into the original sgRNA throughout the guide sequence. Sequence of the original sgRNA is in the top row of the grid. Positions of the original guide sequence are shaded, while the inserted positions are white. Due to identical nucleotides at adjacent positions, some inserted nucleotides can be in multiple positions (marked by 'or').
Figure 14B:
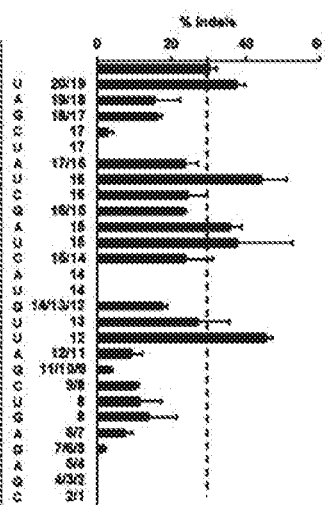
FIG. 14B is a bar graph showing corresponding cleavage activities quantified by T7EI assay in HEK293T cells. Positions relative to PAM and the single nucleotides added are labeled on the y-axis. Error bar, SEM (n=2).

Example 4: sgRNA Variants Containing Single-Base sgRNA Bulges Induce Cas9 Cleavage In addition to Cas9 induced cleavage at off-target sites with single-base DNA bulges, additional studies were designed to investigate if single-base sgRNA bulges (that model single-base deletions in DNA sequence) could induce Cas9 cleavage (FIG. 8B). Again, using sgRNA-DNA interfaces R-01 and R-30 as model systems, single nucleotides were added at positions throughout the original guide sequences, so that the interfaces with target sequences in HBB or CCR5 carries single-base sgRNA bulges (FIG. 13A-13B). For some positions, the addition of single nucleotide A, C, G and U, respectively to the guide sequence was all tested to account for the effect of base identity. As above, HEK293T cells were transfected with plasmids of the Cas9 and sgRNA variants and the T7EI mutation detection assay was used to measure the Cas9 cleavage activity.

sgRNA bulges in the R-30 sgRNA-DNA interface were better tolerated compared to those of R-01. In contrast to the tolerances of DNA bulges adjacent to the PAM, sgRNA bulges close to the PAM prohibited cleavage (FIG. 13A-14B). For the R-01 interface, single-base sgRNA bulges between each of the 11 PAM-proximal guide-strand nucleotides resulted in no detectable activity (FIG. 13A-13B). Single-base sgRNA bulges of the four nucleotides closest to the PAM in R-30 also eliminated T7EI activity (FIG. 14A-14B). The sgRNA bulges 3' to the position 11 in R-30 resulted in reduced cleavage activities (FIG. 14A-14B). The lack of activity with PAM-proximal sgRNA bulges in R-01 and low levels of activity with PAM-proximal sgRNA bulges in R-30 are consistent with the reduced mismatch tolerance in the 'seed sequence' reported in previous studies (Jinek, et al., Science, 337:816-821 (2012); Cong, et al., Science, 339:819-823 (2013); Sapranauskas, et al., Nucleic Acids Res., 39:9275-9282 (2011)). Nucleotide additions in sgRNA sometimes created consecutive identical nucleotides, such as adding a G before or after position 14 of R-01 or before or after position 15 of R-30. These sgRNA variants model a G-bulge that can be at either position in the sgRNA (FIG. 13A-14B). In many cases sgRNA bulges with a single U gave rise to high nuclease activities. Among all sgRNA variants with activities higher than the original sgRNAs, ~71% (5/7) were targeted to the loci with a U-bulge. Overall, single-base sgRNA bulges induced higher Cas9 cleavage activities at many more positions than that with single-base DNA bulges. This is not surprising since RNA molecules are more flexible than DNA molecules, thus having smaller binding energy penalty with single-base RNA bulges, resulting in a higher tolerance (Alberts, et al., *Garland Science* (2007)).

Figure 15A:
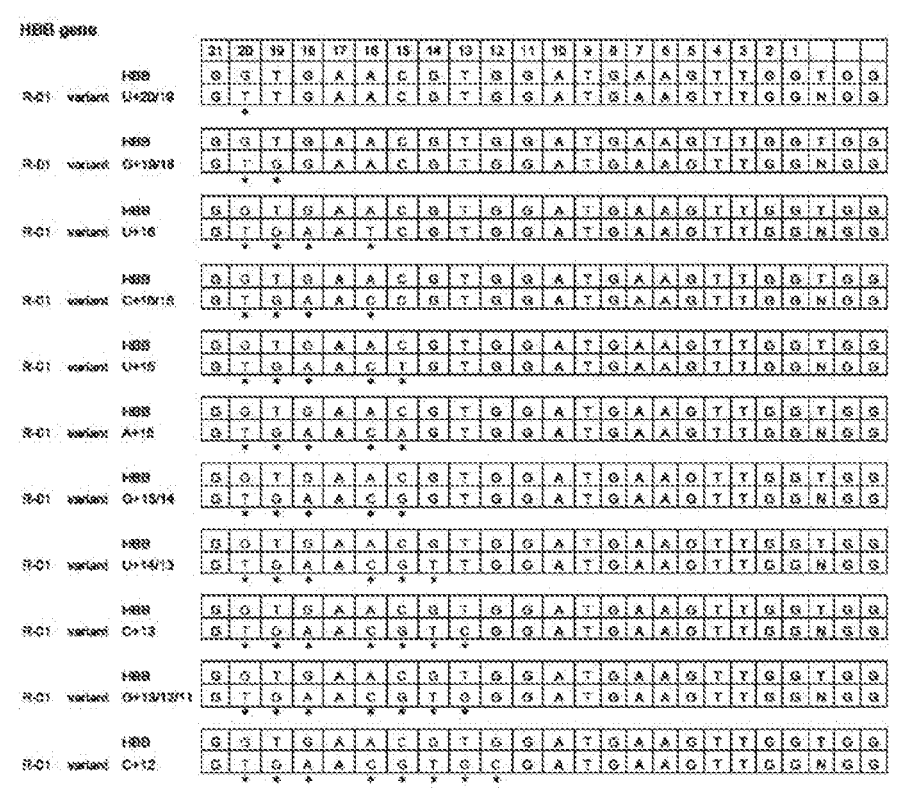
Figure 15B:
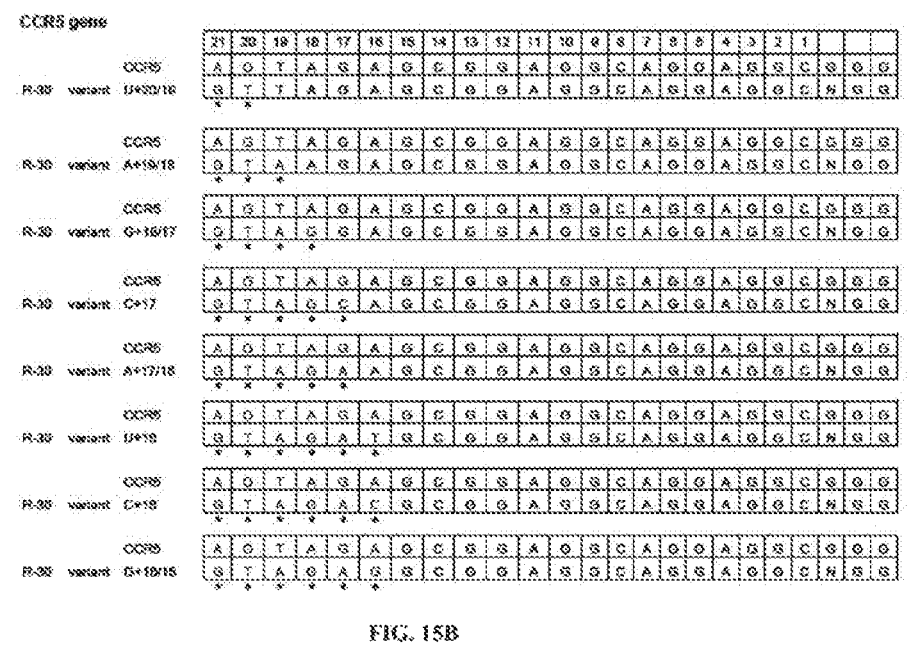
Figure 15B:
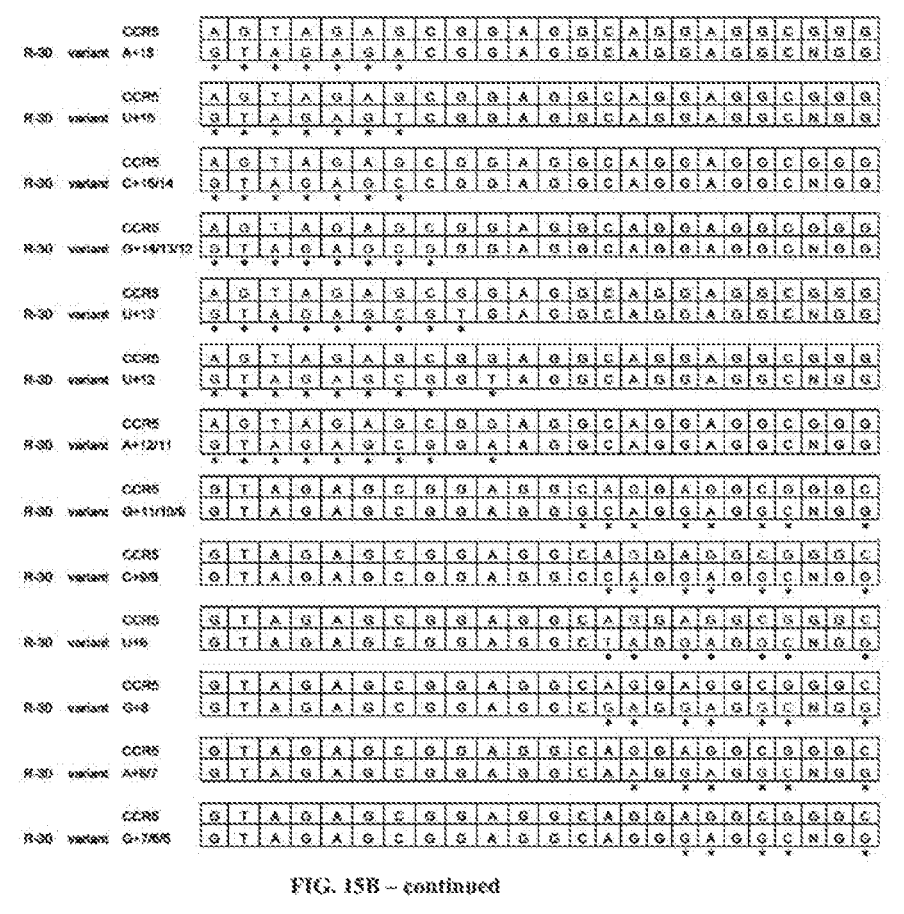

RNA-DNA interfaces with single-base RNA bulges can also be viewed as sequences with various mismatches in the guide sequence and PAM (FIG. 15A-15B). Specifically, sgRNA bulges at the 5'-end of guide RNA sequences (e.g. U+20/19 for R-01 and R-30 interfaces) can be alternatively viewed as having one to a few base mismatches with the 3'-end of DNA sequences (FIG. 15A-15B), which are often tolerated, similar to deletions of 1-2 bp at the 5' end of guide strands (FIG. 12A-12B). SgRNA bulges close to the 3'-end of guide sequence can be alternatively viewed as having base mismatches in the 3'-end region, including those at the third base of PAM (R-30 variants) (the last six variants in FIG. 15B). Among all sgRNA variants with considerable activities (FIG. 15A-15B), most of them could not be explained by tolerance of base mismatches, since they would contain more than five mismatches or change in the third base of PAM, which was shown to abolish cleavage activity (Hsu, et al., *Nat. Biotechnol*, 31:827-832 (2013)).

Figure 16A:
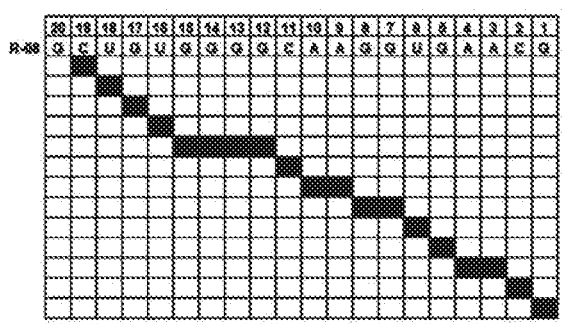
FIGS. 16A and 16C are grids showing the activity of Cas9 at the HBB target site carrying single-base DNA bulges (SEQ ID NOS 971-984, respectively, in order of appearance) (16A) or sgRNA bulges (SEQ ID NOS 971-984, respectively, in order of appearance) (16C) associated with different variants of the original sgRNAs R-08.
Figure 16B:
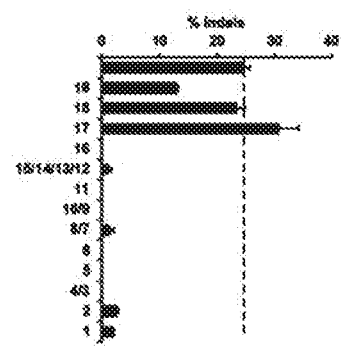
FIGS. 16B and 16D are bar graphs showing corresponding cleavage activities of 16A and 16C, respectively, quantified by T7EI assay in HEK293T cells. Positions relative to PAM and the single nucleotides added are labeled on the y-axis. Error bar, SEM (n=2).
Figure 16C:
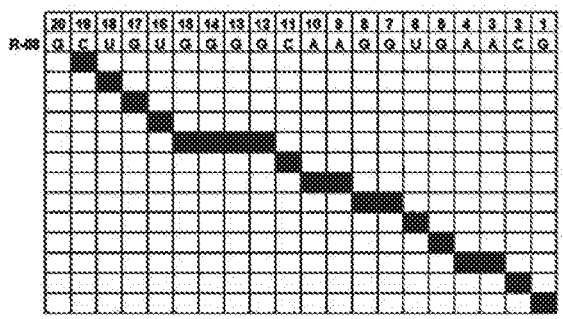
Figure 16D:
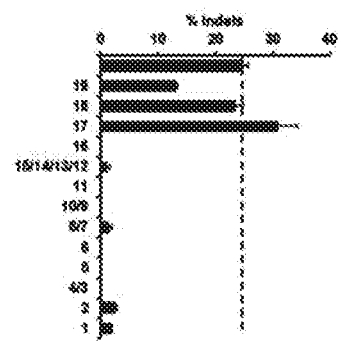

Example 5: GC (Guanine-Cytosine) Content of sgRNAs Effects the Tolerance of Single-Base sgRNA Bulges The specificity profile (location and level of off-target cleavage) of R-01 variants is substantially different from that of R-30 variants. R-30, which showed a higher level of tolerance to DNA and RNA bulges than R-01, has a GC content of 70%, whereas R-01 has a GC content of 50%. It was hypothesized that the GC content of guide strands R-01 and R-30 played a significant role in causing this difference. To investigate this hypothesis, two additional sets of guide strands targeted to HBB and CCR5 genes, respectively, were tested with different GC contents compared to R-01 and R-30 (Table 10).

to 70%). Cas9 induced cleavage with sgRNA variants of R-08 and R-25 was individually tested to quantify the bulge tolerance in HEK 293T cells. For the guide strand R-25, which contains a low percentage of GC, all R-25 variants tested showed non-detectable activities using the T7EI assay (Table 5). In contrast, for R-08 variants with bulges throughout the guide sequence, cleavage activities were observed at more positions compared with R-01 (FIG. 16B-16D). These results of bulge tolerance for variants of R-08 and R-25 support the GC dependence hypothesis.

Example 6: sgRNA Variants Containing 2- to 5-Bp Bulges Induce Cas9 Cleavage

Figures 17A, 17B:
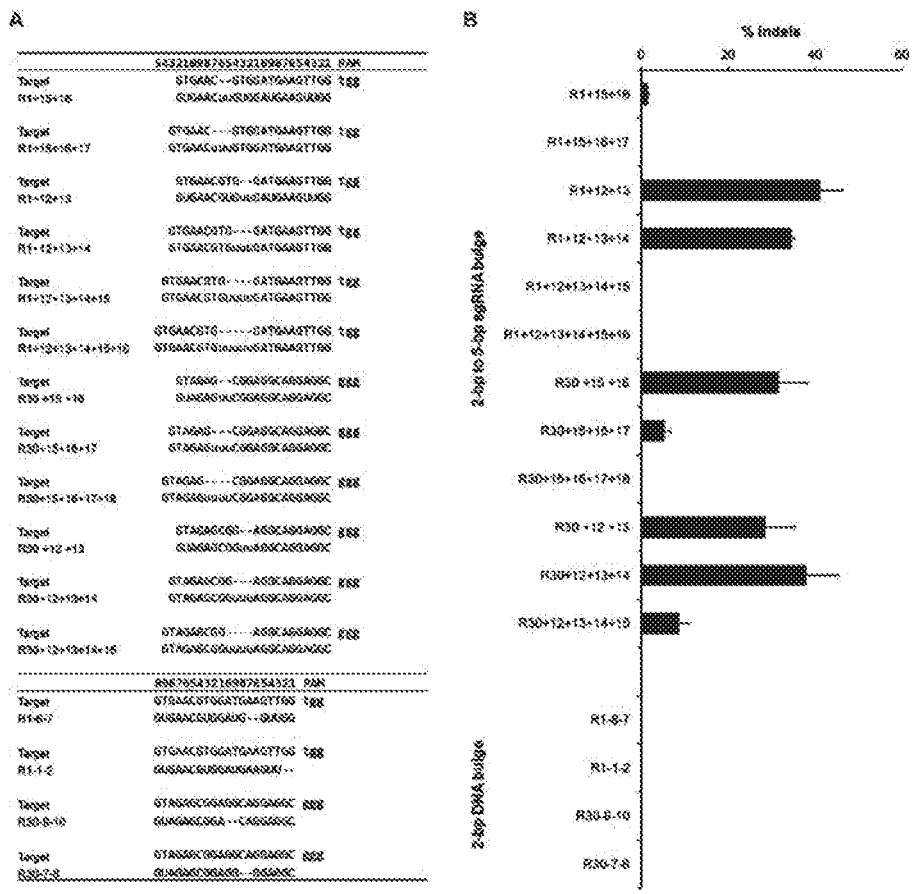
FIG. 17A is a series of sequence alignments comparing guide RNA variants (SEQ ID NOS 986-1002, respectively, in order of appearance) with insertions greater than one nucleotide and their original target sites ('GTGAACGTG-GATGAAGTTGGTGG' disclosed as SEQ ID NO: 985 and 'GTAGAGCGGAGGCAGGAGGCGGG' disclosed as SEQ ID NO: 992) R-01 or R-30. The guide RNAs are named for the position of the insertions.
FIG. 17B is a bar graph showing cleavage activities of the sgRNA variants shown in 17A quantified by T7EI assay in HEK293T cells. Error bar, SEM (n=2).

In addition to single-base bulges between sgRNA and target sequence, it is important to determine if bulges longer than 1 bp can also be tolerated by the CRISPR/Cas9 systems. Consequently, the tolerance of 2- to 5-bp bulges was tested at locations where single-base bulges were well tolerated. For sgRNA bulges, two to five U's 15- or 12-bp upstream of PAM were added into the guide sequences of R-01 and R-30, respectively. To generate DNA bulges, two bases were deleted from the guide sequences of R-01 and R-30 (FIG. 17A). Strikingly, sgRNA variants forming 2-, 3- and 4-bp RNA bulges induced cleavage activities as determined by the T7EI assay in HEK 293T cells (FIG. 17B). Since sgRNA variants forming 2-bp DNA bulges did not show any detectable activity, longer DNA bulges were not tested. The findings that sgRNA bulges of >2-bp are better tolerated than DNA bulges of similar size are consistent with the higher cleavage activities by guide strands with 1-bp sgRNA bulges compared to those with 1-bp DNA bulges as shown in FIGS. (9A-9C, 10A-10C, 13A-13B, and 14A-14B).

Example 7: sgRNA Variants Containing Single-Base Bulges can Mediate Cleavage by Paired Cas9 Nickases Paired Cas9 nickases (Cas9n) were developed to generate DNA double-strand breaks by inducing two closely spaced single-strand nicks using an appropriately designed pair of guide RNAs (Mali, et al., *Nat. Biolechnol*, 31:833-838 (2013); Ran, et al., *Cell*, 154:1380-1389 (2013)). This strategy may lower the off-target cleavage, as double stranded breaks (DSBs) could occur only when both guide RNAs of the pair induced two nicks adjacent to each other at roughly

TABLE 10

Target sites, cleavage activities (% indels by T7EI assay) and GC contents of different guide strands targeted to HBB and CCR5 genes. Table 10 discloses SEQ ID NOS 35, 41, 48 and 44, respectively, in order of appearance.

| Gene | Index | Protospacer Target (5' to 3') | PAM | % indels at target | % GC |
|---|---|---|---|---|---|
| HBB | R-01 | GTGAACGTGGATGAAGTTGG | TGG | 45% | 50% |
| HBB | R-08 | GCTGTGGGGCAAGGTGAACG | TGG | 45% | 65% |
| CCR5 | R-30 | GTAGAGCGGAGGCAGGAGGC | GGG | 30% | 70% |
| CCR5 | R-25 | GTGTTCATCTTTGGTTTTGT | GGG | 27%* | 35% |

*Cleavage activity of R-25 is from reference (Cradick, et al, Nucleic Acids Res., 41: 9584-9592 (2013)).

Specifically, R-08 has a moderately higher GC content compared to R-01 (65%9 compared to 50%), whereas the GC content of R-25 is half of that of R-30 (35% compared the same time. Assays were designed to test if paired Cas9n systems can tolerate bulges by using one bulge-forming guide variant paired with a perfectly matched guide strand.

Figures 18A, 18B:
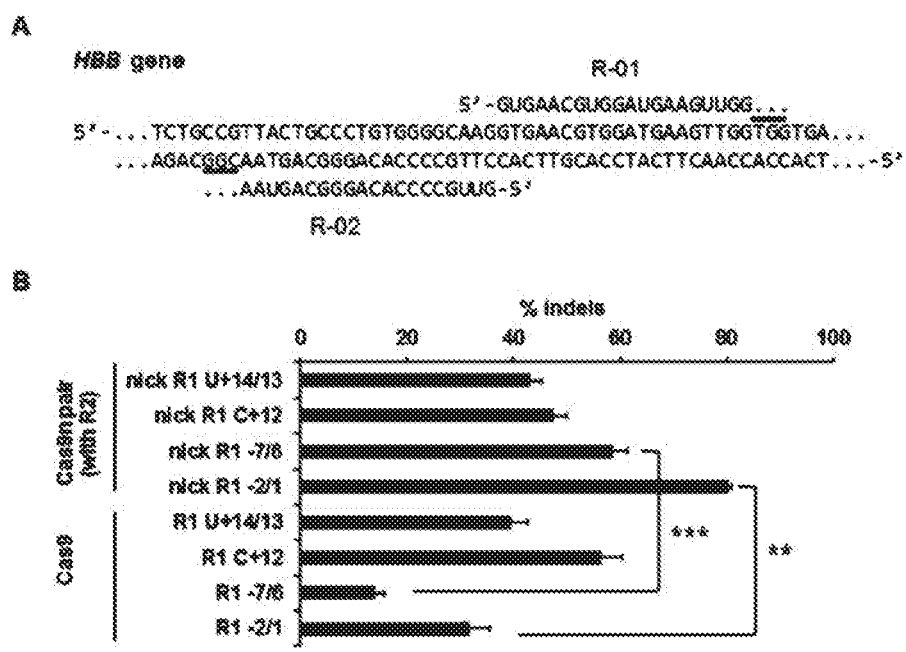
FIG. 18A is a sequence alignment showing the human HBB gene (SEQ ID NO: 1004) targeted by Cas9 nickases (Cas9n) with paired guide strands R-01 (SEQ ID NO: 1003) and R-02 (SEQ ID NO: 1005). PAMs are indicated with bars.
FIG. 18B is a bar graph showing T7EI activities of Cas9n with R-01 bulge-variants paired with R-02, compared with original Cas9 activities of the R-0 bulge-variants as in FIGS. 9-10 and 13-14. Error bar, SEM (n=2). Asterisks indicate P-values from a two-tailed independent two-sample t-test. *P<0.05, P<0.01, *P<0.001.

Specifically, four variants of R-01 showing high activities with Cas9 were paired with R-02, including R1 U+14/13 and R1 C+12 to test sgRNA bulges and R1−7/6 and R1−2/1 to test DNA bulges. Each paired sgRNAs created a 34-bp 5' overhang in the HBB gene (FIG. 18A) (Cradick, et al., *Nucleic Acids Res.*, 41:9584-9592 (2013)), and the Cas9n cleavage activities were determined by the T7EI assay. The results show that both sgRNA and DNA bulges were also well tolerated in the Cas9n system (FIG. 18B). The paired Cas9 nickases with single sgRNA bulges showed activities comparable to Cas9 system having one bulge in R0-1: however, for DNA bulges, the activities of paired Cas9 nickases were >2-fold higher than that of Cas9.

Example 8: Cas9 Cleavage Occurs at Genomic Loci with Both Base Mismatches and DNA or sgRNA Bulges Materials and Methods Identification of Off-Target Sites Potential off-target sites in the human genome (hg19) were identified using TagScan (http://www.isrec.isb-sib.ch/tagger), a web tool providing genome searches for short sequences (Iseli, et al., *PLoS One*, 2:e579 (2007)). Guide sequences containing single-base insertions (represented with an 'N' in the sequence) and single-base deletions at different positions were entered, followed by the PAM sequence 'NGG'. Off-target sites were alternatively searched for using the recently developed bioinformatics program COSMID that can identify potential off-target sites due to insertions and deletions between target DNA and guide RNA sequences (disclosed herein). Primers were individually designed to amplify the genomic loci identified in the output.

Quantitative PCR to Measure the Expression Levels of Different Guide RNAs

HEK 293T cells were transfected with 750 ng sgRNA variants, as described above. Each sgRNA was transfected as biological triplicates in three separate wells and processed independently. Total RNA was isolated from cells using the RNAeasy kit (Qiagen). Extracted RNA was reverse-transcribed using the iScript cDNA Synthesis (BioRad). The cDNA was amplified using the iTaq Universal SYBR Green Supermix (BioRad) and analyzed with quantitative PCR using specific primers that annealed at 60° C. (Tables 6-7). Quantitative PCR was performed in technical triplicates for each cDNA sample from single transfected well. Relative mRNA expression was analyzed using an MX3005P (Agilent) and normalized to glyceraldehyde-3-phosphate dehydrogenase (GAPDH) expression. GAPDH expression remained relatively constant among treatments.

Relative mRNA expression of target genes was calculated with the ddCT method. All target genes were normalized to GAPDH in reactions performed in triplicate. Differences in CT values ($\Delta CT=CT$ gene of interest−CT GAPDH in experimental samples) were calculated for each target mRNA by subtracting the mean value of GAPDH. $\Delta CT$ values were subsequently normalized to the reference sample (mock transfected cells) to get $\Delta\Delta CT$ or ddCT (relative expression=$2-\Delta\Delta CT$).

Deep Sequencing to Determine Activities at Genomic Loci

Genomic DNAs from mock and nuclease-treated cells that were prepared for T7EI assays were used as templates for the first round of PCR using locus-specific primers that contained overhang adapter sequences to be used in the second PCR. Table 11 shows primers used in PCRs for deep sequencing by an Illumina Miseq 2X250 paired-end read. These reactions were sequenced as in Lin *Nucleic Acids Research* 2014. Primers for reaction 1 contains adapter sequences shown (same adapter sequences also present in reaction-2 primers), in addition to gene-specific sequences. In the final pooled sample containing all the amplicons, each barcode has similar occurrence to insure diversity required by Illumina sequencing. Customer sequencing primers for read 1 (forward), read 2 (reverse), and index read (read barcodes) are used in place of standard Illumina sequencing primers.

TABLE 11

Sequencing primers (SEQ ID NOS 564-581, respectively, in order of appearance)

| Primer for illumina reaction 1 | |
|---|---|
| Forwars | TCTACAGTCCGACGATCA-gene specific sequence |
| Reverse | GACGTGTGCTCTTCCGATC-gene specific sequence |

Primers for illumina reaction 2
Forward primer
Rxn2For
Reverse primer with 12 different barcodes

| | | |
|---|---|---|
| Kozich_bar_1 | CAAGCAGAAGACGGCATACGAGatATACTTCG | ATGTGACTGGAGTTCAGACGTGTGCTCTTCCGATC |
| Kozich_bar_2 | CAAGCAGAAGACGGCATACGAGatATACTTCG | ATGTGACTGGAGTTCAGACGTGTGCTCTTCCGATC |
| Kozich_bar_3 | CAAGCAGAAGACGGCATACGAGatAGCTGCTA | ATGTGACTGGAGTTCAGACGTGTGCTCTTCCGATC |
| Kozich_bar_4 | CAAGCAGAAGACGGCATACGAGatCATAGAGA | ATGTGACTGGAGTTCAGACGTGTGCTCTTCCGATC |
| Kozich_bar_5 | CAAGCAGAAGACGGCATACGAGatCGTAGATC | ATGTGACTGGAGTTCAGACGTGTGCTCTTCCGATC |
| Kozich_bar_6 | CAAGCAGAAGACGGCATACGAGatCTCGTTAC | ATGTGACTGGAGTTCAGACGTGTGCTCTTCCGATC |
| Kozich_bar_7 | CAAGCAGAAGACGGCATACGAGatGCGCACGT | ATGTGACTGGAGTTCAGACGTGTGCTCTTCCGATC |
| Kozich_bar_8 | CAAGCAGAAGACGGCATACGAGatGGTACTAT | ATGTGACTGGAGTTCAGACGTGTGCTCTTCCGATC |
| Kozich_bar_9 | CAAGCAGAAGACGGCATACGAGatGTATACGA | ATGTGACTGGAGTTCAGACGTGTGCTCTTCCGATC |

TABLE 11-continued

Sequencing primers (SEQ ID NOS 564-581, respectively, in order of appearance)

| | | |
|---|---|---|
| Kozich_bar_10 | CAAGCAGAAGACGGCATACGAGatTACGAGCA | ATGTGACTGGAGTTCAGACGTGTGCTCTTCCGATC |
| Kozich_bar_11 | CAAGCAGAAGACGGCATACGAGatTCAGCGTT | ATGTGACTGGAGTTCAGACGTGTGCTCTTCCGATC |
| Kozich_bar_12 | CAAGCAGAAGACGGCATACGAGatTCGCTACG | ATGTGACTGGAGTTCAGACGTGTGCTCTTCCGATC |

Custom sequencing primer

| | |
|---|---|
| NewIndex_Read | GATCGGAAGAGCACACGTCTGAACTCCAGTCACAT |
| NewRead_1 | TCTACACGTTCAGAGTTCTACAGTCCGACGATCA |
| NewRead_2 | TGTGACTGGAGTTCAGACGTGTGCTGTTCCGATC |

PCR reactions for each locus were performed independently for eight touchdown cycles in which annealing temperature was lowered by 1° C. each cycle from 65 to 57° C., followed by 35 cycles with annealing temperature at 57° C. PCR products were purified using Agencourt AmPure XP (Beckman Coulter) following manufacturer's protocol. The second PCR amplification was performed for each individual amplicon from first PCR using primers containing the adapter sequences from the first PCR, P5/P7 adapters and sample barcodes in the reverse primers (Table 11). PCR products were purified as in first PCR, pooled in an equimolar ratio, and subjected to 2×250 paired-end sequencing with an Illumina MiSeq.

Paired-end reads from MiSeq were filtered by an average Phred quality (Q score) greater than 20 and merged into a longer single read from each pair with a minimum overlap of 10 nucleotides. Alignments were performed using Borrows-Wheeler Aligner (BWA) for each barcode (Li, et al., Bioinformatics, 26:589-595 (2010)) and percentage of insertions and deletions containing bases within a ±10-bp window of the predicted cut sites were quantified. Error bounds for indel percentages are Wilson score intervals calculated using binom package for R statistical software (version 3.0.3) with a confidence level of 95% (32). To determine if each off-target indel percentage from a CRISPR-treated sample is significant compared to a mock-treated sample, a two-tailed P-value was calculated using Fisher's exact test.

Results

Figures 19A, 19B:
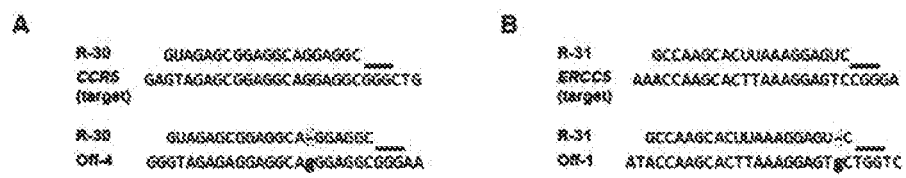
FIGS. 19A and 19B are sequence alignments showing on-target and off-target alignments containing bulges for sgRNAs R-30 targeted to CCR5 gene (SEQ ID NOS 1006-1007, 1006 and 1008, respectively, in order of appearance) (19A), and R-31 target to ERCC5 gene (SEQ ID NOS 1009-1010, 1009 and 1011, respectively, in order of appearance) (19B). Upper: guide strands aligned to target sequences (CCR5 and ERCC5). Lower: guide strands (R-30 and R-31) aligned to off-target sequences (Off-4 and Off-1) each with a DNA bulge compared to the sgRNA (R-30 and R-31) tested. Off-4 has a mismatch with R-30, 14 nt from the PAM. Horizontal lines indicate the PAM. The mismatch shown between the initial G in sgRNA R-31 and the corresponding nt in its target site or in Off-1 does not affect binding, or cleavage. After transfection of R-30 and R-31 expression plasmids, and tissue culture for 2 days, the genomic DNA was harvested and amplified by flanking primers.
Figures 19C, 19D, 19E:
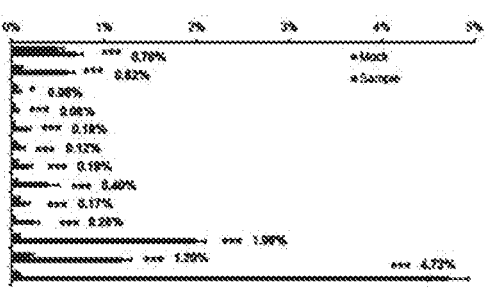
FIGS. 19C and 19D display the mutations, insertions and deletions introduced by mis-repair after cleavage at these sites. The Sanger sequencing reads of amplified off-target sites are aligned to the wild-type genomic sequence and sgRNAs for R-30 (SEQ ID NOS 1012-1024, respectively, in order of appearance) (19C) and R-31 (SEQ ID NOS 1025-1028, respectively, in order of appearance) (19D). The number of times each sequence occurred is indicated to the left of the alignment, if greater than one. Unmodified reads are indicated by 'WT'. Deletions are marked with a dash ('-') and insertions marked in shaded.
FIG. 19E is a bar graph showing activities (indel percent) analyzed by deep sequencing at genomic off-target loci containing bulges coupled with mismatches and in some cases alternative NAG-PAMs. The level after CRISPR treatment with the indicated guide strand is graphed against mutations detected in mock treated samples (likely by mis-reads) (top bar in each pair, outlined) and treated samples (bottom bar in each pair) with sgRNAs at off-target loci (SEQ ID NOS 1029-1041, respectively, in order of appearance) shown in the table to the left. The table on the left shows numbers of mismatches at off-target loci in addition to bulge (no. of mis), bulge types, positions of bulges from PAM (bulge pos), labels for the loci and sequences of off-target sites including PAMs. In these off-target genomic sequences, mismatches are lighter, deleted base compared to sgRNA marked as '-' (sgRNA bulge), inserted base compared to sgRNA marked as underlined letters (DNA bulge). Error bars, Wilson intervals (see 'Materials and Methods' section). *P≤0.05, ***P≤0.001 as determined by Fisher's exact test. The % indel values of treated samples are also indicated.
Figures 23A, 23B, 23C:
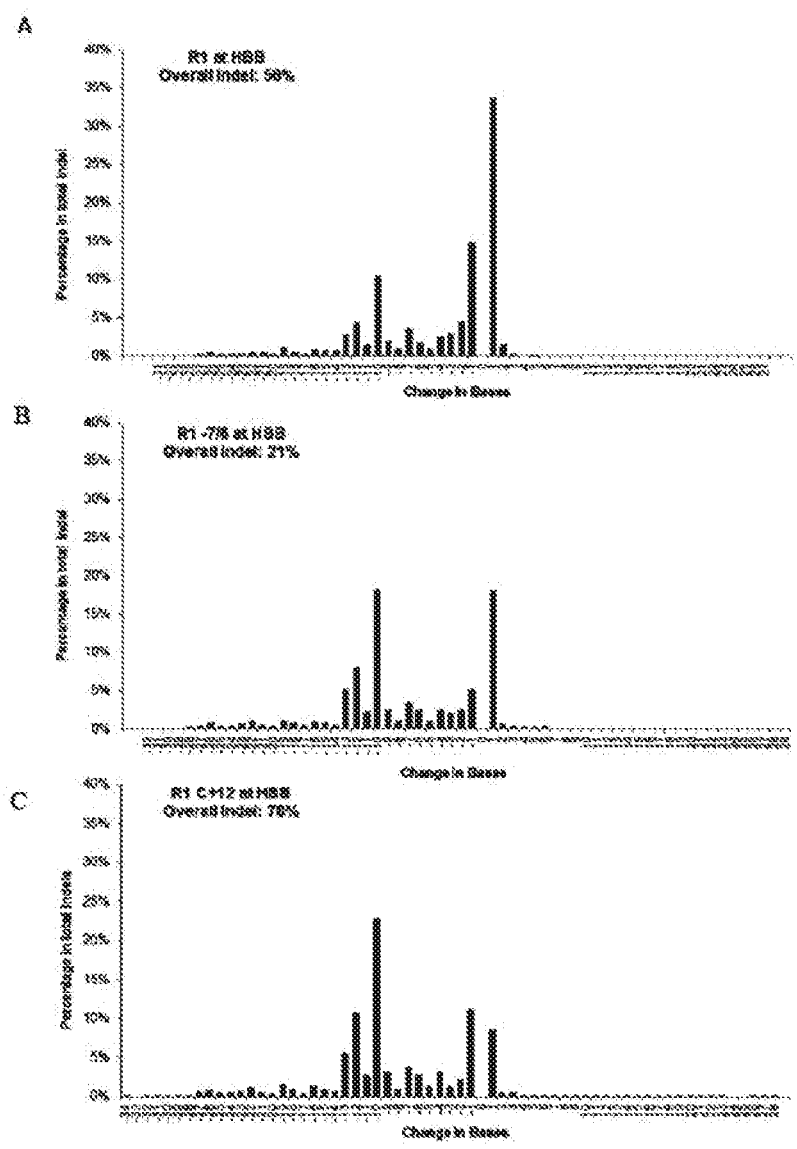
FIGS. 23A-23C are bar graphs showing the range of insertions and deletions introduced with matching guide strand and guide strands with bulges (the indel spectra, the percent in total indels mapped against change in bases) for original sgRNAs and sgRNA variants determined using deep sequencing for R-01 original sgRNA (23A), and variants for DNA bulge (R1−7/6) (23B) and sgRNA bulge (R1 C+12) (23C). The change in bases at predicted cut sites resulting from indicated sgRNAs was calculated from ~$10^4$ reads per sample. The y-axis represents percentages in all indel-reads for that sgRNA. Overall % indel in total reads are indicated in each graph.
Figures 24A, 24B, 24C:
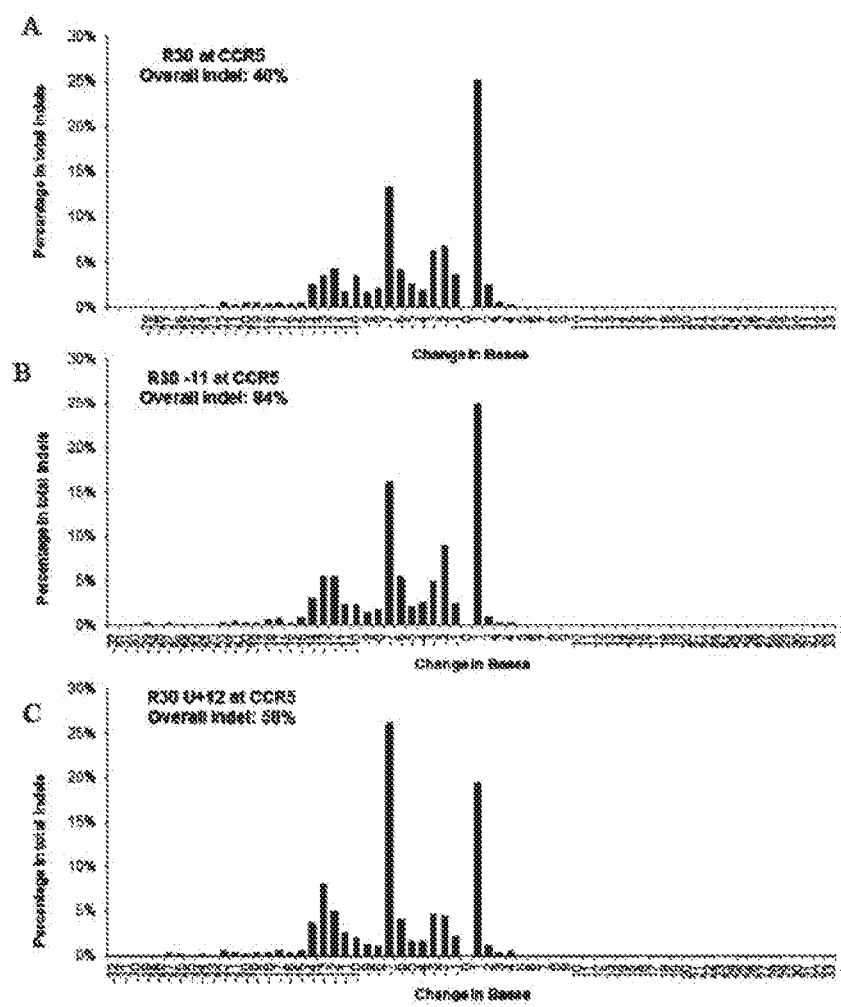
FIGS. 24A-24C are bar graphs showing indel spectra (percent in total indels mapped against change in number of bases) for original sgRNAs and sgRNA variants determined using deep sequencing for R-30 original sgRNA (24A), and variants for DNA bulge (R30−11) (24B) and sgRNA bulge (R30 U+12) (24C). The change in bases at predicted cut sites resulting from indicated sgRNAs was calculated from ~$10^4$ reads per sample. The y-axis represents percentages in all indel-reads for that sgRNA. Overall % indel in total reads are indicated in each graph. Expression of Cas9 and the original guide strand or guide strand with indels result in insertions or ranges of deletions.

To gain a better understanding of CRISPR/Cas9 off-target activity, 27 different sgRNAs targeting six different genes (Table 4), seven targeted HBB, two for EGFP, five for CCR5, seven for ERCC5, four for TARDBP and two for HPRT1, respectively, were examined. Off-target analyses of these sgRNAs were performed by searching the human genome for potential off-target sites and found that for the sgRNAs searched, single-base DNA or sgRNA bulges were not located without mismatches in the human genome. Therefore, for each sgRNA, a subset of the potential sites with one to three mismatches was selected and avoided mismatches close to the PAM as much as possible. All of these sgRNAs efficiently induced mutations at their intended target loci in human HEK293T cells, as measured by the T7EI assay. Using the T7EI assay, 18 potential off-target sites containing target-site insertions and 62 containing deletions were investigated (Table 8). Two sgRNAs targeted to CCR5 and ERCC5, respectively, also induced cleavage at two off-target sites each bearing one DNA bulge and one mismatch (FIGS. 19A and 19B). For R-30, the identified off-target site R-30 Off-4 contains a single-base DNA bulge at position 5, 6 or 7 and a base mismatch at position 14. The off-target gene modification rate determined by T7EI is 9%, almost one third of the 30% on-target activity at the CCR5 gene (FIG. 19A). For an R-31 off-target site with a single-base DNA bulge at position 2 and a mismatch at position 20, the off-target gene modification rate determined by T7EI was 3%, compared to 60% on-target activity at the ERCC5 gene (FIG. 19B). Due to the high frequency of small indels (insertions and deletions) that result from repair of Cas9 induced cleavage, which may be poorly detected by the T7EI assay, the mutagenesis at these off-target sites was verified using Sanger sequencing (FIGS. 19C and 19D). For both off-target sites, the mutation frequencies quantified by Sanger sequencing are higher than those by T7EI, which is consistent with a previous study (Cradick, et al., Nucleic Acids Res., 41:9584-9592 (2013)). No off-target cleavage was observed for the 62 sites tested with both sgRNA bulge and base mismatch, although in the model systems with sgRNA bulges only, high cleavage activities were observed (FIG. 13A-14B). This discrepancy indicates that sites forming sgRNA bulges may be less tolerant to additional base mismatches and vice versa.

Two genomic off-target sites for guide strand R-30, Off-4 and Off-5, have identical target sequences (Table 8), but were cleaved at different rates. Specifically, R-30 Off-4 had a cleavage rate of 9%, while the cleavage at Off-5 was undetectable with the T7EI assay (FIG. 20). Sanger sequencing revealed a 45.5% mutation rate at the R-30 Off-4 locus (FIG. 19C), compared to a 4.2% mutation rate at R-30 Off-5 (FIG. 20). Since R-30 Off-4 and R-30 Off-5 sites have identical sequences, the results indicate that off-target cleavage of Cas9 nuclease is very dependent on genomic context (Cradick, et al., Nucleic Acids Res., 41:9584-9592 (2013)). Further investigation of these two sites using the ENCODE annotation from UCSC genome browser (Rosenbloom, et al., Nucleic Acids Res., 41:D56-D63 (2013): Landt, et al., Genome Res., 22:1813-1831 (2012)) revealed that R-30 Off-4, which had high off-target activity, targeted a site within 400 bp of the 3' end of a long non-coding RNA (RP4-756H11.3) and 12 kb of the protein-coding gene RABGEF. Analysis of the ENCODE data for chromatin structure in normal human embryonic kidney cells (NHEK) cells, the cell type of origin for the HEK293 cells used in this study shows Off-4 to be within 3 kb of a strong enhancer (marked by H3K27Ac and H3K4me1) and a strong DNAse1 hypersensitive site, indicative of an open chromatin structure. In contrast, R-30 Off-5, which had low activity, targeted a site in a 162-kb intergenic region between the WBSCR28 and ELN genes that is marked by the more heterochromatic H3K27me3, and hence may be less accessible for Cas9 induced cleavage (FIGS. 21A and 21B). Taken together, these data lead to a conclusion that differences in the local chromatin structure may underlie the observed differences in cleavage efficiency between Off-4 and Off-5.

Deep sequencing was performed at 55 putative off-target sites corresponding to single-base sgRNA bulges and 21 sites corresponding to single-base DNA bulges. The sites were amplified from genomic DNA harvested from HEK 293T cells transfected with Cas9 and sgRNAs. The 55 sites with sgRNA bulges contain 35 sites tested in the preliminary T7EI assay, and the 21 sites with DNA bulges include seven sites tested in the T7EI assay. Putative bulge-forming loci containing one to three PAM-distal mismatches were chosen, since sites associated with a bulge without any base mismatch were not found. Some of the bulge-forming sites with a high level of sequence similarity, but containing an alternative NAG-PAM were also selected. For comparison, the deep sequencing also investigated 16 on-target sites of the sgRNAs tested. Each locus was sequenced from mock-transfected cells as control.

An additional 13 bulge-forming off-target sites with low, but significant cleavage activities resulted from CRISPR/Cas9 systems compared to the mock-transfected samples (FIG. 19E). The number of genomic off-target cleavage sites associated with sgRNA bulges was relatively small (some of these cases are indistinguishable from a few mismatches at 5' end), but there was considerable activity at genomic sites with DNA bulges coupled with one to three additional base mismatches, even with an alternative NAG-PAM (R30_ins_10 and R30_ins_14). Similar results showing more off-target effect with DNA bulges plus mismatches compared to sgRNA bulges plus mismatches were observed in the preliminary T7EI assay (FIGS. 19A and 19B). The positions of these tolerated DNA bulges are 1-3 and 7-10 bp from PAM, consistent with the results from the model systems using sgRNA variants. The majority of the sites with off-target activities detected, as shown in FIGS. 19A, 19B and 19E are associated with the sgRNA R-30, which has a high GC content (70%). Other sgRNAs that resulted in off-target cleavage at bulge-forming loci have GC content≥50%.

In summary, Examples 3-8 show that CRISPR/Cas9 systems can have off-target cleavage when DNA sequences have an extra base (DNA bulge) or a missing base (sgRNA bulge) at various locations compared with the corresponding RNA guide strand. sgRNA bulges of up to 4-bp could be tolerated by CRISPR/Cas9 systems (FIGS. 17A-17B). The correlation between cleavage activity and the position of DNA bulge or sgRNA bulge relative to the PAM appears to be loci and sequence dependent when comparing the specificity profiles of guide sequences R-01 and R-30.

It is believed that the following design guidelines will help reduce potential off-target effects of CRISPR/Cas9 systems: (i) conservatively choose target sequences with relatively low GC contents (e.g. ≤35%), (ii) avoid target sequences (with either NGG- and NAG-PAM) with ≤3 mismatches that form DNA bulges at 5' end, 3' ends or around 7-10 bp from PAM and (iii) if possible, avoid potential sgRNA bulges further than 12 bp from PAM.

Different specificity profiles of R-01 and R-30 guide sequences (and variants) are not due to different expression levels of the sgRNAs. Quantitative PCR of inactive R-01 variants and active R-30 variants indicated similar sgRNA expression levels (FIG. 22). It is believed that high GC-content, which makes the RNA/DNA hybrids more stable (Sugimoto, et al., Biochemistry, 34:11211-11216 (1995)), may be responsible for increased tolerance of DNA bulges and sgRNA bulges. Consistent with this belief, guide strand R-30 (70% GC) showed the highest tolerance to sgRNA and DNA bulges among the four guide strands tested (R-01, R-08, R-25 and R-30), while guide strand R-25 (35% GC) does not seem to tolerate any bulges. Guide sequences showing bulge-related off-target activity in FIGS. 19A-19E all have GC contents≥50%, which further confirms that it is important to consider DNA-bulges for sgRNAs with high GC content, even with up to three base mismatches, when investigating off-target effects.

As shown in FIGS. 11A-11B and 12A-12B, bulges in the PAM distal or PAM proximal regions can reflect either mismatch tolerance or RNA-DNA bulge tolerance. In a bioinformatics search considering base mismatches only, some of the potential off-target sites identified may overlap with a search considering bulges. Although in both scenarios the mismatch and bulge-containing sites should be tested for off-target cleavage, a better understanding of the bulge tolerance as well as the difference in the mechanisms underlying these two scenarios is needed. One study revealed that a Cas9 ortholog from *Streptococcus thermophilus* has a PAM located 2 bps downstream of the protospacer (Chen, et al., *J. Biol. Chem.*, (2014). in press.). Thus, the cleavage resulting from the variant R-01-2/1 (FIGS. 9A-9B) may reflect the tolerance of a linker between the target sequence and PAM instead of a DNA-bulge. On the other hand, Cas9 cleavage with RNA or DNA bulges in the middle of the target sequence may reflect only the bulge tolerance.

An interesting finding from this study is that sgRNA variants with bulges had different indel spectra than sgRNA without bulges (FIGS. 23A-23C and 24A-24C). Indel spectra for original sgRNAs R-01 and R-30, as well as sgRNA variants R1–7/6, R1 C+12, R30–11 and R30 U+12, were quantified using deep sequencing with around $10^4$ reads for each sample. Bulge-forming sgRNA variants showed higher ratios of larger deletions (Δ10 or Δ7), whereas the original sgRNAs without bulges generate mostly 1-bp insertions. This effect is more prominent for variants forming sgRNA bulges (R1 C+12 and R30 U+12). Bulge-forming sgRNA variants may be more effective than regular sgRNAs in creating larger deletions that might be preferred in certain applications, such as targeted disruption of genomic elements. These larger deletions may also occur at off-target loci, which strengthens the need to include them in genomic searches.

Recently, paired Cas9 nickases have been shown to increase target specificity of CRISPR/Cas9 systems. However, only off-target activity associated with single guide RNAs were investigated (Mali, et al., *Nat. Biotechnol*, 31:833-838 (2013); Ran, et al., *Cell*, 154:1380-1389 (2013)), and the effect of cooperative nicking at potential off-target sites with sequence similarity to a pair of guide RNAs has not been characterized. Examples 3-8 show that Cas9n is able to cleave efficiently at target sites despite a single-base bulge in one of the paired guide RNAs. The results of this work provide some insight into off-target cleavage of the paired Cas9 nickases, as nicking of opposite DNA strands is likely to be independent events and the knowledge of bulge tolerance at the sgRNA-DNA interface would be applicable to off-target cleavage of Cas9 nickases.

Recent studies on the specificity of CRISPR/Cas9 systems revealed that a broad range of partial matches between sgRNA and DNA sequences could induce off-target cleavage (Fu, et al., *Nat. Biotechnol*, 31:822-826 (2013): Hsu, et al., *Nat. Biotechnol*, 31:827-832 (2013): Pattanayak, et al.,

*Nat. Biotechnol*, 31:839-843 (2013); Cradick, et al., *Nucleic Acids Res.*, 41:9584-9592 (2013)), which may limit the choice of sgRNA designs. While the use of existing bioinformatic tools based on base mismatches is certainly useful for predicting the most likely potential off-target sites, it might miss some important sites, since there would be too many base mismatches if bulges were not allowed to form in the middle of a target sequence, so the potential off-target sites with bulges are not likely to be included in the output of these search tools. Therefore, based on these results, it is preferable to search partially matched sequences including base mismatches, deletions and insertions and their combinations in identifying off-target sites. Since there might be a large number of potential off-target sites due to the many partially matched sequences, and the effect of sgRNA-DNA sequence differences on off-target cleavage is target-site and genome-context dependent, experimentally determining the true off-target activities is preferred, including the use of deep sequencing.

Example 9: COSMID Search Algorithm and Web Interface

Materials and Methods
COSMID Search Inputs
To perform a COSMID search, the genome of interest, guide strand, PAM sequence, and the number of base mismatches, insertions, and deletions allowed are specified (FIG. 25A, FIG. 26A-26G, Table 12 below). Three types of indel query are allowed: (i) the number of mismatches with no insertion or deletion (No indels); (ii) the number of mismatches in addition to a single-base deletion (Del); and (iii) the number of mismatches in addition to a single-base insertion (Ins). Up to three mismatches without indels, and up to two mismatches together with a one-base insertion or deletion could be chosen. If primers are desired, primer design parameter settings and parameter templates should also be entered (FIG. 25A). PAM variants, such as NRG can be entered in the suffix box, as well as other PAM sequences (Fischer, et al., *J Biol Chem*, 287:33351-33363 (2012)). The spacer (Ns) and required nucleotides are entered into the suffix box, such as "NNNNGATT" (Hou, et al., *Proc Natl Acad Sci USA*, 110: 15644-15649 (2013)), and include genomic sites with any nucleotide at the N positions in the output.

Before performing the search. COSMID constructs a series of search entries according to the user-specified guide strand and search criteria (FIG. 25B). The search entries include all insertions and deletions at each possible location (FIG. 25C), and are subsequently used to perform rapid and accurate searches of the entire sequence of the interested genome, while allowing for the user-specified number of mismatches. These searches took ~4 seconds without primer design (FIG. 26A-26G).

Although multi-base deletions (RNA bulges) and insertions (DNA bulges) could be tolerated (Lin, et al., *Nucleic Acids Res*, 42:7473-7485 (2014)), they are less common, and search for a wide range of insertions and deletions will likely result in a very large number of returned sites. Therefore, COSMID only allows searches for single-base insertions and deletions in the DNA sequence compared with the guide strand (FIG. 25A). For the potential off-target sites, the search algorithm allows some ambiguities (such as N for any nucleotide). Ambiguities included in the search string are marked in red in the HTML results (as are mismatches and indels), but are not counted toward the user-specified mismatch limits. The use of ambiguities allows the inclusion of the matching genomic base with the output sequences. One possibility is to include an "N" in positions that can have substitutions, such as the first base in a guide strand that is often a G primarily to aid in transcription, but does not need to match the complementary target sequence (Hsu, et al., *Nat Biotechnol*, 31: 827-832 (2013); Cradick, et al., *Nucleic Acids Res*, 41:9584-9592 (2013); Mali, et al., *Science*, 339: 823-826 (2013). One can leave off this base when performing a search, or include a 5' N in the search string, which allows COSMID to output and align to the "N," the corresponding 5' bases at each locus.

COSMID Search Outputs
COSMID outputs all genomic sequences that match the user-supplied search criteria in comparison with the entered guide strand. The first column of the HTML output shows the genomic sequence ("hit") aligned to the query sequence with matches shown in black. Nucleotides that are not a direct match are shown, including mismatches, insertions, and deletions (Table 12). Ambiguities in the query sequence, such as the N in the PAM sequence NGG, are also shown in red, though they do not count as mismatches. The second column lists the query type, including (i) no deletion or insertion (No indel), (ii) deletions (Del), or (iii) insertions (Ins). This column indicates if there are insertions or deletions, and specifies the indel positions as the number of nucleotides away from the PAM. The third column lists the number of mismatched bases between the query and target sequences. When two repeated bases appear in the guide strand, a deletion of either one of them in the target sequence gives the same query sequence, so the ambiguity is noted in the query column. The fourth column indicates if the PAM in the hit ends in RG, as NGG is the Cas9 PAM with the highest activity, followed by NAG (Hsu, et al., *Nat Biotechnol*. 31: 827-832 (2013)). This column helps in ruling out genomic sites with unlikely PAMs. This function must be added to the excel spreadsheet for other PAMs. The fifth, sixth, and seventh columns contain respectively the chromosomal location of the matching sequence, its strand and the chromosomal location of the cleavage site. The predicted cleavage position is based on the fact that Cas9 primarily cleaves both DNA strands three nucleotides from the PAM (Jinek, et al., *Science*, 337: 816-821 (2012)). The HTML links included in the COSMID output are directed to the chromosomal sites in the UCSC genome browser. This allows determination of the gene that best matches the target sequence and if the target site is in an exon, intron, or other region. This information is helpful as mutations may be better tolerated in regions that are noncoding and nonfunctional.

The output is grouped by query types, including (i) genomic sites with base mismatches, but no insertions or deletions (No indels). (ii) sites with deletions (Del), and (iii) sites with insertions (Ins) between the query and potential off-target sites (Table 12). Within each category, sites with mismatches further from the PAM are listed first, which are more likely to result in off-target cleavage (Fu, et al., *Nat Biotechnol*, 31: 822-826 (2013); Hsu, et al., *Nat Biotechnol*, 31: 827-832 (2013); Cradick, et al., *Nucleic Acids Res*, 41:9584-9592 (2013). The same genomic location may satisfy two or more search criteria, such as those sites that satisfy the mismatched base limit without and with an insertion or deletion. For example, mismatches at the base farthest from the PAM and deletions of this base will give the same set of genomic locations. This can also occur when the guide strand contains consecutively repeated bases. Since genomic locations can be specified through multiple criteria (examples shown in FIGS. 28A and 28B), they are listed in each of the corresponding groupings to aid further evaluation and scoring. Duplicate sites can be removed in the spreadsheet, as described below.

COSMID also outputs the potential off-target sites identified in a spreadsheet to allow for further processing, such as sorting by attributes or adding weight matrixes to rank the most likely off-target sites. The accumulation of additional experiments on CRISPR off-target activity will allow creation of a more predictive scoring system. It is thought that mutations in the PAM are least well tolerated followed by sites closest to the PAM; however, little is known about how the guide strand sequence influences these effects (Jinek, et al., *Elife* 2:e00471 (2013); Fu, et al., *Nat Biotechnol*, 31: 822-826 (2013); Hsu, et al., *Nat Biotechnol*, 31: 827-832 (2013); Cradick, et al., *Nucleic Acids Res*, 41:9584-9592 (2013)). The spreadsheet can also be used to indicate duplicate genomic sequences found using different search criteria, as mentioned above. The output list of off-target sites allows a user to compare the number and score of off-target sites for the input target sites.

COSMID Primer Design

COSMID's primer design function is used to assay for off-target cleavage after cells or animals are treated with CRISPR guide strands and nuclease. Primers are designed that fit the criteria needed for the particular assay or sequencing platform using an automated primer pair design process, not found in other CRISPR programs. The algorithm was developed for the zinc finger nucleases and TAL effector nucleases off-target search program PROGNOS and found to give a single specific band in ~93% of amplifications (Fine, et al., *Nucleic Acids Res*, 42:e42 (2013)). The automated primer design alleviates the need for the iterative steps of primer design and verification of the resulting fragment sizes, that slow primer design, especially for mutation detection assays where the cleavage product sizes determine how easily the cleavage bands can be distinguished on gels. The recommended parameters for use in Surveyor assays resolved on 2% agarose gels are: Minimum Distance Between Cleavage Bands—100 bp, Minimum Separation Between Uncleaved and Cleaved Products—150 bp. Users can also input the number of bases the cleavage site must be from each amplicon's edge to ensure sequencing coverage depending on the different sequencing platforms. For single molecule, real-time (SMRT) sequencing, the recommended parameters are: Minimum Distance Between Cleavage Bands—0, Minimum Separation Between Uncleaved and Cleaved Products—125 bp. The output primers can be easily modified in the spreadsheet, such as to add flanking sequences for additional amplification and/or barcodes for sequencing.

Results

The COSMID algorithm is based on sequence homology: it searches a genome of interest for sites similar to CRISPR guide strands using the efficient FetchGWI search program that has powered search tools including TagScan34 and ZFN-site (Cradick, et al., *BMC Bioinformatics*, 12:152 (2011)). FetchGWI operates on indexed genome sequences that are precompiled and stored (FIGS. 26A-26G). It can identify genomic locations with sequences that match any of the series of search entries. FetchGWI saves run time by searching indexed files that represent the genome sequences, rather than the sequences themselves. There is one index entry for each nucleotide in the genome, which allows a rapid and exhaustive search. This is a key advantage of COSMID over BLAST and other programs that scan non-overlapping words and may miss potential off-target sites (Cradick, et al., *BMC Bioinformatics*, 12:152 (2011)). COSMID currently allows searching the human, mouse, *Caenorhabditis elegans*, and rhesus macaque genomes.

COSMID is a CRISPR off-target search tool with a web interface that allows directed and exhaustive genomic searches to identify potential off-target sites for guide strand choice or experimental validation. To perform a search, a user chooses the genome of interest from the list, and enters the guide strand and PAM sequences (FIG. 25A). By clicking the appropriate selection buttons, a user can choose to include (i) ≤2 base mismatches with an insertion and/or deletion, or (ii) ≤3 base mismatches without any indels (FIG. 25A). The user has the option to have primers as part of the output. Primers are designed by COSMID that are optimized to the specified criteria or to the defaults given for particular applications (FIG. 25A). COSMID exhaustively scans the genome based on these input parameters (FIG. 25B), allowing consideration of mismatches, insertions, and/or deletions (FIG. 25C, FIG. 26A-26G).

COSMID outputs a ranked list of perfectly matched (on-target site and possibly other sites) and partially matched (potential off-target) sites in the genome, their ranking score, along with reference sequences and primer designs that can be used for sequencing and/or mutation detection assays (Table 12). Each line of the output file describes one genomic locus matching the search criteria. A locus may appear on multiple lines if it can be modeled and found in multiple ways.

An exemplary COSMID Output includes the following text, a hyperlink for viewing the raw search results in a txt file and Table 12.

TABLE 12

Exemplary COSMID Output - Search Results (Table 12 discloses the 'Result' sequences as SEQ ID NOS 582, 583, 584, 583, 585, 583, 586, 583, 587, 583, 588, 583, 589, 583, 590, 583, 591, 583, 592, 583, 593 and 583, respectively, in order of appearance. Table 12 discloses the 'PCR primer left' sequences as SEQ ID NOS 594-604, respectively, in order of appearance)

| Result | Query type | Mismatch | Hit ends in RG | CHr position |
|---|---|---|---|---|
| GTGAACGTGGATGAAGTTGGTGG - hit<br>NTGAACGTGGATGAAGTTGGNRG - query | No indel | 0 | Yes | Chr11: 5226945-5226967 |
| AAAAACATGGATGAAGTTGGAGG - hit<br>NTGAACGTGGATGAAGTTGGNRG - query | No indel | 3 | Yes | CHr5: 159482356-159482378 |
| AACAACATGGATGAAGTTGGAGG - hit<br>NTGAACGTGGATGAAGTTGGNRG - query | No indel | 3 | Yes | Chr14: 76242458-76242480 |

TABLE 12-continued

Exemplary COSMID Output - Search Results (Table 12 discloses the
'Result' sequences as SEQ ID NOS 582, 583, 584, 583, 585, 583, 586, 583,
587, 583, 588, 583, 589, 583, 590, 583, 591, 583, 592, 583, 593 and 583,
respectively, in order of appearance. Table 12 discloses the 'PCR primer left'
sequences as SEQ ID NOS 594-604, respectively, in order of appearance)

```
AACAACTTGGATGAAGTTGGAGG - hit    No indel    3    Yes    Chr19: 30481960-30481982
NTGAACGTGGATGAAGTTGGNRG - query GACAACGTGGATAAAGTTGGAAG - hit    No indel    3    Yes    Chr14: 46616960-46616982
NTGAACGTGGATGAAGTTGGNRG - query AACAACGTGGATGAAATTGGAGG - hit    No indel    3    Yes    Chr16: 13962384-13962406
NTGAACGTGGATGAAGTTGGNRG - query GACAACGTGGATGAACTTGGAAG - hit    No indel    3    Yes    Chr7: 108476834-108476856
NTGAACGTGGATGAAGTTGGNRG - query AACAACGTGGATGAACTTGGAGG - hit    No indel    3    Yes    Chr9: 8126912-8126934
NTGAACGTGGATGAAGTTGGNRG - query AACAACGTGGATGAACTTGGAGG - hit    No indel    3    Yes    Chr13: 49740941-49740963
NTGAACGTGGATGAAGTTGGNRG - query TACAACGTGGATGAACTTGGAGG - hit    No indel    3    Yes    Chr6: 49662176-49662198
NTGAACGTGGATGAAGTTGGNRG - query AACAACGTGGATGAAGCTGGAGG - hit    No indel    3    Yes    Chr6: 32139214-32139236
NTGAACGTGGATGAAGTTGGNRG - query
```

| Result | Strand | Cut site | Score | PCR primer left |
|---|---|---|---|---|
| GTGAACGTGGATGAAGTTGGTGG - hit<br>NTGAACGTGGATGAAGTTGGNRG - query | − | 5226948 | 0 | ACCAATAGGCAGAGAGAGTCAGTG |
| AAAAACATGGATGAAGTTGGAGG - hit<br>NTGAACGTGGATGAAGTTGGNRG - query | − | 159482359 | 0.51 | AGGTGTCCTTTATCCCAAAGCTCC |
| AACAACATGGATGAAGTTGGAGG - hit<br>NTGAACGTGGATGAAGTTGGNRG - query | + | 76242477 | 0.51 | CCTGGTAACCACCATTCTACTCTG |
| AACAACTTGGATGAAGTTGGAGG - hit<br>NTGAACGTGGATGAAGTTGGNRG - query | − | 30481963 | 0.51 | CAACCTAAGTACCCACTGATCAACG<br>AAAG |
| GACAACGTGGATAAAGTTGGAAG - hit<br>NTGAACGTGGATGAAGTTGGNRG - query | + | 46616979 | 1.38 | GTGCCAGATATGGAAATCATCTAAG<br>CATCAG |
| AACAACGTGGATGAAATTGGAGG - hit<br>NTGAACGTGGATGAAGTTGGNRG - query | − | 13962387 | 2.58 | CAACCTAAGTGTCTAGCAACAGGC |
| GACAACGTGGATGAACTTGGAAG - hit<br>NTGAACGTGGATGAAGTTGGNRG - query | + | 108476853 | 2.58 | GGCAACCACCATTCTCCTCTG |
| AACAACGTGGATGAACTTGGAGG - hit<br>NTGAACGTGGATGAAGTTGGNRG - query | − | 8126915 | 2.58 | CCTCACCCCTAGCAACCATC |
| AACAACGTGGATGAACTTGGAGG - hit<br>NTGAACGTGGATGAAGTTGGNRG - query | − | 49740944 | 2.58 | AAGGAATCAGCCCAAATGTCCACC |
| TACAACGTGGATGAACTTGGAGG - hit<br>NTGAACGTGGATGAAGTTGGNRG - query | + | 49662195 | 2.58 | GCCACCACCCATTTTCTGTCTG |
| AACAACGTGGATGAAGCTGGAGG - hit<br>NTGAACGTGGATGAAGTTGGNRG - query | − | 32139217 | 3.28 | GAACTGCTGAGCTCGAGTGATC |

Table 12 shows an exemplary COSMID output in HTML and includes the genomic sites matching the user-supplied criteria in comparison to guide strand R-01 with chromosomal location. Scoring of the mismatches is provided for ranking, as are PCR primers and reference sequence. The right primers, in silico link, amplicon, and digest sizes are provided in the output, but not shown here. Links are provided to each location in the UCSC genome browser, and to the output file as a spreadsheet for further manipulation and primer ordering.

Each hit is appropriately aligned to the query shown in the "Result" box (Table 12). DNA bases corresponding to mismatches, indels, ambiguity codes, such as N, are shown in the query line to identify the matching genomic bases. To the right of the "Result" box are boxes with the query type, number of mismatches, chromosomal position, score, primers, and other features. The web page showing COSMID output also includes links to test each primer pair and to reformat the output file as text or in a spreadsheet. The spreadsheet output allows thorough evaluation of the number and scores of the low-scoring sites that are predicted to be more likely off-target sites, which may provide important guidelines when evaluating and choosing guide strands and/or testing for true cleavage events using DNA samples from cells after CRISPR/Cas treatment.

COSMID uses the TagScan algorithm to minimize run times while still performing exhaustive genome searches (Iseli, et al., *PLoS One,* 2:e579 (2007)). With the primer design option off, the run times averaged 4 seconds for the guide strands without indels (Table 13).

The boxes in the 'Allowed indels and mismatch' of the Search Options section are checked to indicate if genome sites to be searched include genomic sites that have No indels (with ≤3 mismatches but the same length), have 1-base Del (are 1-base shorter), or have 1-base Ins (are 1-base longer) (FIG. 26C).

TABLE 13

Run Times ('Guide strand' sequences disclosed as SEQ ID NOS 605-607, 607, 607, 607-610, 610, 610-611 and 611, respectively, in order of appearance)

| Guide strand search | PAM | No Indel | Ins | Del | Primers | Hits | Average run and load time | SD |
|---|---|---|---|---|---|---|---|---|
| NTGAACGTGGATGAAGTTGG | NGG | 3 | — | — | paired 250 | 376 | 3:13 | 5.6 |
| TGAACGTGGATGAAGTTGG | NGG | 3 | — | — | paired 250 | 376 | 3:07 | 2.6 |
| GTGAACGTGGATGAAGTTGG | NGG | 3 | — | — | paired 250 | 91 | 0:44 | 0.6 |
| GTGAACGTGGATGAAGTTGG | NGG | 3 | — | — | — | 91 | 0:04 | 0.6 |
| GTGAACGTGGATGAAGTTGG | NGG | 3 | 2 | 2 | paired 250 | 563 | 5:11 | 28.3 |
| GTGAACGTGGATGAAGTTGG | NRG | 3 | 2 | 2 | — | 1195 | 0:42 | 2.9 |
| NTAGAGCGGAGGCAGGAGGC | NGG | 3 | — | — | paired 250 | 190 | 1:42 | 1.0 |
| TAGAGCGGAGGCAGGAGGC | NGG | 3 | — | — | paired 250 | 190 | 1:32 | 0.6 |
| GTAGAGCGGAGGCAGGAGGC | NGG | 3 | — | — | paired 250 | 89 | 0:48 | 0.6 |
| GTAGAGCGGAGGCAGGAGGC | NGG | 3 | — | — | — | 89 | 0:04 | 0.0 |
| GTAGAGCGGAGGCAGGAGGC | NGG | 3 | 2 | 2 | paired 250 | 556 | 4:49 | 3.1 |
| GTAGAGCGGAGGCAGGAGGC | NRG | 3 | 2 | 2 | paired 250 | 799 | 7:19 | 11.6 |
| GTAGAGCGGAGGCAGGAGGC | NRG | 3 | 2 | 2 | — | 799 | 0:36 | 0.6 |

Run times were measured for COSMID using variations of guide strands R-01 and R-30, with and without a 5'G, using standard (NGG) or relaxed PAM (NRG). All runs included sites matching the guide strand with three or less mismatches without indels. More matching loci "hits" were identified by allowing single-base insertions or deletions together with ≤2 base mismatches.

Allowing insertions or deletions in addition to mismatches increases run time. For example, when searching with a 19-nt guide strand and an NRG PAM, and including two mismatches with either an insertion or an deletion resulted in run times averaging 42 seconds for R-01 and 36 seconds for R-30. The run times for the search with three mismatches without insertions or deletions were similar. Including primer design increased the run times proportional to the number of primer sets and reference sequences returned.

FIGS. 26A-26G and Table 14 illustrate an exemplary search string processing by COSMID include examples showing the input, and portions of the web results and spreadsheet output for a search of the human genome using guide strand R-01.

The genome of interest is chosen from the Target Genome list (FIG. 26A). The target sequence is entered in the Query Sequence box (FIG. 26B). The required protospacer adjacent motif (PAM) is entered into the 'Add suffix' Box of the Search Options section (FIG. 26C). The spacers (Ns) and required bases are included, such as NGG or NRG.

The boxes in the PCR Primer Design Options section are chosen, which allow COSMID to design primers matching the specific application. Primer design parameters are set by pressing the button for 'Default', 'Illumina 250', 'Illumina 250 paired', 'SMRT' or 'enzyme' (when using other enzymes). Any of the parameters can be entered by hand to further customize.

For each genome included in COSMID, the genwin program was used to transform the DNA sequence from FASTA formatted files into unsorted index entries, which have all possible 25 bases-long tags in the DNA sequence. After that, the sortGWI program was used to sort the index entries, and store the result as a binary index file. sortGWI subdivided the whole index file into 16,777,216 parts, each representing entries having identical first 12 nucleotides. A secondary index, recording the position in the main index file where each part starts, was added to the end of the index file to enable faster search and reduce file size. The index files are stored in the COSMID server.

When the submit button is clicked, the sequence tags in COSMID are used to generate a series of additional tags that contain indels if the insertion or deletion boxes are checked. Identical tags are removed if they are duplications for strings containing consecutive identical bases. The resulting tags are all searched against the user-selected genome. For example, if guide strand R-01 is entered, the tags illustrated in FIGS. 26E and 26F are generated and used to search the human genome.

To search the query sequences against the user selected genome, the FetchGWI program is used. If the user specifies a search with one or more mismatches, FetchGWI generates all possible sequence tags by replacing the specified number of nucleotides with all other possibilities. After that, Fetch-GWI sorts all the query tags and search for matches in the index file, using an efficient method called binary search. FetchGWI reports the search results by appending the actual sequence tag found, along with the accession number and position offset within the sequence for each matched query tags.

For each match that FetchGWI finds, COSMID generates a score that reflects the empirical expectation of how likely it is an off-target site.

Figures 26G, 27:
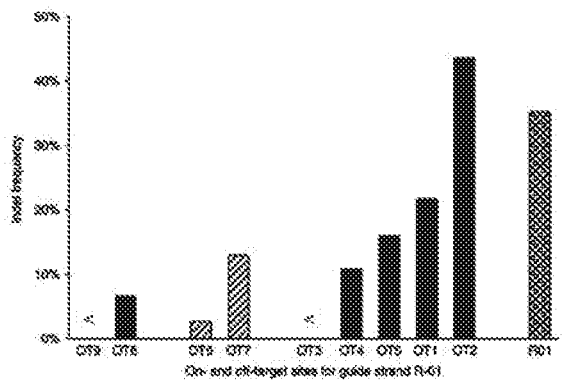
FIG. 26G is an exemplary COSMID HTML output that shows query type, number of mismatches if the PAM ends in RG (NAG or NGG), the chromosomal position, strand, cut site, the ranking score and left PCR primer. The right primer is off screen here.
FIG. 27 is a bar graph showing on- and off-target cleavage rates (% indel frequency) for guide strand R-01 for groups of identical sites. This experiment indicated that other factors in addition to complementary sequence may play in mutation rate—these features may be added into the search calculations, scoring and ranking in other embodiments.
Figure 29A:
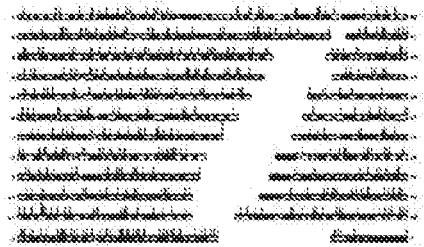
FIGS. 29A-29D are genetic maps showing the number and location of the additional genomic loci found while searching for putative off-target sites with and without indels for R-01 (29A, 29C) and R-30 (29B, 29D).
Figure 29B:
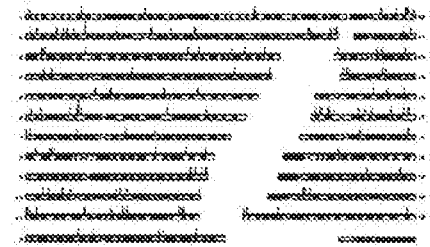
Figure 29C:
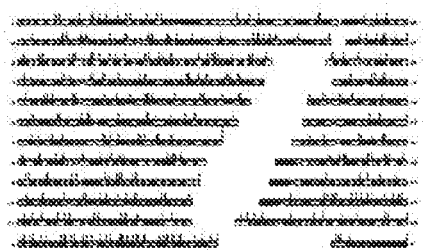
Figure 29D:
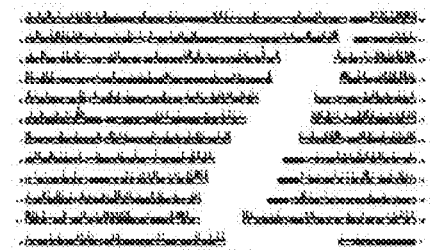

COSMID web output includes links for html, txt and excel files (FIG. 26G). Links are provided to test each primer pair using the UCSC in-silico PCR web site. The excel output is sorted for unique sites with the lowest mismatch and indel score to locate the most likely off-target sites. Here the Score+ column contains a ranking to place NGG ahead of NAG sites (+0.3 points added to the COSMID default scoring). The second column represents the query type, then the chromosomal location, the ranked number and a grid showing the mismatches, insertions and deletions (Table 14). Different sections of the output are illustrated in Table 14.

TABLE 14

Exemplary COSMID excel output (Table 14 discloses SEQ ID NOS 612-646, respectively, in order of appearance)

| Score+ | Ct | Chr. Location | # | 28 | 19 | 18 | 17 | 16 | 15 | 14 | 13 | 12 | 11 | 18 | 9 | 8 | 7 | 6 | 5 | 4 | 3 | 2 | 1 |
|---|---|---|---|---|---|---|---|---|---|---|---|---|---|---|---|---|---|---|---|---|---|---|---|
| 0.00 | No indel | 3,046,372,994 | 1 | T | A | G | A | C | G | G | A | G |   |   | G | C | A | G | G | A | G | G C N R G |  |
| 0.28 | No indel | 2,240,965,315 | 2 | G | T |   |   |   |   |   |   |   |   |   |   |   |   |   |   |   |   | A | G |
| 0.32 | No indel | 2,046,297,170 | 3 | A |   |   | T |   |   |   |   |   |   |   |   |   |   |   |   |   |   | G | G |
| 0.40 | No indel | 17,048,477,505 | 4 | A |   |   |   |   |   | A |   |   |   |   |   |   |   |   |   |   |   | A | G |
| 0.42 | No indel | 20,056,787,697 | 5 |   |   |   |   | G | A |   |   |   |   |   |   |   |   |   |   |   |   | A | G |
| 0.45 | No indel | 9,136,858,805 | 6 | A | G | A |   |   |   |   |   |   |   |   |   |   |   |   |   |   |   | T | G |
| 0.45 | No indel | 23,104,270,496 | 7 | A | T | T |   |   |   |   |   |   |   |   |   |   |   |   |   |   |   | G | G |
| 0.50 | No indel | 13,027,183,485 | 8 |   |   |   |   | G | T |   |   |   |   |   |   |   |   |   |   |   |   | T | G |
| 0.51 | No indel | 2,112,729,675 | 9 | A | G |   |   |   | A |   |   |   |   |   |   |   |   |   |   |   |   | A | G |
| 0.51 | No indel | 17,073,435,677 | 10 | C | G |   |   |   | A |   |   |   |   |   |   |   |   |   |   |   |   | A | G |
| 0.51 | No indel | 17,077,330,111 | 11 | A | G |   |   |   | A |   |   |   |   |   |   |   |   |   |   |   |   | A | G |
| 0.51 | No indel | 19,035,352,907 | 12 | A | G |   |   |   | A |   |   |   |   |   |   |   |   |   |   |   |   | A | G |
| 0.53 | No indel | 10,077,175,845 | 13 | G |   | A |   |   | G |   |   |   |   |   |   |   |   |   |   |   |   | A | G |
| 0.53 | No indel | 20,034,549,863 | 14 | C |   |   | C | A |   |   |   |   |   |   |   |   |   |   |   |   |   | A | G |
| 0.55 | No indel | 2,239,034,824 | 15 |   | G | C |   |   | A |   |   |   |   |   |   |   |   |   |   |   |   | T | G |
| 0.55 | No indel | 8,020,261,890 | 16 | G |   |   | G | A |   |   |   |   |   |   |   |   |   |   |   |   |   | G | G |
| 0.55 | No indel | 11,008,330,436 | 17 | G |   |   | G | T |   |   |   |   |   |   |   |   |   |   |   |   |   | A | G |
| 0.55 | No indel | 11,121,722,489 | 18 | A |   | T | A |   |   |   |   |   |   |   |   |   |   |   |   |   |   | C | G |
| 0.55 | No indel | 12,002,556,210 | 19 |   | C | C |   | G |   |   |   |   |   |   |   |   |   |   |   |   |   | T | G |
| 0.55 | No indel | 19,003,081,047 | 20 | G | G |   |   |   |   | T |   |   |   |   |   |   |   |   |   |   |   | A | G |
| 0.55 | No indel | 21,042,771,441 | 21 | G |   |   | G | A |   |   |   |   |   |   |   |   |   |   |   |   |   | T | G |
| 0.55 | No indel | 23,051,894,668 | 22 | G |   |   | G | T |   |   |   |   |   |   |   |   |   |   |   |   |   | T | G |
| 0.57 | No indel | 3,170,356,688 | 23 |   | G | G | T |   |   |   |   |   |   |   |   |   |   |   |   |   |   | T | G |
| 0.57 | No indel | 6,140,303,969 | 24 | G |   |   | C | A |   |   |   |   |   |   |   |   |   |   |   |   |   | T | G |
| 0.87 | No indel | 2,232,121,970 | 53 | G |   |   | C | T |   |   |   |   |   |   |   |   |   |   |   |   |   | C | A |
| 0.87 | Del 14 | 13,026,017,539 | 54 | C |   |   | ~ |   |   |   |   |   |   |   |   |   |   |   |   |   |   | T | G |
| 0.89 | No indel | 17,078,928,364 | 55 | G |   | G |   | T |   |   |   |   |   |   |   |   |   |   |   |   |   | C | A |
| 0.89 | Del 14 | 3,128,344,215 | 56 |   | G |   | ~ |   |   |   |   |   |   |   |   |   |   |   |   |   |   | A | G |
| 0.89 | Del 14 | 11,030,753,345 | 57 | G |   |   | ~ |   |   |   |   |   |   |   |   |   |   |   |   |   |   | A | G |

TABLE 14-continued

Exemplary COSMID excel output (Table 14 discloses SEQ ID NOS 612-646, respectively, in order of appearance)

| Score+ | Ct | Chr. | Location | # | 28 | 19 | 18 | 17 | 16 | 15 | 14 | 13 | 12 | 11 | 18 | 9 | 8 | 7 | 6 | 5 | 4 | 3 | 2 | 1 |
|---|---|---|---|---|---|---|---|---|---|---|---|---|---|---|---|---|---|---|---|---|---|---|---|---|
| 0.89 | Del | 14 | 16,028,313,664 | 58 | | G | | | | | ~ | | | | | | | | | | | | T | G |
| 0.90 | No indel | | 2,240,468,349 | 59 | C | | | | | | A | | G | | | | | | | | | | A | G |
| 0.90 | No indel | | 17,017,914,203 | 60 | A | | | | | | A | | G | | | | | | | | | | A | G |
| 0.91 | Del | 14 | 14,100,290,418 | 61 | | | | C | | | ~ | | | | | | | | | | | | G | G |
| 1.62 | Ins | 13 | 9,130,450,122 | 330 | | G | | | | | A | | G | | | | | | | | | | A | G |
| 1.63 | Ins | 16 | 1,187,469,204 | 331 | | | | A | | T | G | | | | | | | | | | | | C | A |

Example 10: COSMID Searches and Identifies Putative Off-Target Cleavage Sites

Materials and Methods

CRISPR Transfection and Mutation Detection Assays

The on- and off-target cleavage activity of Cas9 and guide strand R-01 was measured using the mutation rates resulting from the imperfect repair of double-stranded breaks by non-homologous end joining. An amaxa Nucleofector 4D was used to transfect 200,000 K-562 cells with 1 μg px330 expressing R-01 sgRNA, following manufacturer's instructions. The genomic DNA was harvested after 3 days using QuickExtract DNA extraction solution (Epicentre, Madison, Wis.), as described (Guschin, et al., *Methods Mol Biol*, 649: 247-256 (2010)). On- and off-target loci were amplified using AccuPrime Taq DNA Polymerase High Fidelity (Life Technologies, Carlsbad, Calif.) following manufacturer's instructions for 40 cycles (94° C., 30 seconds; 52-60° C., 30 seconds: 68° C., 60 seconds) in 50 μl reactions containing 1 μl of the cell lysate, and 1 μl of each 10 μmol/l amplification primer. The T7EI mutation detection assays were performed, as per manufacturers protocol (Reyon, et al., *Nat Biotechnol*, 30: 460-465 (2012)), with the digestions separated on 2% agarose gels (FIG. 2a) and quantified using ImageJ (FIG. 2b) (Guschin, et al., *Methods Mol Biol*, 649: 247-256 (2010)). This guide strand was shown to have on-target cleavage at beta-globin and off-target cleavage at delta-globin,24 so a range of off-target sites were chosen, including two pairs of identical sites (OT6-OT7 and OT8-OT9) and five identical sites (OT1-OT5) to test for off-target mutations and evaluate the role of genomic context on cleavage and mutation rates. It is hoped that increased cellular data, such as provided in ENCODE for some cell lines, may prove useful in this regard.

TABLE 15

Genomic sequences and chromosomal positions of the off-target sites tested using the mutation detection assay in FIG. 27. (Table 15 discloses SEQ ID NOS 647-657, respectively, in order of appearance)

| Loci ID | Genomic Sequence | Chromosomal Location |
|---|---|---|
| R01 | gTGAACGTGGATGAAGTTGGtGG | Chr11: 5248175-5248197 |
| R01_OT1 | aGGAACATGGATGAAGTTGGaGG | Chr2: 104339432-104339454 |
| R01_OT2 | aGGAACATGGATGAAGTTGGaGG | Chr5: 77278964-77278986 |
| R01_OT3 | gGGAACATGGATGAAGTTGGaGG | Chr1: 187156560-187156582 |
| R01_OT4 | gGGAACATGGATGAAGTTGGaGG | Chr4: 36043493-36043515 |
| R01_OT5 | gGGAACATGGATGAAGTTGGaGG | Chr14: 97573865-97573887 |
| R01_OT6 | aGGAACGTGGATGGAGTTGGaGG | Chr4: 162915337-162915359 |
| R01_OT7 | aGGAACGTGGATGGAGTTGGaGG | Chr9: 91958548-91958570 |
| R01_OT8 | aGGAACGTGGATGAAGCTGGaGG | Chr10: 114331596-114331618 |
| R01_OT9 | gGGAACGTGGATGAAGCTGGaGG | Chr2: 116826852-116826874 |
| R01_OT10 | gTGAAAATGGATGAAGTTGGaGG | Chr13: 84213286-84213308 |

The nucleotides in position 20 and in the first position of the NGG PAM are lowercase, as there are not mismatches at these positions.

Results

To validate COSMID predictions, mutation detection assays were performed to determine if off-target cleavage occurred at putative off-target sites identified by COSMID. A search for the guide strand R-01 (GTGAACGTGGAT-GAAGTTGG (SEQ ID NO: 658)), which targets the human beta-globin gene (Cradick, et al., *Nucleic Acids Res,* 41:9584-9592 (2013)), gave 1,040 potential off-target sites in the human genome when allowing for up to three mismatches without any indels, and up to two mismatches with a one-base deletion or one-base insertion, adjacent to a NRG PAM (FIG. 25A).

Using primers as part of COSMID output, mutation detection assays were performed based on PCR amplification of the genomic loci (Guschin, et al., *Methods Mol Biol,* 649: 247-256 (2010)) after transfecting K-562 cells with a plasmid expressing Cas9 and guide strand R-01. A range of potential off-target sites without indels were studied in order to compare COSMID with other available bioinformatics tools. Of the 10 off-target sites tested, 8 sites, all with two mismatches, had off-target mutagenesis that could be detected by the T7EI mutation detection assay (FIG. 27, Table 15), including an off-target site with higher activity than the on-target cleavage rate (44% versus 35%, Table 16, below). Similar to previous results, the level of off-target activity was generally diminished at sites with mismatches closer to the PAM (Gasiunas, et al., *Proc Natl Acad Sci USA,* 109:E2579-E2586 (2012); Jinek, et al., *Elife* 2:e00471 (2013); Jiang, et al., *Nat Biotechnol,* 31: 233-239 (2013); Fu, et al., *Nat Biotechnol,* 31: 822-826 (2013); Hsu, et al., *Nat Biotechnol,* 31: 827-832 (2013); Cradick, et al., *Nucleic Acids Res,* 41:9584-9592 (2013)).

Five different genomic sites with identical sequences, containing two mismatches respectively 14 and 19 bases from the PAM, had cleavage activities ranging from below the detection limit to 44%. The 10 sites chosen also contained two pairs of duplicated sites that had different mutation rates (13% versus 3%, and 7% versus below detection). The large variation in mutation rates at identical sequences, but different genomic regions may be due to the difference in gRNA/Cas9 accessibility and/or binding affinity at different genomic loci. This exemplifies the role genomic context can play in Cas9-induced cleavage and the difficulty in ranking off-target sites solely based on target sequences. See also, FIG. 2C which compares the mutation rates at two identical sequences.

Table 16 lists these eight experimentally validated off-target sites in decreasing order of mutation rate (%), their ranking by COSMID, as well as that by other on-line CRISPR tools.

TABLE 16

Composition of COSMID with other available tools in predicting off-target sites with two mismatches for guide strand R-01.

| Loci ID | COSMID (rank) | Cas online designer (rank) | ZiFit | CRISPR design tool | Cas offinder (Sorted) | Mutation rate (%) | Gene |
|---|---|---|---|---|---|---|---|
| R01_OT2 | 2-6 | 2-7 | 15 | — | 18-139 | 43.6 | None |
| R01 | 1 | 1 | on | 1 | on | 35.2 | HBB |
| R01_OT10 | 7 | 2-7 | 3 | — | 3-17 | 23.4 | None |
| R01_OT1 | 2-6 | 2-7 | 16 | — | — | 21.8 | None |
| R01_OT5 | 2-6 | 2-7 | 5 | — | 3-17 | 15.9 | None |
| R01_OT7 | 143-145 | 73-76 | 24 | — | 18-139 | 12.9 | SECISBP2 |
| R01_OT4 | 2-6 | 2-7 | 7 | — | 3-17 | 10.8 | None |
| R01_OT8 | 355-357 | 238-241 | 34 | — | 18-139 | 6.6 | VTI1A |
| R01_OT6 | 143-145 | 73-76 | 25 | — | 18-139 | 2.7 | FST L5 |

The cleavage rates at R-01 on-target site and off-target sites OT1-OT10 are listed by decreasing T7EI activity in Table 16. OT3 and OT9 had activities below T7EI detection limit. Annotated genes corresponding to the sites are listed. Off-target analysis was performed with different online search tools. If the genomic sites with measurable T7EI activity (FIG. 27) were identified by a specific tool (such as Cas OFFinder), their rankings in its output (if sortable) are shown. Sites not in the output of that tool are indicated by a dash in a grey box (e.g., R01_OT1 under "Cas OFFinder").

The output from COSMID was also compared with the output from other web tools for their ability to identify off-target sites that contain an extra bases (DNA bulge) or a missed base (RNA bulge) relative to the complementary genomic DNA sequence (Lin, et al., *Nucleic Acids Res,* 42:7473-7485 (2014)) (Table 17). The off-target sites in Table 17 might also be modeled as sites with four mismatches or noncanonical PAMs compared with the on-target site, though it is less likely that binding of Cas9 would occur without an NGG or NAG PAM. The columns corresponding to the individual tools follow from Table 16, above. When an extra base is present in the genomic sequence, next to one or more of the same nucleotide, the DNA bulge may occur in multiple locations, such as in the off-target site R30_Ins9 where the additional G in the genomic sequence might be the first, second, or third of the three adjacent Gs, at locations 2, 3, or 4 nucleotides from the PAM (Table 18).

TABLE 17

Comparison of search results for off-target sites that contain deletions or insertions, in which sequence-verified off-target sites with insertions or deletions, which can also be modeled as loci with four mismatches or alternate PAM considered.

| Loci ID | | | | | | Mismatches | Bulge type | Bulge position | Indel/alternate model |
|---|---|---|---|---|---|---|---|---|---|
| R30_Del1 | Yes | — | Yes | Yes | Yes | 2 | RNA | 17 | 4 mismatches |
| R01_Del1 | Yes | Yes | Yes | — | — | 2 | RNA | 15/14 | 4 mismatches |
| R30_Ins9 | Yes | — | — | Yes | — | 2 | DNA | 4/3/2 | Alternate PAM |
| R01_Ins1 | Yes | — | — | — | — | 3 | DNA | 1 | Alternate PAM |
| R30_Ins14 | Yes | Yes | — | — | — | 2 | DNA | 1 | Alternate PAM |

TABLE 18

Sequence-verified off-target sites with mismatches and 1-base insertion (Ins) or deletion (Del). (Table 18 discloses SEQ ID NOS 659-668, respectively, in order of appearance)

| Loci ID | Mismatches | Bulge Type | Bulge Position | Genomic Sequence* |
|---|---|---|---|---|
| R30_Del1 | 2 | RNA | 17 | AGA-AGCGGAGGCAGGAGGCtGG |
| R01_Del1 | 2 | RNA | 15/14 | GGGAAT-TGGATGAAGTTGGgGG |
| R30_Ins9 | 2 | DNA | 4/3/2 | GAAGAGGGGAGGCAGGAGGGCaGG |
| R01_Ins1 | 3 | DNA | 1 | AGGAACGTGGATGAACTTGGAaGG |
| R30_Ins14 | 2 | DNA | 1 | GGAGAGCGGCGGCAGGAGGCGtAG |
| R30_Del10 | 3 | RNA | 10/9 | AGAGAGAGGA-GCAGGAGGCtGG |
| R30_Ins10 | 2 | DNA | 10 | GCAGAGCCGAGAGCAGGAGGCgAG |
| R30_Ins4 | 2 | DNA | 9/8 | GGAGAGCGGGGGCCAGGAGGCcGG |
| R30_Ins7 | 2 | DNA | 7/6/5 | GAAGAGTGGAGGCAGGGAGGCtGG |
| R30_Ins8 | 2 | DNA | 4/3/2 | GAAGAGAGGAGGCAGGAGGGCtGG |

Genomic sequences of the off-target sites are given, together with the number of mismatches, bulge type (guide bulge or gDNA bulge) and bulge position relative to PAM.
*gDNA mismatches compared to guide strand are shown by alignment; insertions are underlined, and deletions (guide bulge) are represented as dashes. The first nucleotide in PAM is in lower case.

In addition to being modeled as having one insertion with two mismatches, this off-target site can be modeled as having three mismatches with a shift in the PAM from NGG to NAG. Further, the off-target site R01_Ins1 may be modeled as having a NAG PAM. Without a bulge, R30_Ins14 would need to have the unlikely GTA PAM, so it remains unclear how it was modeled by Cas Online Designer. Each site in Tables 17 and 19 are marked "yes" when found by COSMID (first column) or other search method: if any of the confirmed off-target site could not be identified by a search tool, it is shown as a box with a dash. Specifically, of the six off-target sites identified by COSMID (and previously sequence confirmed) (Lin, et al., *Nucleic Acids Res*, 42:7473-7485 (2014)), Cas Online Designer, ZiFit, and CRISPR tools each only found two, and Cas OFFinder only found one. Table 19 lists the sequence confirmed, off-target sites containing DNA or RNA bulges that could not be represented by other means, with COSMID in the first column and the columns the same as in Table 16. Each of these sequence-verified off-target sites was identified by COSMID, but they were not output by these search tools, as they fail to locate sites with insertions or deletions.

TABLE 19

The sequence-verified off-target sites with insertions or deletions that cannot be modeled as four mismatches or alternate PAM can only be predicted by COSMID.

| | | | | | | | | |
|---|---|---|---|---|---|---|---|---|
| R30_Del10 | Yes | — | — | — | — | 3 | RNA | 10/9 |
| R30_Ins10 | Yes | — | — | — | — | 2 | DNA | 10 |
| R30_Ins4 | Yes | — | — | — | — | 2 | DNA | 9/8 |
| R30_Ins7 | Yes | — | — | — | — | 2 | DNA | 7/6/5 |
| R30_Ins8 | Yes | — | — | — | — | 2 | DNA | 4/3/2 |

COSMID has better ability in identifying off-target sites with indels. Although a number of bioinformatics programs can be used for CRISPR designs, COSMID provides exhaustive genomic searches for off-target sites due to mismatches, deletions, and insertions, as well as providing primers for experimental validation of predicted off-target sites. The results shown in Tables 16, 17, and 19 give examples of validated off-target sites identified by COSMID, but not found by other search tools, including Cas Online Designer (Hsu, et al., *Nat Biotechnol*, 31: 827-832 (2013)), ZiFit (Sander, et al., *Nucleic Acids Res*, 38 (suppl.): W462-468 (2010)), CRISPR Tools (Hsu, et al., *Nat Biotech-* nol, 31: 827-832 (2013)), and Cas OFFinder (Bae, et al., Bioinformatics, 30:1473-1475 (2014)), which have different functions, such as determining CRISPR guide sequences (Grissa, et al., Nucleic Acids Res, 35: W52-W57 (2007); Grissa, et al., BMC Bioinformatics, 8:172 (2007); Rousseau, et al., Bioinformatics, 25: 3317-3318 (2009); Bland, et al., BMC Bioinformatics, 8:209 (2007)), scanning a genome for possible target sites, and comparing the potential off-target sites (Hsu, et al., Nat Biotechnol, 31: 827-832 (2013); Montague, et al., Nucleic Acids Res, 42:W401-W407 (2014); Ronda, et al., Biotechnol Bioeng, 11:1604-1616 (2014)).

In addition to providing optimized primer designs for sequencing and mutation detection for confirming putative off-target sites, COSMID also provides the reference sequence to facilitate sequencing. The reference sequence and knowledge of the cut site location facilitates mutation detection assays, including surveyor and T7EI, and possibly other uses, such as searching for restriction sites that may overlap the cut site.

To illustrate the ability of COSMID and importance of locating indels, search results for two guide strands were compared with validated activity and known off-target cleavage, including the guide strand R-01 that targets the human HBB gene, and the guide strand R-30 (GTAGAGCGGAGGCAGGAGC (SEQ ID NO: 669)) that targets the human HIV co-receptor CCR5 gene (Cradick, et al., Nucleic Acids Res, 41:9584-9592 (2013); Lin, et al., Nucleic Acids Res, 42:7473-7485 (2014)). The results of COSMID searches were compared with the output given by other existing search tools. When off-target sites contain insertions or deletions in addition to mismatches, only COSMID searches could identify all of the 10 sequence-validated off-target sites (Tables 15, 16, and 17). Note that the deletion contained in off-target sites R-01_Del1 or R-30_Del1 (Table 17) could be modeled as four mismatches, and the insertion in off-target sites R-01_Ins1, R-30_Ins9, or R-30_Ins14 (Table 17) could be modeled as having alternative PAMs. These alternative interpretations of the insertions and deletions for the sites shown in Table 17 explain why some existing bioinformatics tools such as Cas Online Designer, ZiFit, CRISPR Tools, and Cas OFFinder could still identify some of the off-sites listed in Table 17, although these tools do not allow insertions or deletions to be considered in the searches. Since the insertions or deletions in off-target sites R-30_Del10, R-30_Ins4, R-30_Ins7, R-30_Ins8, R-30_Ins10 (Table 19) could not be modeled as either mismatches or having alternative PAM, they were not found by any other tools at this time.

Example 11: Extensive Searches for HBB-Targeted (R-01) and CCR5-Targeted (R-30) Guide Strands, Allowing Indels Greatly Increases the Number of Putative Off-Target Sites In addition to off-target sites of the same length as the guide strand but with mismatches, many similar sites exist in a genome with insertions (DNA bulges) and deletions (RNA bulges). Cas9 can tolerate DNA and RNA bulges and induce cleavage at genomic loci with high rates, sometimes even higher than the target site (Lin, et al., Nucleic Acids Res, 42:7473-7485 (2014)). To further demonstrate the capabilities of COSMID, the guide strands R-01 and R-30 (Cradick, et al., Nucleic Acids Res, 41:9584-9592 (2013); Lin, et al., Nucleic Acids Res, 42:7473-7485 (2014)) were extensively analyzed using COSMID to search the human genome for sites similar to the R-01 or R-30 guide strands, having (i) up to three mismatches with no indels, (ii) up to two mismatches with a single-base insertion, and (iii) up to two mismatches with a single-base deletion. Since matching a guide strand's initial G is not essential, it was omitted in these searches. The off-target sites with a mismatched A at this position (OT1 and OT2) happened to have higher mutation rates than the three sites with a matching G (OT3-5) (FIG. 27). The outputs provided many possible off-target sites, including those with insertions or deletions.

The number of putative genomic off-target sites output by COSMID increased drastically when indels were allowed in the search. For example, allowing one-base insertions together with two mismatches increased the number of genomic sites adjacent to a NAG or NGG PAM ~3 and ~7 times for R-01 and R-30 respectively compared with those without indels and two mismatches (166 versus 49 for R-01 and 224 versus 34 for R-30, Table 20).

TABLE 20

Comparison of search results for guide strands R-01 and R-30 with deletion or insertion permitted.

|  | R-01 search | | | | R-30 search | | | |
| --- | --- | --- | --- | --- | --- | --- | --- | --- |
| Mismatches | 0 | ≤1 | ≤2 | ≤3 | 0 | ≤1 | ≤2 | ≤3 |
| No indels | 1 | 2 | 49 | 675 | 1 | 1 | 34 | 257 |
| One deletion | 1 | 60 | 883 | — | 1 | 36 | 883 | — |
| One insertion | 0 | 6 | 166 | — | 0 | 9 | 224 | — |

The number of possible unique genomic sites with NAG or NGG PAMs with ≤2 mismatches was significantly higher when the searches allowing either one deletion or one insertion than without.

When one-base deletions are allowed together with two mismatches, the number of genomic sites identified is even higher, ~18 and ~26 times higher for R-01 and R-30 respectively compared with those without indels (883 sites for R-01 and 883 sites for R-30) (Table 20). With one-base insertion or one-base deletion in addition to base mismatches, the number of unique loci found was greatly increased compared with the corresponding number without indels. For example, when a one-base deletion was allowed in addition to ≤2 mismatches, the unique off-target loci found by COSMID is 333 for R-01 and 761 for R-30 (Table 21).

TABLE 21

Off-target loci when a one-base deletion was allowed in addition to ≤2 mismatches.

|  | R-01 search | | | R-30 search | | |
| --- | --- | --- | --- | --- | --- | --- |
| Mismatches | 0 | ≤1 | ≤2 | 0 | ≤1 | ≤2 |
| One deletion | 0 | 0 | 333 | 0 | 0 | 761 |
| One insertion | 0 | 0 | 52 | 0 | 2 | 196 |

When allowing (i) up to three mismatches with no indels, or (ii) up to two mismatches with a one-base insertion, or (iii) up to two mismatches with a one-base deletion, COSMID searches of off-target sites for guide strands R-01 and R-30 with NRG PAM located 1,040 unique putative off-target sites for R-01 and 1,218 for R-30. There were many identical sites located by multiple query types (examples shown in FIGS. 28A and 28B). The results varied between the two guide strands R-01 and R-30 (each targets a coding sequence), as can be expected in a nonrandom genome (FIGS. 29A-29D). R-01 had a markedly larger number of matching sites with no indels. Of note was a particular 3-mismatch hit in 69 sites.

In summary, identifying off-target cleavage by CRISPR/Cas9 systems in a genome of interest is important, especially in treating human disease and creating model organisms, as CRISPR off-target cleavage (Fu, et al., *Nat Biotechnol,* 31: 822-826 (2013); Hsu, et al., *Nat Biotechnol,* 31: 827-832 (2013)) can result in mutations, deletions, inversions, and translocations (Cradick, et al., *Nucleic Acids Res,* 41:9584-9592 (2013); Xiao, et al., *Nucleic Acids Res,* 41:e141 (2013)) inducing detrimental biological consequences and potentially causing disease. However, accurate and complete genome-wide analysis of off-target efforts is a daunting task, since unbiased sequencing of a full genome to determine off-target activity is very costly, and many nuclease-treated clones would have to be sequenced. Therefore, a bioinformatics-based tool that can predict and/or rank potential off-target cleavage sites can greatly aid the off-target analysis, and provide valuable guidance for guide strand designs. In particular, it is important to perform extensive bioinformatics searches for potential off-target sites that contain base mismatches, insertions, and deletions compared with the intended CRISPR target site.

COSMID can quickly and exhaustively search a genome for DNA sequences that partially match the target sequence of the guide strand, but contain insertions or deletions in addition to base mismatches. As shown in Table 21, a large number of potential off-target sites would be missed using search tools that only consider base mismatches, but not insertions or deletions. COSMID outputs potential off-target sites ("hits") corresponding to allowed mismatches and indels, the PAM sequence and the chromosomal location of the hits. COSMID also outputs primer designs for experimental validation of the off-target sites. Further processing of the COSMID results from the output spreadsheets extends COSMIDs utility to different CRISPR/Cas platforms, including the use of Cas9 nickase pairs (Ran, et al., *Cell,* 154:1380-1389 (2013)), Cas9/FokI fusion (Tsai, et al., *Nat Biotechnol,* 32:569-576 (2014): Guilinger, et al., *Nat Biotechnol,* 32: 577-582 (2014)), and multiplexed targeting (Cong, et al., *Science,* 339: 819-823 (2013)) by searching for multiple (sometimes paired) sites within a user-input chromosomal proximity. In addition to aiding the design of CRISPR/Cas systems for DNA cleavage, COSMID can be used to identify potential off-target sites of CRISPR activators, repressors, or other effector domains (Cheng, et al., *Cell Res,* 23: 1163-1171 (2013)).

The on-target and potential off-target sites given in the COSMID output can be tested experimentally using mutation detection assays (Guschin, et al., *Methods Mol Biol,* 649: 247-256 (2010)) or deep sequencing with genomic DNA harvested from cells treated by CRISPR/Cas. Mutation detection assays, including Surveyor and T7EI, are very commonly used to measure on- and off-target cleavage and mutagenesis (Guschin, et al., *Methods Mol Biol,* 649: 247-256 (2010)). COSMID facilitates these assays by automatically designing primers to enable facile gel separation of the uncleaved and cleavage bands. The output also includes the genomic reference sequence for comparison to the sequencing results.

COSMID scores the potential off-target sites based on the number and location of base mismatches, allowing ranking of the more likely off-target sites. Bioinformatics based ranking of CRISPR/Cas off-target sites may be influenced by the effects of genomic context and DNA modifications. As exemplified herein, identical genomic sites and duplicated sites may have differences in off-target activity. The indel rate at off-target site R-01_OT2 was 44%, though other loci with the same complementary sequence have much less, or no activity, possibly due to nuclease blocking. It is believed that incorporating parameters such as the effects of chromatin condensation, DNA availability and other factors into the COSMID search algorithm will improve the scoring and ranking of the target sites.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

The described methods are applicable for active nucleases, for nucleases that are temporally or otherwise controlled, partially inactivated or inactivated nuclease systems. As these systems have similar binding, they share similar capacity for mismatch and indel/bulge tolerance. Therefore analysis of the possible target sites is important using each of these systems.

We claim:

1. A computer-implemented method for identifying binding locations of an enzymatically inactive nucleotide guided nuclease for testing and selecting the nuclease with the fewest off-target binding locations comprising:
proving a database having one or more guide strand sequence variants wherein the variants are selected from the group comprising one or more nucleotide insertions, deletions, and nucleotide substitutions relative to the guide sequence;
identifying a series of query sequences in the database according to the user-specified guide strand and search criteria comprising a guide strand sequence and one or more guide strand sequence variants;
searching the genomic sequence for target binding locations matching user-supplied search criteria, wherein the criteria comprise number of mismatches, number and size of differences in length (bulges), allowed protospacer adjacent motif (PAM) suffixes, or combinations thereof, compared to the query sequence;
identifying potential binding locations that may include mismatches and/or bulges;
assigning a score to the identified binding locations, wherein the target binding locations comprising the genomic sequences having higher sequence identity to the guide sequence are assigned a lower score relative to the target cleavage locations comprising genomic sequences having lower sequence identity to the guide sequence, wherein increasing numbers of substitutions, deletions, and insertions at the target binding location increase the score, wherein the score is increased more for deletion(s) in the genomic sequence relative to the guide sequence (RNA bulges) than for insertions in the genomic sequence relative to the guide sequence (DNA bulges), and wherein a target binding locations located closer to a PAM motif is given a lower score than that of a target binding site locations located further from a PAM motif;
ranking the target binding locations based on their scores;
selecting the enzymatically inactive nucleotide guided nuclease with the lower likelihood of predictive off-target binding sites, wherein the enzymatically inactive nucleotide guided nuclease with the lower likelihood of predictive off-target binding sites is the nuclease with the lowest score; and
assaying the identified genomic locations after treatment with the selected enzymatically inactive nucleotide guided nuclease to confirm specific DNA binding.

2. The method of claim 1, wherein the series of query sequences comprises all possible guide strand sequence variants comprising between 0 and 10 nucleotide insertions relative to the guide sequence, between 0 and 10 nucleotide deletions relative to the guide sequence, between 0 and 10 nucleotide substitutions relative to the guide sequence, or a combination thereof.

3. The method of claim 1, wherein the user-supplied search criteria comprise 5 or fewer mismatches, 5 or fewer insertions, 5 or fewer deletions, and combinations thereof.

4. The method of claim 1, wherein the user-supplied search criteria comprise zero, one, two, or three mismatches, zero insertions, and zero deletions; zero, one or two mismatches with one insertion, and zero deletions; one or two mismatches with zero insertions, and one deletions; or one or two mismatches with one insertion, and one deletion; and combinations thereof.

5. The method of claim 1, wherein the score further includes other factors relating to the genomic context, chromatin, methylation, acetylation, and bound proteins.

6. The method of claim 1, further comprising producing the enzymatically inactive nucleotide-guided nuclease selected to have the lowest likelihood of predictive off-target binding sites.

7. The method of claim 6, wherein producing the enzymatically inactive nucleotide guided nuclease comprises conjugating the selected nuclease with one or more transcriptional activators, transcriptional repressors, chromatic or epigenetic modifiers, imaging agents, or a combination thereof.

8. The method of claim 1, wherein the series of query sequences comprises all possible guide strand sequence variants comprising between 0 and 10 nucleotide insertions relative to the guide sequence, between 0 and 10 nucleotide deletions relative to the guide sequence, between 0 and 10 nucleotide substitutions relative to the guide sequence, or a combination thereof.

9. The method of claim 1, wherein the user-supplied search criteria comprise 5 or fewer mismatches, 5 or fewer insertions, 5 or fewer deletions, and combinations thereof.

10. The method of claim 1, wherein the user-supplied search criteria comprise zero, one, two, or three mismatches, zero insertions, and zero deletions; zero, one or two mismatches with one insertion, and zero deletions; one or two mismatches with zero insertions, and one deletions; or one or two mismatches with one insertion, and one deletion; and combinations thereof.

11. The method of claim 1, wherein the user-supplied search criteria comprise a PAM suffix ending with the sequence RG.

12. The method of claim 1, wherein the user-supplied search criteria comprise a PAM suffix having any of the following sequences NGG, NAG, NGA, NGT, NAA and NRG.

13. The method of claim 1, wherein the user-supplied search criteria comprise a PAM suffix having any of the following sequences NNRG, NNAG, NNGG, NAGNRG, NNGRRT, NGRRT, NGRRN, NNNNGATT, NNNNRYAC, NNNNGHTT, NNAGAAW, and NAAAAC.

14. The method of claim 1, wherein the user-supplied search criteria comprise a PAM suffix having any of the following sequences TTN, YTN, TTA, TTC, TTG, TTTA, TTTC, or TTTG.

15. The method of claim 1, wherein the RNA-guided nuclease is an active nuclease.

16. The method of claim 15, wherein the RNA-guided nuclease is Cpf1 or Cas13.

17. The method of claim 15, wherein the RNA-guided nuclease is from a CRISPR system selected from the group consisting of *Staphylococcus aureus* (Sa), *Streptococcus thermophilus* (St1 or St3), *Neisseria meningitidis* (Nm or Nme), *Campylobacter jejuni* (Cj), *Treponema denticola* (Td), or engineered variants.

18. The method of claim 1, wherein the RNA-guided nuclease is a nickase.

19. The method of claim 18, wherein the nickase is from a CRISPR system selected from the group consisting of *Staphylococcus aureus* (Sa), *Streptococcus thermophilus* (St1 or St3), *Neisseria meningitidis* (Nm or Nme), *Campylobacter jejuni* (Cj), *Treponema denticola* (Td), or engineered variants.

20. The method of claim 1, wherein the nucleotide-guided nuclease is used for other purposes besides cleavage, including pull downs, for visualization (such as with antibodies or fluorescent proteins), for testing for SNPs or other mutations, gene, plasmid, virus or other pathogen identification, etc.

\* \* \* \* \*

SEQUENCE LISTING

<160> NUMBER OF SEQ ID NOS: 1134

<210> SEQ ID NO 1
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 1
acattgaggc actacttg                                                 18

<210> SEQ ID NO 2
<211> LENGTH: 14
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 2
acattgaggc acta                                                         14

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
gcacagggtg aacaagatg g                                                  21

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
gaccacccca aaggtgaccg t                                                 21

<210> SEQ ID NO 5
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
ttgaacaagg acgcatttcc ccag                                              24

<210> SEQ ID NO 6
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
caaagaccca ctcatttgca gcag                                              24

<210> SEQ ID NO 7
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
ccaataggca gagagagtca gtg                                               23
```

```
<210> SEQ ID NO 8
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
agccagggct gggcataaaa g                                          21

<210> SEQ ID NO 9
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
gaggttgtcc aggtgagcca ggccatcac                                  29

<210> SEQ ID NO 10
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
ctgctgaaag agatgcggtg gggagatatg ta                              32

<210> SEQ ID NO 11
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
aaggcagggc agagtcga                                              18

<210> SEQ ID NO 12
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
cacatgccca gtttctattg gt                                         22

<210> SEQ ID NO 13
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 13
gcaaggtgaa cgtggatga                                                   19

<210> SEQ ID NO 14
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
gtgaacgtgg atgaagttgg tgg                                              23

<210> SEQ ID NO 15
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
gtgaacgtgg atgcagttgg tgg                                              23

<210> SEQ ID NO 16
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
cttgccccac agggcagtaa cgg                                              23

<210> SEQ ID NO 17
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
tcagccccac agggcagtaa cgg                                              23

<210> SEQ ID NO 18
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
cacgttcacc ttgccccaca ggg                                              23

<210> SEQ ID NO 19
<211> LENGTH: 23
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 19
cacgttcact ttgccccaca ggg                                            23

<210> SEQ ID NO 20
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
ccacgttcac cttgccccac agg                                            23

<210> SEQ ID NO 21
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
ccacgttcac tttgccccac agg                                            23

<210> SEQ ID NO 22
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 22
agtctgccgt tactgccctg ngg                                            23

<210> SEQ ID NO 23
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 23
cgttactgcc ctgtggggca ngg                                            23

<210> SEQ ID NO 24
<211> LENGTH: 23
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 24
aaggtgaacg tggatgaagt tgg                                          23

<210> SEQ ID NO 25
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
aaggtgaacg tggatgcagt tgg                                          23

<210> SEQ ID NO 26
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
cctgtggggc aaggtgaacg tgg                                          23

<210> SEQ ID NO 27
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
cctgtggggc aaagtgaacg tgg                                          23

<210> SEQ ID NO 28
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
gtgttcatct ttggttttgt ggg                                          23

<210> SEQ ID NO 29
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
gtgttcatct ttggttttgt ggg                                          23
```

```
<210> SEQ ID NO 30
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
gctgccgccc agtgggactt tgg                                           23

<210> SEQ ID NO 31
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
ggcagcatag tgagcccaga ggg                                           23

<210> SEQ ID NO 32
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 32
gtgagtagag cggaggcagg ngg                                           23

<210> SEQ ID NO 33
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
gtagagcgga ggcaggaggc ggg                                           23

<210> SEQ ID NO 34
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
gtagagcgga ggcaggagtt ggg                                           23

<210> SEQ ID NO 35
<211> LENGTH: 23
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 35
gtgaacgtgg atgaagttgg tgg                                              23

<210> SEQ ID NO 36
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
gacgttcacc ttgccccaca ggg                                              23

<210> SEQ ID NO 37
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
gcacgttcac cttgccccac agg                                              23

<210> SEQ ID NO 38
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
ggtctgccgt tactgccctg tgg                                              23

<210> SEQ ID NO 39
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
ggttactgcc ctgtggggca agg                                              23

<210> SEQ ID NO 40
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gaggtgaacg tggatgaagt tgg                                              23

```
<210> SEQ ID NO 41
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
gctgtggggc aaggtgaacg tgg                                              23

<210> SEQ ID NO 42
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
ggtggtgcag atgaacttca ggg                                              23

<210> SEQ ID NO 43
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
gaccaggatg ggcaccaccc cgg                                              23

<210> SEQ ID NO 44
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
gtgttcatct ttggttttgt ggg                                              23

<210> SEQ ID NO 45
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
gctgccgccc agtgggactt tgg                                              23

<210> SEQ ID NO 46
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 46
ggcagcatag tgagcccaga agg                                              23

<210> SEQ ID NO 47
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
gtgagtagag cggaggcagg agg                                              23

<210> SEQ ID NO 48
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
gtagagcgga ggcaggaggc ggg                                              23

<210> SEQ ID NO 49
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
gccaagcact taaaggagtc cgg                                              23

<210> SEQ ID NO 50
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
gcaagcactt aaaggagtcc ggg                                              23

<210> SEQ ID NO 51
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
gtgagttccc atggcgatcc cgg                                              23

<210> SEQ ID NO 52
<211> LENGTH: 23
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 52
gctattgaag aaacagactt tgg                                            23

<210> SEQ ID NO 53
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
gattttctat tgagttccca tgg                                            23

<210> SEQ ID NO 54
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
ggaaacaaag tgagaagatg agg                                            23

<210> SEQ ID NO 55
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
gcctattttt gtgtttgatg ggg                                            23

<210> SEQ ID NO 56
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
gcagagcagt tggggtatga tgg                                            23

<210> SEQ ID NO 57
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
ggcagcacta cagagcagtt ggg                                            23
```

<210> SEQ ID NO 58
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 58
gcagcactac agagcagttg ggg                                              23

<210> SEQ ID NO 59
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 59
gcctgactgg ttctgctggc tgg                                              23

<210> SEQ ID NO 60
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 60
gtttgtgtca ttagtgaaac tgg                                              23

<210> SEQ ID NO 61
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 61
gcaacttgaa ctctcatctt agg                                              23

<210> SEQ ID NO 62
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 62
ggaacgugga ugaaguugg                                                   19

<210> SEQ ID NO 63
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 63
guaacgugga ugaaguugg                                              19

<210> SEQ ID NO 64
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
gugacgugga ugaaguugg                                              19

<210> SEQ ID NO 65
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
gugaagugga ugaaguugg                                              19

<210> SEQ ID NO 66
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
gugaacugga ugaaguugg                                              19

<210> SEQ ID NO 67
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
gugaacggga ugaaguugg                                              19

<210> SEQ ID NO 68
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
gugaacguga ugaaguugg                                              19

<210> SEQ ID NO 69
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
gugaacgugg ugaaguugg                                                    19

<210> SEQ ID NO 70
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
gugaacgugg agaaguugg                                                    19

<210> SEQ ID NO 71
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
gugaacgugg auaaguugg                                                    19

<210> SEQ ID NO 72
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
gugaacgugg augaguugg                                                    19

<210> SEQ ID NO 73
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
gugaacgugg augaauugg                                                    19

<210> SEQ ID NO 74
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
gugaacgugg augaagugg                                                    19
```

-continued

```
<210> SEQ ID NO 75
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
gugaacgugg augaaguug                                                        19

<210> SEQ ID NO 76
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
ggaacgugga ugaaguugg                                                        19

<210> SEQ ID NO 77
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
gaacguggau gaaguugg                                                         18

<210> SEQ ID NO 78
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
gacguggaug aaguugg                                                          17

<210> SEQ ID NO 79
<211> LENGTH: 16
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
gcguggauga aguugg                                                           16

<210> SEQ ID NO 80
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
```

```
            Synthetic oligonucleotide"

<400> SEQUENCE: 80
gguggaugaa guugg                                                  15

<210> SEQ ID NO 81
<211> LENGTH: 14
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
guggaugaag uugg                                                   14

<210> SEQ ID NO 82
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
gagagcggag gcaggaggc                                              19

<210> SEQ ID NO 83
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
gugagcggag gcaggaggc                                              19

<210> SEQ ID NO 84
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
guaagcggag gcaggaggc                                              19

<210> SEQ ID NO 85
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
guaggcggag gcaggaggc                                              19

<210> SEQ ID NO 86
<211> LENGTH: 19
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
guagacggag gcaggaggc                                                       19

<210> SEQ ID NO 87
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
guagagggag gcaggaggc                                                       19

<210> SEQ ID NO 88
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
guagagcgag gcaggaggc                                                       19

<210> SEQ ID NO 89
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
guagagcggg gcaggaggc                                                       19

<210> SEQ ID NO 90
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
guagagcgga gcaggaggc                                                       19

<210> SEQ ID NO 91
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
```
guagagcgga ggaggaggc        19

<210> SEQ ID NO 92
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
guagagcgga ggcggaggc        19

<210> SEQ ID NO 93
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
guagagcgga ggcagaggc        19

<210> SEQ ID NO 94
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
guagagcgga ggcaggggc        19

<210> SEQ ID NO 95
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
guagagcgga ggcaggagc        19

<210> SEQ ID NO 96
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
guagagcgga ggcaggagg        19

<210> SEQ ID NO 97
<211> LENGTH: 19
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 97 gugugggca aggugaacg                                                   19

<210> SEQ ID NO 98
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98 gcgugggca aggugaacg                                                   19

<210> SEQ ID NO 99
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99 gcuugggca aggugaacg                                                   19

<210> SEQ ID NO 100
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100 gcuggggca aggugaacg                                                   19

<210> SEQ ID NO 101
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
gcugugggca aggugaacg                                                  19

<210> SEQ ID NO 102
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
gcugugggga aggugaacg                                                  19

<210> SEQ ID NO 103
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103 gcugugggc aggugaacg                                                    19

<210> SEQ ID NO 104
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104 gcugugggc aagugaacg                                                    19

<210> SEQ ID NO 105
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105 gcugugggc aagggaacg                                                    19

<210> SEQ ID NO 106
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106 gcugugggc aagguaacg                                                    19

<210> SEQ ID NO 107
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107 gcugugggc aaggugacg                                                    19

<210> SEQ ID NO 108
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
```
gcuguggggc aaggugaag                                                   19

<210> SEQ ID NO 109
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
gcuguggggc aaggugaac                                                   19

<210> SEQ ID NO 110
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
gguucaucuu ugguuuugu                                                   19

<210> SEQ ID NO 111
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
guuucaucuu ugguuuugu                                                   19

<210> SEQ ID NO 112
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
gugucaucuu ugguuuugu                                                   19

<210> SEQ ID NO 113
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
guguuaucuu ugguuuugu                                                   19

<210> SEQ ID NO 114
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 114
guguucucuu ugguuuugu                                                   19

<210> SEQ ID NO 115
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
guguucacuu ugguuuugu                                                   19

<210> SEQ ID NO 116
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
guguucauuu ugguuuugu                                                   19

<210> SEQ ID NO 117
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
guguucaucu ugguuuugu                                                   19

<210> SEQ ID NO 118
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
guguucaucu uuguuuugu                                                   19

<210> SEQ ID NO 119
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
guguucaucu uugguuugu                                                   19
```

```
<210> SEQ ID NO 120
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
guguucaucu uugguuuuu                                                  19

<210> SEQ ID NO 121
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
guguucaucu uugguuuug                                                  19

<210> SEQ ID NO 122
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
guugaacgug gaugaaguug g                                               21

<210> SEQ ID NO 123
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
guggaacgug gaugaaguug g                                               21

<210> SEQ ID NO 124
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
guguaacgug gaugaaguug g                                               21

<210> SEQ ID NO 125
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 125
gugauacgug gaugaaguug g                                               21

<210> SEQ ID NO 126
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
gugaaucgug gaugaaguug g                                               21

<210> SEQ ID NO 127
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
gugaaacgug gaugaaguug g                                               21

<210> SEQ ID NO 128
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
gugaaccgug gaugaaguug g                                               21

<210> SEQ ID NO 129
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129 gugaacgug gaugaaguug g                                                21

<210> SEQ ID NO 130
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
gugaacagug gaugaaguug g                                               21

<210> SEQ ID NO 131
<211> LENGTH: 21
<212> TYPE: RNA
<213> ORGANISM: Artificial Sequence
```

```
-continued

<220> FEATURE:
<221> NAME/KEY: source
<223> OTHER INFORMATION: /note="Description of Artificial Sequence:
      Synthetic oligonucleotide"

<400> SEQUENCE: 131
gugaacggug gaugaaguug g                                          21

<210> SEQ ID NO 132
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
gugaacgcug gaugaaguug g                                          21

<210> SEQ ID NO 133
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
gugaacgaug gaugaaguug g                                          21

<210> SEQ ID NO 134
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
gugaacguug gaugaaguug g                                          21

<210> SEQ ID NO 135
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
gugaacguag gaugaaguug g                                          21

<210> SEQ ID NO 136
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
gugaacgucg gaugaaguug g                                          21
```

<210> SEQ ID NO 137
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
gugaacgugg gaugaaguug g                                              21

<210> SEQ ID NO 138
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
gugaacgugc gaugaaguug g                                              21

<210> SEQ ID NO 139
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
gugaacgugg caugaaguug g                                              21

<210> SEQ ID NO 140
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
gugaacgugg aaugaaguug g                                              21

<210> SEQ ID NO 141
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
gugaacgugg auugaaguug g                                              21

<210> SEQ ID NO 142
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 142
gugaacgugg auggaaguug g                                      21

<210> SEQ ID NO 143
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
gugaacgugg augaaaguug g                                      21

<210> SEQ ID NO 144
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
gugaacgugg augaagguug g                                      21

<210> SEQ ID NO 145
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
gugaacgugg augaaguuug g                                      21

<210> SEQ ID NO 146
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
gugaacgugg augaaguugg g                                      21

<210> SEQ ID NO 147
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
guuagagcgg aggcaggagg c                                      21

<210> SEQ ID NO 148
<211> LENGTH: 21
<212> TYPE: RNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
guaagagcgg aggcaggagg c                                              21

<210> SEQ ID NO 149
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
guaggagcgg aggcaggagg c                                              21

<210> SEQ ID NO 150
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
guagcagcgg aggcaggagg c                                              21

<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
guaguagcgg aggcaggagg c                                              21

<210> SEQ ID NO 152
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
guagaagcgg aggcaggagg c                                              21

<210> SEQ ID NO 153
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
guagaugcgg aggcaggagg c                                              21
```

<210> SEQ ID NO 154
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 154
guagacgcgg aggcaggagg c                                      21

<210> SEQ ID NO 155
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 155
guagaggcgg aggcaggagg c                                      21

<210> SEQ ID NO 156
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 156
guagagacgg aggcaggagg c                                      21

<210> SEQ ID NO 157
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 157
guagagucgg aggcaggagg c                                      21

<210> SEQ ID NO 158
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 158
guagagccgg aggcaggagg c                                      21

<210> SEQ ID NO 159
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

-continued

```
      Synthetic oligonucleotide"

<400> SEQUENCE: 159
guagagcagg aggcaggagg c                                           21

<210> SEQ ID NO 160
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
guagagcugg aggcaggagg c                                           21

<210> SEQ ID NO 161
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
guagagcggg aggcaggagg c                                           21

<210> SEQ ID NO 162
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
guagagcgug aggcaggagg c                                           21

<210> SEQ ID NO 163
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
guagagcggu aggcaggagg c                                           21

<210> SEQ ID NO 164
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
guagagcgga aggcaggagg c                                           21

<210> SEQ ID NO 165
<211> LENGTH: 21
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
guagagcgga gggcaggagg c                                              21

<210> SEQ ID NO 166
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
guagagcgga ggccaggagg c                                              21

<210> SEQ ID NO 167
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
guagagcgga ggcuaggagg c                                              21

<210> SEQ ID NO 168
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
guagagcgga ggcgaggagg c                                              21

<210> SEQ ID NO 169
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
guagagcgga ggcaaggagg c                                              21

<210> SEQ ID NO 170
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
```
guagagcgga ggcagggagg c                                            21

<210> SEQ ID NO 171
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
guagagcgga ggcaggaagg c                                            21

<210> SEQ ID NO 172
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
guagagcgga ggcaggaggg c                                            21

<210> SEQ ID NO 173
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
guagagcgga ggcaggaggc c                                            21

<210> SEQ ID NO 174
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
gucugugggg caaggugaac g                                            21

<210> SEQ ID NO 175
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175 gcugugggg caaggugaac g                                             21

<210> SEQ ID NO 176
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 176
gcucgugggg caaggugaac g                                              21

<210> SEQ ID NO 177
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
gcuguugggg caaggugaac g                                              21

<210> SEQ ID NO 178
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gcugucgggg caaggugaac g                                              21

<210> SEQ ID NO 179
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
gcuguguggg caaggugaac g                                              21

<210> SEQ ID NO 180
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
gcuguggugg caaggugaac g                                              21

<210> SEQ ID NO 181
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
gcugugggug caaggugaac g                                              21

<210> SEQ ID NO 182
```

```
-continued

<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182 gcugugggu caaggugaac g                                          21

<210> SEQ ID NO 183
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183 gcugugggc uaaggugaac g                                          21

<210> SEQ ID NO 184
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184 gcugugggc auaggugaac g                                          21

<210> SEQ ID NO 185
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185 gcugugggc aauggugaac g                                          21

<210> SEQ ID NO 186
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186 gcugugggc aagugugaac g                                          21

<210> SEQ ID NO 187
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
```

-continued gcugugggc aagguugaac g                                       21

<210> SEQ ID NO 188
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188 gcugugggc aaggucgaac g                                       21

<210> SEQ ID NO 189
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189 gcugugggc aagguguaac g                                       21

<210> SEQ ID NO 190
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190 gcugugggc aaggugauac g                                       21

<210> SEQ ID NO 191
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191 gcugugggc aaggugaauc g                                       21

<210> SEQ ID NO 192
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192 gcugugggc aaggugaacu g                                       21

<210> SEQ ID NO 193
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 193
guuguucauc uuugguuuug u                                              21

<210> SEQ ID NO 194
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
gucguucauc uuugguuuug u                                              21

<210> SEQ ID NO 195
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
guguuucauc uuugguuuug u                                              21

<210> SEQ ID NO 196
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
gugucucauc uuugguuuug u                                              21

<210> SEQ ID NO 197
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
guguuccauc uuugguuuug u                                              21

<210> SEQ ID NO 198
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
guguucuauc uuugguuuug u                                              21
```

```
<210> SEQ ID NO 199
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
guguucauuc uuugguuuug u                                              21

<210> SEQ ID NO 200
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
guguucaucc uuugguuuug u                                              21

<210> SEQ ID NO 201
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
guguucaucu uuugguuuug u                                              21

<210> SEQ ID NO 202
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
guguucaucu cuugguuuug u                                              21

<210> SEQ ID NO 203
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
guguucaucu ucugguuuug u                                              21

<210> SEQ ID NO 204
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 204
guguucaucu uucgguuuug u                                              21

<210> SEQ ID NO 205
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
guguucaucu uuguguuuug u                                              21

<210> SEQ ID NO 206
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
guguucaucu uugguuuuug u                                              21

<210> SEQ ID NO 207
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
guguucaucu uuggucuuug u                                              21

<210> SEQ ID NO 208
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
guguucaucu uugguucuug u                                              21

<210> SEQ ID NO 209
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
guguucaucu uugguuucug u                                              21

<210> SEQ ID NO 210
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 210
guguucaucu uugguuuucg u                                                  21

<210> SEQ ID NO 211
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
guguucaucu uugguuuugu u                                                  21

<210> SEQ ID NO 212
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
gugaacuugu ggaugaaguu gg                                                 22

<210> SEQ ID NO 213
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
gugaacgugu ugaugaaguu gg                                                 22

<210> SEQ ID NO 214
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
guagaguucg gaggcaggag gc                                                 22

<210> SEQ ID NO 215
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
guagagcggu uaggcaggag gc                                                 22
```

```
<210> SEQ ID NO 216
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
gugaacgugg augguugg                                                       18

<210> SEQ ID NO 217
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
gugaacgugg augaaguu                                                       18

<210> SEQ ID NO 218
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
guagagcgga caggaggc                                                       18

<210> SEQ ID NO 219
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
guagagcgga ggggaggc                                                       18

<210> SEQ ID NO 220
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
gugaacuuug uggaugaagu ugg                                                 23

<210> SEQ ID NO 221
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 221
gugaacgugu uugaugaagu ugg                                          23

<210> SEQ ID NO 222
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
guagaguuuc ggaggcagga ggc                                          23

<210> SEQ ID NO 223
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
guagagcggu uuaggcagga ggc                                          23

<210> SEQ ID NO 224
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
gugaacgugu uuugaugaag uugg                                         24

<210> SEQ ID NO 225
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
guagaguuuu cggaggcagg aggc                                         24

<210> SEQ ID NO 226
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
guagagcggu uuuaggcagg aggc                                         24

<210> SEQ ID NO 227
<211> LENGTH: 25
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
gugaacgugu uuuugaugaa guugg                                         25

<210> SEQ ID NO 228
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 228
cgatacaagg ctgttagaga gataattgg                                     29

<210> SEQ ID NO 229
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 229
ccaactccta agccagtgcc agaagag                                       27

<210> SEQ ID NO 230
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 230
agtcagtgcc tatcagaaac ccaagag                                       27

<210> SEQ ID NO 231
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 231
taatacgact cactataggg                                               20

<210> SEQ ID NO 232
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 232
tgccgtcctc gatgttgtgg cg                                            22
```

<210> SEQ ID NO 233
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 233
gcacagggtg gaacaagatg g                                              21

<210> SEQ ID NO 234
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 234
accaccccaa aggtgaccgt                                                20

<210> SEQ ID NO 235
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 235
tgaggatgaa gagaaaaatc ccggag                                         26

<210> SEQ ID NO 236
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 236
atcattgtac ccatgatgaa ctctcataaa ac                                  32

<210> SEQ ID NO 237
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 237
caatagcaat agacagttag aaagaagtgg aag                                 33

<210> SEQ ID NO 238
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic primer"

<400> SEQUENCE: 238
gctgcaccag aattagagcc actataagag                                30

<210> SEQ ID NO 239
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 239
caatccgccc aagggaact gatag                                      25

<210> SEQ ID NO 240
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 240
tgctttgttt tcaaaagata cactcccca                                 29

<210> SEQ ID NO 241
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 241
gttttagagc tagaaatagc aagttaaaat aaggc                          35

<210> SEQ ID NO 242
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 242
aaaagcaccg actcggtgcc ac                                        22

<210> SEQ ID NO 243
<211> LENGTH: 24
<212> TYPE: DNA
<213> ORGANISM: Homo sapiens

<400> SEQUENCE: 243
ttgtaacatg gatgaagttg gagg                                      24

<210> SEQ ID NO 244
<211> LENGTH: 24
<212> TYPE: DNA
<213> ORGANISM: Homo sapiens
<220> FEATURE:
<221> NAME/KEY: modified_base

```
<222> LOCATION: (4)..(4)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 244
gtgnaacgtg gatgaagttg gngg                                              24

<210> SEQ ID NO 245
<211> LENGTH: 24
<212> TYPE: DNA
<213> ORGANISM: Homo sapiens

<400> SEQUENCE: 245
ctgcaacgtg gatgaagctg gagg                                              24

<210> SEQ ID NO 246
<211> LENGTH: 24
<212> TYPE: DNA
<213> ORGANISM: Homo sapiens
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 246
gtgnaacgtg gatgaagttg gngg                                              24

<210> SEQ ID NO 247
<211> LENGTH: 24
<212> TYPE: DNA
<213> ORGANISM: Homo sapiens

<400> SEQUENCE: 247
gctctgccgt ttactgccct gtgg                                              24

<210> SEQ ID NO 248
<211> LENGTH: 24
<212> TYPE: DNA
<213> ORGANISM: Homo sapiens
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 248
ggtctgccgn ttactgccct gngg                                              24

<210> SEQ ID NO 249
<211> LENGTH: 24
<212> TYPE: DNA
<213> ORGANISM: Homo sapiens

<400> SEQUENCE: 249
aagatgaacg tggagtgaag tggg                                              24

<210> SEQ ID NO 250
```

```
<211> LENGTH: 24
<212> TYPE: DNA
<213> ORGANISM: Homo sapiens
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 250
gaggtgaacg tggantgaag tngg                                              24

<210> SEQ ID NO 251
<211> LENGTH: 24
<212> TYPE: DNA
<213> ORGANISM: Homo sapiens

<400> SEQUENCE: 251
cgccaagatg ggcagccacc ccgg                                              24

<210> SEQ ID NO 252
<211> LENGTH: 24
<212> TYPE: DNA
<213> ORGANISM: Homo sapiens
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 252
gaccaggatg ggcanccacc cngg                                              24

<210> SEQ ID NO 253
<211> LENGTH: 24
<212> TYPE: DNA
<213> ORGANISM: Homo sapiens

<400> SEQUENCE: 253
atccaggatg ggcaccacac ccgg                                              24

<210> SEQ ID NO 254
<211> LENGTH: 24
<212> TYPE: DNA
<213> ORGANISM: Homo sapiens
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 254
gaccaggatg ggcaccacnc cngg                                              24

<210> SEQ ID NO 255
<211> LENGTH: 24
<212> TYPE: DNA
<213> ORGANISM: Homo sapiens

<400> SEQUENCE: 255
```
atgttcttct ttggcttttg ttgg       24

<210> SEQ ID NO 256
<211> LENGTH: 24
<212> TYPE: DNA
<213> ORGANISM: Homo sapiens
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 256
gtgttcatct ttggnttttg tngg       24

<210> SEQ ID NO 257
<211> LENGTH: 24
<212> TYPE: DNA
<213> ORGANISM: Homo sapiens

<400> SEQUENCE: 257
tatttcatct ttggttttag tggg       24

<210> SEQ ID NO 258
<211> LENGTH: 24
<212> TYPE: DNA
<213> ORGANISM: Homo sapiens
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 258
gtgttcatct ttggttttng tngg       24

<210> SEQ ID NO 259
<211> LENGTH: 24
<212> TYPE: DNA
<213> ORGANISM: Homo sapiens

<400> SEQUENCE: 259
aggttcaact ttggttttgg tggg       24

<210> SEQ ID NO 260
<211> LENGTH: 24
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 260
gtgttcatct ttggttttgn tngg       24

<210> SEQ ID NO 261

```
<211> LENGTH: 24
<212> TYPE: DNA
<213> ORGANISM: Homo sapiens

<400> SEQUENCE: 261
atgttcatat ttggttttgt gtgg                                              24

<210> SEQ ID NO 262
<211> LENGTH: 24
<212> TYPE: DNA
<213> ORGANISM: Homo sapiens
<220> FEATURE:
<221> NAME/KEY: modified_base
<222> LOCATION: (21)..(22)
<223> OTHER INFORMATION: a, c, t, g, unknown or other

<400> SEQUENCE: 262
gtgttcatct ttggttttgt nngg                                              24

<210> SEQ ID NO 263
<211> LENGTH: 24
<212> TYPE: DNA
<213> ORGANISM: Homo sapiens

<400> SEQUENCE: 263
tttgcccccc agtgggacat ttgg                                              24

<210> SEQ ID NO 264
<211> LENGTH: 24
<212> TYPE: DNA
<213> ORGANISM: Homo sapiens
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 264
gctgccgccc agtgggacnt tngg                                              24

<210> SEQ ID NO 265
<211> LENGTH: 24
<212> TYPE: DNA
<213> ORGANISM: Homo sapiens

<400> SEQUENCE: 265
gtgtgagcgg aggcaggagg cagg                                              24

<210> SEQ ID NO 266
<211> LENGTH: 24
<212> TYPE: DNA
<213> ORGANISM: Homo sapiens
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 266
gtnagagcgg aggcaggagg cngg                                              24
```

```
<210> SEQ ID NO 267
<211> LENGTH: 24
<212> TYPE: DNA
<213> ORGANISM: Homo sapiens

<400> SEQUENCE: 267
gtaggagagg aggcaggagg cagg                                              24

<210> SEQ ID NO 268
<211> LENGTH: 24
<212> TYPE: DNA
<213> ORGANISM: Homo sapiens
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 268
gtangagcgg aggcaggagg cngg                                              24

<210> SEQ ID NO 269
<211> LENGTH: 24
<212> TYPE: DNA
<213> ORGANISM: Homo sapiens

<400> SEQUENCE: 269
ccagaagcgg aggcaggagg ctgg                                              24

<210> SEQ ID NO 270
<211> LENGTH: 24
<212> TYPE: DNA
<213> ORGANISM: Homo sapiens
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 270
gtagnagcgg aggcaggagg cngg                                              24

<210> SEQ ID NO 271
<211> LENGTH: 24
<212> TYPE: DNA
<213> ORGANISM: Homo sapiens

<400> SEQUENCE: 271
gtagagagga ggcagggagg cggg                                              24

<210> SEQ ID NO 272
<211> LENGTH: 24
<212> TYPE: DNA
<213> ORGANISM: Homo sapiens
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other
```

```
<400> SEQUENCE: 272
gtagagcgga ggcanggagg cngg                                              24

<210> SEQ ID NO 273
<211> LENGTH: 24
<212> TYPE: DNA
<213> ORGANISM: Homo sapiens

<400> SEQUENCE: 273
gtagagagga ggcagggagg cggg                                              24

<210> SEQ ID NO 274
<211> LENGTH: 24
<212> TYPE: DNA
<213> ORGANISM: Homo sapiens
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 274
gtagagcgga ggcanggagg cngg                                              24

<210> SEQ ID NO 275
<211> LENGTH: 24
<212> TYPE: DNA
<213> ORGANISM: Homo sapiens

<400> SEQUENCE: 275
accaagcact taaggagtg ctgg                                               24

<210> SEQ ID NO 276
<211> LENGTH: 24
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 276
gccaagcact taaggagtn cngg                                               24

<210> SEQ ID NO 277
<211> LENGTH: 24
<212> TYPE: DNA
<213> ORGANISM: Homo sapiens

<400> SEQUENCE: 277
tccagcacta cagagcagat ttgg                                              24

<210> SEQ ID NO 278
<211> LENGTH: 24
<212> TYPE: DNA
<213> ORGANISM: Homo sapiens
<220> FEATURE:
<221> NAME/KEY: modified_base
<222> LOCATION: (19)..(19)
<223> OTHER INFORMATION: a, c, t, g, unknown or other
```

```
<220> FEATURE:
<221> NAME/KEY: modified_base
<222> LOCATION: (22)..(22)
<223> OTHER INFORMATION: a, c, t, g, unknown or other

<400> SEQUENCE: 278
ggcagcacta cagagcagnt tngg                                              24

<210> SEQ ID NO 279
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 279
tcagtctttt actcggggat accaa                                             25

<210> SEQ ID NO 280
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 280
ttcatctatc gtaacgcttg gcaat                                             25

<210> SEQ ID NO 281
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 281
gaacagaatg atgaggaagg gaaga                                             25

<210> SEQ ID NO 282
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 282
aacctagatg cccatcaata gtgga                                             25

<210> SEQ ID NO 283
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 283
ttgagatgcc gttgtttcat gccaa                                             25
```

<210> SEQ ID NO 284
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 284
attgctcaca ccacatcaga aagcc                                              25

<210> SEQ ID NO 285
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 285
ccaggcatcc tgctgatctt ttgtt                                              25

<210> SEQ ID NO 286
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 286
ttaggggtta aagggcttgc tggtg                                              25

<210> SEQ ID NO 287
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 287
gacggcgtct gtgacaagta caatg                                              25

<210> SEQ ID NO 288
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 288
gaggtctctt acaaaaggcc cagga                                              25

<210> SEQ ID NO 289
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

```
<400> SEQUENCE: 289
ggtaccttgg agggatctat tgcct                                    25

<210> SEQ ID NO 290
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 290
ctgacacttc tgcagccttg ggtag                                    25

<210> SEQ ID NO 291
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 291
tgaccaatga gcaaagaaat tatccaca                                 28

<210> SEQ ID NO 292
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 292
acatcccaaa gaatgaagtt ggaga                                    25

<210> SEQ ID NO 293
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 293
gcacactagt ggactactca gggtat                                   26

<210> SEQ ID NO 294
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 294
acaggcatat catattgtat gtcagagtg                                29

<210> SEQ ID NO 295
<211> LENGTH: 25
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 295
aagaaacagg gatccgtgca taaat                                            25

<210> SEQ ID NO 296
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 296
aatttctttg ttggaaaacc ctgga                                            25

<210> SEQ ID NO 297
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 297
cattgattgt ttcatcccga cagtt                                            25

<210> SEQ ID NO 298
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 298
ggctaaggtg aaaaacaaag ccaat                                            25

<210> SEQ ID NO 299
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 299
gctacatctg gttctggttt gaggc                                            25

<210> SEQ ID NO 300
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 300
tccaccctat ccaatgtcag caaca                                            25
```

<210> SEQ ID NO 301
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 301
aggaatgctt tagcgaggag gaag                                           24

<210> SEQ ID NO 302
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 302
ctctccactc ctcctctggt tctc                                           24

<210> SEQ ID NO 303
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 303
tgatgcactt gaggacagct actct                                          25

<210> SEQ ID NO 304
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 304
tgtgcctggc ttcaaatatg tctta                                          25

<210> SEQ ID NO 305
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 305
ccactttgcc ttctttgaaa ctgg                                           24

<210> SEQ ID NO 306
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 306
aacacgatct gatggagaag gaaag				25

<210> SEQ ID NO 307
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 307
ctcgggaaat ggcaccatca tcatc				25

<210> SEQ ID NO 308
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 308
caggtcatgg tgaacctcag agcta				25

<210> SEQ ID NO 309
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 309
ttctgtaatt ctgaggccca cggag				25

<210> SEQ ID NO 310
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 310
tgatgaacct cagagccatt tgggg				25

<210> SEQ ID NO 311
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 311
acctcccaca tgtaccttgc ttttt				25

<210> SEQ ID NO 312
<211> LENGTH: 25

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 312
gcctttcatg tctggaacat ttttg                                          25

<210> SEQ ID NO 313
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 313
ccaacctcaa aaggaccttg ctgtc                                          25

<210> SEQ ID NO 314
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 314
ttcactttcc agagaagagt cctcc                                          25

<210> SEQ ID NO 315
<211> LENGTH: 22
<212> TYPE: DNA
<213> ORGANISM: Homo sapiens

<400> SEQUENCE: 315
gggaattgga tgaagttggg gg                                             22

<210> SEQ ID NO 316
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 316
gtgaagtgga tgaagttggn gg                                             22

<210> SEQ ID NO 317
<211> LENGTH: 22
<212> TYPE: DNA
<213> ORGANISM: Homo sapiens

<400> SEQUENCE: 317
ctgaagtgga taaagttggt gg                                             22

<210> SEQ ID NO 318
<211> LENGTH: 22
<212> TYPE: DNA
<213> ORGANISM: Homo sapiens
<220> FEATURE:
```

```
<221> NAME/KEY: modified_base
<222> LOCATION: (20)..(20)
<223> OTHER INFORMATION: a, c, t, g, unknown or other

<400> SEQUENCE: 318
gtgaagtgga tgaagttggn gg                                            22

<210> SEQ ID NO 319
<211> LENGTH: 22
<212> TYPE: DNA
<213> ORGANISM: Homo sapiens

<400> SEQUENCE: 319
gggaacggga tgaaggtggt gg                                            22

<210> SEQ ID NO 320
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 320
gtgaacggga tgaagttggn gg                                            22

<210> SEQ ID NO 321
<211> LENGTH: 22
<212> TYPE: DNA
<213> ORGANISM: Homo sapiens

<400> SEQUENCE: 321
caccttcacc tgccccacac gg                                            22

<210> SEQ ID NO 322
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 322
gacgttcacc tgccccacan gg                                            22

<210> SEQ ID NO 323
<211> LENGTH: 22
<212> TYPE: DNA
<213> ORGANISM: Homo sapiens

<400> SEQUENCE: 323
tcaccttccc ttgccccaca gg                                            22

<210> SEQ ID NO 324
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 324
gcacgttccc ttgccccacn gg                                            22
```

<210> SEQ ID NO 325
<211> LENGTH: 22
<212> TYPE: DNA
<213> ORGANISM: Homo sapiens

<400> SEQUENCE: 325
ggctactgcc ctgggggcag gg                                              22

<210> SEQ ID NO 326
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 326
ggttactgcc ctgggggcan gg                                              22

<210> SEQ ID NO 327
<211> LENGTH: 22
<212> TYPE: DNA
<213> ORGANISM: Homo sapiens

<400> SEQUENCE: 327
gcagtgacgt ggatgaagtt gg                                              22

<210> SEQ ID NO 328
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 328
gaggtgacgt ggatgaagtn gg                                              22

<210> SEQ ID NO 329
<211> LENGTH: 22
<212> TYPE: DNA
<213> ORGANISM: Homo sapiens

<400> SEQUENCE: 329
gtggggacgt ggatgaagtt gg                                              22

<210> SEQ ID NO 330
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 330
gaggtgacgt ggatgaagtn gg                                              22

<210> SEQ ID NO 331
<211> LENGTH: 22
<212> TYPE: DNA
<213> ORGANISM: Homo sapiens

```
<400> SEQUENCE: 331
gagggaacgt ggatgaagct gg                                              22

<210> SEQ ID NO 332
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 332
gagggaacgt ggatgaagtn gg                                              22

<210> SEQ ID NO 333
<211> LENGTH: 22
<212> TYPE: DNA
<213> ORGANISM: Homo sapiens

<400> SEQUENCE: 333
gatgagggga aggtgaacgt gg                                              22

<210> SEQ ID NO 334
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 334
gctgtgggga aggtgaacgn gg                                              22

<210> SEQ ID NO 335
<211> LENGTH: 22
<212> TYPE: DNA
<213> ORGANISM: Homo sapiens

<400> SEQUENCE: 335
gctgggggca acgtgaacgt gg                                              22

<210> SEQ ID NO 336
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 336
gctgggggca aggtgaacgn gg                                              22

<210> SEQ ID NO 337
<211> LENGTH: 22
<212> TYPE: DNA
<213> ORGANISM: Homo sapiens

<400> SEQUENCE: 337
ggtggtcaga tcaacttcag gg                                              22

<210> SEQ ID NO 338
<211> LENGTH: 22
```

```
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 338
ggtggtcaga tgaacttcan gg                                                  22

<210> SEQ ID NO 339
<211> LENGTH: 22
<212> TYPE: DNA
<213> ORGANISM: Homo sapiens

<400> SEQUENCE: 339
gaccaggagg gcagcaccca gg                                                  22

<210> SEQ ID NO 340
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 340
gaccaggagg gcaccacccn gg                                                  22

<210> SEQ ID NO 341
<211> LENGTH: 22
<212> TYPE: DNA
<213> ORGANISM: Homo sapiens

<400> SEQUENCE: 341
gtcttctctt tggttttgta gg                                                  22

<210> SEQ ID NO 342
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 342
gtgttctctt tggttttgtn gg                                                  22

<210> SEQ ID NO 343
<211> LENGTH: 22
<212> TYPE: DNA
<213> ORGANISM: Homo sapiens

<400> SEQUENCE: 343
gtgttcatct tggttttgta cg                                                  22

<210> SEQ ID NO 344
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other
```

```
<400> SEQUENCE: 344
gtgttcatct tggttttgtn gg                                           22

<210> SEQ ID NO 345
<211> LENGTH: 22
<212> TYPE: DNA
<213> ORGANISM: Homo sapiens

<400> SEQUENCE: 345
atgctctctt tggttttgtt gg                                           22

<210> SEQ ID NO 346
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 346
gtgttctctt tggttttgtn gg                                           22

<210> SEQ ID NO 347
<211> LENGTH: 22
<212> TYPE: DNA
<213> ORGANISM: Homo sapiens

<400> SEQUENCE: 347
atggtctctt tggttttgta gg                                           22

<210> SEQ ID NO 348
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 348
gtgttctctt tggttttgtn gg                                           22

<210> SEQ ID NO 349
<211> LENGTH: 22
<212> TYPE: DNA
<213> ORGANISM: Homo sapiens

<400> SEQUENCE: 349
atgttcattt tggttttgtt gg                                           22

<210> SEQ ID NO 350
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 350
gtgttcattt tggttttgtn gg                                           22

<210> SEQ ID NO 351
<211> LENGTH: 22
```

```
<212> TYPE: DNA
<213> ORGANISM: Homo sapiens

<400> SEQUENCE: 351
ttattcattt tggttttgtg gg                                              22

<210> SEQ ID NO 352
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 352
gtgttcattt tggttttgtn gg                                              22

<210> SEQ ID NO 353
<211> LENGTH: 22
<212> TYPE: DNA
<213> ORGANISM: Homo sapiens

<400> SEQUENCE: 353
ggtttcattt tggttttgtt gg                                              22

<210> SEQ ID NO 354
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 354
gtgttcattt tggttttgtn gg                                              22

<210> SEQ ID NO 355
<211> LENGTH: 22
<212> TYPE: DNA
<213> ORGANISM: Homo sapiens

<400> SEQUENCE: 355
gtgttcactt tggttgtgta gg                                              22

<210> SEQ ID NO 356
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 356
gtgttcactt tggttttgtn gg                                              22

<210> SEQ ID NO 357
<211> LENGTH: 22
<212> TYPE: DNA
<213> ORGANISM: Homo sapiens

<400> SEQUENCE: 357
gtgttcttct tggttttgtt gg                                              22
```

```
<210> SEQ ID NO 358
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 358
gtgttcatct tggttttgtn gg                                              22

<210> SEQ ID NO 359
<211> LENGTH: 22
<212> TYPE: DNA
<213> ORGANISM: Homo sapiens

<400> SEQUENCE: 359
ggaagcaagt gagcccagaa gg                                              22

<210> SEQ ID NO 360
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 360
ggcagcaagt gagcccagan gg                                              22

<210> SEQ ID NO 361
<211> LENGTH: 22
<212> TYPE: DNA
<213> ORGANISM: Homo sapiens

<400> SEQUENCE: 361
gaaagcatag tgacccagag gg                                              22

<210> SEQ ID NO 362
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 362
ggcagcatag tgacccagan gg                                              22

<210> SEQ ID NO 363
<211> LENGTH: 22
<212> TYPE: DNA
<213> ORGANISM: Homo sapiens

<400> SEQUENCE: 363
ggcacatagt gagccaagat gg                                              22

<210> SEQ ID NO 364
<211> LENGTH: 22
<212> TYPE: DNA
<213> ORGANISM: Homo sapiens
<220> FEATURE:
<221> NAME/KEY: modified_base
```

```
<222> LOCATION: (20)..(20)
<223> OTHER INFORMATION: a, c, t, g, unknown or other

<400> SEQUENCE: 364
ggcacatagt gagcccagan gg                                              22

<210> SEQ ID NO 365
<211> LENGTH: 22
<212> TYPE: DNA
<213> ORGANISM: Homo sapiens

<400> SEQUENCE: 365
ggcagctagt gagcccagag ga                                              22

<210> SEQ ID NO 366
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 366
ggcagctagt gagcccagan gg                                              22

<210> SEQ ID NO 367
<211> LENGTH: 22
<212> TYPE: DNA
<213> ORGANISM: Homo sapiens

<400> SEQUENCE: 367
ggcagcaagt gaggccagaa gg                                              22

<210> SEQ ID NO 368
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 368
ggcagcaagt gagcccagan gg                                              22

<210> SEQ ID NO 369
<211> LENGTH: 22
<212> TYPE: DNA
<213> ORGANISM: Homo sapiens

<400> SEQUENCE: 369
gagtgtgagc ggaggcagga gg                                              22

<210> SEQ ID NO 370
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 370
gtgagtgagc ggaggcaggn gg                                              22
```

```
<210> SEQ ID NO 371
<211> LENGTH: 22
<212> TYPE: DNA
<213> ORGANISM: Homo sapiens

<400> SEQUENCE: 371
ctgaggaggc ggaggcagga gg                                               22

<210> SEQ ID NO 372
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 372
gtgagtaggc ggaggcaggn gg                                               22

<210> SEQ ID NO 373
<211> LENGTH: 22
<212> TYPE: DNA
<213> ORGANISM: Homo sapiens

<400> SEQUENCE: 373
gtgagtagag ggagggagga gg                                               22

<210> SEQ ID NO 374
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 374
gtgagtagag ggaggcaggn gg                                               22

<210> SEQ ID NO 375
<211> LENGTH: 22
<212> TYPE: DNA
<213> ORGANISM: Homo sapiens

<400> SEQUENCE: 375
gaagggcgga ggaggaggca gg                                               22

<210> SEQ ID NO 376
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 376
gtagagcgga ggaggaggcn gg                                               22

<210> SEQ ID NO 377
<211> LENGTH: 22
<212> TYPE: DNA
<213> ORGANISM: Homo sapiens

<400> SEQUENCE: 377
```

```
ggagagagga ggaggaggct gg                                              22

<210> SEQ ID NO 378
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 378
gtagagcgga ggaggaggcn gg                                              22

<210> SEQ ID NO 379
<211> LENGTH: 22
<212> TYPE: DNA
<213> ORGANISM: Homo sapiens

<400> SEQUENCE: 379
gcaaagcgga ggcggaggca gg                                              22

<210> SEQ ID NO 380
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 380
gtagagcgga ggcggaggcn gg                                              22

<210> SEQ ID NO 381
<211> LENGTH: 22
<212> TYPE: DNA
<213> ORGANISM: Homo sapiens

<400> SEQUENCE: 381
gcagcgcgga ggcggaggcg gg                                              22

<210> SEQ ID NO 382
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 382
gtagagcgga ggcggaggcn gg                                              22

<210> SEQ ID NO 383
<211> LENGTH: 22
<212> TYPE: DNA
<213> ORGANISM: Homo sapiens

<400> SEQUENCE: 383
ctagggcgga ggcggaggcg gg                                              22

<210> SEQ ID NO 384
<211> LENGTH: 22
<212> TYPE: DNA
```

```
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 384
gtagagcgga ggcggaggcn gg                                              22

<210> SEQ ID NO 385
<211> LENGTH: 22
<212> TYPE: DNA
<213> ORGANISM: Homo sapiens

<400> SEQUENCE: 385
gtggagggag gcaggaggca gg                                              22

<210> SEQ ID NO 386
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 386
gtagagggag gcaggaggcn gg                                              22

<210> SEQ ID NO 387
<211> LENGTH: 22
<212> TYPE: DNA
<213> ORGANISM: Homo sapiens

<400> SEQUENCE: 387
gaaggaggag gcaggaggct gg                                              22

<210> SEQ ID NO 388
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 388
gtaggcggag gcaggaggcn gg                                              22

<210> SEQ ID NO 389
<211> LENGTH: 22
<212> TYPE: DNA
<213> ORGANISM: Homo sapiens

<400> SEQUENCE: 389
ggaggtggag gcaggaggct gg                                              22

<210> SEQ ID NO 390
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 390
```

-continued gtaggcggag gcaggaggcn gg                                                22

<210> SEQ ID NO 391
<211> LENGTH: 22
<212> TYPE: DNA
<213> ORGANISM: Homo sapiens

<400> SEQUENCE: 391
ggtgagggag gcaggaggca gg                                                22

<210> SEQ ID NO 392
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 392
gtagagggag gcaggaggcn gg                                                22

<210> SEQ ID NO 393
<211> LENGTH: 22
<212> TYPE: DNA
<213> ORGANISM: Homo sapiens

<400> SEQUENCE: 393
gcagggcggg gcaggaggct gg                                                22

<210> SEQ ID NO 394
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 394
gtagagcggg gcaggaggcn gg                                                22

<210> SEQ ID NO 395
<211> LENGTH: 22
<212> TYPE: DNA
<213> ORGANISM: Homo sapiens

<400> SEQUENCE: 395
ggctagcatt aaaggagtca gg                                                22

<210> SEQ ID NO 396
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 396
gccaagcatt aaaggagtcn gg                                                22

<210> SEQ ID NO 397
<211> LENGTH: 22
<212> TYPE: DNA

```
<213> ORGANISM: Homo sapiens

<400> SEQUENCE: 397
gcaagactta aagcagtccg gg                                              22

<210> SEQ ID NO 398
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 398
gcaagactta aaggagtccn gg                                              22

<210> SEQ ID NO 399
<211> LENGTH: 22
<212> TYPE: DNA
<213> ORGANISM: Homo sapiens

<400> SEQUENCE: 399
gtgaggtccc aggcgatcct gg                                              22

<210> SEQ ID NO 400
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 400
gtgagttccc aggcgatccn gg                                              22

<210> SEQ ID NO 401
<211> LENGTH: 22
<212> TYPE: DNA
<213> ORGANISM: Homo sapiens

<400> SEQUENCE: 401
gctagtaaga aacagactta gg                                              22

<210> SEQ ID NO 402
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 402
gctattaaga aacagacttn gg                                              22

<210> SEQ ID NO 403
<211> LENGTH: 22
<212> TYPE: DNA
<213> ORGANISM: Homo sapiens

<400> SEQUENCE: 403
gattttcttt gaggtcccaa gg                                              22
```

```
<210> SEQ ID NO 404
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 404
gattttcttt gagttcccan gg                                              22

<210> SEQ ID NO 405
<211> LENGTH: 22
<212> TYPE: DNA
<213> ORGANISM: Homo sapiens

<400> SEQUENCE: 405
ggaatcaaat gagaagatgt gg                                              22

<210> SEQ ID NO 406
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 406
ggaaacaaat gagaagatgn gg                                              22

<210> SEQ ID NO 407
<211> LENGTH: 22
<212> TYPE: DNA
<213> ORGANISM: Homo sapiens

<400> SEQUENCE: 407
gaagacaaag gagaagatga gg                                              22

<210> SEQ ID NO 408
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 408
ggaaacaaag gagaagatgn gg                                              22

<210> SEQ ID NO 409
<211> LENGTH: 22
<212> TYPE: DNA
<213> ORGANISM: Homo sapiens

<400> SEQUENCE: 409
agaatcaaag gagaagatga gg                                              22

<210> SEQ ID NO 410
<211> LENGTH: 22
<212> TYPE: DNA
<213> ORGANISM: Homo sapiens
<220> FEATURE:
<221> NAME/KEY: modified_base
<222> LOCATION: (20)..(20)
```

```
<223> OTHER INFORMATION: a, c, t, g, unknown or other

<400> SEQUENCE: 410
ggaaacaaag gagaagatgn gg                                              22

<210> SEQ ID NO 411
<211> LENGTH: 22
<212> TYPE: DNA
<213> ORGANISM: Homo sapiens

<400> SEQUENCE: 411
ggaaaaaagt gagaacatgt gg                                              22

<210> SEQ ID NO 412
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 412
ggaaaaaagt gagaagatgn gg                                              22

<210> SEQ ID NO 413
<211> LENGTH: 22
<212> TYPE: DNA
<213> ORGANISM: Homo sapiens

<400> SEQUENCE: 413
ggaaacaaag gagaagatgt gc                                              22

<210> SEQ ID NO 414
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 414
ggaaacaaag gagaagatgn gg                                              22

<210> SEQ ID NO 415
<211> LENGTH: 22
<212> TYPE: DNA
<213> ORGANISM: Homo sapiens

<400> SEQUENCE: 415
ggaaacaaag tagaagaaga gg                                              22

<210> SEQ ID NO 416
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 416
ggaaacaaag tagaagatgn gg                                              22
```

-continued

```
<210> SEQ ID NO 417
<211> LENGTH: 22
<212> TYPE: DNA
<213> ORGANISM: Homo sapiens

<400> SEQUENCE: 417
ggaaacaaaa tgaaagatga gg                                              22

<210> SEQ ID NO 418
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 418
ggaaacaaag tgaaagatgn gg                                              22

<210> SEQ ID NO 419
<211> LENGTH: 22
<212> TYPE: DNA
<213> ORGANISM: Homo sapiens

<400> SEQUENCE: 419
gcctgttttt tgtttgatgt gg                                              22

<210> SEQ ID NO 420
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 420
gcctattttt tgtttgatgn gg                                              22

<210> SEQ ID NO 421
<211> LENGTH: 22
<212> TYPE: DNA
<213> ORGANISM: Homo sapiens

<400> SEQUENCE: 421
gcctattttt ggtttgaagg gg                                              22

<210> SEQ ID NO 422
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 422
gcctattttt ggtttgatgn gg                                              22

<210> SEQ ID NO 423
<211> LENGTH: 22
<212> TYPE: DNA
<213> ORGANISM: Homo sapiens

<400> SEQUENCE: 423
```

```
gcagacagtt ggggtgtgat gg                                              22
```

<210> SEQ ID NO 424
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 424

```
gcagacagtt ggggtatgan gg                                              22
```

<210> SEQ ID NO 425
<211> LENGTH: 22
<212> TYPE: DNA
<213> ORGANISM: Homo sapiens

<400> SEQUENCE: 425

```
tccagcctac agagcagttt gg                                              22
```

<210> SEQ ID NO 426
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 426

```
ggcagcctac agagcagttn gg                                              22
```

<210> SEQ ID NO 427
<211> LENGTH: 22
<212> TYPE: DNA
<213> ORGANISM: Homo sapiens

<400> SEQUENCE: 427

```
ggcagcacac agagcagatt gg                                              22
```

<210> SEQ ID NO 428
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 428

```
ggcagcacac agagcagttn gg                                              22
```

<210> SEQ ID NO 429
<211> LENGTH: 22
<212> TYPE: DNA
<213> ORGANISM: Homo sapiens

<400> SEQUENCE: 429

```
ggcagcacta agagcagtcg gg                                              22
```

<210> SEQ ID NO 430
<211> LENGTH: 22
<212> TYPE: DNA
<213> ORGANISM: Homo sapiens

```
<220> FEATURE:
<221> NAME/KEY: modified_base
<222> LOCATION: (20)..(20)
<223> OTHER INFORMATION: a, c, t, g, unknown or other

<400> SEQUENCE: 430
ggcagcacta agagcagttn gg                                              22

<210> SEQ ID NO 431
<211> LENGTH: 22
<212> TYPE: DNA
<213> ORGANISM: Homo sapiens

<400> SEQUENCE: 431
ccagaataca gagcagttgg gg                                              22

<210> SEQ ID NO 432
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 432
gcagcataca gagcagttgn gg                                              22

<210> SEQ ID NO 433
<211> LENGTH: 22
<212> TYPE: DNA
<213> ORGANISM: Homo sapiens

<400> SEQUENCE: 433
gcctgctggt gctgctggca gg                                              22

<210> SEQ ID NO 434
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 434
gcctgctggt tctgctggcn gg                                              22

<210> SEQ ID NO 435
<211> LENGTH: 22
<212> TYPE: DNA
<213> ORGANISM: Homo sapiens

<400> SEQUENCE: 435
gttttgtcat tagtgaaatg gg                                              22

<210> SEQ ID NO 436
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 436
```

```
gttttgtcat tagtgaaacn gg                                             22
```

<210> SEQ ID NO 437
<211> LENGTH: 22
<212> TYPE: DNA
<213> ORGANISM: Homo sapiens

<400> SEQUENCE: 437

```
acaagttgac tctcatcttg gg                                             22
```

<210> SEQ ID NO 438
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 438

```
gcaacttgac tctcatcttn gg                                             22
```

<210> SEQ ID NO 439
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 439

```
gaatgcagta aatttaaaag cccaagg                                        27
```

<210> SEQ ID NO 440
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 440

```
catcacagaa caccagaaag acagc                                          25
```

<210> SEQ ID NO 441
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 441

```
gcaaatctgg gtggatgtac tgttg                                          25
```

<210> SEQ ID NO 442
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 442
cctgcacgat ctcactatgt cttgc                                              25

<210> SEQ ID NO 443
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 443
tttacatggt ggaggacagg acttc                                              25

<210> SEQ ID NO 444
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 444
ccaatgatga ttatctccgt gactg                                              25

<210> SEQ ID NO 445
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 445
aattcacttt ccttcctttc ttttg                                              25

<210> SEQ ID NO 446
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 446
ctcacactcc caggttcaaa caatc                                              25

<210> SEQ ID NO 447
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 447
gttgaaattt gatccccagc attg                                               24

<210> SEQ ID NO 448
<211> LENGTH: 25
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 448
agagaggtgt gaaggagagg gaaag                                  25

<210> SEQ ID NO 449
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 449
ttgatgccgt ctgtgtactc aagca                                  25

<210> SEQ ID NO 450
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 450
gtttggtctc tttccaaggg gaagc                                  25

<210> SEQ ID NO 451
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 451
gttcccattg ttgtttggtt ttctg                                  25

<210> SEQ ID NO 452
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 452
tgctactata aagacgcatg cacac                                  25

<210> SEQ ID NO 453
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 453
gtgagtgaga acatgtggtg ttca                                   24
```

```
<210> SEQ ID NO 454
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 454
tggtgctatt cacaacagca aagag                                  25

<210> SEQ ID NO 455
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 455
agacgtggaa tcaacacaaa tgccc                                  25

<210> SEQ ID NO 456
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 456
acagatgtgc gatgtcaaga tcacc                                  25

<210> SEQ ID NO 457
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 457
atagagactg cttggaaagc gtgtg                                  25

<210> SEQ ID NO 458
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 458
agccttaccg aggactcctt ttacc                                  25

<210> SEQ ID NO 459
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 459
ctgagtcgtg ggagatctgt tgctg                                    25

<210> SEQ ID NO 460
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 460
atacacctga ccgcaaactt tgagac                                   26

<210> SEQ ID NO 461
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 461
ccctgagata caagaggagc ctgac                                    25

<210> SEQ ID NO 462
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 462
cgtcctctga acttcaattg ccctg                                    25

<210> SEQ ID NO 463
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 463
gaatgacatg gagatgctag agcaga                                   26

<210> SEQ ID NO 464
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 464
agaggctttc cataccctatg tgcca                                   25

<210> SEQ ID NO 465
<211> LENGTH: 28
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 465
tgcccagtaa gcattggcta taataatc                                          28

<210> SEQ ID NO 466
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 466
gtcccatatc atcctccaga aatcc                                             25

<210> SEQ ID NO 467
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 467
gctttaggat ctgctgccct cctat                                             25

<210> SEQ ID NO 468
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 468
cgtcttaatg gaccctgtat gttgct                                            26

<210> SEQ ID NO 469
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 469
gacccggctg cttaaattac aaatg                                             25

<210> SEQ ID NO 470
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 470
ttgttccaga caaggaaaag ctgac                                             25
```

<210> SEQ ID NO 471
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 471
tgtttctttt gggggaaact tagag                                                25

<210> SEQ ID NO 472
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 472
tttcttacca aatgatgaaa ctcgac                                               26

<210> SEQ ID NO 473
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 473
gagaacataa ctaaaaacaa aaagagaaac                                           30

<210> SEQ ID NO 474
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 474
gcaagaaatc ctcttctgtt aagaaacc                                             28

<210> SEQ ID NO 475
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 475
acaaaaaggg gattttggag gtagg                                                25

<210> SEQ ID NO 476
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 476
cagtgctctc caggctcact ctc    23

<210> SEQ ID NO 477
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 477
cagaagatgt tcagaaacaa gcaagg    26

<210> SEQ ID NO 478
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 478
attctgtctg tgaggcgtgt ctttc    25

<210> SEQ ID NO 479
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 479
ctcaccattg caggagagag gaagt    25

<210> SEQ ID NO 480
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 480
gaatgggaag aaggaatctg gctgc    25

<210> SEQ ID NO 481
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 481
aagttactca cctgtcccct agagtg    26

<210> SEQ ID NO 482
<211> LENGTH: 25
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 482
attttgcctg aggctggcct tcata                                       25

<210> SEQ ID NO 483
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 483
gaacacggga gttggttgga aat                                         23

<210> SEQ ID NO 484
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 484
ataggtgatt gtgaaaagaa gc                                          22

<210> SEQ ID NO 485
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 485
aattatcact gatttttact gagaactg                                    28

<210> SEQ ID NO 486
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 486
actgggctat tgtttaatat gatgg                                       25

<210> SEQ ID NO 487
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 487
gacccagcca tcccattact tggta                                       25
```

<210> SEQ ID NO 488
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 488
tctgaaaagc gcaatattcg ggtgg                                    25

<210> SEQ ID NO 489
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 489
catccgtgca caataccagg ctaag                                    25

<210> SEQ ID NO 490
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 490
gctgcttgca aatcaaccag gtttc                                    25

<210> SEQ ID NO 491
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 491
agtccaagtc agatggtcag aaagca                                   26

<210> SEQ ID NO 492
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 492
tccttgcatg ccaagagcag agatt                                    25

<210> SEQ ID NO 493
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 493
caatagctgt cattgtgcct ttgtc                                    25

<210> SEQ ID NO 494
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 494
cctggaagtg acatcctatg caaac                                    25

<210> SEQ ID NO 495
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 495
cgagccagaa gtatattcct acgtg                                    25

<210> SEQ ID NO 496
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 496
cctgggcaac aaagtgagac c                                        21

<210> SEQ ID NO 497
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 497
atataccagc caacttggga tgcct                                    25

<210> SEQ ID NO 498
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 498
acaagttttc agtgagggga gggaa                                    25

<210> SEQ ID NO 499
<211> LENGTH: 25

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 499
agggctgtaa gaccaatcag aggac                                     25

<210> SEQ ID NO 500
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 500
acctgctccc cttttcattg g                                         21

<210> SEQ ID NO 501
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 501
cagagtcttc tgccctggca tc                                        22

<210> SEQ ID NO 502
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 502
agaagggcac cacagcctca g                                         21

<210> SEQ ID NO 503
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 503
agccacttgg cctgtagttt ttctt                                     25

<210> SEQ ID NO 504
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 504
```
gaggtcagga gtttgagaac agcct                                          25

<210> SEQ ID NO 505
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 505
cctagcaatt tgggctgaa caac                                            24

<210> SEQ ID NO 506
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 506
aaacttctca gcctctcgct ccag                                           24

<210> SEQ ID NO 507
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 507
gctgggctgg agagaaggtg                                                20

<210> SEQ ID NO 508
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 508
gtccttgcaa actcccgttc c                                              21

<210> SEQ ID NO 509
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 509
tgtgtgcaga ggtgagatcc tatgag                                         26

<210> SEQ ID NO 510
<211> LENGTH: 25
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 510
ggacctgggt tcgtaggaag aaaac                                        25

<210> SEQ ID NO 511
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 511
aggctgctga ccacagtgcc tac                                          23

<210> SEQ ID NO 512
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 512
ggagtttatt tccctcctct tgaagc                                       26

<210> SEQ ID NO 513
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 513
aactgtgagt gcggtgactc tgaag                                        25

<210> SEQ ID NO 514
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 514
agcacacctc tgctctcatg gac                                          23

<210> SEQ ID NO 515
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 515
ttggcttcct tggagcctag c                                            21

<210> SEQ ID NO 516
```

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 516
caaggaggaa aggggagagc ag                                           22

<210> SEQ ID NO 517
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 517
gtaatttgcc cgcccctctc                                              20

<210> SEQ ID NO 518
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 518
ccctactcca ctcctcttcc ctcag                                        25

<210> SEQ ID NO 519
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 519
tgtgtaacaa attgccacaa atttagc                                      27

<210> SEQ ID NO 520
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 520
gatgttgata gctgcaagaa actgg                                        25

<210> SEQ ID NO 521
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 521
```

```
ctcatggggc aaatggtctt caacc                                         25
```

<210> SEQ ID NO 522
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 522

```
ccccatcaca tgagagaatg tgggt                                         25
```

<210> SEQ ID NO 523
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 523

```
gacgctggag acacatagaa tccct                                         25
```

<210> SEQ ID NO 524
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 524

```
gtgttcaatg ggctatcagg cttcc                                         25
```

<210> SEQ ID NO 525
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 525

```
tctcattgat cctcattgca ctctg                                         25
```

<210> SEQ ID NO 526
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 526

```
aaagcaaatg tctttggcca cattg                                         25
```

<210> SEQ ID NO 527
<211> LENGTH: 25
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 527
ggcttctcca taaatgcccc cattg                                              25

<210> SEQ ID NO 528
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 528
caccgggtag gaagtctatc cacag                                              25

<210> SEQ ID NO 529
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 529
aatgcacacc aatgccaata ctacc                                              25

<210> SEQ ID NO 530
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 530
ggcctatagg agccactttc aagc                                               24

<210> SEQ ID NO 531
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 531
tggtcccatc ctatagcacc ttctc                                              25

<210> SEQ ID NO 532
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 532
aggcagtcct ggaatctcag acac                                               24
```

```
<210> SEQ ID NO 533
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 533
gaaggtgttc agctgtggag gtg                                              23

<210> SEQ ID NO 534
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 534
tgacccagta tgctcctttc atcag                                            25

<210> SEQ ID NO 535
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 535
gtaaacgtct gccatgctgg tctg                                             24

<210> SEQ ID NO 536
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 536
agcagtggaa ctgaataata gcagagt                                          27

<210> SEQ ID NO 537
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 537
cccacttcag atcactccca cctac                                            25

<210> SEQ ID NO 538
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 538
tatcaagatg gtgagcatgg gagca                                          25

<210> SEQ ID NO 539
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 539
atatgaacaa acacctgaac ggggc                                          25

<210> SEQ ID NO 540
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 540
ggatgcatct ccattcctgt accct                                          25

<210> SEQ ID NO 541
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 541
aacgcacagc aattgtatat ggaga                                          25

<210> SEQ ID NO 542
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 542
tggcaagatt aaccaattta gctacccac                                      29

<210> SEQ ID NO 543
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 543
tagtcactgt tggtaagcac atttct                                         26

<210> SEQ ID NO 544
<211> LENGTH: 24
<212> TYPE: DNA
<213> ORGANISM: Artificial Sequence
```

```
-continued

<220> FEATURE:
<221> NAME/KEY: source
<223> OTHER INFORMATION: /note="Description of Artificial Sequence:
      Synthetic primer"

<400> SEQUENCE: 544
agcccaaact ccaatggtaa agca                                           24

<210> SEQ ID NO 545
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 545
aacacgtcta gggtcatacc atgtca                                         26

<210> SEQ ID NO 546
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 546
tcgttggttg aacatctttc tcagtct                                        27

<210> SEQ ID NO 547
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 547
aataacagca cctccttcac aggct                                          25

<210> SEQ ID NO 548
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 548
catgagattg tagatggtgt caggtcc                                        27

<210> SEQ ID NO 549
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 549
atgagaccac tcccaaacga attg                                           24
```

```
<210> SEQ ID NO 550
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 550
tgaccaaatt ctatcaggtt tataccac                                         28

<210> SEQ ID NO 551
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 551
taccacagaa tgcagccttg aatcc                                            25

<210> SEQ ID NO 552
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 552
acaaaaatta gccaggcatg gtggt                                            25

<210> SEQ ID NO 553
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 553
ggtctcggga aaggagcatt ttgac                                            25

<210> SEQ ID NO 554
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 554
aagtcccagt ctgcaggtaa caagt                                            25

<210> SEQ ID NO 555
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 555
cagctaggac acaggctttg agg    23

<210> SEQ ID NO 556
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 556
atcacctcag ctctcacatc taggg    25

<210> SEQ ID NO 557
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 557
actgagtact gcctcatctg ctgtg    25

<210> SEQ ID NO 558
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 558
caatggccac gatggagaaa taggc    25

<210> SEQ ID NO 559
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 559
attgaaaagt ggagtattgg taagaccat    29

<210> SEQ ID NO 560
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 560
cccagttacg gactcactgg gatag    25

<210> SEQ ID NO 561
<211> LENGTH: 25
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 561
tgggcttatt aatcaatggc atcag                                            25

<210> SEQ ID NO 562
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 562
acacatgagg cattattgga cttgg                                            25

<210> SEQ ID NO 563
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 563
tgtaaaacga cggccagt                                                    18

<210> SEQ ID NO 564
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 564
tctacagtcc gacgatca                                                    18

<210> SEQ ID NO 565
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 565
gacgtgtgct cttccgatc                                                   19

<210> SEQ ID NO 566
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 566
aatgatacgg cgaccaccga gatctacacg ttcagagttc tacagtccga cgatca          56
```

<210> SEQ ID NO 567
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 567
caagcagaag acggcatacg agataagtcg agatgtgact ggagttcaga cgtgtgctct    60
tccgatc                                                              67

<210> SEQ ID NO 568
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 568
caagcagaag acggcatacg agatatactt cgatgtgact ggagttcaga cgtgtgctct    60
tccgatc                                                              67

<210> SEQ ID NO 569
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 569
caagcagaag acggcatacg agatagctgc taatgtgact ggagttcaga cgtgtgctct    60
tccgatc                                                              67

<210> SEQ ID NO 570
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 570
caagcagaag acggcatacg agatcataga gaatgtgact ggagttcaga cgtgtgctct    60
tccgatc                                                              67

<210> SEQ ID NO 571
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 571
caagcagaag acggcatacg agatcgtaga tcatgtgact ggagttcaga cgtgtgctct    60

-continued tccgatc 67

<210> SEQ ID NO 572
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 572
caagcagaag acggcatacg agatctcgtt acatgtgact ggagttcaga cgtgtgctct    60
tccgatc                                                              67

<210> SEQ ID NO 573
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 573
caagcagaag acggcatacg agatgcgcac gtatgtgact ggagttcaga cgtgtgctct    60
tccgatc                                                              67

<210> SEQ ID NO 574
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 574
caagcagaag acggcatacg agatggtact atatgtgact ggagttcaga cgtgtgctct    60
tccgatc                                                              67

<210> SEQ ID NO 575
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 575
caagcagaag acggcatacg agatgtatac gcatgtgact ggagttcaga cgtgtgctct    60
tccgatc                                                              67

<210> SEQ ID NO 576
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 576
caagcagaag acggcatacg agattacgag catgtgact ggagttcaga cgtgtgctct     60

```
tccgatc                                                            67

<210> SEQ ID NO 577
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 577
caagcagaag acggcatacg agattcagcg ttatgtgact ggagttcaga cgtgtgctct   60
tccgatc                                                            67

<210> SEQ ID NO 578
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 578
caagcagaag acggcatacg agattcgcta cgatgtgact ggagttcaga cgtgtgctct   60
tccgatc                                                            67

<210> SEQ ID NO 579
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 579
gatcggaaga gcacacgtct gaactccagt cacat                             35

<210> SEQ ID NO 580
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 580
tctacacgtt cagagttcta cagtccgacg atca                              34

<210> SEQ ID NO 581
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 581
tgtgactgga gttcagacgt gtgctcttcc gatc                              34

<210> SEQ ID NO 582
```

```
<211> LENGTH: 23
<212> TYPE: DNA
<213> ORGANISM: Homo sapiens

<400> SEQUENCE: 582
gtgaacgtgg atgaagttgg tgg                                              23

<210> SEQ ID NO 583
<211> LENGTH: 23
<212> TYPE: DNA
<213> ORGANISM: Homo sapiens
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 583
ntgaacgtgg atgaagttgg nrg                                              23

<210> SEQ ID NO 584
<211> LENGTH: 23
<212> TYPE: DNA
<213> ORGANISM: Homo sapiens

<400> SEQUENCE: 584
aaaaacatgg atgaagttgg agg                                              23

<210> SEQ ID NO 585
<211> LENGTH: 23
<212> TYPE: DNA
<213> ORGANISM: Homo sapiens

<400> SEQUENCE: 585
aacaacatgg atgaagttgg agg                                              23

<210> SEQ ID NO 586
<211> LENGTH: 23
<212> TYPE: DNA
<213> ORGANISM: Homo sapiens

<400> SEQUENCE: 586
aacaacttgg atgaagttgg agg                                              23

<210> SEQ ID NO 587
<211> LENGTH: 23
<212> TYPE: DNA
<213> ORGANISM: Homo sapiens

<400> SEQUENCE: 587
gacaacgtgg ataagttgg aag                                               23

<210> SEQ ID NO 588
<211> LENGTH: 23
<212> TYPE: DNA
<213> ORGANISM: Homo sapiens

<400> SEQUENCE: 588
aacaacgtgg atgaaattgg agg                                              23

<210> SEQ ID NO 589
<211> LENGTH: 23
```

```
<212> TYPE: DNA
<213> ORGANISM: Homo sapiens

<400> SEQUENCE: 589
gacaacgtgg atgaacttgg aag                                              23

<210> SEQ ID NO 590
<211> LENGTH: 23
<212> TYPE: DNA
<213> ORGANISM: Homo sapiens

<400> SEQUENCE: 590
aacaacgtgg atgaacttgg agg                                              23

<210> SEQ ID NO 591
<211> LENGTH: 23
<212> TYPE: DNA
<213> ORGANISM: Homo sapiens

<400> SEQUENCE: 591
aacaacgtgg atgaacttgg agg                                              23

<210> SEQ ID NO 592
<211> LENGTH: 23
<212> TYPE: DNA
<213> ORGANISM: Homo sapiens

<400> SEQUENCE: 592
tacaacgtgg atgaacttgg agg                                              23

<210> SEQ ID NO 593
<211> LENGTH: 23
<212> TYPE: DNA
<213> ORGANISM: Homo sapiens

<400> SEQUENCE: 593
aacaacgtgg atgaagctgg agg                                              23

<210> SEQ ID NO 594
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 594
accaataggc agagagagtc agtg                                             24

<210> SEQ ID NO 595
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 595
aggtctcctt tatcccaaag ctcc                                             24

<210> SEQ ID NO 596
<211> LENGTH: 24
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 596
cctggtaacc accattctac tctg                                          24

<210> SEQ ID NO 597
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 597
caacctaagt acccactgat caacgaaag                                     29

<210> SEQ ID NO 598
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 598
gtgccagata tggaaatcat ctaagcatca g                                  31

<210> SEQ ID NO 599
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 599
caacctaagt gtctagcaac aggc                                          24

<210> SEQ ID NO 600
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 600
ggcaaccacc attctcctct g                                             21

<210> SEQ ID NO 601
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 601
cctcacccct agcaaccatc                                               20
```

<210> SEQ ID NO 602
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 602
aaggaatcag cccaaatgtc cacc                                          24

<210> SEQ ID NO 603
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 603
gccaccaccc attttctgtc tg                                            22

<210> SEQ ID NO 604
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 604
gaactgctga gctcgagtga tc                                            22

<210> SEQ ID NO 605
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 605
ntgaacgtgg atgaagttgg ngg                                           23

<210> SEQ ID NO 606
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(20)
<223> OTHER INFORMATION: a, c, t, g, unknown or other

```
<400> SEQUENCE: 606
tgaacgtgga tgaagttggn gg                                    22

<210> SEQ ID NO 607
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 607
gtgaacgtgg atgaagttgg ngg                                   23

<210> SEQ ID NO 608
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 608
ntagagcgga ggcaggaggc ngg                                   23

<210> SEQ ID NO 609
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(20)
<223> OTHER INFORMATION: a, c, t, g, unknown or other

<400> SEQUENCE: 609
tagagcggag gcaggaggcn gg                                    22

<210> SEQ ID NO 610
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 610
gtagagcgga ggcaggaggc ngg                                   23
```

```
<210> SEQ ID NO 611
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 611
gtagagcgga ggcaggaggc nrg                                              23

<210> SEQ ID NO 612
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 612
tagagcggag gcaggaggcn rg                                               22

<210> SEQ ID NO 613
<211> LENGTH: 22
<212> TYPE: DNA
<213> ORGANISM: Homo sapiens

<400> SEQUENCE: 613
gtgagcggag gcaggaggca gg                                               22

<210> SEQ ID NO 614
<211> LENGTH: 22
<212> TYPE: DNA
<213> ORGANISM: Homo sapiens

<400> SEQUENCE: 614
aagtgcggag gcaggaggcg gg                                               22

<210> SEQ ID NO 615
<211> LENGTH: 22
<212> TYPE: DNA
<213> ORGANISM: Homo sapiens

<400> SEQUENCE: 615
aagagcagag gcaggaggca gg                                               22

<210> SEQ ID NO 616
<211> LENGTH: 22
<212> TYPE: DNA
<213> ORGANISM: Homo sapiens

<400> SEQUENCE: 616
tagggaggag gcaggaggca gg                                               22

<210> SEQ ID NO 617
<211> LENGTH: 22
<212> TYPE: DNA
<213> ORGANISM: Homo sapiens
```

```
<400> SEQUENCE: 617
agaagcggag gcaggaggct gg                                              22

<210> SEQ ID NO 618
<211> LENGTH: 22
<212> TYPE: DNA
<213> ORGANISM: Homo sapiens

<400> SEQUENCE: 618
attagcggag gcaggaggcg gg                                              22

<210> SEQ ID NO 619
<211> LENGTH: 22
<212> TYPE: DNA
<213> ORGANISM: Homo sapiens

<400> SEQUENCE: 619
tagaggtgag gcaggaggct gg                                              22

<210> SEQ ID NO 620
<211> LENGTH: 22
<212> TYPE: DNA
<213> ORGANISM: Homo sapiens

<400> SEQUENCE: 620
aggagaggag gcaggaggca gg                                              22

<210> SEQ ID NO 621
<211> LENGTH: 22
<212> TYPE: DNA
<213> ORGANISM: Homo sapiens

<400> SEQUENCE: 621
cggagaggag gcaggaggca gg                                              22

<210> SEQ ID NO 622
<211> LENGTH: 22
<212> TYPE: DNA
<213> ORGANISM: Homo sapiens

<400> SEQUENCE: 622
aggagaggag gcaggaggca gg                                              22

<210> SEQ ID NO 623
<211> LENGTH: 22
<212> TYPE: DNA
<213> ORGANISM: Homo sapiens

<400> SEQUENCE: 623
aggagaggag gcaggaggca gg                                              22

<210> SEQ ID NO 624
<211> LENGTH: 22
<212> TYPE: DNA
<213> ORGANISM: Homo sapiens

<400> SEQUENCE: 624 gaaagggag gcaggaggca gg                                               22

<210> SEQ ID NO 625
<211> LENGTH: 22
<212> TYPE: DNA
<213> ORGANISM: Homo sapiens
```

```
<400> SEQUENCE: 625
cagcacggag gcaggaggca gg                                              22

<210> SEQ ID NO 626
<211> LENGTH: 22
<212> TYPE: DNA
<213> ORGANISM: Homo sapiens

<400> SEQUENCE: 626
tgcagaggag gcaggaggct gg                                              22

<210> SEQ ID NO 627
<211> LENGTH: 22
<212> TYPE: DNA
<213> ORGANISM: Homo sapiens

<400> SEQUENCE: 627
gagggaggag gcaggaggcg gg                                              22

<210> SEQ ID NO 628
<211> LENGTH: 22
<212> TYPE: DNA
<213> ORGANISM: Homo sapiens

<400> SEQUENCE: 628
gagggtggag gcaggaggca gg                                              22

<210> SEQ ID NO 629
<211> LENGTH: 22
<212> TYPE: DNA
<213> ORGANISM: Homo sapiens

<400> SEQUENCE: 629
aagtgaggag gcaggaggcc gg                                              22

<210> SEQ ID NO 630
<211> LENGTH: 22
<212> TYPE: DNA
<213> ORGANISM: Homo sapiens

<400> SEQUENCE: 630
tccaggggag gcaggaggct gg                                              22

<210> SEQ ID NO 631
<211> LENGTH: 22
<212> TYPE: DNA
<213> ORGANISM: Homo sapiens

<400> SEQUENCE: 631
gggagctgag gcaggaggca gg                                              22

<210> SEQ ID NO 632
<211> LENGTH: 22
<212> TYPE: DNA
<213> ORGANISM: Homo sapiens

<400> SEQUENCE: 632
gagggaggag gcaggaggct gg                                              22

<210> SEQ ID NO 633
<211> LENGTH: 22
<212> TYPE: DNA
```

```
<213> ORGANISM: Homo sapiens

<400> SEQUENCE: 633
gagggtggag gcaggaggct gg                                    22

<210> SEQ ID NO 634
<211> LENGTH: 22
<212> TYPE: DNA
<213> ORGANISM: Homo sapiens

<400> SEQUENCE: 634
tggggtggag gcaggaggct gg                                    22

<210> SEQ ID NO 635
<211> LENGTH: 22
<212> TYPE: DNA
<213> ORGANISM: Homo sapiens

<400> SEQUENCE: 635
gagacaggag gcaggaggct gg                                    22

<210> SEQ ID NO 636
<211> LENGTH: 22
<212> TYPE: DNA
<213> ORGANISM: Homo sapiens

<400> SEQUENCE: 636
gagactggag gcaggaggcc ag                                    22

<210> SEQ ID NO 637
<211> LENGTH: 21
<212> TYPE: DNA
<213> ORGANISM: Homo sapiens

<400> SEQUENCE: 637
cagagggagg caggaggctg g                                     21

<210> SEQ ID NO 638
<211> LENGTH: 22
<212> TYPE: DNA
<213> ORGANISM: Homo sapiens

<400> SEQUENCE: 638
gagggctgag gcaggaggcc ag                                    22

<210> SEQ ID NO 639
<211> LENGTH: 21
<212> TYPE: DNA
<213> ORGANISM: Homo sapiens

<400> SEQUENCE: 639
tggagggagg caggaggcag g                                     21

<210> SEQ ID NO 640
<211> LENGTH: 21
<212> TYPE: DNA
<213> ORGANISM: Homo sapiens

<400> SEQUENCE: 640
tggagggagg caggaggcag g                                     21

<210> SEQ ID NO 641
<211> LENGTH: 21
```

```
<212> TYPE: DNA
<213> ORGANISM: Homo sapiens

<400> SEQUENCE: 641 tgagggagg caggaggctg g                                              21

<210> SEQ ID NO 642
<211> LENGTH: 22
<212> TYPE: DNA
<213> ORGANISM: Homo sapiens

<400> SEQUENCE: 642
cagagcaggg gcaggaggca gg                                            22

<210> SEQ ID NO 643
<211> LENGTH: 22
<212> TYPE: DNA
<213> ORGANISM: Homo sapiens

<400> SEQUENCE: 643
aagagcaggg gcaggaggca gg                                            22

<210> SEQ ID NO 644
<211> LENGTH: 21
<212> TYPE: DNA
<213> ORGANISM: Homo sapiens

<400> SEQUENCE: 644
tacagggagg caggaggcgg g                                             21

<210> SEQ ID NO 645
<211> LENGTH: 22
<212> TYPE: DNA
<213> ORGANISM: Homo sapiens

<400> SEQUENCE: 645
gagagagggg gcaggaggca gg                                            22

<210> SEQ ID NO 646
<211> LENGTH: 22
<212> TYPE: DNA
<213> ORGANISM: Homo sapiens

<400> SEQUENCE: 646
taaatgggag gcaggaggcc ag                                            22

<210> SEQ ID NO 647
<211> LENGTH: 23
<212> TYPE: DNA
<213> ORGANISM: Homo sapiens

<400> SEQUENCE: 647
gtgaacgtgg atgaagttgg tgg                                           23

<210> SEQ ID NO 648
<211> LENGTH: 23
<212> TYPE: DNA
<213> ORGANISM: Homo sapiens

<400> SEQUENCE: 648
aggaacatgg atgaagttgg agg                                           23

<210> SEQ ID NO 649
```

```
<211> LENGTH: 23
<212> TYPE: DNA
<213> ORGANISM: Homo sapiens

<400> SEQUENCE: 649
aggaacatgg atgaagttgg agg                                              23

<210> SEQ ID NO 650
<211> LENGTH: 23
<212> TYPE: DNA
<213> ORGANISM: Homo sapiens

<400> SEQUENCE: 650
gggaacatgg atgaagttgg agg                                              23

<210> SEQ ID NO 651
<211> LENGTH: 23
<212> TYPE: DNA
<213> ORGANISM: Homo sapiens

<400> SEQUENCE: 651
gggaacatgg atgaagttgg agg                                              23

<210> SEQ ID NO 652
<211> LENGTH: 23
<212> TYPE: DNA
<213> ORGANISM: Homo sapiens

<400> SEQUENCE: 652
gggaacatgg atgaagttgg agg                                              23

<210> SEQ ID NO 653
<211> LENGTH: 23
<212> TYPE: DNA
<213> ORGANISM: Homo sapiens

<400> SEQUENCE: 653
aggaacgtgg atggagttgg agg                                              23

<210> SEQ ID NO 654
<211> LENGTH: 23
<212> TYPE: DNA
<213> ORGANISM: Homo sapiens

<400> SEQUENCE: 654
aggaacgtgg atggagttgg agg                                              23

<210> SEQ ID NO 655
<211> LENGTH: 23
<212> TYPE: DNA
<213> ORGANISM: Homo sapiens

<400> SEQUENCE: 655
aggaacgtgg atgaagctgg agg                                              23

<210> SEQ ID NO 656
<211> LENGTH: 23
<212> TYPE: DNA
<213> ORGANISM: Homo sapiens

<400> SEQUENCE: 656
gggaacgtgg atgaagctgg agg                                              23
```

```
<210> SEQ ID NO 657
<211> LENGTH: 23
<212> TYPE: DNA
<213> ORGANISM: Homo sapiens

<400> SEQUENCE: 657
gtgaaaatgg atgaagttgg agg                                            23

<210> SEQ ID NO 658
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
gtgaacgtgg atgaagttgg                                                20

<210> SEQ ID NO 659
<211> LENGTH: 22
<212> TYPE: DNA
<213> ORGANISM: Homo sapiens

<400> SEQUENCE: 659
agaagcggag gcaggaggct gg                                             22

<210> SEQ ID NO 660
<211> LENGTH: 22
<212> TYPE: DNA
<213> ORGANISM: Homo sapiens

<400> SEQUENCE: 660
gggaattgga tgaagttggg gg                                             22

<210> SEQ ID NO 661
<211> LENGTH: 24
<212> TYPE: DNA
<213> ORGANISM: Homo sapiens

<400> SEQUENCE: 661
gaagagggga ggcaggaggg cagg                                           24

<210> SEQ ID NO 662
<211> LENGTH: 24
<212> TYPE: DNA
<213> ORGANISM: Homo sapiens

<400> SEQUENCE: 662
aggaacgtgg atgaacttgg aagg                                           24

<210> SEQ ID NO 663
<211> LENGTH: 24
<212> TYPE: DNA
<213> ORGANISM: Homo sapiens

<400> SEQUENCE: 663
ggagagcggc ggcaggaggc gtag                                           24

<210> SEQ ID NO 664
<211> LENGTH: 22
<212> TYPE: DNA
<213> ORGANISM: Homo sapiens
```

```
<400> SEQUENCE: 664
agagagagga gcaggaggct gg                                              22

<210> SEQ ID NO 665
<211> LENGTH: 24
<212> TYPE: DNA
<213> ORGANISM: Homo sapiens

<400> SEQUENCE: 665
gcagagccga gagcaggagg cgag                                            24

<210> SEQ ID NO 666
<211> LENGTH: 24
<212> TYPE: DNA
<213> ORGANISM: Homo sapiens

<400> SEQUENCE: 666
ggagagcggg ggccaggagg ccgg                                            24

<210> SEQ ID NO 667
<211> LENGTH: 24
<212> TYPE: DNA
<213> ORGANISM: Homo sapiens

<400> SEQUENCE: 667
gaagagtgga ggcagggagg ctgg                                            24

<210> SEQ ID NO 668
<211> LENGTH: 24
<212> TYPE: DNA
<213> ORGANISM: Homo sapiens

<400> SEQUENCE: 668
gaagagagga ggcaggaggg ctgg                                            24

<210> SEQ ID NO 669
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
gtagagcgga ggcaggagc                                                  19

<210> SEQ ID NO 670
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 670
gtgaacgtgg atgaagttgg ngg                                             23

<210> SEQ ID NO 671
<211> LENGTH: 23
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(3)
<223> OTHER INFORMATION: a, c, t, g, unknown or other

<400> SEQUENCE: 671
ccnttactgc cctgtggggc aac                                              23

<210> SEQ ID NO 672
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(3)
<223> OTHER INFORMATION: a, c, t, g, unknown or other

<400> SEQUENCE: 672
ccntgtgggg caaggtgaac gtc                                              23

<210> SEQ ID NO 673
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(3)
<223> OTHER INFORMATION: a, c, t, g, unknown or other

<400> SEQUENCE: 673
ccngtggggc aaggtgaacg tgc                                              23

<210> SEQ ID NO 674
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 674
ggtctgccgt tactgccctg ngg                                              23

<210> SEQ ID NO 675
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: modified_base
<222> LOCATION: (21)..(21)
<223> OTHER INFORMATION: a, c, t, g, unknown or other

<400> SEQUENCE: 675
ggttactgcc ctgtggggca ngg                                    23

<210> SEQ ID NO 676
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 676
gaggtgaacg tggatgaagt ngg                                    23

<210> SEQ ID NO 677
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 677
gctgtggggc aaggtgaacg ngg                                    23

<210> SEQ ID NO 678
<211> LENGTH: 65
<212> TYPE: DNA
<213> ORGANISM: Homo sapiens

<400> SEQUENCE: 678
tggagaagtc tgccgttact gccctgtggg gcaaggtgaa cgtggatgaa gttggtggtg    60
aggcc                                                               65

<210> SEQ ID NO 679
<211> LENGTH: 65
<212> TYPE: DNA
<213> ORGANISM: Homo sapiens

<400> SEQUENCE: 679
aggagaagac tgctgtcaat gccctgtggg gcaaagtgaa cgtggatgca gttggtggtg    60
aggcc                                                               65

<210> SEQ ID NO 680
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
```

```
<222> LOCATION: (21)..(21)
<223> OTHER INFORMATION: a, c, t, g, unknown or other

<400> SEQUENCE: 680
gacgttcacc ttgccccaca ngg                                              23

<210> SEQ ID NO 681
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 681
gctgtggggc aaggtgaacg ngg                                              23

<210> SEQ ID NO 682
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 682
gtgaacgtgg atgaagttgg ngg                                              23

<210> SEQ ID NO 683
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 683
gcacgttcac cttgccccac ngg                                              23

<210> SEQ ID NO 684
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 684
gaggtgaacg tggatgaagt ngg                                              23
```

<210> SEQ ID NO 685
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 685
ggtctgccgt tactgccctg ngg                                              23

<210> SEQ ID NO 686
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 686
gttgccccac agggcagtaa ngg                                              23

<210> SEQ ID NO 687
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 687
ggttactgcc ctgtggggca ngg                                              23

<210> SEQ ID NO 688
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 688
gtgttcatct ttggttttgt ngg                                              23

<210> SEQ ID NO 689
<211> LENGTH: 23
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"
<220> FEATURE:
<221> NAME/KEY: modified_base
<222> LOCATION: (3)..(3)
<223> OTHER INFORMATION: a, c, t, g, unknown or other

<400> SEQUENCE: 689
ccncctgcct ccgctctact cac                                              23

<210> SEQ ID NO 690
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(3)
<223> OTHER INFORMATION: a, c, t, g, unknown or other

<400> SEQUENCE: 690
ccngcctcct gcctccgctc tac                                              23

<210> SEQ ID NO 691
<211> LENGTH: 66
<212> TYPE: DNA
<213> ORGANISM: Homo sapiens

<400> SEQUENCE: 691
tcgcagcccg cctcctgcct ccgctctact cactggtgtt catctttggt tttgtgggca      60
acatgc                                                                 66

<210> SEQ ID NO 692
<211> LENGTH: 66
<212> TYPE: DNA
<213> ORGANISM: Homo sapiens

<400> SEQUENCE: 692
ttggggccca actcctgcct ccgctctact cgctggtgtt catctttggt tttgtgggca      60
acatgc                                                                 66

<210> SEQ ID NO 693
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 693
gctgccgccc agtgggactt ngg                                              23

<210> SEQ ID NO 694
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

```
    Synthetic oligonucleotide"
<220> FEATURE:
<221> NAME/KEY: modified_base
<222> LOCATION: (3)..(3)
<223> OTHER INFORMATION: a, c, t, g, unknown or other

<400> SEQUENCE: 694
ccntctgggc tcactatgct gcc                                              23

<210> SEQ ID NO 695
<211> LENGTH: 66
<212> TYPE: DNA
<213> ORGANISM: Homo sapiens

<400> SEQUENCE: 695
ccttcttact gtccccttct gggctcacta tgctgccgcc cagtgggact ttggaaatac     60
aatgtg                                                                66

<210> SEQ ID NO 696
<211> LENGTH: 66
<212> TYPE: DNA
<213> ORGANISM: Homo sapiens

<400> SEQUENCE: 696
tcttattact ctcccattgt gggctcactc tgctgcaaat gagtgggtct ttgggaatgc     60
aatgtg                                                                66

<210> SEQ ID NO 697
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 697
gtgttcatct ttggttttgt ngg                                              23

<210> SEQ ID NO 698
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 698
gtagagcgga ggcaggaggc ngg                                              23

<210> SEQ ID NO 699
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<220> FEATURE:
<221> NAME/KEY: modified_base
<222> LOCATION: (21)..(21)
<223> OTHER INFORMATION: a, c, t, g, unknown or other

<400> SEQUENCE: 699
gctgccgccc agtgggactt ngg                                              23

<210> SEQ ID NO 700
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 700
ggcagcatag tgagcccaga ngg                                              23

<210> SEQ ID NO 701
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 701
gtgagtagag cggaggcagg ngg                                              23

<210> SEQ ID NO 702
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 702
gagggtaaaa ttaagcacag ngg                                              23

<210> SEQ ID NO 703
<211> LENGTH: 43
<212> TYPE: DNA
<213> ORGANISM: Homo sapiens

<400> SEQUENCE: 703
accaccaact tcagggcagt aacggcagac ttctcctcag gag                        43

<210> SEQ ID NO 704
<211> LENGTH: 50
<212> TYPE: DNA
<213> ORGANISM: Homo sapiens
```

```
<400> SEQUENCE: 704
accaccaact tcatccacgt tcaccttgcc ggcagacttc tcctcaggag            50

<210> SEQ ID NO 705
<211> LENGTH: 56
<212> TYPE: DNA
<213> ORGANISM: Homo sapiens

<400> SEQUENCE: 705
accaccaact tcatccacgt tcaccttgcc cctaacggca gacttctcct caggag      56

<210> SEQ ID NO 706
<211> LENGTH: 62
<212> TYPE: DNA
<213> ORGANISM: Homo sapiens

<400> SEQUENCE: 706
accaccaact tcatccacgt tcaccttgca cagggcagta acggcggact tctcctcagg  60
ag                                                                62

<210> SEQ ID NO 707
<211> LENGTH: 63
<212> TYPE: DNA
<213> ORGANISM: Homo sapiens

<400> SEQUENCE: 707
accaccaact tcatccacgt tcaccttgcc ccagggcagt aacggcagac ttctcctcag  60
gag                                                               63

<210> SEQ ID NO 708
<211> LENGTH: 64
<212> TYPE: DNA
<213> ORGANISM: Homo sapiens

<400> SEQUENCE: 708
accaccaact tcatccacgt tcaccttgcc cacagggcag taacggcaga cttctcctca  60
ggag                                                              64

<210> SEQ ID NO 709
<211> LENGTH: 64
<212> TYPE: DNA
<213> ORGANISM: Homo sapiens

<400> SEQUENCE: 709
accaccaact catccacgtt caccttgccc cacagggcag taacggcaga cttctcctca  60
ggag                                                              64

<210> SEQ ID NO 710
<211> LENGTH: 65
<212> TYPE: DNA
<213> ORGANISM: Homo sapiens

<400> SEQUENCE: 710
accaccaact tcatccacgt tcaccttgcc ccacagggca gtaacggcag acttctcctc  60
aggag                                                             65

<210> SEQ ID NO 711
<211> LENGTH: 65
<212> TYPE: DNA
<213> ORGANISM: Homo sapiens
```

<400> SEQUENCE: 711
accaccaact tcatccacgt tcaccttgcc ccacagggca gtaacggcag acttctcctc    60
aggag    65

<210> SEQ ID NO 712
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 712
gacgttcacc ttgccccaca ngg    23

<210> SEQ ID NO 713
<211> LENGTH: 65
<212> TYPE: DNA
<213> ORGANISM: Homo sapiens

<400> SEQUENCE: 713
accaccaact tcatccacgt tcaccttgcc cccacagggc agtaacggca gacttctcct    60
tagga    65

<210> SEQ ID NO 714
<211> LENGTH: 65
<212> TYPE: DNA
<213> ORGANISM: Homo sapiens

<400> SEQUENCE: 714
accaccaact tcatccacgt tcaccttgcc ttgttcaccg ttacagggca gtaacggcag    60
acttc    65

<210> SEQ ID NO 715
<211> LENGTH: 65
<212> TYPE: DNA
<213> ORGANISM: Homo sapiens

<400> SEQUENCE: 715
accaccaact tcatccacgt tctcatccac gttcaccttg cccacagggc agtaacggca    60
gactt    65

<210> SEQ ID NO 716
<211> LENGTH: 43
<212> TYPE: DNA
<213> ORGANISM: Homo sapiens

<400> SEQUENCE: 716
accaccaact gcatccacgt tccagcagtc ttctcctcaa gag    43

<210> SEQ ID NO 717
<211> LENGTH: 47
<212> TYPE: DNA
<213> ORGANISM: Homo sapiens

<400> SEQUENCE: 717

```
accaccaact gcatccacgt tcactacagc agtcttctcc tcaggag        47

<210> SEQ ID NO 718
<211> LENGTH: 59
<212> TYPE: DNA
<213> ORGANISM: Homo sapiens

<400> SEQUENCE: 718
accaccaact gcatccacgt tcactttgcc cccattgaca gcagtcttct cctcaggag        59

<210> SEQ ID NO 719
<211> LENGTH: 60
<212> TYPE: DNA
<213> ORGANISM: Homo sapiens

<400> SEQUENCE: 719
accaccaact gcatccacgt tcacttcaca gggcattgac agcagtcttc tcctcaggag        60

<210> SEQ ID NO 720
<211> LENGTH: 62
<212> TYPE: DNA
<213> ORGANISM: Homo sapiens

<400> SEQUENCE: 720
accaccaact gcatccacgt tcactttca cagggcattg acagcagtct tctcctcagg        60
ag                                                                     62

<210> SEQ ID NO 721
<211> LENGTH: 63
<212> TYPE: DNA
<213> ORGANISM: Homo sapiens

<400> SEQUENCE: 721
accaccaact gcatccacgt tcactttgcc acagggcatt gacagcagtc ttctcctcag        60
gag                                                                    63

<210> SEQ ID NO 722
<211> LENGTH: 64
<212> TYPE: DNA
<213> ORGANISM: Homo sapiens

<400> SEQUENCE: 722
accaccaact gcatccacgt tcactttgcc cacagggcat tgacagcagt cttctcctca        60
ggag                                                                   64

<210> SEQ ID NO 723
<211> LENGTH: 65
<212> TYPE: DNA
<213> ORGANISM: Homo sapiens

<400> SEQUENCE: 723
accaccaact gcatccacgt tcactttgcc ccacagggca ttgacagcag tcttctcctc        60
aggag                                                                  65

<210> SEQ ID NO 724
<211> LENGTH: 65
<212> TYPE: DNA
<213> ORGANISM: Homo sapiens

<400> SEQUENCE: 724
accaccaact gcatccacgt tcactttgcc ccacagggca ttgacagcag tcttctcctc        60
``` aggag                                                              65

<210> SEQ ID NO 725
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 725
gacgttcacc ttgccccaca ngg                                          23

<210> SEQ ID NO 726
<211> LENGTH: 65
<212> TYPE: DNA
<213> ORGANISM: Homo sapiens

<400> SEQUENCE: 726
accaccaact gcatccacgt tcactttgcc cccacagggc attgacagca gtcttctcct   60
cagga                                                              65

<210> SEQ ID NO 727
<211> LENGTH: 65
<212> TYPE: DNA
<213> ORGANISM: Homo sapiens

<400> SEQUENCE: 727
accaccaact gcatccacgt tcactttgcc ccccagggc attgacagca gtcttctcct    60
cagga                                                              65

<210> SEQ ID NO 728
<211> LENGTH: 65
<212> TYPE: DNA
<213> ORGANISM: Homo sapiens

<400> SEQUENCE: 728
accaccaact gcatccacgt tcactttgcc ccaatccctc ccagcatcag ggtcttttcc   60
aatga                                                              65

<210> SEQ ID NO 729
<211> LENGTH: 65
<212> TYPE: DNA
<213> ORGANISM: Homo sapiens

<400> SEQUENCE: 729
accaccaact gcatccacgt tcactttgcc ccggcgtcaa tacgggataa taccgcgcca   60
catag                                                              65

<210> SEQ ID NO 730
<211> LENGTH: 10
<212> TYPE: DNA
<213> ORGANISM: Homo sapiens

<400> SEQUENCE: 730
tgcacagggc                                                         10

-continued

```
<210> SEQ ID NO 731
<211> LENGTH: 14
<212> TYPE: DNA
<213> ORGANISM: Homo sapiens

<400> SEQUENCE: 731
gccccacaca gggc                                                           14

<210> SEQ ID NO 732
<211> LENGTH: 12
<212> TYPE: DNA
<213> ORGANISM: Homo sapiens

<400> SEQUENCE: 732
ttgccacagg gc                                                             12

<210> SEQ ID NO 733
<211> LENGTH: 13
<212> TYPE: DNA
<213> ORGANISM: Homo sapiens

<400> SEQUENCE: 733
ttgcccacag ggc                                                            13

<210> SEQ ID NO 734
<211> LENGTH: 10
<212> TYPE: DNA
<213> ORGANISM: Homo sapiens

<400> SEQUENCE: 734
ttgcccgggc                                                                10

<210> SEQ ID NO 735
<211> LENGTH: 14
<212> TYPE: DNA
<213> ORGANISM: Homo sapiens

<400> SEQUENCE: 735
ttgcagtaca gggc                                                           14

<210> SEQ ID NO 736
<211> LENGTH: 14
<212> TYPE: DNA
<213> ORGANISM: Homo sapiens

<400> SEQUENCE: 736
ttgccttaca gggc                                                           14

<210> SEQ ID NO 737
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 737
gacgttcacc ttgccccaca ngg                                                 23

<210> SEQ ID NO 738
<211> LENGTH: 14
<212> TYPE: DNA
<213> ORGANISM: Homo sapiens
```

```
<400> SEQUENCE: 738
ttgccccaca gggc                                                        14

<210> SEQ ID NO 739
<211> LENGTH: 14
<212> TYPE: DNA
<213> ORGANISM: Homo sapiens

<400> SEQUENCE: 739
ttgccccaca gggc                                                        14

<210> SEQ ID NO 740
<211> LENGTH: 29
<212> TYPE: DNA
<213> ORGANISM: Homo sapiens

<400> SEQUENCE: 740
ccgctctact cactggtgtt catctttgg                                        29

<210> SEQ ID NO 741
<211> LENGTH: 65
<212> TYPE: DNA
<213> ORGANISM: Homo sapiens

<400> SEQUENCE: 741
ccgctctact cactggtgtt catctttggt tgtgggctca ctctgctgca aatgagtggg      60
tcttt                                                                  65

<210> SEQ ID NO 742
<211> LENGTH: 65
<212> TYPE: DNA
<213> ORGANISM: Homo sapiens

<400> SEQUENCE: 742
ccgctctact cactggtgtt catctttggt tttgtgggca acatgctggt catcctcatc      60
ctgat                                                                  65

<210> SEQ ID NO 743
<211> LENGTH: 65
<212> TYPE: DNA
<213> ORGANISM: Homo sapiens

<400> SEQUENCE: 743
ccgctctact cactggtgtt catctttggt tttgtgggca acatgctggt catcctcatc      60
ctgat                                                                  65

<210> SEQ ID NO 744
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 744
gtgttcatct ttggttttgt ngg                                              23
```

```
<210> SEQ ID NO 745
<211> LENGTH: 65
<212> TYPE: DNA
<213> ORGANISM: Homo sapiens

<400> SEQUENCE: 745
ccgctctact cactggtgtt catctttggt ttatgtgggc aacatgctgg tcgtcctcat      60
cttaa                                                                 65

<210> SEQ ID NO 746
<211> LENGTH: 45
<212> TYPE: DNA
<213> ORGANISM: Homo sapiens

<400> SEQUENCE: 746
ccgctctact cgctggtgca acatgctggt cgtcctcatc ttaat                     45

<210> SEQ ID NO 747
<211> LENGTH: 64
<212> TYPE: DNA
<213> ORGANISM: Homo sapiens

<400> SEQUENCE: 747
ccgctctact cgctggtgtt catctttggt ttgtgggcaa catgctggtc gtcctcatct     60
taat                                                                 64

<210> SEQ ID NO 748
<211> LENGTH: 65
<212> TYPE: DNA
<213> ORGANISM: Homo sapiens

<400> SEQUENCE: 748
ccgctctact cgccggtgtt catctttggt tttgtgggca acatgctggt cgtcctcatc     60
ttaat                                                                 65

<210> SEQ ID NO 749
<211> LENGTH: 65
<212> TYPE: DNA
<213> ORGANISM: Homo sapiens

<400> SEQUENCE: 749
ccgctctact cgctggtgtt catctttggt tttgtgggca acatgctggt cgtcctcatc     60
ttaat                                                                 65

<210> SEQ ID NO 750
<211> LENGTH: 65
<212> TYPE: DNA
<213> ORGANISM: Homo sapiens

<400> SEQUENCE: 750
ccgctctact cgctggtgtt catctttggt tttgtgggca acatgctggt cgtcctcatc     60
ttaat                                                                 65

<210> SEQ ID NO 751
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: modified_base
<222> LOCATION: (21)..(21)
<223> OTHER INFORMATION: a, c, t, g, unknown or other

<400> SEQUENCE: 751
gtgttcatct ttggttttgt ngg                                              23

<210> SEQ ID NO 752
<211> LENGTH: 65
<212> TYPE: DNA
<213> ORGANISM: Homo sapiens

<400> SEQUENCE: 752
ccgctctact cgctggtgtt catctttggt ttatgtgggc aacatgctgg tcgtcctcat      60
cttaa                                                                  65

<210> SEQ ID NO 753
<211> LENGTH: 65
<212> TYPE: DNA
<213> ORGANISM: Homo sapiens

<400> SEQUENCE: 753
ccgctctact cgctggtgtt catctttggt ttttgtgggc aacatgctgg tcgtcctcat      60
cttaa                                                                  65

<210> SEQ ID NO 754
<211> LENGTH: 65
<212> TYPE: DNA
<213> ORGANISM: Homo sapiens

<400> SEQUENCE: 754
ccgctctact cgctggtgtt catctttggt tttttgtggg caacatgctg gtcgtcctca      60
tctta                                                                  65

<210> SEQ ID NO 755
<211> LENGTH: 19
<212> TYPE: DNA
<213> ORGANISM: Homo sapiens

<400> SEQUENCE: 755
ctggtgttca tctttggtc                                                   19

<210> SEQ ID NO 756
<211> LENGTH: 31
<212> TYPE: DNA
<213> ORGANISM: Homo sapiens

<400> SEQUENCE: 756
ctggtgttca tctgtgggca acatgctggt c                                     31

<210> SEQ ID NO 757
<211> LENGTH: 31
<212> TYPE: DNA
<213> ORGANISM: Homo sapiens

<400> SEQUENCE: 757
ctggtgttca tctttgggca acatgctggt c                                     31

<210> SEQ ID NO 758
<211> LENGTH: 33
<212> TYPE: DNA
```

<213> ORGANISM: Homo sapiens

<400> SEQUENCE: 758
ctggtgttca tctttggtgg caacatgctg gtc          33

<210> SEQ ID NO 759
<211> LENGTH: 33
<212> TYPE: DNA
<213> ORGANISM: Homo sapiens

<400> SEQUENCE: 759
ctggtgttca tctttggttt aaacatgctg gtc          33

<210> SEQ ID NO 760
<211> LENGTH: 33
<212> TYPE: DNA
<213> ORGANISM: Homo sapiens

<400> SEQUENCE: 760
ctggtgttca tctttgtggg caacatgctg gtc          33

<210> SEQ ID NO 761
<211> LENGTH: 34
<212> TYPE: DNA
<213> ORGANISM: Homo sapiens

<400> SEQUENCE: 761
ctggtgttca tctttggtgg gcaacatgct ggtc         34

<210> SEQ ID NO 762
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 762
gtgttcatct ttggttttgt ngg                    23

<210> SEQ ID NO 763
<211> LENGTH: 39
<212> TYPE: DNA
<213> ORGANISM: Homo sapiens

<400> SEQUENCE: 763
ctggtgttca tctttggttt tgtgggcaac atgctggtc    39

<210> SEQ ID NO 764
<211> LENGTH: 39
<212> TYPE: DNA
<213> ORGANISM: Homo sapiens

<400> SEQUENCE: 764
ctggtgttca tctttggttt tgtgggcaac atgctggtc    39

<210> SEQ ID NO 765
<211> LENGTH: 20
<212> TYPE: DNA
<213> ORGANISM: Homo sapiens

```
<400> SEQUENCE: 765
ttcatccacg ttcaggtgga                                              20

<210> SEQ ID NO 766
<211> LENGTH: 20
<212> TYPE: DNA
<213> ORGANISM: Homo sapiens

<400> SEQUENCE: 766
ttcatccacg ttcacgtgga                                              20

<210> SEQ ID NO 767
<211> LENGTH: 42
<212> TYPE: DNA
<213> ORGANISM: Homo sapiens

<400> SEQUENCE: 767
ttcatccacg ttcaccagac ttctcctcag gagtcaggtg ca                     42

<210> SEQ ID NO 768
<211> LENGTH: 43
<212> TYPE: DNA
<213> ORGANISM: Homo sapiens

<400> SEQUENCE: 768
ttcatccaca taacggcaga cttctcctca ggagtcaggt gca                    43

<210> SEQ ID NO 769
<211> LENGTH: 46
<212> TYPE: DNA
<213> ORGANISM: Homo sapiens

<400> SEQUENCE: 769
ttcatccacg ttcaccttgc agacttctcc tcaggagtca ggtgca                 46

<210> SEQ ID NO 770
<211> LENGTH: 48
<212> TYPE: DNA
<213> ORGANISM: Homo sapiens

<400> SEQUENCE: 770
ttcatccacg ttcaccttgc cccacagggc agtcaggagt caggtgca               48

<210> SEQ ID NO 771
<211> LENGTH: 49
<212> TYPE: DNA
<213> ORGANISM: Homo sapiens

<400> SEQUENCE: 771
ttcatccacg ttcacctaac ggcagacttc tcctcaggag tcaggtgca              49

<210> SEQ ID NO 772
<211> LENGTH: 54
<212> TYPE: DNA
<213> ORGANISM: Homo sapiens

<400> SEQUENCE: 772
ttcatccacg ttcaccttgc cccacggcag acttctcctc aggagtcagg tgca        54

<210> SEQ ID NO 773
<211> LENGTH: 55
<212> TYPE: DNA
```

<213> ORGANISM: Homo sapiens

<400> SEQUENCE: 773
ttcatccacg ttcaccttgc cctaacggca gacttctcct caggagtcag gtgca    55

<210> SEQ ID NO 774
<211> LENGTH: 56
<212> TYPE: DNA
<213> ORGANISM: Homo sapiens

<400> SEQUENCE: 774
tccatccacg ttcaccttgc cccacacggc agacttctcc tcaggagtca ggtgca    56

<210> SEQ ID NO 775
<211> LENGTH: 56
<212> TYPE: DNA
<213> ORGANISM: Homo sapiens

<400> SEQUENCE: 775
ttcatccacg ttcaccttgc cccacagggc agacttctcc tcaggagtca ggtgca    56

<210> SEQ ID NO 776
<211> LENGTH: 56
<212> TYPE: DNA
<213> ORGANISM: Homo sapiens

<400> SEQUENCE: 776
ttcatccacg ttcaccttgc cccacagggt agacttctcc tcaggagtca ggtgca    56

<210> SEQ ID NO 777
<211> LENGTH: 57
<212> TYPE: DNA
<213> ORGANISM: Homo sapiens

<400> SEQUENCE: 777
ttcatccacg ttcaccttgc cccacagggc aggacttctc ctcaggagtc aggtgca    57

<210> SEQ ID NO 778
<211> LENGTH: 58
<212> TYPE: DNA
<213> ORGANISM: Homo sapiens

<400> SEQUENCE: 778
ttcatccacg ttcaccttgc cccactaacg gcagacttct cctcaggagt caggtgca    58

<210> SEQ ID NO 779
<211> LENGTH: 59
<212> TYPE: DNA
<213> ORGANISM: Homo sapiens

<400> SEQUENCE: 779
ttcatccacg ttcaccttgc cccacagggc agcagacttc tcctcaggag tcaggtgca    59

<210> SEQ ID NO 780
<211> LENGTH: 59
<212> TYPE: DNA
<213> ORGANISM: Homo sapiens

<400> SEQUENCE: 780
ttcatccacg ttcaccttgc cccacataac ggcagacttc tcctcaggag tcaggtgca    59

<210> SEQ ID NO 781
<211> LENGTH: 60

```
<212> TYPE: DNA
<213> ORGANISM: Homo sapiens

<400> SEQUENCE: 781
ttcatccacg ttcaccttgc cccacagggc aggcagactt ctcctcagga gtcaggtgca      60

<210> SEQ ID NO 782
<211> LENGTH: 60
<212> TYPE: DNA
<213> ORGANISM: Homo sapiens

<400> SEQUENCE: 782
ttcatccacg ttcaccttgc cccacagtaa cggcagactt ctcctcagga gtcaggtgca      60

<210> SEQ ID NO 783
<211> LENGTH: 62
<212> TYPE: DNA
<213> ORGANISM: Homo sapiens

<400> SEQUENCE: 783
ttcatccacg ttcaccttgc cccacagggt aacggcagac ttctcctcag gagtcaggtg      60
ca                                                                    62

<210> SEQ ID NO 784
<211> LENGTH: 63
<212> TYPE: DNA
<213> ORGANISM: Homo sapiens

<400> SEQUENCE: 784
ttcatccacg ttcaccttgc cccacagcag taacggcaga cttctcctca ggagtcaggt      60
gca                                                                   63

<210> SEQ ID NO 785
<211> LENGTH: 63
<212> TYPE: DNA
<213> ORGANISM: Homo sapiens

<400> SEQUENCE: 785
ttcatccacg ttcaccttgc cccacagggc taacggcaaa cttctcctca ggagtcaggt      60
gca                                                                   63

<210> SEQ ID NO 786
<211> LENGTH: 63
<212> TYPE: DNA
<213> ORGANISM: Homo sapiens

<400> SEQUENCE: 786
ttcatccacg ttcaccttgc cccacagggc aaacggcaga cttctcctca ggagtcaggt      60
gca                                                                   63

<210> SEQ ID NO 787
<211> LENGTH: 64
<212> TYPE: DNA
<213> ORGANISM: Homo sapiens

<400> SEQUENCE: 787
ttcatccacg ttcaccttgc cccacagggc agaacggcag acttctcctc aggagtcagg      60
tgca                                                                  64

<210> SEQ ID NO 788
```

```
<211> LENGTH: 64
<212> TYPE: DNA
<213> ORGANISM: Homo sapiens

<400> SEQUENCE: 788
ttcatccacg ttcaccttgc cccacagggc ataacggcag acttctcctc aggagtcagg    60
tgca                                                                 64

<210> SEQ ID NO 789
<211> LENGTH: 65
<212> TYPE: DNA
<213> ORGANISM: Homo sapiens

<400> SEQUENCE: 789
ttcatccacg ttcaccttgc cccacagggc attgacagca gacttctcct caggagtcag    60
gtgca                                                                65

<210> SEQ ID NO 790
<211> LENGTH: 65
<212> TYPE: DNA
<213> ORGANISM: Homo sapiens

<400> SEQUENCE: 790
ttcatccacg ttcaccttgc cccacagggc agtaacggca gacttctcct caggagtcag    60
gtgca                                                                65

<210> SEQ ID NO 791
<211> LENGTH: 65
<212> TYPE: DNA
<213> ORGANISM: Homo sapiens

<400> SEQUENCE: 791
ttcatccacg ttcaccttgc cccacagggc agtaacggca gacttctcct caggagtcag    60
gtgca                                                                65

<210> SEQ ID NO 792
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 792
gttgccccac agggcagtaa ngg                                            23

<210> SEQ ID NO 793
<211> LENGTH: 65
<212> TYPE: DNA
<213> ORGANISM: Homo sapiens

<400> SEQUENCE: 793
ttcatccacg ttcaccttgc cccacagggc agttaacggc agacttctcc tcaggagtca    60
ggtgc                                                                65

<210> SEQ ID NO 794
<211> LENGTH: 65
```

```
<212> TYPE: DNA
<213> ORGANISM: Homo sapiens

<400> SEQUENCE: 794
ttcatccacg ttcaccttgc cccacagggc agataacggc agacttctcc tcaggagtca    60
ggtgc                                                                65

<210> SEQ ID NO 795
<211> LENGTH: 65
<212> TYPE: DNA
<213> ORGANISM: Homo sapiens

<400> SEQUENCE: 795
ttcatccacg ttcaccttgc cccacagggc aagtaacggc agacttctcc tcaggagtca    60
ggtgc                                                                65

<210> SEQ ID NO 796
<211> LENGTH: 65
<212> TYPE: DNA
<213> ORGANISM: Homo sapiens

<400> SEQUENCE: 796
ttcatccacg ttcaccttgc cccacagggc aggtaacggc agacttctcc tcaggagtca    60
ggtgc                                                                65

<210> SEQ ID NO 797
<211> LENGTH: 65
<212> TYPE: DNA
<213> ORGANISM: Homo sapiens

<400> SEQUENCE: 797
ttcatccacg ttcaccttgc cccacagggc agagtaacgg cagacttctc ctcaggagtc    60
aggtg                                                                65

<210> SEQ ID NO 798
<211> LENGTH: 65
<212> TYPE: DNA
<213> ORGANISM: Homo sapiens

<400> SEQUENCE: 798
ttcatccacg ttcaccttgc cccacagggc aatattaacg gcagacttct cctcaggagt    60
caggt                                                                65

<210> SEQ ID NO 799
<211> LENGTH: 33
<212> TYPE: DNA
<213> ORGANISM: Homo sapiens

<400> SEQUENCE: 799
agtcagagca gtgcttcagc cccacagggg ctg                                  33

<210> SEQ ID NO 800
<211> LENGTH: 35
<212> TYPE: DNA
<213> ORGANISM: Homo sapiens

<400> SEQUENCE: 800
agtcagagca gtgcttcagc cccacagggc cctgt                                35

<210> SEQ ID NO 801
```

<211> LENGTH: 51
<212> TYPE: DNA
<213> ORGANISM: Homo sapiens

<400> SEQUENCE: 801
agtcagagca gtgcttcagc cccacagggc agctctaaat accagattcc c    51

<210> SEQ ID NO 802
<211> LENGTH: 56
<212> TYPE: DNA
<213> ORGANISM: Homo sapiens

<400> SEQUENCE: 802
agtcagagca gtgcttcagc cccacagggc agccttcctc taaataccag attccc    56

<210> SEQ ID NO 803
<211> LENGTH: 64
<212> TYPE: DNA
<213> ORGANISM: Homo sapiens

<400> SEQUENCE: 803
agtcagagca gtgcttcagc cccacagggc ataagggcag ccttcctcta ataccagat    60 tccc    64

<210> SEQ ID NO 804
<211> LENGTH: 65
<212> TYPE: DNA
<213> ORGANISM: Homo sapiens

<400> SEQUENCE: 804
agtcagagca gtgcttcagc cccacagggc agtaagggca gccttcctct aaataccaga    60
ttccc    65

<210> SEQ ID NO 805
<211> LENGTH: 65
<212> TYPE: DNA
<213> ORGANISM: Homo sapiens

<400> SEQUENCE: 805
agtcagagca gtgcttcagc cccacagggc agtaagggca gccttcctct aaataccaga    60
ttccc    65

<210> SEQ ID NO 806
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 806
gttgccccac agggcagtaa ngg    23

<210> SEQ ID NO 807
<211> LENGTH: 65
<212> TYPE: DNA
<213> ORGANISM: Homo sapiens

<400> SEQUENCE: 807

```
agtcagagca gtgcttcagc cccacagggc agttaagggc agccttcctc taaataccag    60
attcc                                                                65

<210> SEQ ID NO 808
<211> LENGTH: 65
<212> TYPE: DNA
<213> ORGANISM: Homo sapiens

<400> SEQUENCE: 808
agtcagagca gtgcttcagc cccacagggc agctaagggc agccttcctc taaataccag    60
attcc                                                                65

<210> SEQ ID NO 809
<211> LENGTH: 65
<212> TYPE: DNA
<213> ORGANISM: Homo sapiens

<400> SEQUENCE: 809
agtcagagca gtgcttcagc cccacagggc agtataaggg cgccttcctc taaataccag    60
attcc                                                                65

<210> SEQ ID NO 810
<211> LENGTH: 58
<212> TYPE: DNA
<213> ORGANISM: Homo sapiens

<400> SEQUENCE: 810
gatgaacacc agcgagtaga gcggaggcag gacccaattt gcttcacgtc aaatttat     58

<210> SEQ ID NO 811
<211> LENGTH: 60
<212> TYPE: DNA
<213> ORGANISM: Homo sapiens

<400> SEQUENCE: 811
gatgaacacc agcgagtaga gcgggggcag ggcctccaat ttgcttcacg tcaaatttat    60

<210> SEQ ID NO 812
<211> LENGTH: 60
<212> TYPE: DNA
<213> ORGANISM: Homo sapiens

<400> SEQUENCE: 812
gatgaacacc agcgagtaga gcggagagtt gggccccaat ttgcttcacg tcaaatttat    60

<210> SEQ ID NO 813
<211> LENGTH: 61
<212> TYPE: DNA
<213> ORGANISM: Homo sapiens

<400> SEQUENCE: 813
gatgaacacc agcgagtaga gcggaggagt tgggccccaa tttgcttcac gtcaaattta    60
t                                                                    61

<210> SEQ ID NO 814
<211> LENGTH: 64
<212> TYPE: DNA
<213> ORGANISM: Homo sapiens

<400> SEQUENCE: 814
```

```
gatgaacacc agcgagtaga gcggaggcag agttgggccc caatttgctt cacgtcaaat    60
ttat                                                                64

<210> SEQ ID NO 815
<211> LENGTH: 64
<212> TYPE: DNA
<213> ORGANISM: Homo sapiens

<400> SEQUENCE: 815
gatgaacacc agcgagtaga gcggaggcag gattgggccc caatttgctt cacgtcaaat    60
ttat                                                                64

<210> SEQ ID NO 816
<211> LENGTH: 65
<212> TYPE: DNA
<213> ORGANISM: Homo sapiens

<400> SEQUENCE: 816
gatgaacacc agcgagtaga gcggaggcag gagttgggcc ccaatttgct tcacgtcaaa    60
tttat                                                               65

<210> SEQ ID NO 817
<211> LENGTH: 65
<212> TYPE: DNA
<213> ORGANISM: Homo sapiens

<400> SEQUENCE: 817
gatgaacacc agcgagtaga gcggaggcag gagttgggcc ccaatttgct tcacgtcaaa    60
tttat                                                               65

<210> SEQ ID NO 818
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 818
gtagagcgga ggcaggaggc ngg                                           23

<210> SEQ ID NO 819
<211> LENGTH: 65
<212> TYPE: DNA
<213> ORGANISM: Homo sapiens

<400> SEQUENCE: 819
gatgaacacc agcgagtaga gcggaggcag gaagttgggc cccaatttgc ttcacgtcaa    60
attta                                                               65

<210> SEQ ID NO 820
<211> LENGTH: 64
<212> TYPE: DNA
<213> ORGANISM: Homo sapiens

<400> SEQUENCE: 820
gatgaacacc agcgagtaga gcggaggcag gagcagttgg gccccaattt gcttcacgtc    60
``` aaat                                                                   64

<210> SEQ ID NO 821
<211> LENGTH: 27
<212> TYPE: DNA
<213> ORGANISM: Homo sapiens
<220> FEATURE:
<221> NAME/KEY: modified_base
<222> LOCATION: (13)..(13)
<223> OTHER INFORMATION: a, c, t, g, unknown or other

<400> SEQUENCE: 821
gagtagagcg gangcaggag gcgggct                                          27

<210> SEQ ID NO 822
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 822
guagagcgga gcaggaggc                                                   19

<210> SEQ ID NO 823
<211> LENGTH: 26
<212> TYPE: DNA
<213> ORGANISM: Homo sapiens

<400> SEQUENCE: 823
gagagagcgg aggcaggagg cgggct                                           26

<210> SEQ ID NO 824
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: a, c, t, g, unknown or other

<400> SEQUENCE: 824
gagagncgga ggcaggaggc                                                  20

<210> SEQ ID NO 825
<211> LENGTH: 29
<212> TYPE: DNA
<213> ORGANISM: Homo sapiens

<400> SEQUENCE: 825
aaggtgaacg tggatgaagt tggtggtga                                        29

<210> SEQ ID NO 826
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 826
gugaacgugg augaaguugg                                               20

<210> SEQ ID NO 827
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 827
ggaacgugga ugaaguugg                                                19

<210> SEQ ID NO 828
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 828
guaacgugga ugaaguugg                                                19

<210> SEQ ID NO 829
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829
gugacgugga ugaaguugg                                                19

<210> SEQ ID NO 830
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 830
gugaagugga ugaaguugg                                                19

<210> SEQ ID NO 831
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 831
gugaacugga ugaaguugg                                                19

<210> SEQ ID NO 832
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 832
gugaacggga ugaaguugg                                              19

<210> SEQ ID NO 833
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 833
gugaacguga ugaaguugg                                              19

<210> SEQ ID NO 834
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 834
gugaacgugg ugaaguugg                                              19

<210> SEQ ID NO 835
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 835
gugaacgugg agaaguugg                                              19

<210> SEQ ID NO 836
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 836
gugaacgugg auaaguugg                                              19

<210> SEQ ID NO 837
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 837
gugaacgugg augaguugg                                              19
```

```
<210> SEQ ID NO 838
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 838
gugaacgugg augaauugg                                                  19

<210> SEQ ID NO 839
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 839
gugaacgugg augaagugg                                                  19

<210> SEQ ID NO 840
<211> LENGTH: 19
<212> TYPE: RNA
<213> ORGANISM: Homo sapiens

<400> SEQUENCE: 840
gugaacgugg augaaguug                                                  19

<210> SEQ ID NO 841
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 841
tgagtagagc ggaggcagga ggcgggctg                                       29

<210> SEQ ID NO 842
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 842
guagagcgga ggcaggaggc                                                 20

<210> SEQ ID NO 843
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843
gagagcggag gcaggaggc                                                  19
```

```
<210> SEQ ID NO 844
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 844
gugagcggag gcaggaggc                                                    19

<210> SEQ ID NO 845
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845
guaagcggag gcaggaggc                                                    19

<210> SEQ ID NO 846
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 846
guaggcggag gcaggaggc                                                    19

<210> SEQ ID NO 847
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 847
guagacggag gcaggaggc                                                    19

<210> SEQ ID NO 848
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 848
guagagggag gcaggaggc                                                    19

<210> SEQ ID NO 849
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 849
guagagcgag gcaggaggc 19

<210> SEQ ID NO 850
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 850
guagagcggg gcaggaggc 19

<210> SEQ ID NO 851
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 851
guagagcgga gcaggaggc 19

<210> SEQ ID NO 852
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 852
guagagcgga ggaggaggc 19

<210> SEQ ID NO 853
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 853
guagagcgga ggcggaggc 19

<210> SEQ ID NO 854
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 854
guagagcgga ggcagaggc 19

<210> SEQ ID NO 855
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 855
guagagcgga ggcaggggc                                                  19

<210> SEQ ID NO 856
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 856
guagagcgga ggcaggagc                                                  19

<210> SEQ ID NO 857
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 857
guagagcgga ggcaggagg                                                  19

<210> SEQ ID NO 858
<211> LENGTH: 23
<212> TYPE: DNA
<213> ORGANISM: Homo sapiens

<400> SEQUENCE: 858
gtgaacgtgg atgaagttgg tgg                                             23

<210> SEQ ID NO 859
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 859
ggaacgtgga tgaagttggn gg                                              22

<210> SEQ ID NO 860
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 860
gtaacgtgga tgaagttggn gg                                              22

<210> SEQ ID NO 861
```

```
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 861
gtgaacgtgg atgagttggn gg                                              22

<210> SEQ ID NO 862
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 862
gtgaacgtgg atgaagttgn gg                                              22

<210> SEQ ID NO 863
<211> LENGTH: 23
<212> TYPE: DNA
<213> ORGANISM: Homo sapiens

<400> SEQUENCE: 863
gtagagcgga ggcaggaggc ggg                                             23

<210> SEQ ID NO 864
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 864
gagagcggag gcaggaggcn gg                                              22

<210> SEQ ID NO 865
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 865
gtgagcggag gcaggaggcn gg                                              22

<210> SEQ ID NO 866
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 866
gtaagcggag gcaggaggcn gg                                              22
```

```
<210> SEQ ID NO 867
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 867
gtaggcggag gcaggaggcn gg                                              22

<210> SEQ ID NO 868
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 868
gtagagcggg gcaggaggcn gg                                              22

<210> SEQ ID NO 869
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 869
gtagagcgga gcaggaggcn gg                                              22

<210> SEQ ID NO 870
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 870
gtagagcgga ggaggaggcn gg                                              22

<210> SEQ ID NO 871
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 871
gtagagcgga ggcggaggcn gg                                              22

<210> SEQ ID NO 872
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other
```

<400> SEQUENCE: 872
gtagagcgga ggcaggagcn gg                                    22

<210> SEQ ID NO 873
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 873
gtagagcgga ggcaggaggn gg                                    22

<210> SEQ ID NO 874
<211> LENGTH: 29
<212> TYPE: DNA
<213> ORGANISM: Homo sapiens

<400> SEQUENCE: 874
aaggtgaacg tggatgaagt tggtggtga                             29

<210> SEQ ID NO 875
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 875
gugaacgugg augaaguugg                                       20

<210> SEQ ID NO 876
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 876
ggaacgugga ugaaguugg                                        19

<210> SEQ ID NO 877
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 877
gaacguggau gaaguugg                                         18

<210> SEQ ID NO 878
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 878
gacguggaug aaguugg                                                      17

<210> SEQ ID NO 879
<211> LENGTH: 16
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 879
gcguggauga aguugg                                                       16

<210> SEQ ID NO 880
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 880
gguggaugaa guugg                                                        15

<210> SEQ ID NO 881
<211> LENGTH: 14
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 881
guggaugaag uugg                                                         14

<210> SEQ ID NO 882
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882
gugaacgugg augaaguugg                                                   20

<210> SEQ ID NO 883
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 883
guugaacgug gaugaaguug g                                                 21

<210> SEQ ID NO 884
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 884
guggaacgug gaugaaguug g                                              21

<210> SEQ ID NO 885
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 885
guguaacgug gaugaaguug g                                              21

<210> SEQ ID NO 886
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 886
gugauacgug gaugaaguug g                                              21

<210> SEQ ID NO 887
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 887
gugaaucgug gaugaaguug g                                              21

<210> SEQ ID NO 888
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 888
gugaaacgug gaugaaguug g                                              21

<210> SEQ ID NO 889
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 889
gugaaccgug gaugaaguug g                                              21
```

```
<210> SEQ ID NO 890
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 890
gugaacugug gaugaaguug g                                              21

<210> SEQ ID NO 891
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 891
gugaacagug gaugaaguug g                                              21

<210> SEQ ID NO 892
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 892
gugaacggug gaugaaguug g                                              21

<210> SEQ ID NO 893
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 893
gugaacgcug gaugaaguug g                                              21

<210> SEQ ID NO 894
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 894
gugaacgaug gaugaaguug g                                              21

<210> SEQ ID NO 895
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

```
            Synthetic oligonucleotide"

<400> SEQUENCE: 895
gugaacguug gaugaaguug g                                              21

<210> SEQ ID NO 896
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 896
gugaacguag gaugaaguug g                                              21

<210> SEQ ID NO 897
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 897
gugaacgucg gaugaaguug g                                              21

<210> SEQ ID NO 898
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 898
gugaacgugg gaugaaguug g                                              21

<210> SEQ ID NO 899
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 899
gugaacgugc gaugaaguug g                                              21

<210> SEQ ID NO 900
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 900
gugaacgugg caugaaguug g                                              21

<210> SEQ ID NO 901
<211> LENGTH: 21
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 901
gugaacgugg aaugaaguug g                                              21

<210> SEQ ID NO 902
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 902
gugaacgugg auugaaguug g                                              21

<210> SEQ ID NO 903
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 903
gugaacgugg auggaaguug g                                              21

<210> SEQ ID NO 904
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 904
gugaacgugg augaaaguug g                                              21

<210> SEQ ID NO 905
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 905
gugaacgugg augaagguug g                                              21

<210> SEQ ID NO 906
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 906
```
gugaacgugg augaaguuug g					21

<210> SEQ ID NO 907
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 907
gugaacgugg augaaguugg g					21

<210> SEQ ID NO 908
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 908
guagagcgga ggcaggaggc					20

<210> SEQ ID NO 909
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 909
guuagagcgg aggcaggagg c					21

<210> SEQ ID NO 910
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 910
guaagagcgg aggcaggagg c					21

<210> SEQ ID NO 911
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 911
guaggagcgg aggcaggagg c					21

<210> SEQ ID NO 912
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 912
guagcagcgg aggcaggagg c                                              21

<210> SEQ ID NO 913
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 913
guaguagcgg aggcaggagg c                                              21

<210> SEQ ID NO 914
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 914
guagaagcgg aggcaggagg c                                              21

<210> SEQ ID NO 915
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 915
guagaugcgg aggcaggagg c                                              21

<210> SEQ ID NO 916
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 916
guagacgcgg aggcaggagg c                                              21

<210> SEQ ID NO 917
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 917
guagaggcgg aggcaggagg c                                              21

<210> SEQ ID NO 918

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 918
guagagacgg aggcaggagg c                                              21

<210> SEQ ID NO 919
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 919
guagagucgg aggcaggagg c                                              21

<210> SEQ ID NO 920
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 920
guagagccgg aggcaggagg c                                              21

<210> SEQ ID NO 921
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 921
guagagcagg aggcaggagg c                                              21

<210> SEQ ID NO 922
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 922
guagagcugg aggcaggagg c                                              21

<210> SEQ ID NO 923
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 923
```
guagagcggg aggcaggagg c          21

<210> SEQ ID NO 924
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 924
guagagcgug aggcaggagg c          21

<210> SEQ ID NO 925
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 925
guagagcggu aggcaggagg c          21

<210> SEQ ID NO 926
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 926
guagagcgga aggcaggagg c          21

<210> SEQ ID NO 927
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 927
guagagcgga gggcaggagg c          21

<210> SEQ ID NO 928
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 928
guagagcgga ggccaggagg c          21

<210> SEQ ID NO 929
<211> LENGTH: 21
<212> TYPE: RNA
<213> ORGANISM: Artificial Sequence
<220> FEATURE:

-continued

```
<221> NAME/KEY: source
<223> OTHER INFORMATION: /note="Description of Artificial Sequence:
      Synthetic oligonucleotide"

<400> SEQUENCE: 929
guagagcgga ggcuaggagg c                                              21

<210> SEQ ID NO 930
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 930
guagagcgga ggcgaggagg c                                              21

<210> SEQ ID NO 931
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 931
guagagcgga ggcaaggagg c                                              21

<210> SEQ ID NO 932
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 932
guagagcgga ggcagggagg c                                              21

<210> SEQ ID NO 933
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 933
guagagcgga ggcaggaagg c                                              21

<210> SEQ ID NO 934
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 934
guagagcgga ggcaggaggg c                                              21
```

```
<210> SEQ ID NO 935
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 935
guagagcgga ggcaggaggc c                                              21

<210> SEQ ID NO 936
<211> LENGTH: 24
<212> TYPE: DNA
<213> ORGANISM: Homo sapiens

<400> SEQUENCE: 936
ggtgaacgtg gatgaagttg gtgg                                           24

<210> SEQ ID NO 937
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 937
gttgaacgtg gatgaagttg gngg                                           24

<210> SEQ ID NO 938
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 938
gtggaacgtg gatgaagttg gngg                                           24

<210> SEQ ID NO 939
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 939
gtgaatcgtg gatgaagttg gngg                                           24

<210> SEQ ID NO 940
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 940
gtgaaccgtg gatgaagttg gngg                                           24
```

```
<210> SEQ ID NO 941
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 941
gtgaactgtg gatgaagttg gngg                                          24

<210> SEQ ID NO 942
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 942
gtgaacagtg gatgaagttg gngg                                          24

<210> SEQ ID NO 943
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 943
gtgaacggtg gatgaagttg gngg                                          24

<210> SEQ ID NO 944
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 944
gtgaacgttg gatgaagttg gngg                                          24

<210> SEQ ID NO 945
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 945
gtgaacgtcg gatgaagttg gngg                                          24

<210> SEQ ID NO 946
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other
```

```
<400> SEQUENCE: 946
gtgaacgtgg gatgaagttg gngg                                          24

<210> SEQ ID NO 947
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 947
gtgaacgtgc gatgaagttg gngg                                          24

<210> SEQ ID NO 948
<211> LENGTH: 24
<212> TYPE: DNA
<213> ORGANISM: Homo sapiens

<400> SEQUENCE: 948
agtagagcgg aggcaggagg cggg                                          24

<210> SEQ ID NO 949
<211> LENGTH: 24
<212> TYPE: DNA
<213> ORGANISM: Homo sapiens

<400> SEQUENCE: 949
gtagagcgga ggcaggaggc gggc                                          24

<210> SEQ ID NO 950
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 950
gttagagcgg aggcaggagg cngg                                          24

<210> SEQ ID NO 951
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 951
gtaagagcgg aggcaggagg cngg                                          24

<210> SEQ ID NO 952
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 952
```
gtaggagcgg aggcaggagg cngg                                        24

<210> SEQ ID NO 953
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 953
gtagcagcgg aggcaggagg cngg                                        24

<210> SEQ ID NO 954
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 954
gtagaagcgg aggcaggagg cngg                                        24

<210> SEQ ID NO 955
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 955
gtagatgcgg aggcaggagg cngg                                        24

<210> SEQ ID NO 956
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 956
gtagacgcgg aggcaggagg cngg                                        24

<210> SEQ ID NO 957
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 957
gtagaggcgg aggcaggagg cngg                                        24

<210> SEQ ID NO 958
<211> LENGTH: 24
<212> TYPE: DNA
<213> ORGANISM: Homo sapiens
<220> FEATURE:
<221> NAME/KEY: modified_base

```
<222> LOCATION: (22)..(22)
<223> OTHER INFORMATION: a, c, t, g, unknown or other

<400> SEQUENCE: 958
gtagagacgg aggcaggagg cngg                                              24

<210> SEQ ID NO 959
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 959
gtagagtcgg aggcaggagg cngg                                              24

<210> SEQ ID NO 960
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 960
gtagagccgg aggcaggagg cngg                                              24

<210> SEQ ID NO 961
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 961
gtagagcggg aggcaggagg cngg                                              24

<210> SEQ ID NO 962
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 962
gtagagcgtg aggcaggagg cngg                                              24

<210> SEQ ID NO 963
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 963
gtagagcggt aggcaggagg cngg                                              24

<210> SEQ ID NO 964
```

```
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 964
gtagagcgga aggcaggagg cngg                                              24

<210> SEQ ID NO 965
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 965
gtagagcgga gggcaggagg cngg                                              24

<210> SEQ ID NO 966
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 966
gtagagcgga ggccaggagg cngg                                              24

<210> SEQ ID NO 967
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 967
gtagagcgga ggctaggagg cngg                                              24

<210> SEQ ID NO 968
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 968
gtagagcgga ggcgaggagg cngg                                              24

<210> SEQ ID NO 969
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 969
```
gtagagcgga ggcaaggagg cngg                                          24

<210> SEQ ID NO 970
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 970
gtagagcgga ggcagggagg cngg                                          24

<210> SEQ ID NO 971
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 971 gcugugggc aaggugaacg                                                20

<210> SEQ ID NO 972
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 972 gugugggca aggugaacg                                                 19

<210> SEQ ID NO 973
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 973 gcgugggca aggugaacg                                                 19

<210> SEQ ID NO 974
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 974
gcuuggggca aggugaacg                                                19

<210> SEQ ID NO 975
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 975 gcuggggca aggugaacg                                                        19

<210> SEQ ID NO 976
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 976
gcugugggca aggugaacg                                                       19

<210> SEQ ID NO 977
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 977 gcuguggga aggugaacg                                                        19

<210> SEQ ID NO 978
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 978 gcugugggc aggugaacg                                                        19

<210> SEQ ID NO 979
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 979 gcugugggc aagugaacg                                                        19

<210> SEQ ID NO 980
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 980 gcugugggc aagggaacg                                                        19
```

```
<210> SEQ ID NO 981
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 981
gcuguggggc aagguaacg                                                    19

<210> SEQ ID NO 982
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 982
gcuguggggc aaggugacg                                                    19

<210> SEQ ID NO 983
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 983
gcuguggggc aaggugaag                                                    19

<210> SEQ ID NO 984
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 984
gcuguggggc aaggugaac                                                    19

<210> SEQ ID NO 985
<211> LENGTH: 23
<212> TYPE: DNA
<213> ORGANISM: Homo sapiens

<400> SEQUENCE: 985
gtgaacgtgg atgaagttgg tgg                                               23

<210> SEQ ID NO 986
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 986
gugaacuugu ggaugaaguu gg                                                22
```

```
<210> SEQ ID NO 987
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 987
gtgaacuuug tggatgaagt tgg                                              23

<210> SEQ ID NO 988
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 988
gugaacgugu ugaugaaguu gg                                               22

<210> SEQ ID NO 989
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 989
gtgaacgtgu uugatgaagt tgg                                              23

<210> SEQ ID NO 990
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 990
gtgaacgtgu uuugatgaag ttgg                                             24

<210> SEQ ID NO 991
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 991
gtgaacgtgu uuugatgaa gttgg                                              25

<210> SEQ ID NO 992
<211> LENGTH: 23
<212> TYPE: DNA
<213> ORGANISM: Homo sapiens

<400> SEQUENCE: 992
gtagagcgga ggcaggaggc ggg                                               23

<210> SEQ ID NO 993
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 993
guagaguucg gaggcaggag gc                                                22

<210> SEQ ID NO 994
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 994
gtagaguuuc ggaggcagga ggc                                               23

<210> SEQ ID NO 995
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 995
gtagaguuuu cggaggcagg aggc                                              24

<210> SEQ ID NO 996
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 996
```
guagagcggu uaggcaggag gc                                                  22

<210> SEQ ID NO 997
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 997
gtagagcggu uuaggcagga ggc                                                 23

<210> SEQ ID NO 998
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 998
gtagagcggu uuuaggcagg aggc                                                24

<210> SEQ ID NO 999
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 999
gugaacgugg augguugg                                                       18

<210> SEQ ID NO 1000
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1000
gugaacgugg augaaguu                                                       18

<210> SEQ ID NO 1001
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1001
guagagcgga caggaggc                                                       18

<210> SEQ ID NO 1002
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1002
guagagcgga ggggaggc                                              18

<210> SEQ ID NO 1003
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1003
gugaacgugg augaaguugg                                            20

<210> SEQ ID NO 1004
<211> LENGTH: 53
<212> TYPE: DNA
<213> ORGANISM: Homo sapiens

<400> SEQUENCE: 1004
tctgccgtta ctgccctgtg gggcaaggtg aacgtggatg aagttggtgg tga       53

<210> SEQ ID NO 1005
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1005
guugccccac agggcaguaa                                            20

<210> SEQ ID NO 1006
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1006
guagagcgga ggcaggaggc                                            20

<210> SEQ ID NO 1007
<211> LENGTH: 28
<212> TYPE: DNA
<213> ORGANISM: Homo sapiens

<400> SEQUENCE: 1007
gagtagagcg gaggcaggag gcgggctg                                   28

<210> SEQ ID NO 1008

```
<211> LENGTH: 28
<212> TYPE: DNA
<213> ORGANISM: Homo sapiens

<400> SEQUENCE: 1008
gggtagagag gaggcaggga ggcgggaa                                          28

<210> SEQ ID NO 1009
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1009
gccaagcacu uaaaggaguc                                                   20

<210> SEQ ID NO 1010
<211> LENGTH: 27
<212> TYPE: DNA
<213> ORGANISM: Homo sapiens

<400> SEQUENCE: 1010
aaaccaagca cttaaaggag tccggga                                           27

<210> SEQ ID NO 1011
<211> LENGTH: 28
<212> TYPE: DNA
<213> ORGANISM: Homo sapiens

<400> SEQUENCE: 1011
ataccaagca cttaaaggag tgctggtc                                          28

<210> SEQ ID NO 1012
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1012
guagagcgga ggcaggaggc                                                   20

<210> SEQ ID NO 1013
<211> LENGTH: 80
<212> TYPE: DNA
<213> ORGANISM: Homo sapiens

<400> SEQUENCE: 1013
ctgttggggg tagagaggag gcagggaggc gggaaggagg ctgtgctggc ctccagggcc       60
aagctggtga tggcttgaca                                                   80

<210> SEQ ID NO 1014
<211> LENGTH: 78
<212> TYPE: DNA
<213> ORGANISM: Homo sapiens

<400> SEQUENCE: 1014
ctgttggggg tagagaggag gcagggacgg gaaggaggct gtgctggcct ccagggccaa       60
gctggtgatg gcttgaca                                                     78
```

<210> SEQ ID NO 1015
<211> LENGTH: 76
<212> TYPE: DNA
<213> ORGANISM: Homo sapiens

<400> SEQUENCE: 1015 ctgttgggggg tagagaggag gcaggcggga aggaggctgt gctggcctcc agggccaagc    60
tggtgatggc ttgaca                                                    76

<210> SEQ ID NO 1016
<211> LENGTH: 73
<212> TYPE: DNA
<213> ORGANISM: Homo sapiens

<400> SEQUENCE: 1016 ctgttgggggg tagagaggag gcagggaagg aggctgtgct ggcctccagg gccaagctgg    60
tgatggcttg aca                                                       73

<210> SEQ ID NO 1017
<211> LENGTH: 61
<212> TYPE: DNA
<213> ORGANISM: Homo sapiens

<400> SEQUENCE: 1017 ctgttgggggg tagagaggag gctgtgctgg cctccagggc caagctggtg atggcttgac    60
a                                                                    61

<210> SEQ ID NO 1018
<211> LENGTH: 80
<212> TYPE: DNA
<213> ORGANISM: Homo sapiens

<400> SEQUENCE: 1018 ctgttgggggg tagagaggag gcagggaagg cgggaaggag gctgtgctgg cctccagggc    60
caagctggtg atggcttgac                                                80

<210> SEQ ID NO 1019
<211> LENGTH: 80
<212> TYPE: DNA
<213> ORGANISM: Homo sapiens

<400> SEQUENCE: 1019 ctgttgggggg tagagaggag gcagggatgg cgggaaggag gctgtgctgg cctccagggc    60
caagctggtg atggcttgac                                                80

<210> SEQ ID NO 1020
<211> LENGTH: 80
<212> TYPE: DNA
<213> ORGANISM: Homo sapiens

<400> SEQUENCE: 1020 ctgttgggggg tagagaggag gcagggaggg cgggaaggag gctgtgctgg cctccagggc    60
caagctggtg atggcttgac                                                80

<210> SEQ ID NO 1021
<211> LENGTH: 80
<212> TYPE: DNA
<213> ORGANISM: Homo sapiens

```
<400> SEQUENCE: 1021 ctgttgggggg tagagaggag gcagggaagg gcgggaagga ggctgtgctg gcctccaggg    60
ccaagctggt gatggcttga                                                80

<210> SEQ ID NO 1022
<211> LENGTH: 80
<212> TYPE: DNA
<213> ORGANISM: Homo sapiens

<400> SEQUENCE: 1022 ctgttgggggg tagagaggag gcagggagag ctagaccacg acatatggtc agattttgtt   60
tggcgggaag gaggctgtgc                                                80

<210> SEQ ID NO 1023
<211> LENGTH: 80
<212> TYPE: DNA
<213> ORGANISM: Homo sapiens

<400> SEQUENCE: 1023 ctgttgggggg tagagaggag gcagggaggc gggaaggaga acaagggcag aagcagtgaa   60
accacctagg cgggaaggag                                                80

<210> SEQ ID NO 1024
<211> LENGTH: 80
<212> TYPE: DNA
<213> ORGANISM: Homo sapiens

<400> SEQUENCE: 1024 ctgttgggggg tagagaggag gcagggaact cccggatgaa cactaagtac gacgagaatg   60
acaagctgat ccggggcggg                                                80

<210> SEQ ID NO 1025
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1025
gccaagcacu uaaaggaguc                                                20

<210> SEQ ID NO 1026
<211> LENGTH: 80
<212> TYPE: DNA
<213> ORGANISM: Homo sapiens

<400> SEQUENCE: 1026
gaggattaag tgttatacca agcacttaaa ggagtgctgg tcctatgtca gcagaactca    60
tagcactgtt aaaatacata                                                80

<210> SEQ ID NO 1027
<211> LENGTH: 76
<212> TYPE: DNA
<213> ORGANISM: Homo sapiens

<400> SEQUENCE: 1027
gaggattaag tgttatacca agcacttaag tgctggtcct atgtcagcag aactcatagc    60
actgttaaaa tacata                                                    76
```

```
<210> SEQ ID NO 1028
<211> LENGTH: 80
<212> TYPE: DNA
<213> ORGANISM: Homo sapiens

<400> SEQUENCE: 1028
gaggattaag tgttatacca agcacttaaa ggaggtgctg gtcctatgtc agcagaactc      60
atagcactgt taaaatacat                                                 80

<210> SEQ ID NO 1029
<211> LENGTH: 22
<212> TYPE: DNA
<213> ORGANISM: Homo sapiens

<400> SEQUENCE: 1029
gggaattgga tgaagttggg gg                                              22

<210> SEQ ID NO 1030
<211> LENGTH: 22
<212> TYPE: DNA
<213> ORGANISM: Homo sapiens

<400> SEQUENCE: 1030
agaagcggag gcaggaggct gg                                              22

<210> SEQ ID NO 1031
<211> LENGTH: 22
<212> TYPE: DNA
<213> ORGANISM: Homo sapiens

<400> SEQUENCE: 1031
agagagagga gcaggaggct gg                                              22

<210> SEQ ID NO 1032
<211> LENGTH: 24
<212> TYPE: DNA
<213> ORGANISM: Homo sapiens

<400> SEQUENCE: 1032
aggaacgtgg atgaacttgg aagg                                            24

<210> SEQ ID NO 1033
<211> LENGTH: 24
<212> TYPE: DNA
<213> ORGANISM: Homo sapiens

<400> SEQUENCE: 1033
aagatgaacg tggagtgaag tggg                                            24

<210> SEQ ID NO 1034
<211> LENGTH: 24
<212> TYPE: DNA
<213> ORGANISM: Homo sapiens

<400> SEQUENCE: 1034
atccaggatg ggcaccacac ccgg                                            24

<210> SEQ ID NO 1035
<211> LENGTH: 24
<212> TYPE: DNA
<213> ORGANISM: Homo sapiens
```

```
<400> SEQUENCE: 1035
gcagagccga gagcaggagg cgag                                          24

<210> SEQ ID NO 1036
<211> LENGTH: 24
<212> TYPE: DNA
<213> ORGANISM: Homo sapiens

<400> SEQUENCE: 1036
ggagagcggc ggcaggaggc gtag                                          24

<210> SEQ ID NO 1037
<211> LENGTH: 24
<212> TYPE: DNA
<213> ORGANISM: Homo sapiens

<400> SEQUENCE: 1037
ggagagcggg ggccaggagg ccgg                                          24

<210> SEQ ID NO 1038
<211> LENGTH: 24
<212> TYPE: DNA
<213> ORGANISM: Homo sapiens

<400> SEQUENCE: 1038
gaagagtgga ggcagggagg ctgg                                          24

<210> SEQ ID NO 1039
<211> LENGTH: 24
<212> TYPE: DNA
<213> ORGANISM: Homo sapiens

<400> SEQUENCE: 1039
gaagagagga ggcaggaggg ctgg                                          24

<210> SEQ ID NO 1040
<211> LENGTH: 24
<212> TYPE: DNA
<213> ORGANISM: Homo sapiens

<400> SEQUENCE: 1040
gaagagggga ggcaggaggg cagg                                          24

<210> SEQ ID NO 1041
<211> LENGTH: 24
<212> TYPE: DNA
<213> ORGANISM: Homo sapiens

<400> SEQUENCE: 1041
gctctgccgt ttactgccct gtgg                                          24

<210> SEQ ID NO 1042
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1042
guagagcgga ggcaggaggc                                               20
```

```
<210> SEQ ID NO 1043
<211> LENGTH: 48
<212> TYPE: DNA
<213> ORGANISM: Homo sapiens

<400> SEQUENCE: 1043
ctggaggggg tagagaggag gcagggaggc ggggaggagg ctgtgctg                    48

<210> SEQ ID NO 1044
<211> LENGTH: 48
<212> TYPE: DNA
<213> ORGANISM: Homo sapiens

<400> SEQUENCE: 1044
ctggaggggg tagagaggag gcagggaagg cggggaggag gctgtgct                    48

<210> SEQ ID NO 1045
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: a, c, t, g, unknown or other

<400> SEQUENCE: 1045
ntgaacgtgg atgaagttgg                                                  20

<210> SEQ ID NO 1046
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1046
gtgaacgtgg atgaagttgg                                                  20

<210> SEQ ID NO 1047
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1047
ggaacgtgga tgaagttg                                                    18

<210> SEQ ID NO 1048
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1048
gtaacgtgga tgaagttg                                                    18
```

```
<210> SEQ ID NO 1049
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1049
gtgacgtgga tgaagttg                                                        18

<210> SEQ ID NO 1050
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1050
gtgaagtgga tgaagttg                                                        18

<210> SEQ ID NO 1051
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1051
gtgaactgga tgaagttg                                                        18

<210> SEQ ID NO 1052
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: a, c, t, g, unknown or other

<400> SEQUENCE: 1052
gntgaacgtg gatgaagttg                                                      20

<210> SEQ ID NO 1053
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(3)
<223> OTHER INFORMATION: a, c, t, g, unknown or other

<400> SEQUENCE: 1053
gtngaacgtg gatgaagttg                                                      20
```

-continued

```
<210> SEQ ID NO 1054
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (4)..(4)
<223> OTHER INFORMATION: a, c, t, g, unknown or other

<400> SEQUENCE: 1054
gtgnaacgtg gatgaagttg                                                    20

<210> SEQ ID NO 1055
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(5)
<223> OTHER INFORMATION: a, c, t, g, unknown or other

<400> SEQUENCE: 1055
gtganacgtg gatgaagttg                                                    20

<210> SEQ ID NO 1056
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: a, c, t, g, unknown or other

<400> SEQUENCE: 1056
gtgaancgtg gatgaagttg                                                    20

<210> SEQ ID NO 1057
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(7)
<223> OTHER INFORMATION: a, c, t, g, unknown or other

<400> SEQUENCE: 1057
gtgaacngtg gatgaagttg                                                    20

<210> SEQ ID NO 1058
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 1058
tgaacgtgga tgaagttgg                                          19

<210> SEQ ID NO 1059
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1059
taacgtggat gaagttggnr g                                       21

<210> SEQ ID NO 1060
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1060
tgacgtggat gaagttggnr g                                       21

<210> SEQ ID NO 1061
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1061
tgaagtggat gaagttggnr g                                       21

<210> SEQ ID NO 1062
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1062
tgaactggat gaagttggnr g                                       21

-continued

```
<210> SEQ ID NO 1063
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1063
tgaacgggat gaagttggnr g                                         21

<210> SEQ ID NO 1064
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1064
tgaacgtgat gaagttggnr g                                         21

<210> SEQ ID NO 1065
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1065
tgaacgtgat gaagttggnr g                                         21

<210> SEQ ID NO 1066
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1066
tgaacgtggt gaagttggnr g                                         21

<210> SEQ ID NO 1067
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1067
tgaacgtgga gaagttggnr g                                                   21

<210> SEQ ID NO 1068
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1068
tgaacgtgga taagttggnr g                                                   21

<210> SEQ ID NO 1069
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1069
tgaacgtgga tgagttggnr g                                                   21

<210> SEQ ID NO 1070
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1070
tgaacgtgga tgaattggnr g                                                   21

<210> SEQ ID NO 1071
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1071
```
tgaacgtgga tgaagtggnr g                                        21

<210> SEQ ID NO 1072
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1072
tgaacgtgga tgaagttgnr g                                        21

<210> SEQ ID NO 1073
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1073
tgaacgtgga tgaagttggr g                                        21

<210> SEQ ID NO 1074
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(20)
<223> OTHER INFORMATION: a, c, t, g, unknown or other

<400> SEQUENCE: 1074
tgaacgtgga tgaagttggn r                                        21

<210> SEQ ID NO 1075
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1075
ngaacgtgga tgaagttggn rg                                       22

<210> SEQ ID NO 1076
<211> LENGTH: 22
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1076
gnaacgtgga tgaagttggn rg                                              22

<210> SEQ ID NO 1077
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1077
ganacgtgga tgaagttggn rg                                              22

<210> SEQ ID NO 1078
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1078
gaancgtgga tgaagttggn rg                                              22

<210> SEQ ID NO 1079
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other
```

<400> SEQUENCE: 1079
gaacngtgga tgaagttggn rg                                              22

<210> SEQ ID NO 1080
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1080
gaacgntgga tgaagttggn rg                                              22

<210> SEQ ID NO 1081
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1081
gaacgtngga tgaagttggn rg                                              22

<210> SEQ ID NO 1082
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1082
gaacgtgnga tgaagttggn rg                                              22

<210> SEQ ID NO 1083
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1083
gaacgtggna tgaagttggn rg                                              22

<210> SEQ ID NO 1084
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1084
gaacgtggan tgaagttggn rg                                              22

<210> SEQ ID NO 1085
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1085
gaacgtggat ngaagttggn rg                                              22

<210> SEQ ID NO 1086
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1086
gaacgtggat gnaagttggn rg                                              22

<210> SEQ ID NO 1087
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1087
gaacgtggat ganagttggn rg                                             22

<210> SEQ ID NO 1088
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1088
gaacgtggat gaangttggn rg                                             22

<210> SEQ ID NO 1089
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1089
gaacgtggat gaagnttggn rg                                             22

<210> SEQ ID NO 1090
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (16)..(16)

```
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1090
gaacgtggat gaagtntggn rg                                              22

<210> SEQ ID NO 1091
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1091
gaacgtggat gaagttnggn rg                                              22

<210> SEQ ID NO 1092
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 1092
gaacgtggat gaagttgngn rg                                              22

<210> SEQ ID NO 1093
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(20)
<223> OTHER INFORMATION: a, c, t, g, unknown or other

<400> SEQUENCE: 1093
gaacgtggat gaagttggnn rg                                              22

<210> SEQ ID NO 1094
<211> LENGTH: 22
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: modified_base
<222> LOCATION: (19)..(20)
<223> OTHER INFORMATION: a, c, t, g, unknown or other

<400> SEQUENCE: 1094
gaacgtggat gaagttggnn rg                                             22

<210> SEQ ID NO 1095
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 1095
gaacgtggat gaagttggnr ng                                             22

<210> SEQ ID NO 1096
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(20)
<223> OTHER INFORMATION: a, c, t, g, unknown or other

<400> SEQUENCE: 1096
tgaacgtgga tgaagttggn rg                                             22

<210> SEQ ID NO 1097
<211> LENGTH: 22
<212> TYPE: DNA
<213> ORGANISM: Homo sapiens

<400> SEQUENCE: 1097
tgaacgtgga tgaagttggt gg                                             22

<210> SEQ ID NO 1098
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 1098
tgaacgtgga tgaagttggn rg                                             22

<210> SEQ ID NO 1099
<211> LENGTH: 22
<212> TYPE: DNA
```

<213> ORGANISM: Homo sapiens

<400> SEQUENCE: 1099
aaaacatgga tgaagttgga gg                                    22

<210> SEQ ID NO 1100
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 1100
tgaacgtgga tgaagttggn rg                                    22

<210> SEQ ID NO 1101
<211> LENGTH: 22
<212> TYPE: DNA
<213> ORGANISM: Homo sapiens

<400> SEQUENCE: 1101
acaacatgga tgaagttgga gg                                    22

<210> SEQ ID NO 1102
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 1102
tgaacgtgga tgaagttggn rg                                    22

<210> SEQ ID NO 1103
<211> LENGTH: 22
<212> TYPE: DNA
<213> ORGANISM: Homo sapiens

<400> SEQUENCE: 1103
acaacttgga tgaagttgga gg                                    22

<210> SEQ ID NO 1104
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 1104
tgaacgtgga tgaagttggn rg                                    22

<210> SEQ ID NO 1105
<211> LENGTH: 22
<212> TYPE: DNA
<213> ORGANISM: Homo sapiens

<400> SEQUENCE: 1105
acaacgtgga taaagttgga ag                                    22

```
<210> SEQ ID NO 1106
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 1106
tgaacgtgga tgaagttggn rg                                              22

<210> SEQ ID NO 1107
<211> LENGTH: 22
<212> TYPE: DNA
<213> ORGANISM: Homo sapiens

<400> SEQUENCE: 1107
acaacgtgga tgaaattgga gg                                              22

<210> SEQ ID NO 1108
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 1108
tgaacgtgga tgaagttggn rg                                              22

<210> SEQ ID NO 1109
<211> LENGTH: 22
<212> TYPE: DNA
<213> ORGANISM: Homo sapiens

<400> SEQUENCE: 1109
acaacgtgga tgaacttgga ag                                              22

<210> SEQ ID NO 1110
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 1110
tgaacgtgga tgaagttggn rg                                              22

<210> SEQ ID NO 1111
<211> LENGTH: 22
<212> TYPE: DNA
<213> ORGANISM: Homo sapiens

<400> SEQUENCE: 1111
acaacgtgga tgaacttgga gg                                              22

<210> SEQ ID NO 1112
<211> LENGTH: 22
<212> TYPE: DNA
<213> ORGANISM: Homo sapiens
<220> FEATURE:
<221> NAME/KEY: modified_base
<222> LOCATION: (20)..(20)
```

```
<223> OTHER INFORMATION: a, c, t, g, unknown or other

<400> SEQUENCE: 1112
tgaacgtgga tgaagttggn rg                                              22

<210> SEQ ID NO 1113
<211> LENGTH: 22
<212> TYPE: DNA
<213> ORGANISM: Homo sapiens

<400> SEQUENCE: 1113
acaacgtgga tgaacttgga gg                                              22

<210> SEQ ID NO 1114
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 1114
tgaacgtgga tgaagttggn rg                                              22

<210> SEQ ID NO 1115
<211> LENGTH: 22
<212> TYPE: DNA
<213> ORGANISM: Homo sapiens

<400> SEQUENCE: 1115
acaacgtgga tgaacttgga gg                                              22

<210> SEQ ID NO 1116
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 1116
tgaacgtgga tgaagttggn rg                                              22

<210> SEQ ID NO 1117
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1117
accaataggc agagagagtc ag                                              22

<210> SEQ ID NO 1118
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1118
```
aggtctcctt tatcccaaag ct                                      22

<210> SEQ ID NO 1119
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1119
cctggtaacc accattctac tc                                      22

<210> SEQ ID NO 1120
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1120
caacctaagt acccactgat ca                                      22

<210> SEQ ID NO 1121
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1121
gtgccagata tggaaatcat ct                                      22

<210> SEQ ID NO 1122
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1122
caacctaagt gtctagcaac ag                                      22

<210> SEQ ID NO 1123
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1123
ggcaaccacc attctcctct g                                       21

<210> SEQ ID NO 1124
<211> LENGTH: 22
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 1124
gccaccaccc attttctgtc tg                                          22

<210> SEQ ID NO 1125
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1125
cctcacccct agcaaccatc                                             20

<210> SEQ ID NO 1126
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1126
aaggaatcag cccaaatgtc ca                                          22

<210> SEQ ID NO 1127
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(20)
<223> OTHER INFORMATION: a, c, t, g, unknown or other

<400> SEQUENCE: 1127
tagagcggag gcaggaggcn gg                                          22

<210> SEQ ID NO 1128
<211> LENGTH: 23
<212> TYPE: DNA
<213> ORGANISM: Homo sapiens

<400> SEQUENCE: 1128
caggagagga ggcaggaggc agg                                         23

<210> SEQ ID NO 1129
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1129
```
agagcggagg caggaggcng g                                   21

<210> SEQ ID NO 1130
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 1130
tangagcgga ggcaggaggc ngg                                 23

<210> SEQ ID NO 1131
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 1131
tagagcggag gcaggaggcn gg                                  22

<210> SEQ ID NO 1132
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1132
tgtgagcgga ggcaggaggc agg                                 23

<210> SEQ ID NO 1133
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, t, g, unknown or other

<400> SEQUENCE: 1133
agagcggagg caggaggcng g                                   21

<210> SEQ ID NO 1134
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:

```
    Synthetic oligonucleotide"
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 1134
tnagagcgga ggcaggaggc ngg                                              23
```